United States Patent
Romero et al.

(10) Patent No.: US 9,340,554 B2
(45) Date of Patent: May 17, 2016

(54) IRAK INHIBITORS AND USES THEREOF

(71) Applicant: Nimbus Iris, Inc., Cambridge, MA (US)

(72) Inventors: Donna L. Romero, Chesterfield, MO (US); Matthew David Wessel, Sisters, OR (US); Shaughnessy Robinson, Westerly, RI (US); Jeremy Robert Greenwood, Brooklyn, NY (US); Karl Shawn Watts, Portland, OR (US); Leah Lynn Frye, Portland, OR (US); Geraldine C. Harriman, Charlestown, RI (US); Alan Franklin Corin, Sudbury, MA (US); Craig E. Masse, Cambridge, MA (US); Mee Shelley, Tigard, OR (US)

(73) Assignee: NIMBUS IRIS, INC., Cambridge, MA (US)

( * ) Notice: Subject to any disclaimer, the term of this patent is extended or adjusted under 35 U.S.C. 154(b) by 0 days.

(21) Appl. No.: 14/189,271

(22) Filed: Feb. 25, 2014

(65) Prior Publication Data

US 2015/0025093 A1    Jan. 22, 2015

Related U.S. Application Data

(63) Continuation of application No. 13/347,610, filed on Jan. 10, 2012, now Pat. No. 8,703,941.

(60) Provisional application No. 61/545,873, filed on Oct. 11, 2011, provisional application No. 61/431,227, filed on Jan. 10, 2011.

(51) Int. Cl.
    *C07D 495/04* (2006.01)

(52) U.S. Cl.
    CPC .................... *C07D 495/04* (2013.01)

(58) Field of Classification Search
    CPC ...................................................... C07D 495/04
    See application file for complete search history.

(56) References Cited

U.S. PATENT DOCUMENTS

| | | | |
|---|---|---|---|
| 6,297,238 B1 | 10/2001 | Doyle et al. |
| 6,482,948 B1 | 11/2002 | Yamada et al. |
| 7,829,570 B2 | 11/2010 | Hirst et al. |
| 8,058,285 B2 | 11/2011 | Reichelt et al. |
| 8,703,941 B2 | 4/2014 | Romero et al. |
| 2002/0058667 A1 | 5/2002 | Castelhano et al. |
| 2003/0119829 A1 | 6/2003 | Stolle et al. |
| 2007/0155777 A1 | 7/2007 | Burkitt et al. |
| 2008/0176871 A1 | 7/2008 | Girardet et al. |
| 2010/0041676 A1 | 2/2010 | Hirst et al. |
| 2010/0063047 A1 | 3/2010 | Borchardt et al. |
| 2010/0143341 A1 | 6/2010 | Taylor et al. |
| 2010/0227853 A1 | 9/2010 | Hoffman et al. |
| 2012/0015962 A1 | 1/2012 | Arora et al. |
| 2012/0283238 A1 | 11/2012 | Romero et al. |
| 2013/0231328 A1 | 9/2013 | Harriman et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |

FOREIGN PATENT DOCUMENTS

| | | | |
|---|---|---|---|
| WO | WO-02/088138 A1 | 11/2002 |
| WO | WO-03/057149 A2 | 7/2003 |
| WO | WO 2004/041285 A1 | 5/2004 |
| WO | WO 2004089312 A2 * | 10/2004 |
| WO | WO 2011/029054 | 3/2011 |
| WO | WO-2012/007375 A1 | 1/2012 |
| WO | WO 2012/012712 | 1/2012 |
| WO | WO-2012/097013 A1 | 7/2012 |
| WO | WO-2013/078126 A1 | 5/2013 |

OTHER PUBLICATIONS

Wang, Zhulun. Current Topics in Medicinal Chemistry, 2009, 9, 724-737.*
WebMD, Psoriasis Health Center, 2014, <http://www.webmd.com/skin-problems-and-treatments/psoriasis/understanding-psoriasis-treatment>.*
National Cancer Institute, Drugs Approced for Melanoma, 2013, <http://www.cancer.gov/cancertopics/druginfo/melanoma/print>.*
International Search Report for PCT/US 12/20845, mailed May 16, 2012.
CAS STN Abstract, RN 1185175-64-7 & 1008036-50-7 (Pub. Mar. 14, 2008 & Sep. 16, 2009).
International Search Report for PCT/US2013/020981, 3 pages (Mar. 18, 2013).
International Search Report for PCT/US2013/050108, 3 pages (Dec. 16, 2013).
International Search Report for PCT/US2013/050113, 2 pages (Dec. 9, 2013).
International Search Report for PCT/US2014/010652, 3 pages (Apr. 30, 2014).
Ngo, VN et al., Oncogenically active MYD88 mutations in human lymphoma, Nature, 470(7332): 115-119 (2011).
Patani, G.A. and Lavoie, E.J., Bioisosterism: A Rational Approach in Drug Design, Chem. Rev., 96: 3147-3176 (1996).
Song, KW et al., The kinase activities of interleukin-1 receptor associated kinase (IRAK)-1 and 4 are redundant in the control of inflammatory cytokine expression in human cells, Molecular Immunology, 46(7): 1458-1466 (2009).
Written Opinion for PCT/US2012/020845, 7 pages (May 16, 2012).
Written Opinion for PCT/US2013/020981, 8 pages (Mar. 18, 2013).
Written Opinion for PCT/US2013/050108, 24 pages (Dec. 16, 2013).
Written Opinion for PCT/US2013/050113, 25 pages (Dec. 9, 2013).
Written Opinion for PCT/US2014/010652, 10 pages (Apr. 30, 2014).

* cited by examiner

*Primary Examiner* — Golam M M Shameem
*Assistant Examiner* — Laura Daniel
(74) *Attorney, Agent, or Firm* — Dechert LLP; Andrea L.C. Reid

(57) ABSTRACT

The present invention provides 5,6,7,8-tetrahydrobenzo[4,5]thieno[2,3-d]pyrimidine compounds and pharmaceutical compositions thereof as inhibitors of IRAK.

9 Claims, No Drawings

IRAK INHIBITORS AND USES THEREOF

CROSS-REFERENCE TO RELATED APPLICATIONS

This application is a continuation of U.S. application Ser. No. 13/347,610, filed on Jan. 10, 2012, granted as U.S. Pat. No. 8,703,941 on Apr. 22, 2014, which claims priority to U.S. Provisional Patent Application Ser. No. 61/431,227, filed on Jan. 10, 2011, and U.S. Provisional Patent Application Ser. No. 61/545,873, filed Oct. 11, 2011, the entire contents of each of which are hereby incorporated by reference.

TECHNICAL FIELD OF THE INVENTION

The present invention relates to compounds and methods useful for inhibiting one or more interleukin-1 receptor-associated kinases ("IRAK"). The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1), interleukin-8 (IL-8) and tumor necrosis factor $\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

DETAILED DESCRIPTION OF CERTAIN EMBODIMENTS

1. General Description of Certain Embodiments of the Invention

Compounds of the present invention, and compositions thereof, are useful as inhibitors of one or more IRAK protein kinases. In some embodiments, a provided compound inhibits IRAK-1 and IRAK-4.

The binding pocket of IRAK-4 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of IRAK-4.

Water molecules occupying hydration sites in the binding pocket of IRAK-4 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

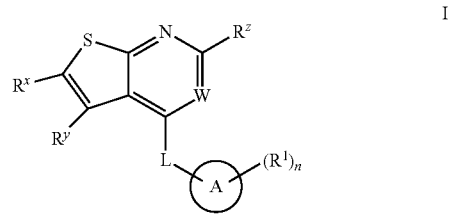

or a pharmaceutically acceptable salt thereof, wherein:

Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

n is 0-4;

each $R^1$ is independently —R, halogen, —CN, —NO$_2$, —OR, —CH$_2$OR, —SR, —N(R)$_2$, —SO$_2$R, —SO$_2$N(R)$_2$, —SOR, —C(O)R, —CO$_2$R, —C(O)N(R)$_2$, —C(O)N(R)—OR, —NRC(O)R, —NRC(O)N(R)$_2$, Cy, or —NRSO$_2$R, or:

two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen, deuterium, or an optionally substituted group selected from $C_{1-6}$ aliphatic, aryl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each of $R^x$ and $R^y$ is independently —R, halogen, —CN, —NO$_2$, —OR, —SR, —N(R)$_2$, —SO$_2$R, —SO$_2$N(R)$_2$, —SOR, —C(O)R, —CO$_2$R, —C(O)N(R)$_2$, —NRC(O)R, —NRC(O)N(R)$_2$, or —NRSO$_2$R, or:

$R^x$ and $R^y$ are taken together with their intervening atoms to form Ring B substituted with m occurrences of $R^2$;

Ring B is a 4-8 membered partially unsaturated carbocyclic fused ring or a 4-8 membered partially unsaturated azacyclic fused ring having one or two nitrogens;

m is 0-4;

each $R^2$ is independently —R, halogen, —CN, —NO$_2$, —OR, —SR, —N(R)$_2$, —SO$_2$R, —SO$_2$N(R)$_2$, —SOR, —C(O)R, —CO$_2$R, —C(O)N(R)$_2$, —NRC(O)R, —NRC(O)N(R)$_2$, or —NRSO$_2$R, or:

two $R^2$ groups are taken together with their intervening atoms to form an optionally substituted 4-7 membered fused, spiro-fused, or bridged bicyclic ring having 0-2 heteroatoms independently selected from nitrogen, oxygen, or sulfur;

W is N or —C($R^3$)—;

$R^z$ is R, CN, NO$^2$, halogen, —C(O)N(R)$_2$, —C(O)OR, —C(O)R, —N(R)$_2$, —OR, or —SO$^2$N(R)$_2$;

$R^3$ is hydrogen, halogen, —CN, $C_{1-4}$ aliphatic, $C_{1-4}$ haloaliphatic, —OR, —C(O)R, or —C(O)N(R)$_2$; and L is a covalent bond or a $C_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

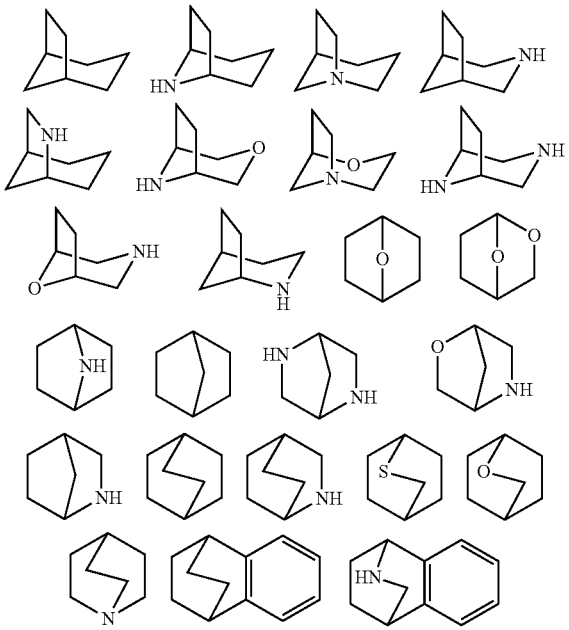

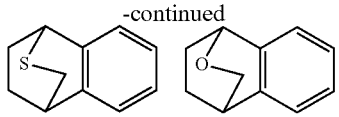

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

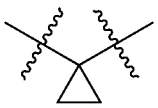

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits IRAK-4 with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof 3. Description of Exemplary Embodiments As described above, in certain embodiments, the present invention provides a compound of formula I:

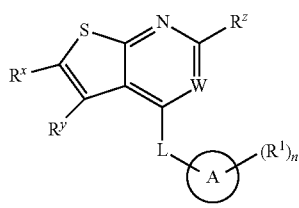

I or a pharmaceutically acceptable salt thereof, wherein:
Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
n is 0-4;
each $R^1$ is independently —R, halogen, —CN, —NO$_2$, —OR, —CH$_2$OR, —SR, —N(R)$_2$, —SO$_2$R, —SO$_2$N(R)$_2$, —SOR, —C(O)R, —CO$_2$R, —C(O)N(R)$_2$, —C(O)N(R)—OR, —NRC(O)R, —NRC(O)N(R)$_2$, Cy, or —NRSO$_2$R, or:
  two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;
each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
each R is independently hydrogen or an optionally substituted group selected from C$_{1-6}$ aliphatic, aryl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;
each of $R^x$ and $R^y$ is independently —R, halogen, —CN, —NO$_2$, —OR, —SR, —N(R)$_2$, —SO$_2$R, —SO$_2$N(R)$_2$, —SOR, —C(O)R, —CO$_2$R, —C(O)N(R)$_2$, —NRC(O)R, —NRC(O)N(R)$_2$, or —NRSO$_2$R, or:
  $R^x$ and $R^y$ are taken together with their intervening atoms to form Ring B substituted with m occurrences of $R^2$;

Ring B is a 4-8 membered partially unsaturated carbocyclic fused ring or a 4-8 membered partially unsaturated azacyclic fused ring having one or two nitrogens;
m is 0-4;
each $R^2$ is independently —R, halogen, —CN, —NO$_2$, —OR, —SR, —N(R)$_2$, —SO$_2$R, —SO$_2$N(R)$_2$, —SOR, —C(O)R, —CO$_2$R, —C(O)N(R)$_2$, —NRC(O)R, —NRC(O)N(R)$_2$, or —NRSO$_2$R, or:
  two $R^2$ groups are taken together with their intervening atoms to form an optionally substituted 4-7 membered fused, spiro-fused, or bridged bicyclic ring having 0-2 heteroatoms independently selected from nitrogen, oxygen, or sulfur;
W is N or —C($R^3$)—;
$R^z$ is R, CN, NO$^2$, halogen, —C(O)N(R)$_2$, —C(O)OR, —C(O)R, —N(R)$_2$, —OR or —SO$^2$N(R)$_2$;
$R^3$ is hydrogen, halogen, —CN, C$_{1-4}$ aliphatic, C$_{1-4}$ haloaliphatic, —OR, —C(O)R, or —C(O)N(R)$_2$; and
L is a covalent bond or a C$_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—.

As defined generally above, the Ring A group of formula I is a 3-7 membered saturated or partially unsaturated carbocyclic ring or a 4-7 membered saturated or partially unsaturated heterocyclic ring having 1-3 heteroatoms independently selected from nitrogen, oxygen, or sulfur. In some embodiments, Ring A is a 3-7 membered saturated or partially unsaturated carbocyclic ring. In certain embodiments, Ring A is a 4-7 membered saturated or partially unsaturated heterocyclic ring having 1-3 heteroatoms independently selected from nitrogen, oxygen, or sulfur.

In some embodiments, Ring A is a 3-7 membered saturated carbocyclic ring. In certain embodiments, Ring A is cyclopentyl or cyclohexyl.

In certain embodiments, Ring A is a 4-7 membered saturated heterocyclic ring having 1-3 heteroatoms independently selected from nitrogen, oxygen, or sulfur. In certain embodiments, Ring A is a 5-6 membered saturated heterocyclic ring having 1-3 heteroatoms independently selected from nitrogen, oxygen, or sulfur. In certain embodiments, Ring A is piperidinyl, piperazinyl, morpholinyl, thiomorpholinyl, tetrahydropyranyl, or tetrahydrofuranyl.

As defined generally above, the n group of formula I is 0-4. In some embodiments, n is 0. In other embodiments, n is 1-4. In certain embodiments, n is 1 or 2.

As defined generally above, each $R^1$ group of formula I is independently —R, halogen, —CN, —NO$_2$, —OR, —CH$_2$OR, —SR, —N(R)$_2$, —SO$_2$R, —SO$_2$N(R)$_2$, —SOR, —C(O)R, —CO$_2$R, —C(O)N(R)$_2$, —C(O)N(R)—OR, —NRC(O)R, —NRC(O)N(R)$_2$, Cy, or —NRSO$_2$R, or $R^1$ is selected from one of the following groups:

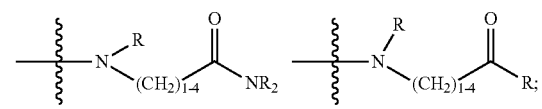

or
  two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur.

In certain embodiments, R¹ is R, —OR, —N(R)₂, —CO₂R, —C(O)N(R)₂, —C(O)N(R)—OR, —SO₂N(R)₂, Cy, or —NRC(O)R. In some embodiments, R¹ is —C(O)NH₂, —C(O)NHCH₃, —C(O)NH—OH, —CH₃, —CH₂CH₃, —SO₂t-butyl, —OH, —C(O)OH, —NH₂, —NHCH₃, —N(CH₃)₂, —N(CH₂CH₃)₂, —NHC(O)CH₃, or —CH₂phenyl. In certain embodiments, R¹ is Cy. In certain embodiments, R1 is —N(R)₂. In certain embodiments, R1 is selected from one of the following groups:

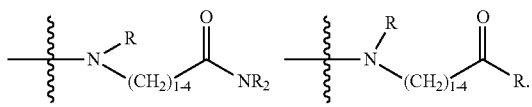

Exemplary R¹ groups include those depicted in Table 1.

In some embodiments, the present invention provides a compound of formula I wherein two R¹ groups are taken together with their intervening atoms to form an optionally substituted 4-7 membered fused, spiro-fused, or bridged bicyclic ring having 0-2 heteroatoms independently selected from nitrogen, oxygen, or sulfur. In certain embodiments, two R¹ groups on adjacent carbon atoms are taken together to form an optionally substituted 4-7 membered ring fused to Ring A. In other embodiments, two R¹ groups on the same carbon atom are taken together to form an optionally substituted 4-7 membered spiro-fused ring. In other embodiments, two R¹ groups on non-adjacent carbon atoms are taken together to form an optionally substituted bridged bicyclic ring with Ring A. In certain embodiments, R¹ is —N(R)₂.

As defined generally above, Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur.

In some embodiments, Cy is a 3-7 membered saturated carbocyclic ring. In certain embodiments, Cy is a 4-7 membered saturated heterocyclic ring containing 1-2 heteroatoms independently selected from nitrogen, oxygen or sulfur. In certain embodiments, Cy is morpholinyl, pyrrolidinyl, azetidinyl, piperidinyl or piperazinyl.

One of ordinary skill in the art will appreciate that an R¹ substituent on a saturated carbon of Ring A forms a chiral center of a chiral compound, or a stereocenter of a meso compound. In some embodiments, that chiral center is in the (R) configuration. In other embodiments, that chiral center is in the (S) configuration. In some embodiments, the stereocenter gives a trans substitution relative to the other stereocenter. In some embodiments, the stereocenter gives a cis substitution relative to the other stereocenter.

As defined generally above, the L group of formula I is a covalent bond or a C₁₋₆ bivalent hydrocarbon chain wherein one or two methylene units of the chain are optionally and independently replaced by —NR—, —N(R)C(O)—, —C(O)N(R)—, —N(R)SO₂—, —SO₂N(R)—, —O—, —C(O)—, —OC(O)—, —C(O)O—, —S—, —SO— or —SO₂—. In some embodiments, L is a covalent bond. In other embodiments, L is a C₁₋₆ bivalent hydrocarbon chain wherein one or two methylene units of the chain are optionally and independently replaced by —NR—, —N(R)C(O)—, —C(O)N(R)—, —N(R)SO₂—, —SO₂N(R)—, —O—, —C(O)—, —OC(O)—, —C(O)O—, —S—, —SO— or —SO₂—.

In some embodiments, L is —NH— (i.e., a C₁ bivalent hydrocarbon chain wherein the methylene unit is replaced by —NH—), —O—, —CH₂O—, —OCH₂—, —NHC(O)—, —CH₂NH—, or —NHCH₂—. Exemplary L groups include those depicted in Table 1.

As defined generally above, the $R^x$ and $R^y$ groups of formula I are each independently —R, halogen, —CN, —NO₂, —OR, —SR, —N(R)₂, —SO₂R, —SO₂N(R)₂, —SOR, —C(O)R, —CO₂R, —C(O)N(R)₂, —NRC(O)R, —NRC(O)N(R)₂, or —NRSO₂R, or $R^x$ and $R^y$ are taken together with their intervening atoms to form Ring B substituted with m occurrences of $R^2$.

In some embodiments, the $R^x$ and $R^y$ groups of formula I are each independently —R, halogen, —CN, —NO₂, —OR, —SR, —N(R)₂, —SO₂R, —SO₂N(R)₂, —SOR, —C(O)R, —CO₂R, —C(O)N(R)₂, —NRC(O)R, —NRC(O)N(R)₂, or —NRSO₂R. In some embodiments, the $R^x$ and $R^y$ groups of formula I are each independently —R, halogen, —N(R)₂, —SO₂R, —SO₂N(R)₂, —SOR, —C(O)R, —CO₂R, —C(O)N(R)₂, —NRC(O)R, —NRC(O)N(R)₂, or —NRSO₂R.

In certain embodiments, $R^x$ is hydrogen and $R^y$ is —R, halogen, —CN, —NO₂, —OR, —SR, —N(R)₂, —SO₂R, —SO₂N(R)₂, —SOR, —C(O)R, —CO₂R, —C(O)N(R)₂, —NRC(O)R, —NRC(O)N(R)₂, or —NRSO₂R. In other embodiments, $R^y$ is hydrogen and $R^x$ is —R, halogen, —CN, —NO₂, —OR, —SR, —N(R)₂, —SO₂R, —SO₂N(R)₂, —SOR, —C(O)R, —CO₂R, —C(O)N(R)₂, —NRC(O)R, —NRC(O)N(R)₂, or —NRSO₂R. In some embodiments, $R^x$ and $R^y$ are both hydrogen. In other embodiments, one of $R^x$ and $R^y$ is optionally substituted C₁₋₆ aliphatic. In other embodiments, both of $R^x$ and $R^y$ are optionally substituted C₁₋₆ aliphatic. In some embodiments, both of $R^x$ and $R^y$ are methyl. Exemplary $R^x$ and $R^y$ groups include those depicted in Table 1.

In other embodiments, the $R^x$ and $R^y$ groups of formula I are taken together with their intervening atoms to form Ring B substituted with m occurrences of $R^2$.

As defined generally above, the Ring B group of formula I is a 4-8 membered partially unsaturated carbocyclic fused ring or a 4-8 membered partially unsaturated azacyclic fused ring having one or two nitrogens. In some embodiments, Ring B is a 4-8 membered partially unsaturated carbocyclic fused ring. In other embodiments, Ring B is a 4-8 membered partially unsaturated azacyclic fused ring having one or two nitrogens. In some embodiments, Ring B is a cyclohexo- or cyclopento-fused ring substituted with m occurrences of $R^2$. In other embodiments, Ring B is a piperidino-fused ring substituted with m occurrences of $R^2$.

As defined generally above, the m group of formula I is 0-4. In some embodiments, m is 0. In other embodiments, m is 1-4. In certain embodiments, m is 1 or 2.

As defined generally above, the R² group of formula I is each R² is independently —R, halogen, —CN, —NO₂, —OR, —SR, —N(R)₂, —SO₂R, —SO₂N(R)₂, —SOR, —C(O)R, —CO₂R, —C(O)N(R)₂, —NRC(O)R, —NRC(O)N(R)₂, or —NRSO₂R, or two R² groups are taken together with their intervening atoms to form an optionally substituted 4-7 membered fused, spiro-fused, or bridged bicyclic ring having 0-2 heteroatoms independently selected from nitrogen, oxygen, or sulfur.

In some embodiments, each R² is R wherein R is optionally substituted C₁₋₆ aliphatic. In certain embodiments, each R² is methyl or ethyl. In other embodiments, R² is methyl and m is 2 wherein both R² groups are on the same carbon atom thereby forming a gem dimethyl substituent. Exemplary R² groups include those depicted in Table 1.

In some embodiments, the present invention provides a compound of formula I wherein two R² groups are taken together with their intervening atoms to form an optionally substituted 4-7 membered fused, spiro-fused, or bridged bicyclic ring having 0-2 heteroatoms independently selected from nitrogen, oxygen, or sulfur. In certain embodiments, two $R^2$ groups on adjacent carbon atoms are taken together to form an optionally substituted 4-7 membered ring fused to Ring B. In other embodiments, two $R^2$ groups on the same carbon atom are taken together to form an optionally substituted 4-7 membered spiro-fused ring. In other embodiments, two $R^2$ groups on non-adjacent carbon atoms are taken together to form an optionally substituted bridged bicyclic ring with Ring B.

One of ordinary skill in the art will appreciate that an $R^2$ substituent on a saturated carbon of Ring B forms a chiral center. In some embodiments, that chiral center is in the (R) configuration. In other embodiments, that chiral center is in the (S) configuration.

As defined generally above, the $R^z$ group of formula I is R, CN, $NO^2$, halogen, —C(O)N(R)$_2$, —C(O)OR, —C(O)R, —N(R)$_2$, —OR, or —SO$^2$N(R)$_2$. In some embodiments, $R^z$ is hydrogen. In other embodiments, $R^z$ is CN, halogen, —N(R)$_2$ or —C(O)N(R)$_2$. In some embodiments $R^z$ is —N(R)$_2$. Exemplary $R^z$ groups include those depicted in Table 1.

In some embodiments, the compound of formula I is not selected from the following compounds:

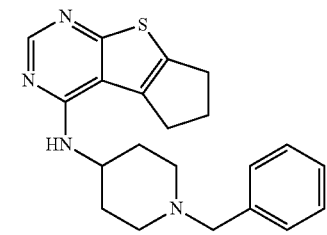

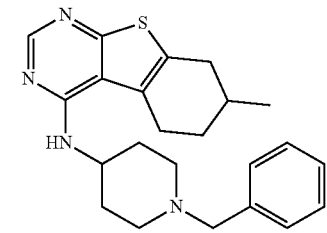

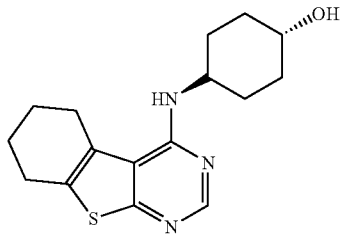

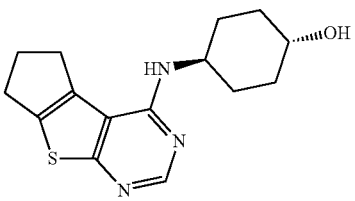

-continued

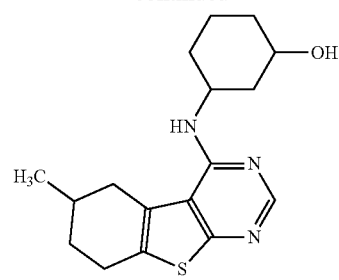

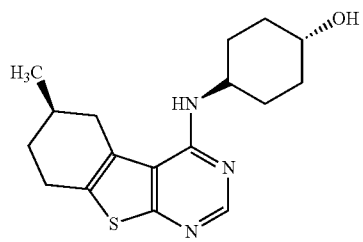

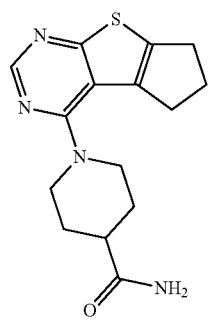

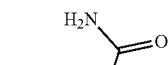

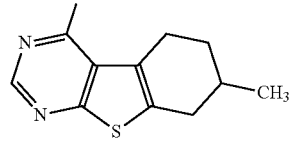

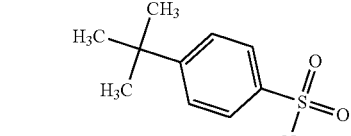

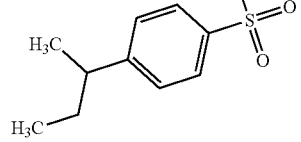

-continued
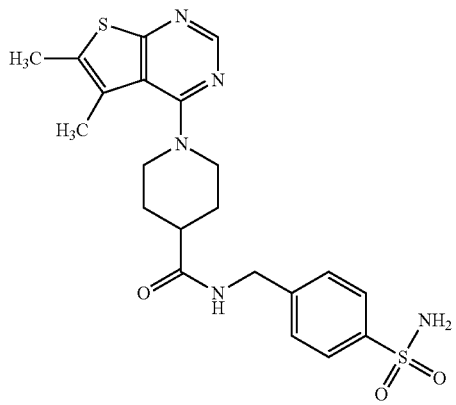
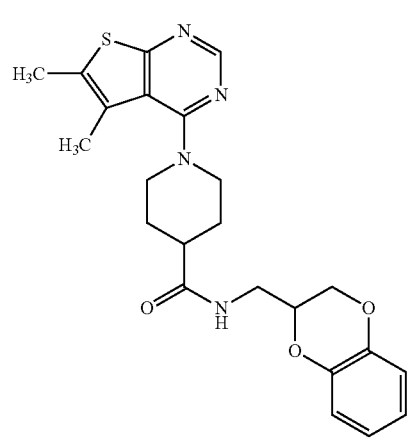
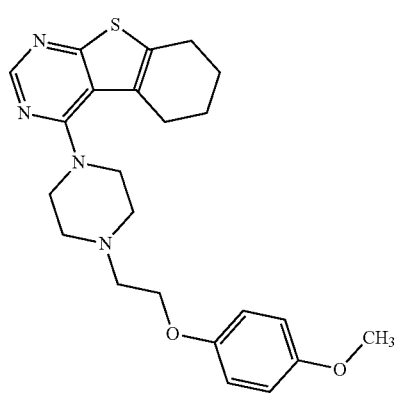
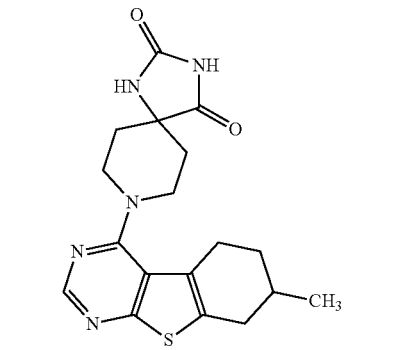
-continued
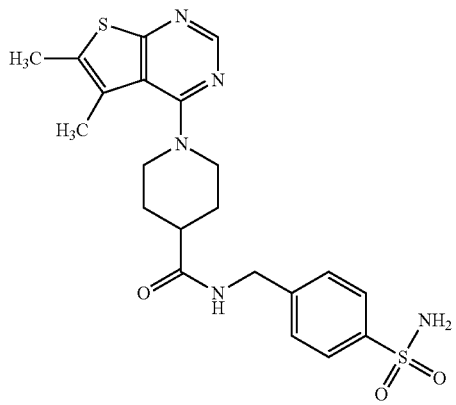
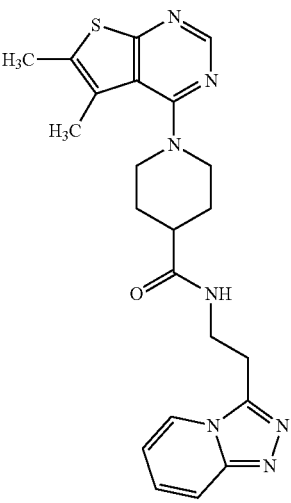
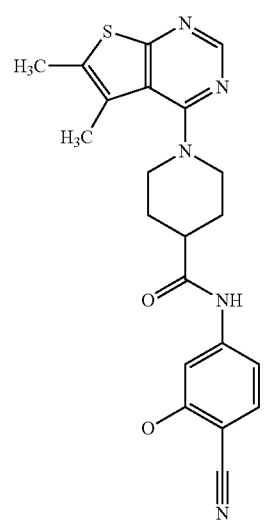
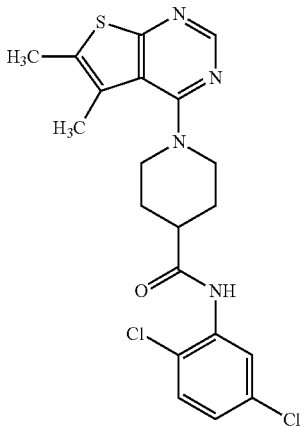

-continued

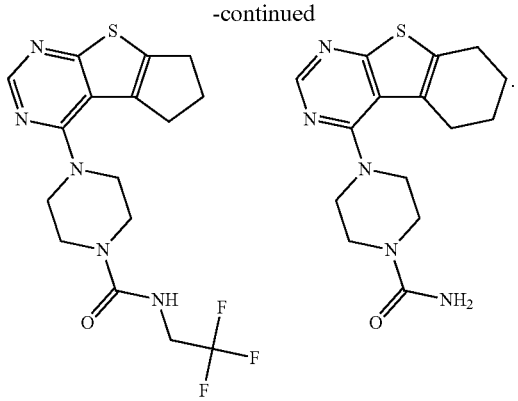

In some embodiments, the present invention provides a compound of formula I wherein L is a covalent bond, thereby forming a compound of formula I-a:

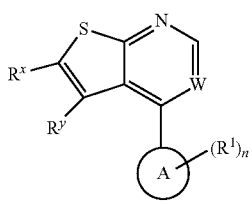

I-a or a pharmaceutically acceptable salt thereof, wherein each of Ring A, $R^1$, n, $R^x$ and $R^y$ is as defined above for formula I and described in embodiments set forth herein, singly and in combination.

In some embodiments, the present invention provides a compound of formula I wherein W is N thereby forming a compound of formula I-b:

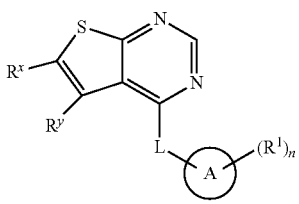

I-b or a pharmaceutically acceptable salt thereof, wherein each of Ring A, L, $R^1$, n, $R^x$ and $R^y$ is as defined above for formula I and described in embodiments set forth herein, singly and in combination.

In some embodiments, the present invention provides a compound of formula I-a wherein W is N, thereby forming a compound of formula I-c:

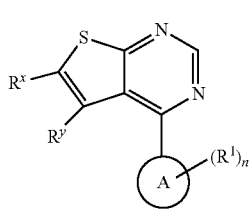

I-c or a pharmaceutically acceptable salt thereof, wherein each of Ring A, $R^1$, n, $R^x$ and $R^y$ is as defined above for formula I and described in embodiments set forth herein, singly and in combination.

In some embodiments, the present invention provides a compound of formula I wherein W is N and Ring A is cyclohexyl, thereby forming a compound of formula I-d:

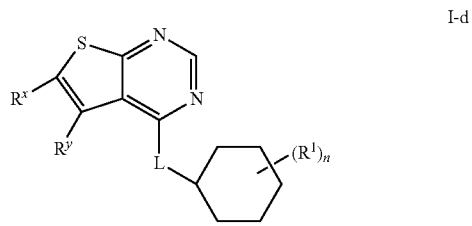

I-d or a pharmaceutically acceptable salt thereof, wherein each of L, $R^1$, n, $R^x$ and $R^y$ is as defined above for formula I and described in embodiments set forth herein, singly and in combination.

In some embodiments, the present invention provides a compound of formula I-c wherein Ring A is piperidin-1-yl, thereby forming a compound of formula I-e:

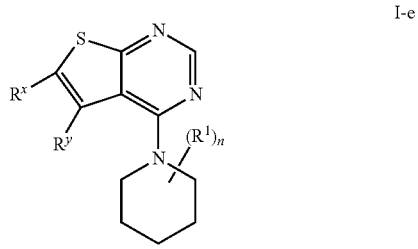

I-e or a pharmaceutically acceptable salt thereof, wherein each of $R^1$, n, $R^x$ and $R^y$ is as defined above for formula I and described in embodiments set forth herein, singly and in combination.

In certain embodiments, the present invention provides a compound of any of formulae I-a, I-b, I-c, I-d, or I-e, wherein $R^x$ and $R^y$ are each independently a $C_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—.

In some embodiments, the present invention provides a compound of formula I wherein $R^x$ and $R^y$ are taken together to form Ring B substituted with m occurrences of $R^2$, thereby forming a compound of formula II:

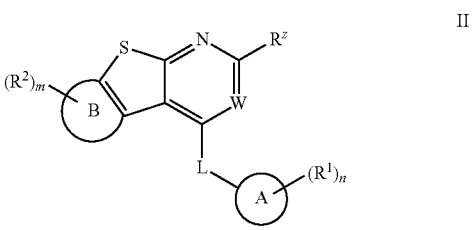

II or a pharmaceutically acceptable salt thereof, wherein each of Ring A, Ring B, W, m, $R^2$ L, $R^1$, and n is as defined above for formula I and described in embodiments set forth herein, singly and in combination.

In some embodiments, the present invention provides a compound of formula II wherein L is a covalent bond, thereby forming a compound of formula II-a:

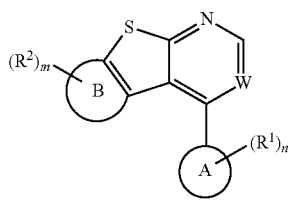

II-a or a pharmaceutically acceptable salt thereof, wherein each of Ring A, Ring B, W, m, $R^2$ $R^1$, and n is as defined above for formula I and described in embodiments set forth herein, singly and in combination.

In some embodiments, the present invention provides a compound of formula II wherein W is N, thereby forming a compound of formula II-b:

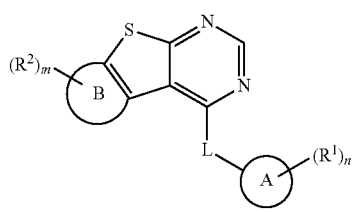

II-b or a pharmaceutically acceptable salt thereof, wherein each of Ring A, Ring B, m, $R^2$ L, $R^1$, and n is as defined above for formula I and described in embodiments set forth herein, singly and in combination.

In some embodiments, the present invention provides a compound of formula II-a wherein W is N, thereby forming a compound of formula II-c:

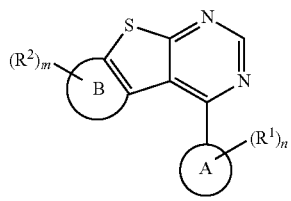

II-c or a pharmaceutically acceptable salt thereof, wherein each of Ring A, Ring B, m, $R^2$ L, $R^1$, and n is as defined above for formula I and described in embodiments set forth herein, singly and in combination.

In some embodiments, the present invention provides a compound of formula II-b wherein Ring A is cyclohexyl, thereby forming a compound of formula II-d:

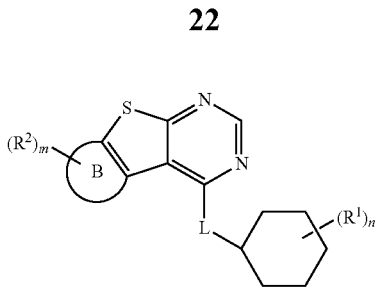

II-d or a pharmaceutically acceptable salt thereof, wherein each of Ring B, m, $R^2$ L, $R^1$, and n is as defined above for formula I and described in embodiments set forth herein, singly and in combination.

In some embodiments, the present invention provides a compound of formula II-c wherein Ring A is piperidin-1-yl, thereby forming a compound of formula II-e:

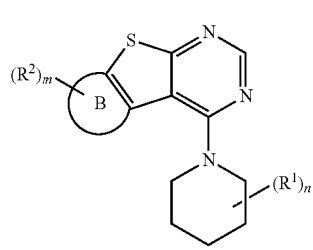

II-e or a pharmaceutically acceptable salt thereof, wherein each of Ring B, m, $R^2$, $R^1$, and n is as defined above for formula I and described in embodiments set forth herein, singly and in combination.

In some embodiments, the present invention provides a compound of formula II wherein W is N, and m is 0, thereby forming a compound of formula II-f:

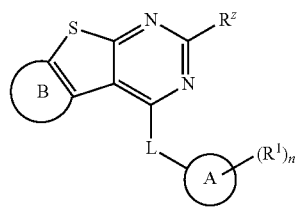

II-f or a pharmaceutically acceptable salt thereof, wherein each of Ring A, Ring B, L, $R^1$, $R^z$, and n is as defined above for formula I and described in embodiments set forth herein, singly and in combination.

In some embodiments, the present invention provides a compound of formula II-f wherein the compound is not one of the following:

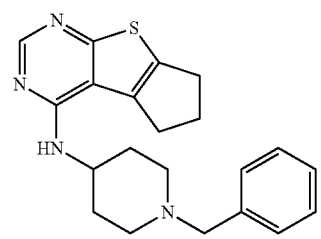

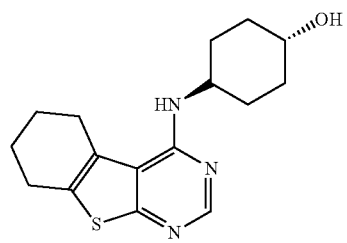

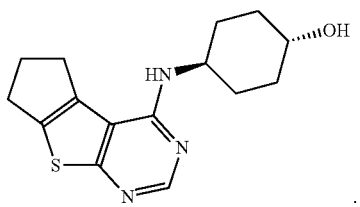

In some embodiments, the present invention provides a compound of formula I wherein Ring B is cyclohexo or cyclopento, thereby forming a compound of formula III or IV:

III

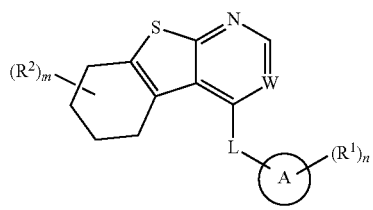

IV

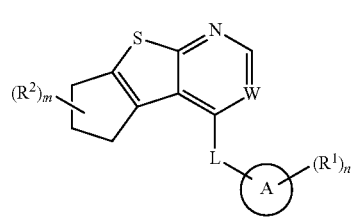

or a pharmaceutically acceptable salt thereof, wherein each of Ring A, m, W, L, $R^2$, $R^1$, and n is as defined above for formula I and described in embodiments set forth herein, singly and in combination.

In some embodiments, the present invention provides a compound of formula III or IV wherein L is a covalent bond, thereby forming a compound of formula III-a or IV-a:

III-a

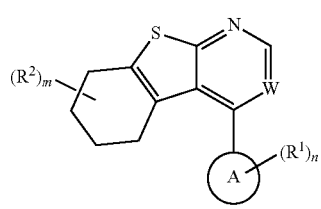

IV-a

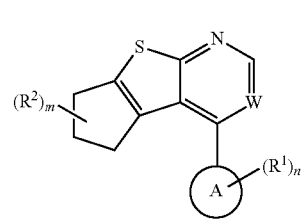

or a pharmaceutically acceptable salt thereof, wherein each of Ring A, m, W, $R^2$, $R^1$, and n is as defined above for formula I and described in embodiments set forth herein, singly and in combination.

In some embodiments, the present invention provides a compound of formula III or IV wherein W is N, thereby forming a compound of formula III-b or IV-b:

III-b

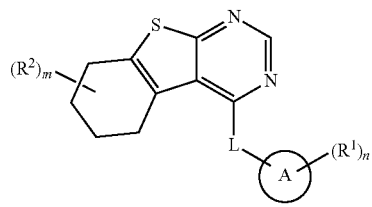

IV-b

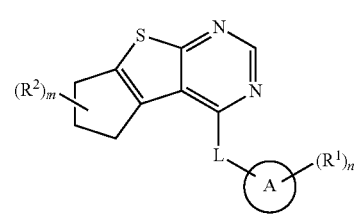

or a pharmaceutically acceptable salt thereof, wherein each of Ring A, m, L, $R^2$, $R^1$, and n is as defined above for formula I and described in embodiments set forth herein, singly and in combination.

In some embodiments, the present invention provides a compound of formula III-a or IV-a wherein W is N, thereby forming a compound of formula III-c or IV-c:

III-c

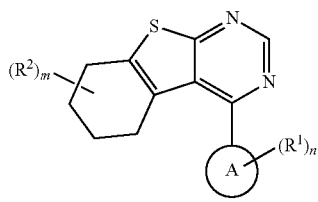

IV-c

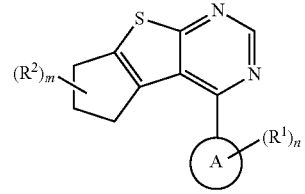

or a pharmaceutically acceptable salt thereof, wherein each of Ring A, m, $R^2$, $R^1$, and n is as defined above for formula I and described in embodiments set forth herein, singly and in combination.

In some embodiments, the present invention provides a compound of formula III-b or IV-b wherein Ring A is cyclohexyl, thereby forming a compound of formula III-d or IV-d:

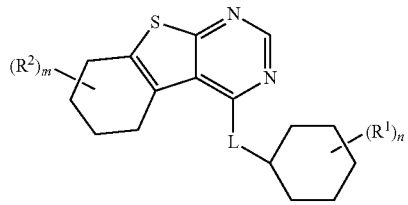

III-d

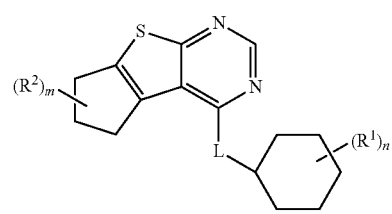

IV-d or a pharmaceutically acceptable salt thereof, wherein each of m, L, $R^2$, $R^1$, and n is as defined above for formula I and described in embodiments set forth herein, singly and in combination.

In some embodiments, the present invention provides a compound of formula III-c or IV-c wherein Ring A is piperidin-1-yl, thereby forming a compound of formula III-e or IV-e:

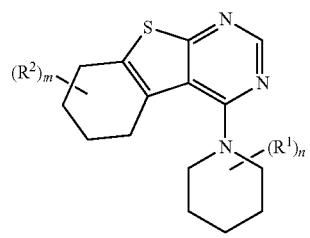

III-e

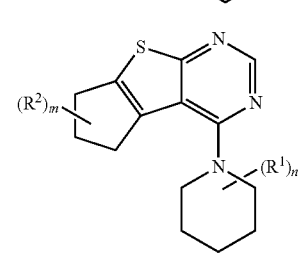

IV-e or a pharmaceutically acceptable salt thereof, wherein each of m, $R^2$, $R^1$, and n is as defined above for formula I and described in embodiments set forth herein, singly and in combination.

In some embodiments, the present invention provides a compound of formula III or IV wherein m is 0, thereby forming a compound of formula III-f or IV-f:

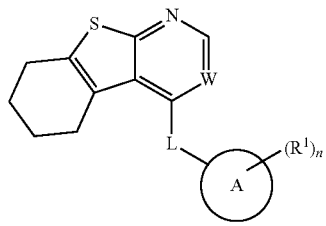

III-f

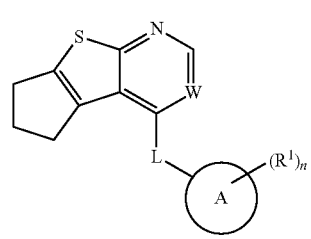

IV-f or a pharmaceutically acceptable salt thereof, wherein each of W, $R^1$, and n is as defined above for formula I and described in embodiments set forth herein, singly and in combination.

In some embodiments, the present invention provides a compound of formula III-f or IV-f wherein W is N, thereby forming a compound of formula III-g or IV-g:

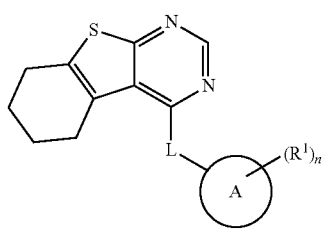

III-g

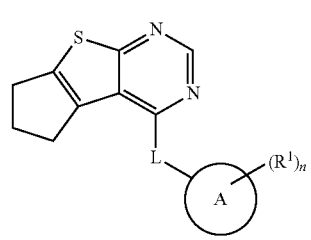

IV-g or a pharmaceutically acceptable salt thereof, wherein each of $R^1$, and n is as defined above for formula I and described in embodiments set forth herein, singly and in combination.

In some embodiments, the present invention provides a compound of formula III-d or IV-d wherein m is 0, thereby forming a compound of formula III-h or IV-h:

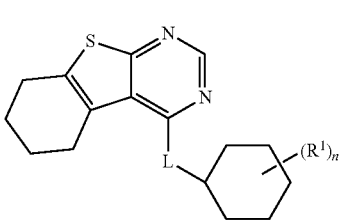

III-h

IV-h

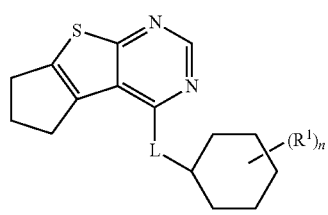

or a pharmaceutically acceptable salt thereof, wherein each of $R^1$, and n is as defined above for formula I and described in embodiments set forth herein, singly and in combination.

In some embodiments the present invention provides a compound of formula III-h or IV-h wherein n is 1, and $R^1$ is —N(R)$_2$, thereby forming a compound of formula III-i or IV-i:

III-i

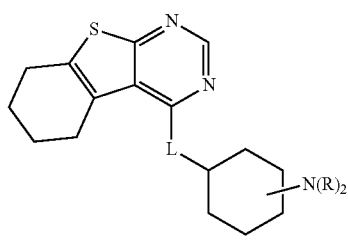

IV-i

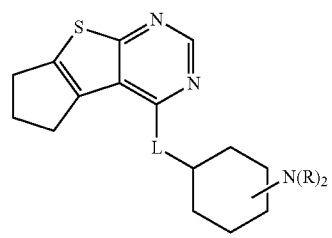

or a pharmaceutically acceptable salt thereof, wherein R is as defined above for formula I and described in embodiments set forth herein, singly and in combination.

In some embodiments the present invention provides a compound of formula III-h or IV-h wherein n is 1, and $R^1$ is morpholinyl, thereby forming a compound of formula III-j or IV-j:

III-j

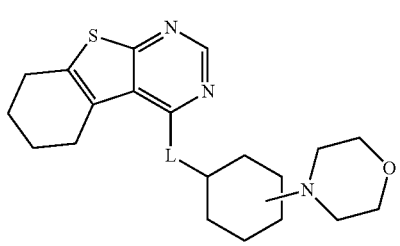

IV-j

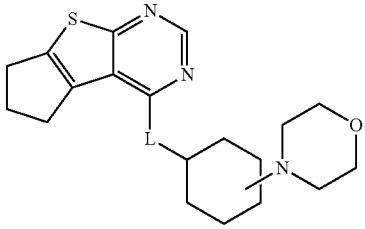

or a pharmaceutically acceptable salt thereof, wherein R is as defined above for formula I and described in embodiments set forth herein, singly and in combination.

In some embodiments the present invention provides a compound of formula III-h or IV-h wherein n is 1 and $R^1$ has one the following formulas:

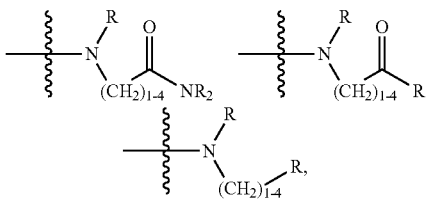

or a pharmaceutically acceptable salt thereof, wherein R is as defined above for formula I and described in embodiments set forth herein, singly and in combination.

In some embodiments, the invention provides a deuterated compound of formula V:

V

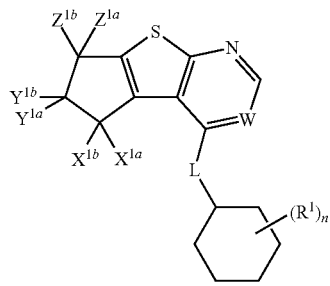

or a pharmaceutically acceptable salt thereof, wherein W, L, n, and $R^1$ are defined above for formula I, and $X^{1a}$, $X^{1b}$, $Y^{1a}$, $Y^{1b}$, $Z^{1a}$, and $Z^{1b}$ are independently selected from hydrogen or deuterium.

In certain embodiments, the deuterated compound of formula V is selected from one of the following structures:

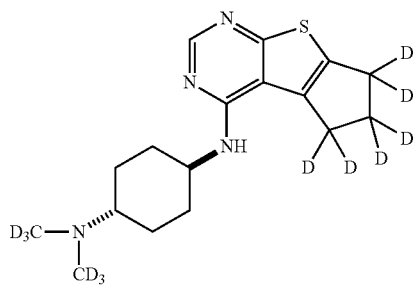

29
-continued
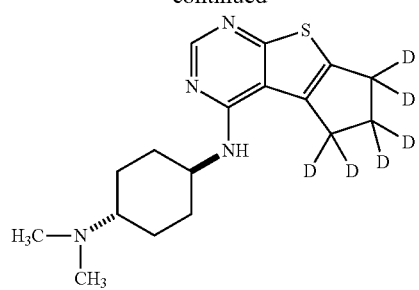
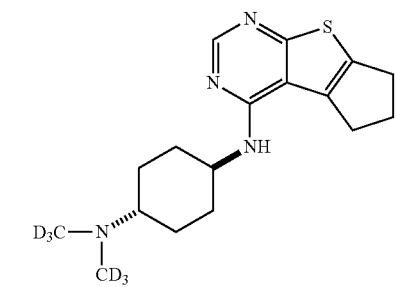
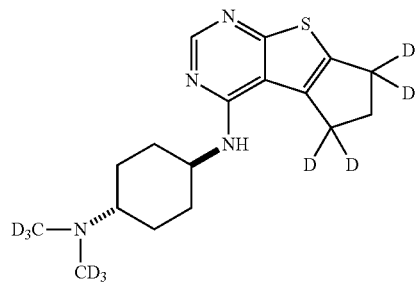
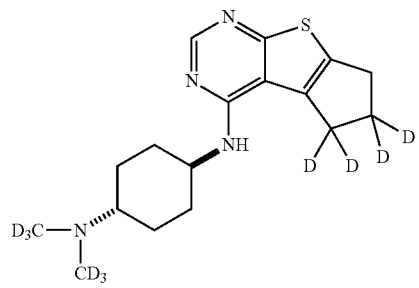
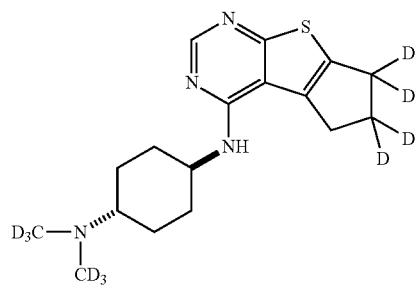
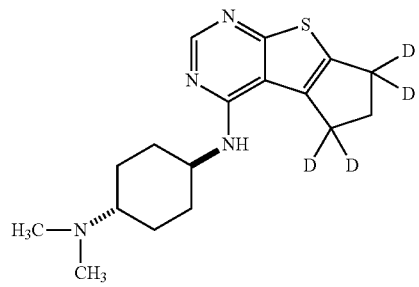
30
-continued
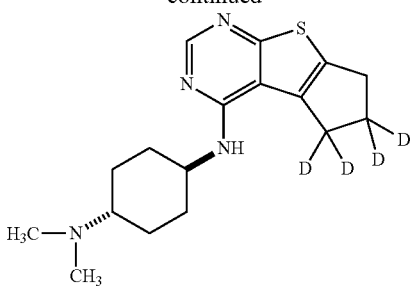
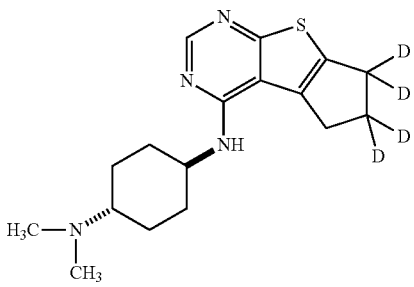
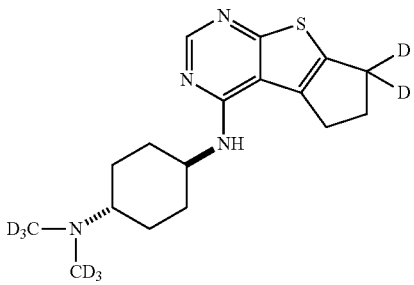
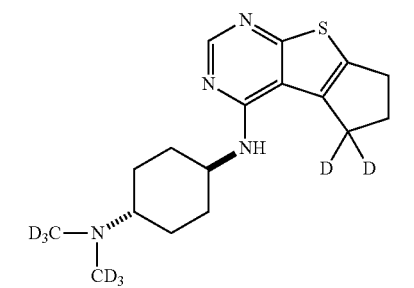
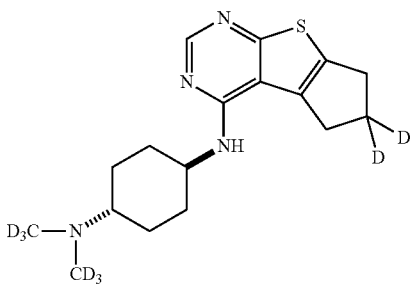
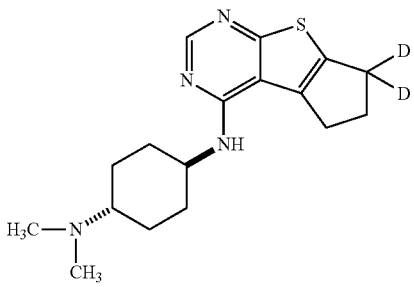

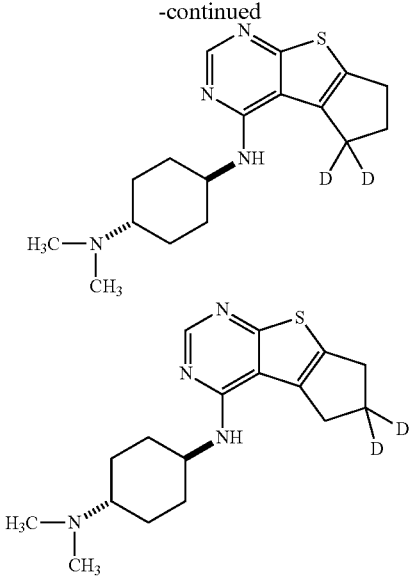
Exemplary compounds are set forth in Table 1, below.
TABLE 1
| Exemplary Compounds | |
|---|---|
| 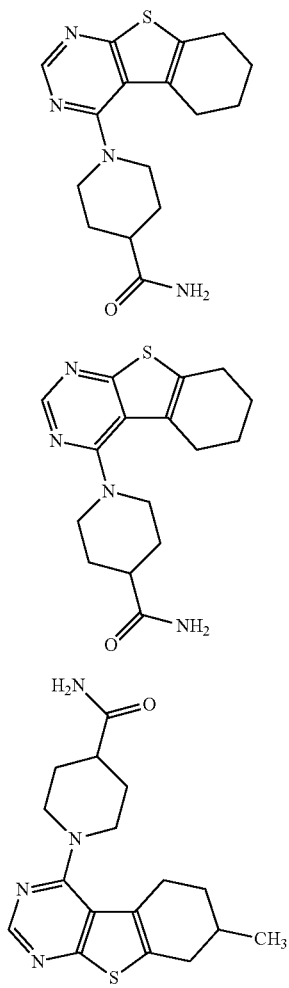 | I-1 |
| | I-2 |
| | I-3 |
TABLE 1-continued
| Exemplary Compounds | |
|---|---|
| 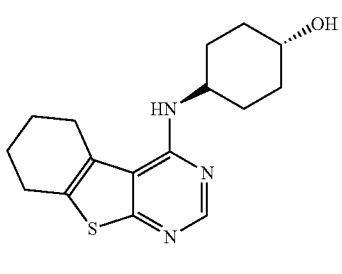 | I-4 |
| 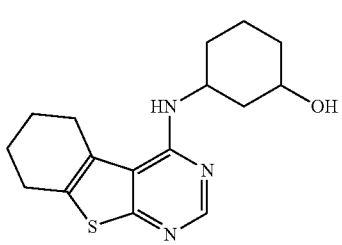 [SMILES: OC1CCCC(Nc2ncnc3sc4c(c23)CCCC4)C1] | I-5 |
| 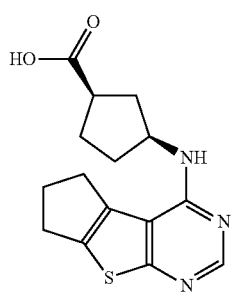 [SMILES: O=C(O)[C@@H]1CC[C@H](Nc2ncnc3sc4c(c23)CCC4)C1] | I-6 |
| 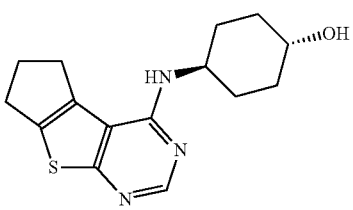 [SMILES: O[C@H]1CC[C@H](Nc2ncnc3sc4c(c23)CCC4)CC1] | I-7 |
| 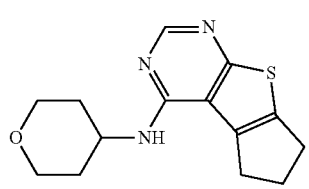 [SMILES: c1nc(NC2CCOCC2)c2c3c(sc2n1)CCC3] | I-8 |
| 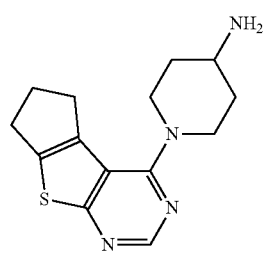 [SMILES: NC1CCN(c2ncnc3sc4c(c23)CCC4)CC1] | I-9 |

TABLE 1-continued

Exemplary Compounds

I-10, I-11, I-12, I-13, I-14, I-15, I-16, I-17, I-18, I-19, I-20, I-21

TABLE 1-continued
Exemplary Compounds
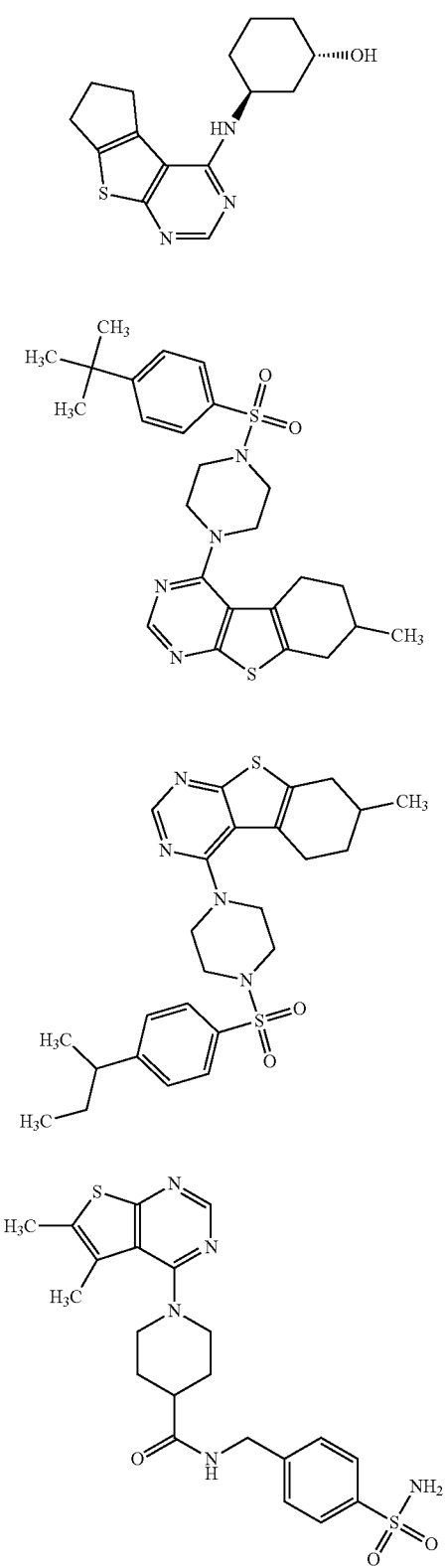
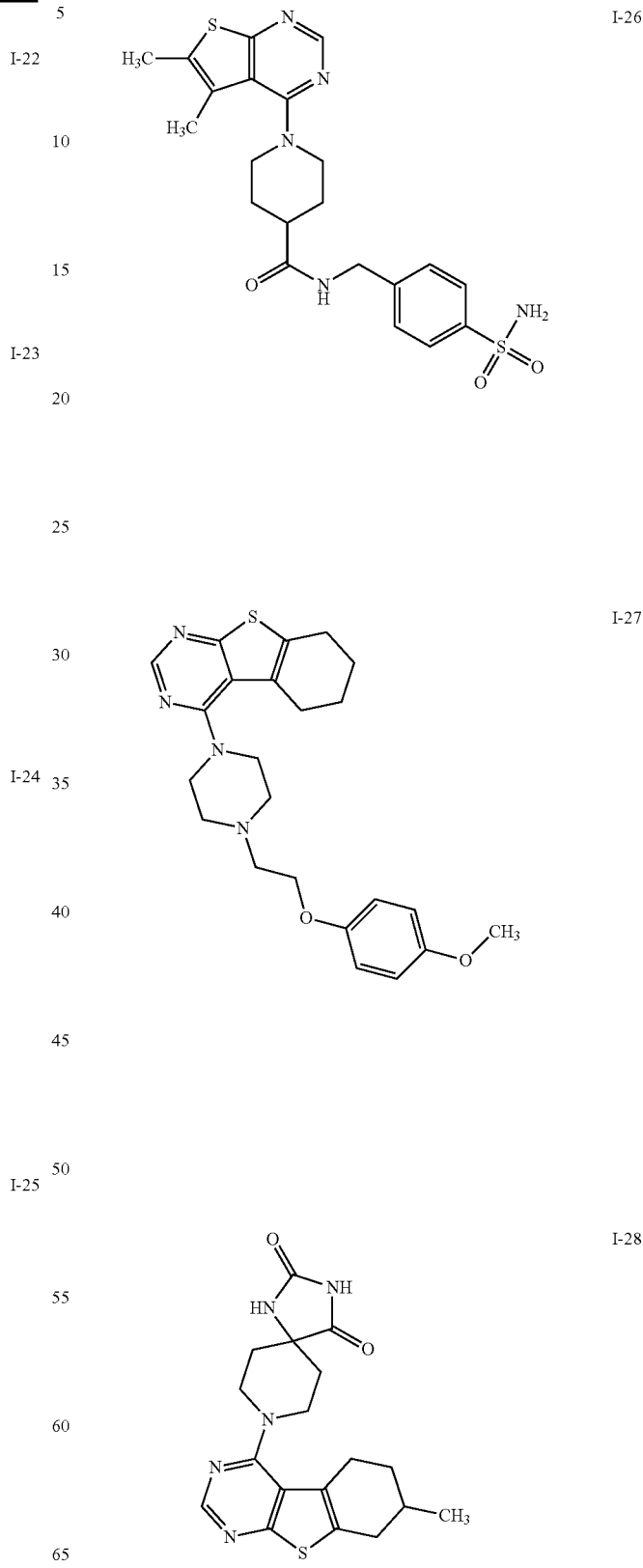

TABLE 1-continued
Exemplary Compounds
I-29
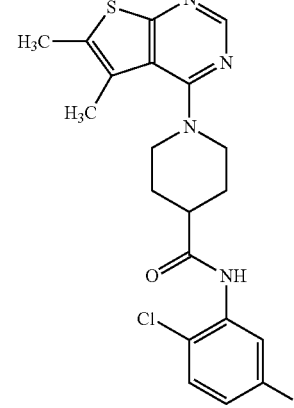
I-30
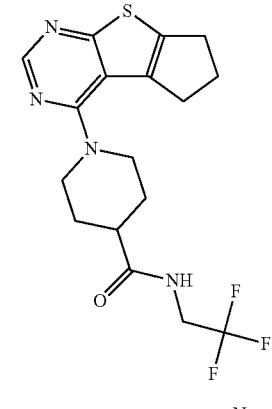
I-31
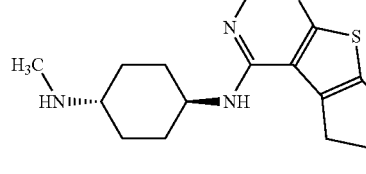
I-32
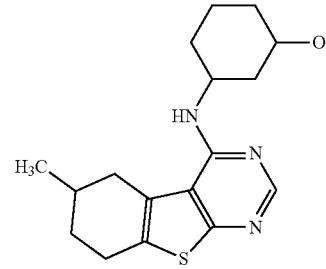
I-33
I-34
I-35
I-36
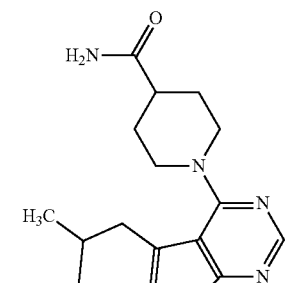

TABLE 1-continued

Exemplary Compounds (Structures I-37 through I-47 are shown as chemical diagrams.)

TABLE 1-continued
Exemplary Compounds
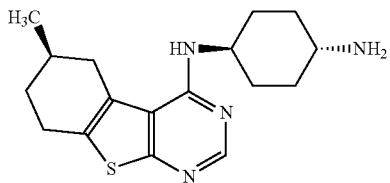 [SMILES: C[C@@H]1CCc2sc3ncnc(N[C@H]4CC[C@H](N)CC4)c3c2C1] I-48
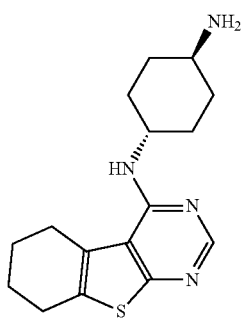 [SMILES: N[C@H]1CC[C@H](Nc2ncnc3sc4c(c23)CCCC4)CC1] I-49
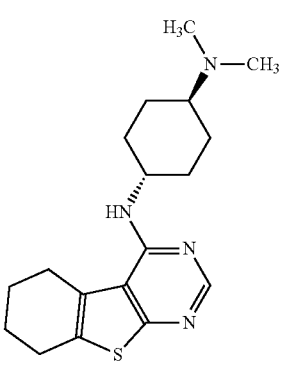 [SMILES: CN(C)[C@H]1CC[C@H](Nc2ncnc3sc4c(c23)CCCC4)CC1] I-50
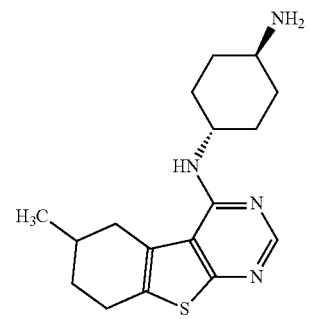 [SMILES: CC1CCc2sc3ncnc(N[C@H]4CC[C@H](N)CC4)c3c2C1] I-51
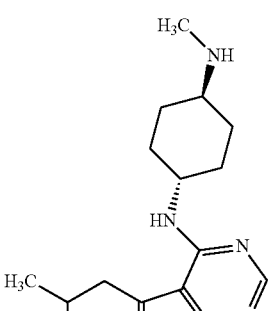 I-52
TABLE 1-continued
Exemplary Compounds
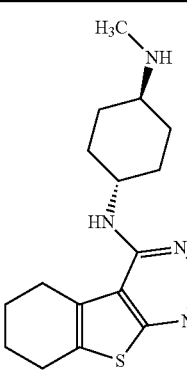 I-53
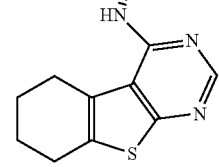 I-54
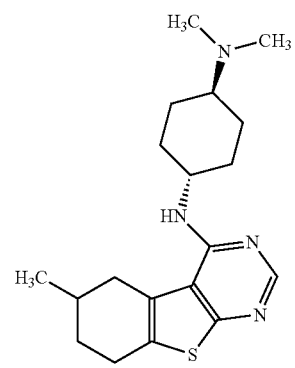 [SMILES: CC1CCc2sc3ncnc(N[C@H]4CC[C@H](N(C)C)CC4)c3c2C1] I-55
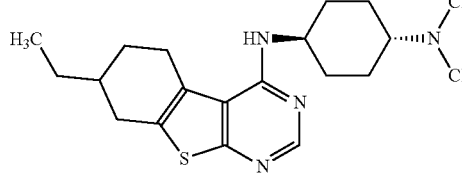 I-56
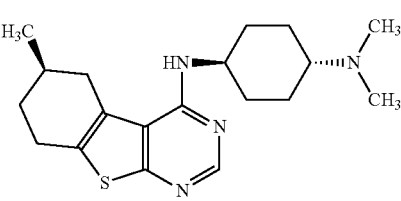 [SMILES: C[C@@H]1CCc2sc3ncnc(N[C@H]4CC[C@H](N(C)C)CC4)c3c2C1] I-57
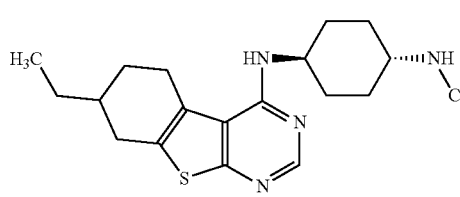 I-58

TABLE 1-continued
Exemplary Compounds
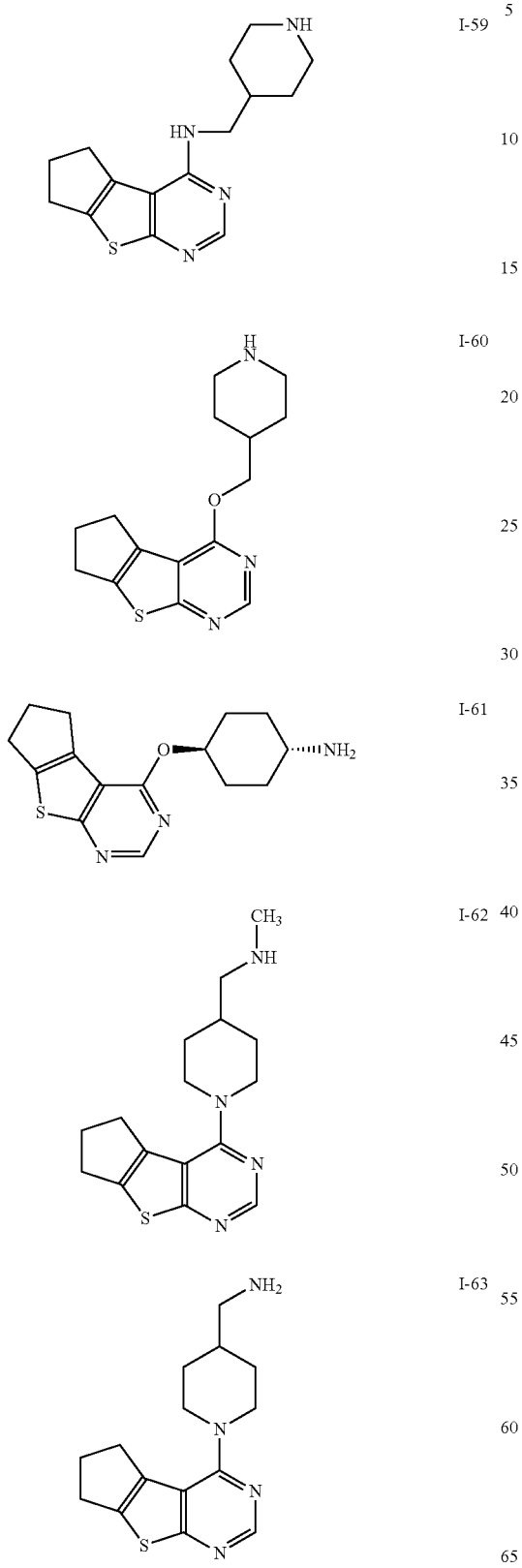
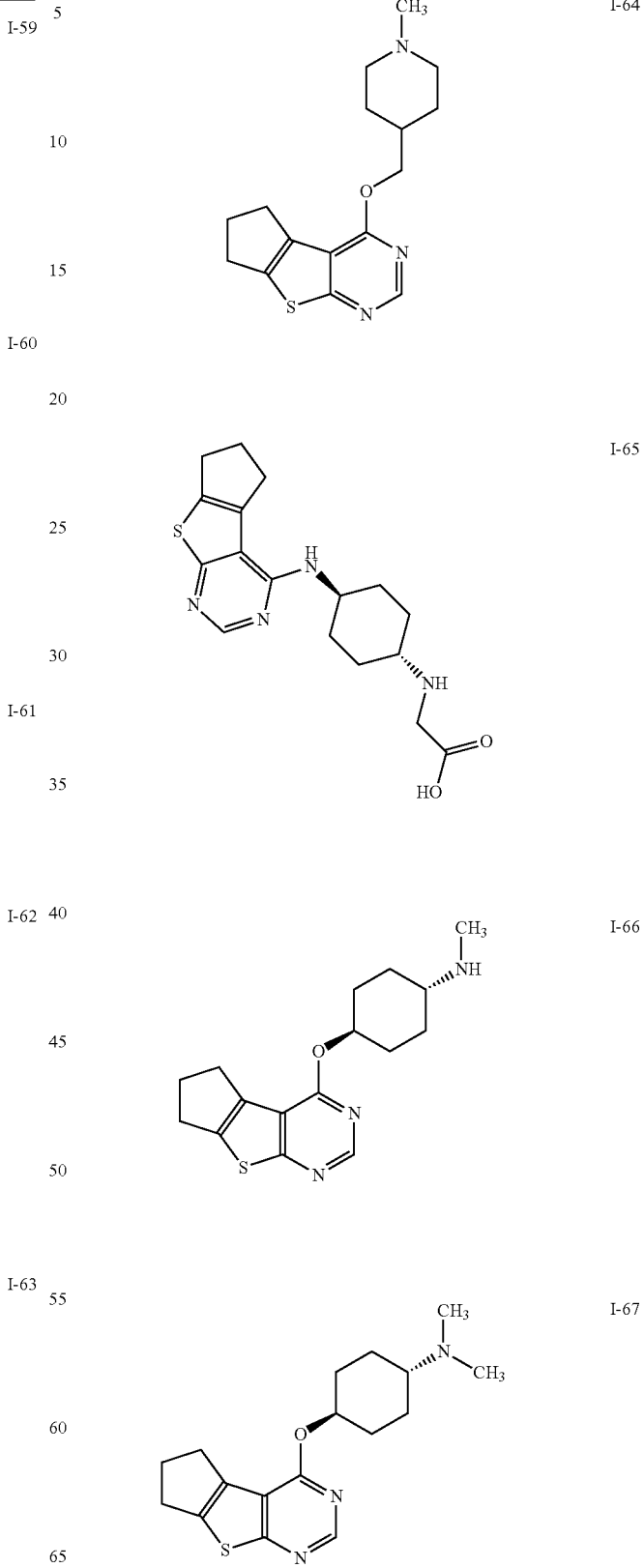

TABLE 1-continued
Exemplary Compounds
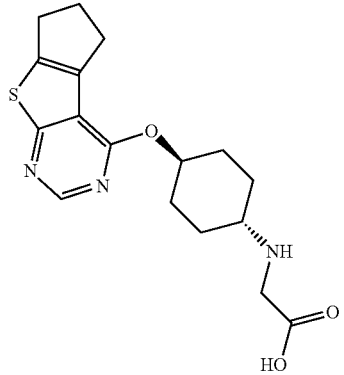 [SMILES: O=C(O)CN[C@H]1CC[C@H](Oc2ncnc3sc4c(c23)CCC4)CC1] I-68
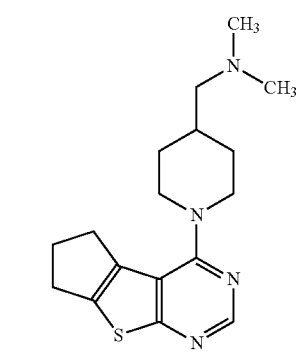 [SMILES: CN(C)CC1CCN(c2ncnc3sc4c(c23)CCC4)CC1] I-69
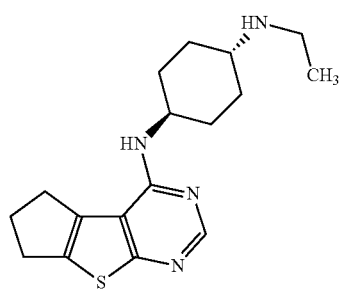 [SMILES: CCN[C@H]1CC[C@H](Nc2ncnc3sc4c(c23)CCC4)CC1] I-70
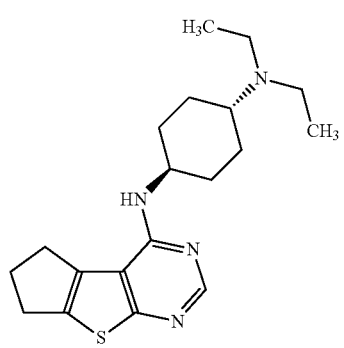 [SMILES: CCN(CC)[C@H]1CC[C@H](Nc2ncnc3sc4c(c23)CCC4)CC1] I-71
TABLE 1-continued
Exemplary Compounds
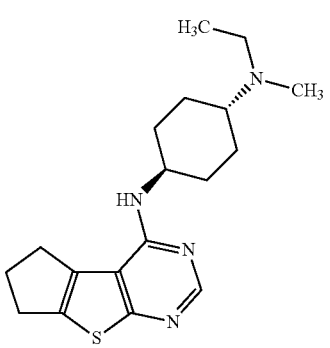 [SMILES: CCN(C)[C@H]1CC[C@H](Nc2ncnc3sc4c(c23)CCC4)CC1] I-72
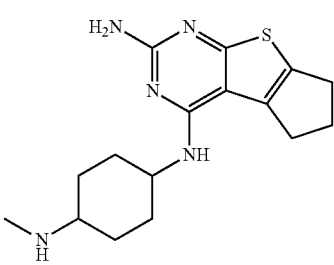 [SMILES: CNC1CCC(Nc2nc(N)nc3sc4c(c23)CCC4)CC1] I-73
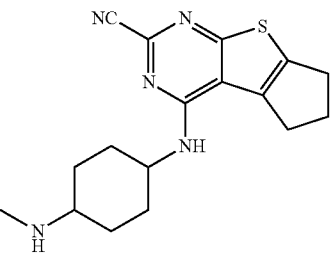 [SMILES: CNC1CCC(Nc2nc(C#N)nc3sc4c(c23)CCC4)CC1] I-74
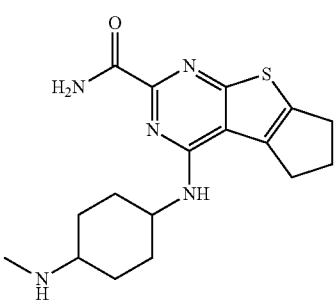 [SMILES: CNC1CCC(Nc2nc(C(N)=O)nc3sc4c(c23)CCC4)CC1] I-75
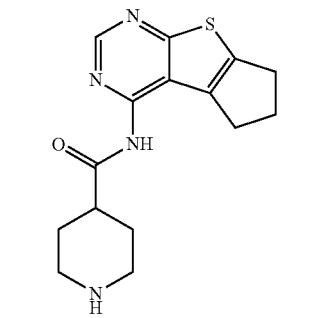 [SMILES: O=C(Nc1ncnc2sc3c(c12)CCC3)C1CCNCC1] I-76

TABLE 1-continued
Exemplary Compounds
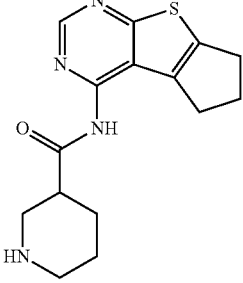 I-77
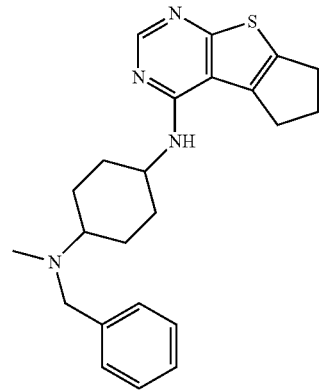 [SMILES: CN(Cc1ccccc1)C1CCC(Nc2ncnc3sc4c(c23)CCC4)CC1] I-78
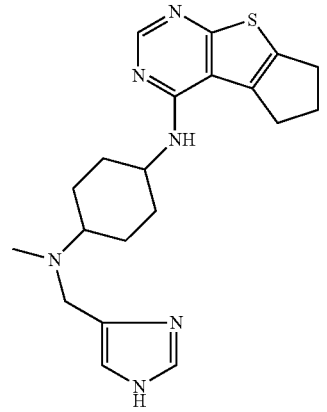 [SMILES: CN(Cc1c[nH]cn1)C1CCC(Nc2ncnc3sc4c(c23)CCC4)CC1] I-79
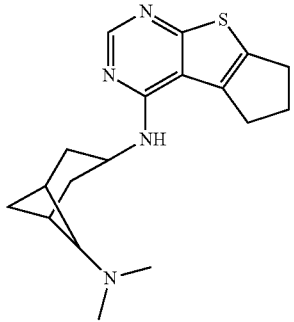 [SMILES: CN(C)C1C2CC(Nc3ncnc4sc5c(c34)CCC5)CC1C2] I-80
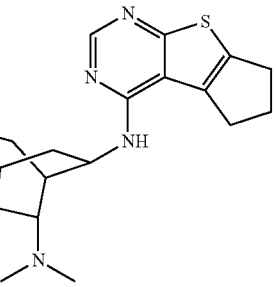 I-81
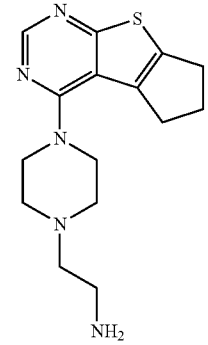 [SMILES: NCCN1CCN(c2ncnc3sc4c(c23)CCC4)CC1] I-82
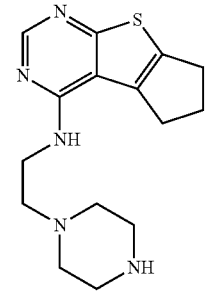 [SMILES: c1nc(NCCN2CCNCC2)c2c3c(sc2n1)CCC3] I-83
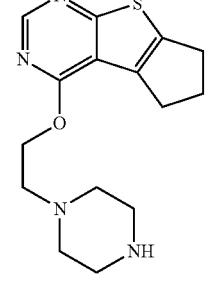 I-84
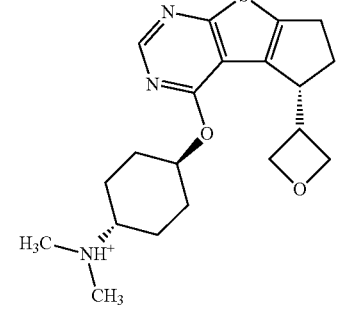 I-85

TABLE 1-continued
Exemplary Compounds
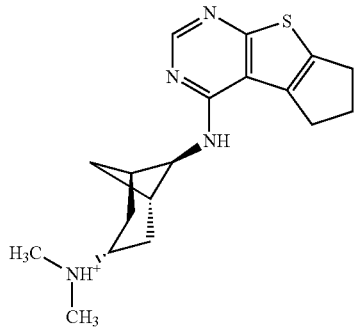 I-86
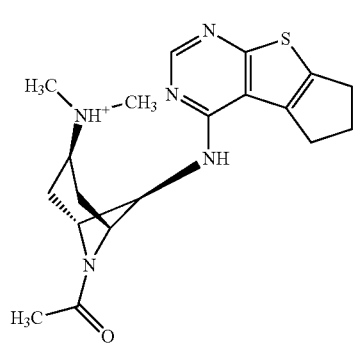 I-87
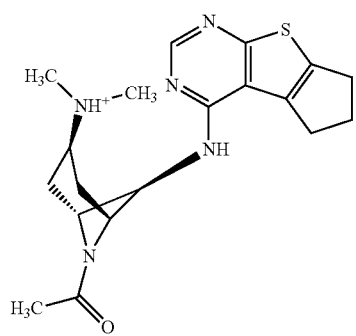 I-88
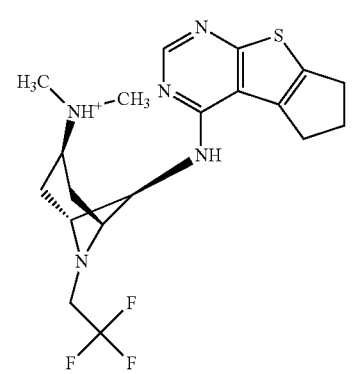 I-89
TABLE 1-continued
Exemplary Compounds
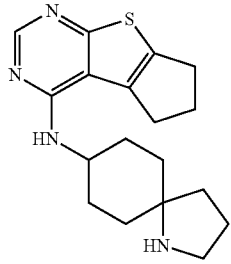 [SMILES: c1nc(NC2CCC3(CCCN3)CC2)c2c3c(sc2n1)CCC3] I-90
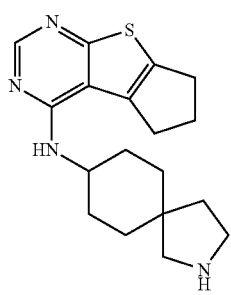 [SMILES: c1nc(NC2CCC3(CCNC3)CC2)c2c3c(sc2n1)CCC3] I-91
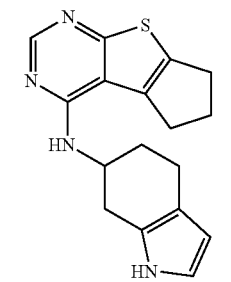 [SMILES: c1nc(NC2CCc3cc[nH]c3C2)c2c3c(sc2n1)CCC3] I-92
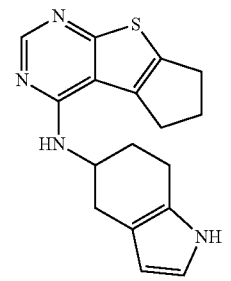 [SMILES: c1nc(NC2CCc3[nH]ccc3C2)c2c3c(sc2n1)CCC3] I-93
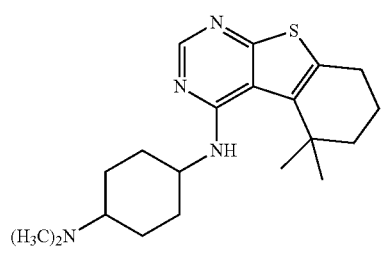 I-94

TABLE 1-continued
Exemplary Compounds
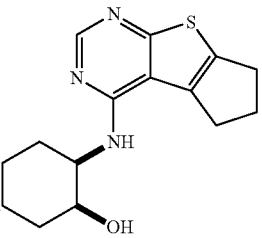 I-95
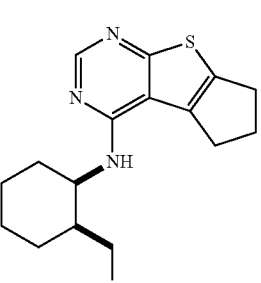 I-96
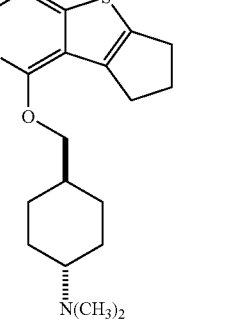 I-97
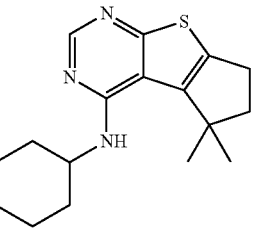 I-98
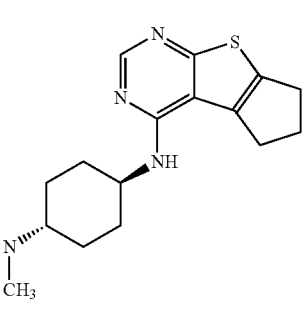 I-99
TABLE 1-continued
Exemplary Compounds
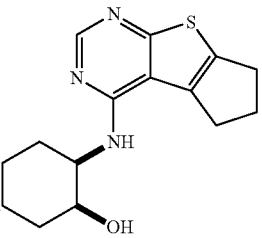 I-100
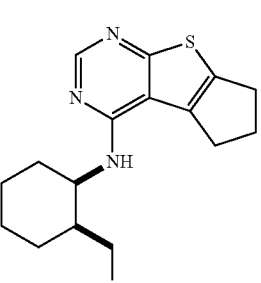 I-101
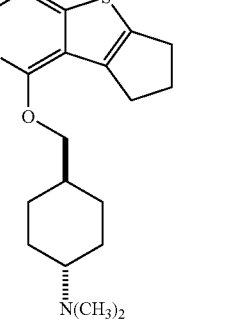 I-102
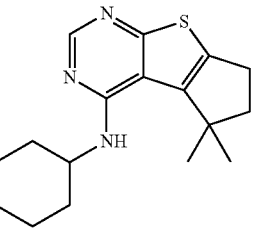 I-103

TABLE 1-continued
Exemplary Compounds
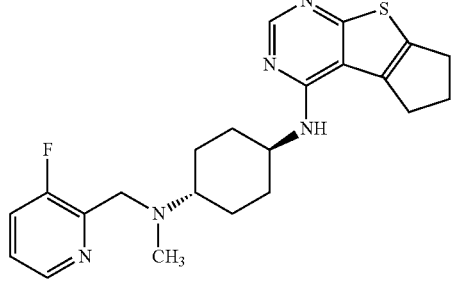 I-104
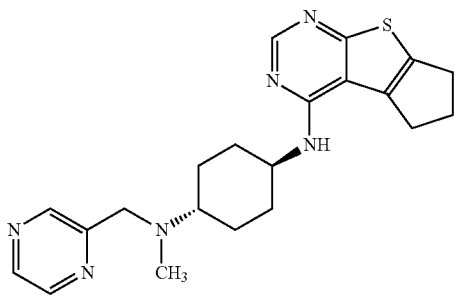 [SMILES: CN(Cc1cnccn1)[C@H]1CC[C@H](Nc2ncnc3sc4c(c23)CCC4)CC1] I-105
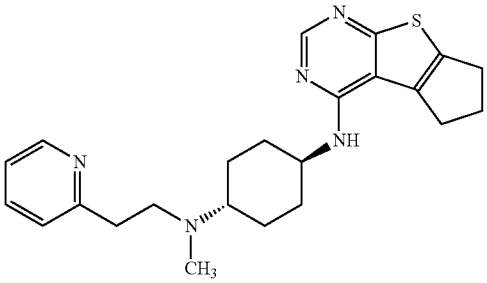 [SMILES: CN(CCc1ccccn1)[C@H]1CC[C@H](Nc2ncnc3sc4c(c23)CCC4)CC1] I-106
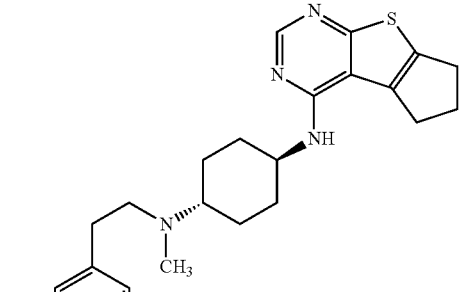 I-107
TABLE 1-continued
Exemplary Compounds
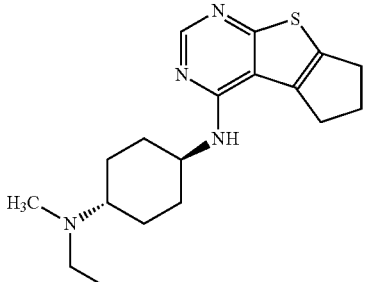 I-108
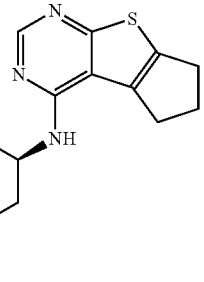 I-109
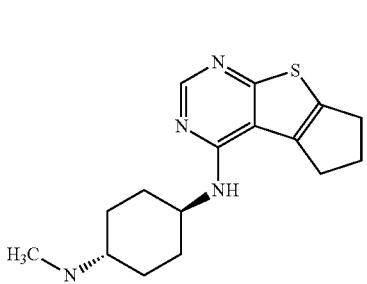 I-110
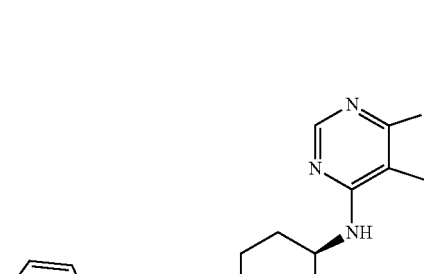 I-111

TABLE 1-continued

Exemplary Compounds

I-112, I-113, I-114, I-115, I-116, I-117, I-118, I-119, I-120, I-121

TABLE 1-continued
Exemplary Compounds
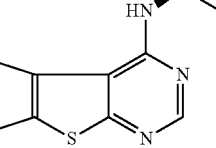 I-122
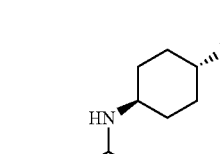 I-123
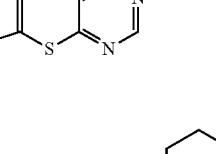 I-124
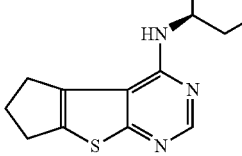 I-125
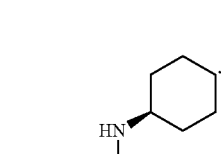 I-126
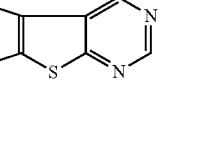 I-127
TABLE 1-continued
Exemplary Compounds
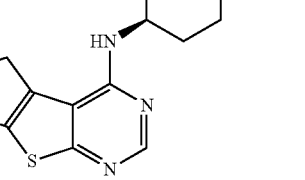 I-128
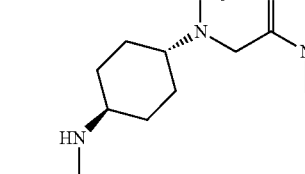 I-129
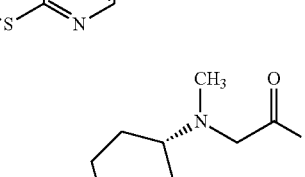 I-130
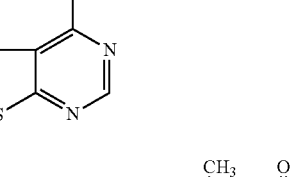 I-131
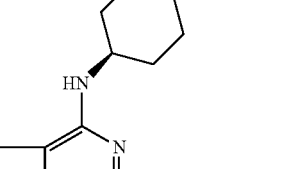 I-132

TABLE 1-continued
Exemplary Compounds
I-133 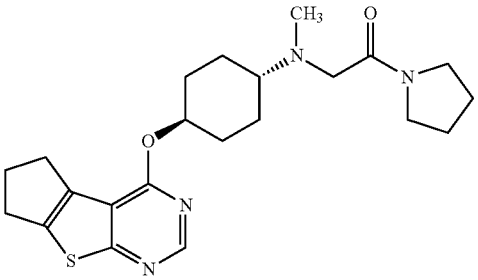 [SMILES: CN(CC(=O)N1CCCC1)[C@H]1CC[C@H](Oc2ncnc3sc4c(c23)CCC4)CC1]
I-134 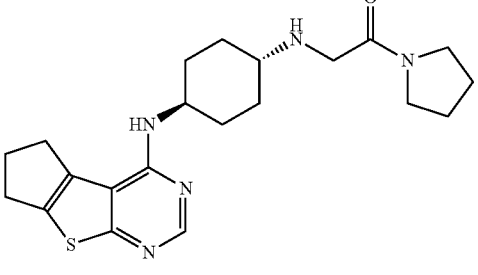
I-135 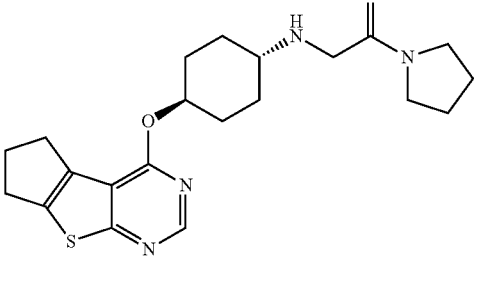
I-136 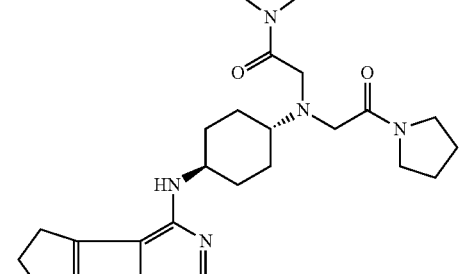
I-137 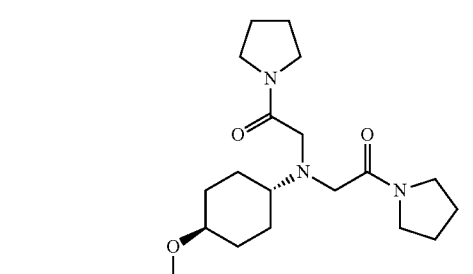
I-138 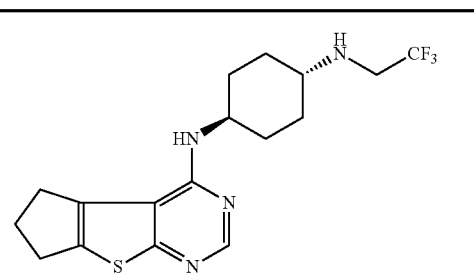
I-139 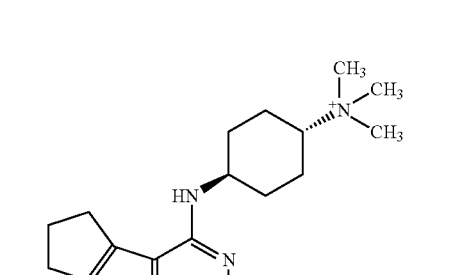
I-140 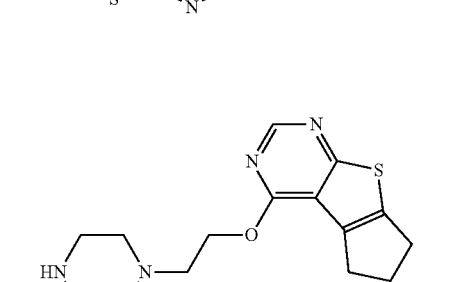
I-141 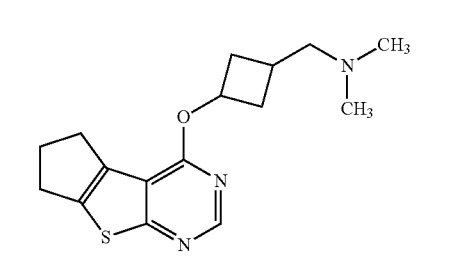 [SMILES: CN(C)CC1CC(Oc2ncnc3sc4c(c23)CCC4)C1]
I-142 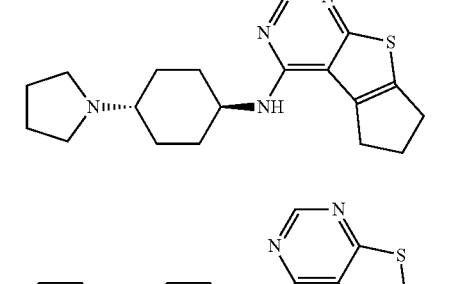
I-143 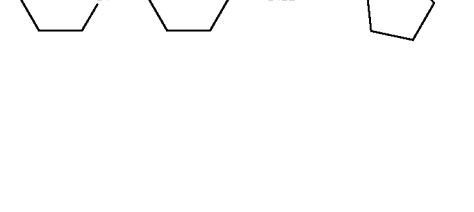

TABLE 1-continued

Exemplary Compounds

I-144, I-145, I-146, I-147, I-148, I-149, I-150, I-151, I-153, I-154, I-155, I-156

TABLE 1-continued
Exemplary Compounds
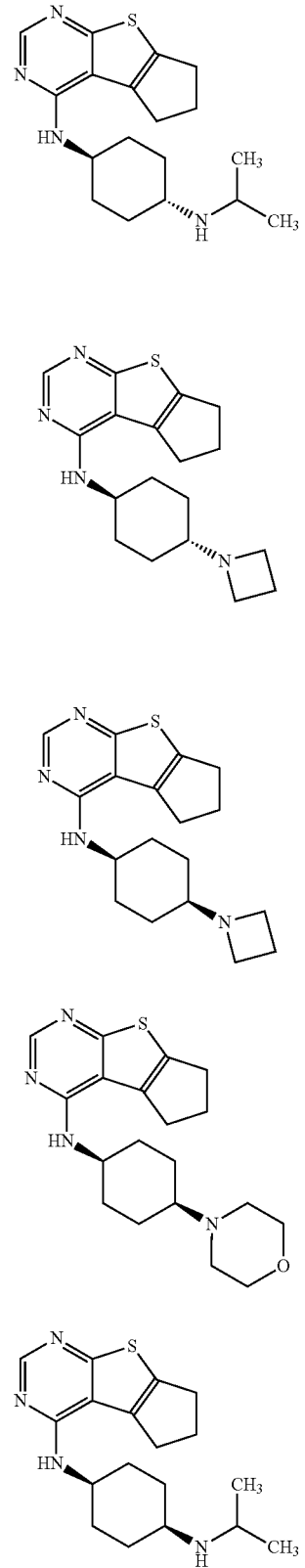
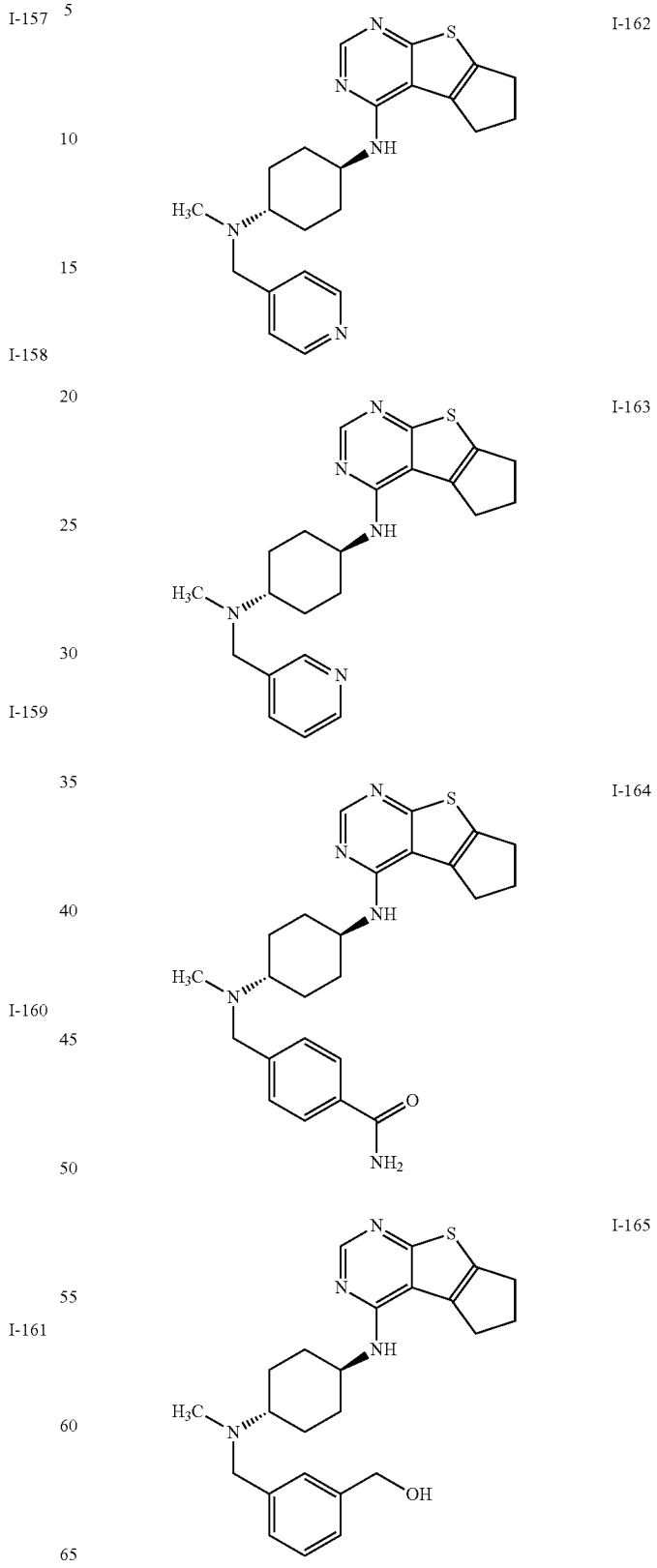

TABLE 1-continued

Exemplary Compounds

I-166

I-167

I-168

I-169

In some embodiments, the present invention provides a compound set forth in Table 1, above, or a pharmaceutically acceptable salt thereof.

In certain embodiments, the present invention provides a compound set forth in Table 1, above, or a pharmaceutically acceptable salt thereof, wherein said compound is other than compound number I-1, I-2, I-3, I-23, I-24, I-25, I-26, I-27, I-28, I-31, I-32, or I-33.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the present invention provides a complex comprising IRAK-4 and an inhibitor, wherein at least one unstable water of IRAK-4 is displaced or disrupted by the inhibitor. In some embodiments, at least two unstable waters selected are displaced or disrupted by the inhibitor.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit an IRAK protein kinase, or a mutant thereof, in a biological sample or in a patient. In certain embodiments, the amount of compound in compositions of this invention is such that is effective to measurably inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes.

Examples of kinases that are inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase," *PNAS* 2002, 99(8), 5567-5572, Flannery et al., "The interleukin-1 receptor-associated kinases: Critical regulators of innate immune signaling" Biochem Pharm 2010, 80(12), 1981-1991 incorporated by reference in its entirety.

The activity of a compound utilized in this invention as an inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204(5), 1025-1036; Lebakken et al., "A Fluorescence Lifetime Based Binding Assay to Characterize Kinase Inhibitors," *J. Biomol. Screen.* 2007, 12(6), 828-841; Maschera et al., "Overexpression of an enzymatically inactive interleukin-1-receptor-associated kinase activates nuclear factor-κB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, each of which is herein incorporated by reference in its entirety. Detailed conditions for assaying a compound utilized in this invention as an inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1 α, IL-6 and IL-8. The kinase activity of IRAK-4 has been shown to play a critical role in the TLR-mediated immune and inflammatory responses. Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medicine (Baltimore)*, 2010, 89(6), 043-25; Li, "IRAK4 in TLR/IL-1R signaling: Possible clinical applications," *Eur. J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80(12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J. Exp. Med.* 2007 204(5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282(18), 13552-13560; Kubo-Murai et al., "IRAK-4-dependent Degradation of IRAK-1 is a Negative Feedback Signal for TLR-mediated NF-κB Activation," *J. Biochem.* 2008, 143, 295-302; Maschera et al., "Overexpression of an enzymatically inactive interleukin-1-receptor-associated kinase activates nuclear factor-κB," *Biochem. J.* 1999, 339, 227-231; Lin et al., "Helical assembly in the MyD88-IRAK4-IRAK2 complex in TLR/IL-1R signalling," *Nature* 2010, 465 (17), 885-891; Suzuki et al., "IRAK-4 as the central TIR signaling mediator in innate immunity," *TRENDS in Immunol.* 2002, 23(10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), each of which is herein incorporated by reference in its entirety. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204(10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets*, 12(7), pp: 883-903 (2008); Gearing, A. "Targeting toll-like receptors for drug development: a summary of commercial approaches," *Immunology and Cell Biology*, 85, pp: 490-494 (2007); Dinarello, C. "IL-1: Discoveries, controversies and future directions," *European Journal of Immunology*, 40, pp: 595-653 (2010), each of which is herein incorporated by reference in its entirety. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wng et al., "IRAK-4 Inhibitors for Inflammation," *Curr. Topics in Med. Chem.* 2009, 9, 724-737, each of which is herein incorporated by reference in its entirety.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature, vol.* 000, pp: 1-7 (2010); Lust, J. et al., "Induction of a Chronic Disease State in patients With Smoldering of Indolent Multiple Myeloma by Targeting Interleukin 113-Induced Interleukin 6 Production and the Myeloma Proliferative Component," *Mayo Clinic Proceedings*, 84(2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of anti-inflammatory drugs," *Curr. Opin. Cell Bio.* 2009, 21:317-324) and rheumatoid arthritis (see, e.g., Geyer, M. et al., "Actual status of antiinterleukin-1 therapies in rheumatic diseases," *Current Opinion in Rheumatology*, 22, pp: 246-251 (2010)), autoinflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.,* 14, pp: 411-421 (2008)), inflammation (see, e.g., Dinarello, C. "Interleukin 1 and interleukin 18 as mediators of inflammation and the aging process," *The American Journal of Clinical Nutrition*, 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases*, 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomised, single-blind pilot study," *Annals of Rheumatic Diseases*, 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases*, 68, pp: 1602-1608 (2009)), neurological disorders, metabolic syndrome (see, e.g., Troseid, M. "The role of interleukin-18 in the metabolic syndrome," *Cardiovascular Diabetology*, 9:11, pp: 1-8 (2010)), immunodeficiency disorders such as AIDS and HIV (see, e.g., Iannello, A. et al., "Role of Interleukin-18 in the Development and Pathogenesis of AIDS," *AIDS Reviews*, 11, pp: 115-125 (2009)), destructive bone disorders (see, e.g., Hennessy, E., et al., "Targeting Toll-like receptors: emerging therapeutics?" *Nature Reviews, vol.* 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" 53rd ASH Annual Meeting; Xu, et al., "A somatic variant in MYD88 (L256P) revealed by whole genome sequencing differentiates lymphoplasmacytic lymphoma from marginal zone lymphomas" 53rd ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53$^{rd}$ ASH Annual Meeting; Iriyama et al., "Clinical significance of genetic mutations of CD79B, CARD11, MYD88, and EZH2 genes in diffuse large B-cell lymphoma patients" 53$^{rd}$ ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably inhibit IRAK-1 only, IRAK-2-only, IRAK-4-only and/or IRAK1- and IRAK4 kinase activity.

Compounds of the current invention are useful in the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, Waldenström's macroglobulinemia, a mammary carcinoma, follicular carcinoma, undifferentiated carcinoma, papillary carcinoma, seminoma, melanoma, an MYD88-driven disorder, DLBCL, ABC DLBCL, an IL-1-driven disorder, Smoldering of indolent multiple myeloma, or a leukemia.

In some embodiments the proliferative disease which can be treated according to the methods of this invention is an MYD88-driven disorder. In some embodiments, the MYD88-driven disorder which can be treated according to the methods of this invention is selected from ABC DLBCL and Waldenstrom's macroglobulinemia.

In some embodiments the proliferative disease which can be treated according to the methods of this invention is an IL-1-driven disorder. In some embodiments, the IL-1-driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Graves' disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, dermatomyositis, polymyositis, inclusion body myositis, myasthenia gravis, thyroiditis, Addison's disease, lichen planus, Type 1 diabetes, or Type 2 diabetes.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin-Associated Periodic Syndromes (CAPS), or osteoarthritis.

In some embodiments, the inflammatory disease which can be treated according to the methods of this invention is selected from a TH17-mediated disease. In some embodiments, the TH17-mediated disease is selected from Systemic lupus erythematosus, Multiple sclerosis, inflammatory bowel disease including Crohn's or ulcerative colitis.

In some embodiments, the inflammatory disease which can be treated according to the methods of this invention is selected from Sjogren's syndrome allergic disorders, osteoarthritis. Conditions of the eye such as ocular allergy, conjunctivitis, keratoconjunctivitis sicca, and vernal conjunctivitis, diseases affecting the nose including allergic rhinitis.

In some embodiments, the inflammatory disease which can be treated according to the methods of this invention is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

Cardiovascular diseases which can be treated according to the methods of this invention include, but are not limited to, restenosis, cardiomegaly, atherosclerosis, myocardial infarction, ischemic stroke and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia, epilepsy, In some embodiments, the disease which can be treated according to the methods of this invention is selected from organ transplantation, organ transplant rejection, graft versus host disease.

In some embodiments, the metabolic disease which can be treated according to the methods of this invention is selected from, Type 1 diabetes, Type 2 diabetes, metabolic syndrome including obesity.

In some embodiments, the cardiovascular disease which can be treated according to the methods of this invention is heart disease or atherosclerosis.

In some embodiments, the neurodegenerative disease which can be treated according to the methods of this invention is epilepsy.

In some embodiments, the viral disease which can be treated according to the methods of this invention is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease or an obstructive respiratory disease, a cardiovascular disease, a neurological disease or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif¯), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In one embodiment, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In one embodiment, the present invention provides a method of treating lupus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In another embodiment, the present invention provides a method of treating inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In another embodiment, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In another embodiment, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating HIV comprising administering to a patient in need thereof a compound of formula I and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®) and prednisone, and combinations thereof.

In another embodiment, the present invention provides a method of treating multiple myeloma comprising administering to a patient in need thereof a compound of formula I and one or more additional therapeutic agents selected from bortezomib (Velcase®), and dexamethasone (Decadron®) in combination with lenalidomide (Revlimid®).

In another embodiment, the present invention provides a method of treating multiple myeloma comprising administering to a patient in need thereof a compound of formula I and one or more additional therapeutic agents selected from bortezomib (Velcade®), and dexamethasone (Decadron®) in combination with lenalidomide (Revlimid®).

In another embodiment, the present invention provides a method of treating Waldenström's macroglobulinemia comprising administering to a patient in need thereof a compound of formula I and one or more additional therapeutic agents selected from chlorambucil (Leukeran®), cyclophosphamide (Cytoxan®, Neosar®), fludarabine (Fludara®), cladribine (Leustatin®), and rituximab (Rituxan®).

In another embodiment, the present invention provides a method of treating organ transplant rejection or graft vs. host disease comprising administering to a patient in need thereof a compound of formula I and one or more additional therapeutic agents selected from a steroid, cyclosporin, FK506, or rapamycin.

The compounds and compositions, according to the method of the present invention, may be administered using any amount and any route of administration effective for treating or lessening the severity of cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting IRAK-1, IRAK-2, and/or IRAK-4, or a mutant thereof, activity in a biological sample comprising the step of contacting said biological sample with a compound of this invention, or a composition comprising said compound. In certain embodiments, the invention relates to a method of irreversibly inhibiting IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof and blood, saliva, urine, feces, semen, tears, or other body fluids or extracts thereof.

Inhibition of protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or more of IRAK-1, IRAK-2, and/or IRAK-4, or a mutant thereof, activity in a patient comprising the step of administering to said patient a compound of the present invention, or a composition comprising said compound. According to certain embodiments, the invention relates to a method of irreversibly inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino- 17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (Thalomid™) and TNP-470.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™ Pamidronic acid is marketed under the trade name Aredia™. Alendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloro anilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHU-Fab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Intermediate A

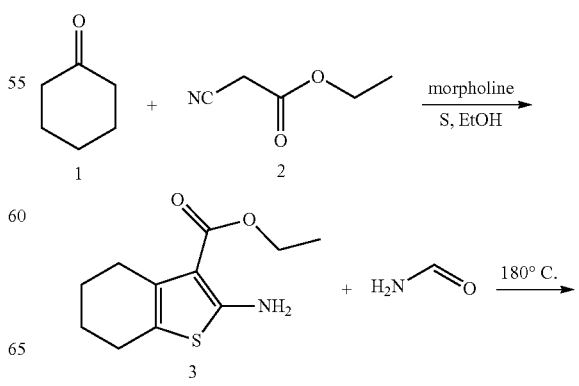

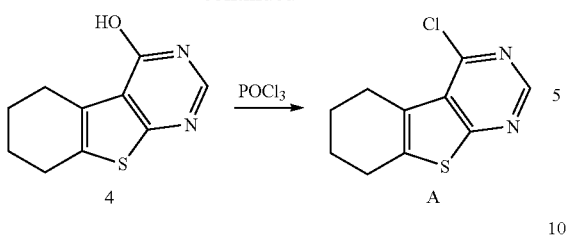
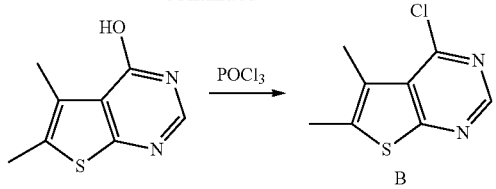

Synthesis of Compound 3

In to a mixture of cyclohexanone (compound 1) (49 g, 0.5 mol, 1.0 eq), ethyl 2-cyanoacetate (compound 2) (56 g, 0.5 mol, 1.0 eq), and sulphur (16 g, 0.5 mol, 1.0 eq) in 150 mL of ethanol was added morpholine (44 g, 0.5 mol, 1.0 eq). The mixture was stirred for 8 h at room temperature. The reaction mixture was diluted with water and the precipitate was collected by filtration and recrystallized from ethanol to afford compound 3 as yellow solid (62 g, 55%).

Synthesis of Compound 4

The mixture of compound 3 (35 g, 0.16 mol) in 150 mL of formamide was heated at 180° C. for 4 h and cooled down. The mixture was poured into 200 mL of water and filtered. The solid was collected and recrystallized from ethanol to afford compound 4 as yellow solid (25 g, 75%). $^1$H NMR (400 MHz, DMSO-$d_6$) δ 1.75-1.82 (m, 4H), 2.72-2.75 (m, 2H), 2.85-2.88 (m, 2H), 8.00 (s, 1H), 12.31 (br s, 1H). MS: m/z 207.0 (M+H)$^+$.

Synthesis of Compound A

A suspension of compound 4 (25 g, 0.12 mol) in 150 mL of POC$_3$ was heated at reflux for 2 h. POC$_3$ was removed at reduced pressure and the residue was poured onto ice and filtered. The solid was washed with water and dried to afford compound A as brown solid (23 g, 85%). $^1$H NMR (400 MHz, CDCl$_3$) δ 1.92-1.95 (m, 4H), 2.88-2.90 (m, 2H), 3.10-3.12 (m, 2H), 8.72 (s, 1H). MS: m/z 225.0 (M+H)$^+$.

Example 2

Synthesis of Intermediate B

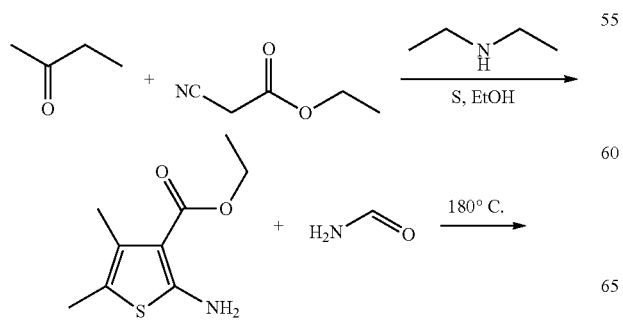

Synthesis of ethyl 2-amino-4,5-dimethylthiophene-3-carboxylate

Into a mixture of butan-2-one (20 g, 0.28 mol, 1.0 eq), ethyl 2-cyanoacetate (31.4 g, 0.28 mol, 1.0 eq), and sulphur (8.9 g, 0.28 mol, 1.0 eq) in 100 mL of ethanol was added diethyl amine (21 g, 0.28 mol, 1.0 eq). The mixture was stirred for 8 h at room temperature. The reaction mixture was diluted with water and the precipitate was collected by filtration and recrystallized from ethanol to afford ethyl 2-amino-4,5-dimethylthiophene-3-carboxylate as yellow solid (41 g, 75%).

Synthesis of 5,6-dimethylthieno[2,3-d]pyrimidin-4-ol

The mixture of ethyl 2-amino-4,5-dimethylthiophene-3-carboxylate (30 g, 0.15 mol) in 150 mL of formamide was heated at 180° C. for 4 h and cooled down. The mixture was poured into 200 mL of water and filtered. The solid was collected and recrystallized from ethanol to afford 5,6-dimethylthieno[2,3-d]pyrimidin-4-ol as yellow solid (23 g, 85%).

Synthesis of Compound B

A suspension of compound 4 (20 g, 0.11 mol) in 150 mL of POC$_3$ was heated at reflux for 2 h. POC$_3$ was removed at reduced pressure and the residue was poured onto ice and filtered. The solid was washed with water and dried to afford compound A as brown solid (17 g, 76%). $^1$H NMR (400 MHz, CDCl$_3$) δ 2.53 (s, 3H), 2.56 (s, 3H), 8.72 (s, 1H). MS: m/z 199.0 (M+H)$^+$.

Example 3

Synthesis of Intermediate C

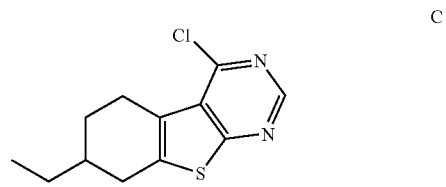 [SMILES: CCC1CCc2c(sc3ncnc(Cl)c23)C1]

Compound C was synthesized in a manner consistent with Example 1. Isolated a brown solid in 73% yield. $^1$H NMR (400 MHz, CDCl$_3$) δ 1.01 (t, J=7.2 Hz, 3H), 1.43-1.54 (m, 3H), 1.77-1.80 (m, 1H), 2.06-2.10 (m, 1H), 2.47-2.55 (m, 1H), 2.92-3.02 (m, 2H), 3.26-3.32 (m, 1H), 8.71 (s, 1H). MS: m/z 253.1 (M+H)+.

Example 4

Synthesis of Intermediate D

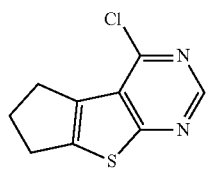

D

Compound D was synthesized in a manner consistent with Example 2. Isolated a brown solid in 72% yield. $^1$H NMR (400 MHz, CDCl$_3$) δ 2.51-2.58 (m, 2H), 3.08 (t, J=6.8 Hz, 2H), 3.16-3.20 (m, 2H), 8.72 (s, 1H). MS: m/z 211.1 (M+H)+.

Example 5

Synthesis of Intermediate E

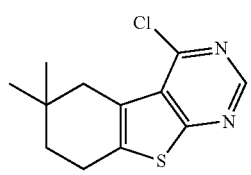

E

Compound E was synthesized in a manner consistent with Example 2. Isolated a brown solid in 70% yield. $^1$H NMR (400 MHz, CDCl$_3$) δ 1.01 (s, 6H), 1.62 (t, J=6.4 Hz, 2H), 2.82-2.85 (m, 4H), 8.65 (s, 1H). MS: m/z 253.1 (M+H)+.

Example 6

Synthesis of Intermediate F

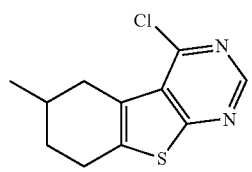

F

Compound F was synthesized in a manner consistent with Example 2. Isolated a brown solid in 85% yield. $^1$H NMR (400 MHz, CDCl$_3$) δ 1.16 (d, J=6.4 Hz, 3H), 1.52-1.65 (m, 1H), 1.94-2.03 (m, 2H), 2.52-2.59 (m, 1H), 2.90-2.94 (m, 2H), 3.32 (dd, J=5.2, 16.8 Hz, 1H), 8.71 (s, 1H). MS: m/z 239.0 (M+H)+.

Example 7

Synthesis of Intermediate G

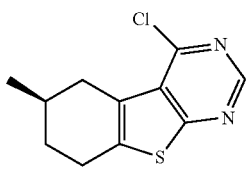

G

Compound G was synthesized in a manner consistent with Example 2. Isolated a brown solid in 80% yield. $^1$H NMR (400 MHz, CDCl$_3$) δ 1.16 (d, J=6.4 Hz, 3H), 1.52-1.65 (m, 1H), 1.94-2.03 (m, 2H), 2.52-2.59 (m, 1H), 2.90-2.94 (m, 2H), 3.32 (dd, J=5.2, 16.8 Hz, 1H), 8.71 (s, 1H). MS: m/z 239.0 (M+H)+.

Example 8

Synthesis of trans-4-((5,6,7,8-tetrahydrobenzo[4,5]thieno[2,3-d]pyrimidin-4-yl)amino)cyclohexanol (I-4)

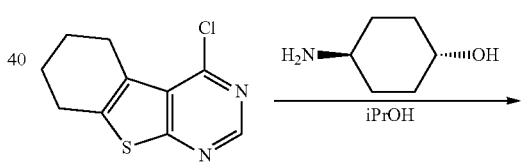

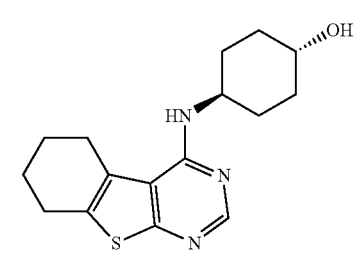

The mixture of A (500 mg, 2.38 mmol, 1.0 eq) and trans-4-aminocyclohexanol (1031 mg, 7.0 mmol, 3.0 eq) in iPrOH (10 mL) was heated at reflux for 12 h. The solvent was removed under vacuum and water (20 mL) was added. The aqueous phase was extracted by CH$_2$Cl$_2$ (3×40 mL). The combined organic phases was washed (brine), dried (Na$_2$SO$_4$), filtered and concentrated. The residue was purified by column chromatography on silica gel (DCM/MeOH/Et$_3$N=30:2:1) to give the product as pale solid (580 mg, 86%). $^1$H NMR (400 MHz, DMSO-d$_6$) δ 1.26-1.32 (m, 2H), 1.44-1.47 (m, 2H), 1.81-1.94 (m, 8H), 2.74-2.77 (m, 2H), 2.93-

2.95 (m, 2H), 3.40-3.44 (m, 1H), 4.01-4.03 (m, 1H), 4.59-4.60 (m, 1H), 5.83 (d, J=7.8 Hz, 1H), 8.25 (s, 1H). MS: m/z 304.1 (M+H)+.

Example 9

Synthesis of 3-((5,6,7,8-tetrahydrobenzo[4,5]thieno[2,3-d]pyrimidin-4-yl)amino)cyclohexanol (I-5)

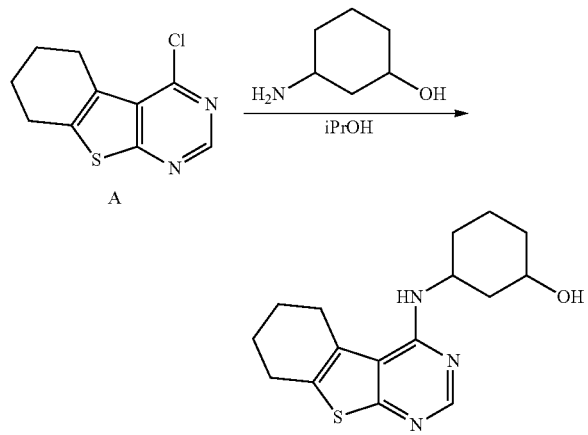

Compound I-5 was synthesized in a manner consistent with Example 8. Isolated a white solid in 70% yield. $^1$H NMR (400 MHz, DMSO-d$_6$) δ 1.25-1.47 (m, 2H), 1.53-1.69 (m, 4H), 1.72-1.85 (m, 5H), 1.94 (d, J=12.0 Hz, 1H), 2.75 (s, 2H), 2.94 (s, 2H), 3.77 (d, J=3.0 Hz, 1H), 4.30 (t, J=6.0 Hz, 1H), 5.01 (s, 1H), 8.42 (d, J=5.2 Hz, 1H), 8.24 (s, 1H). MS: m/z 304.2 (M+H)+.

Example 10

Synthesis of trans-4-((7-ethyl-5,6,7,8-tetrahydrobenzo[4,5]thieno[2,3-d]pyrimidin-4-yl)amino)cyclohexanol

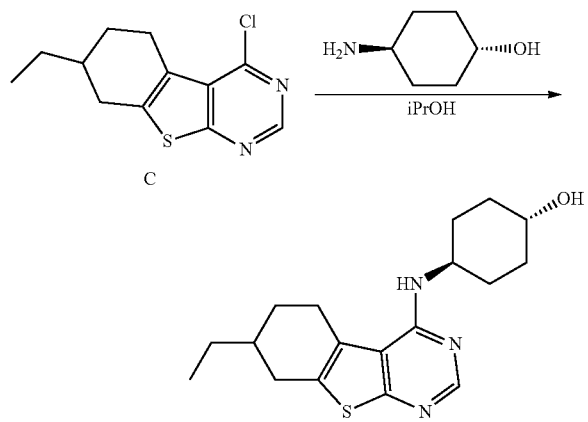

Trans-4-((7-ethyl-5,6,7,8-tetrahydrobenzo[4,5]thieno[2,3-d]pyrimidin-4-yl)amino)cyclohexanol was synthesized in a manner consistent with Example 8. Isolated a white solid in 72% yield. $^1$H NMR (400 MHz, DMSO-d$_6$) δ 0.95 (t, J=7.3 Hz, 3H), 1.16-1.47 (m, 6H), 1.67 (s, 1H), 1.84-1.94 (m, 6H),
2.35-2.39 (m, 1H), 2.85-3.00 (m, 2H), 4.00-4.02 (m, 1H), 4.03-4.05 (m, 1H), 4.60 (s, 1H), 5.86 (d, J=8.0 Hz, 1H), 7.82 (s, 1H), 8.25 (s, 1H). MS: m/z 332.2 (M+H)+.

Example 11

Synthesis of trans-4-((6,7-dihydro-5H-cyclopenta[4,5]thieno[2,3-d]pyrimidin-4-yl)amino)cyclohexanol (I-7)

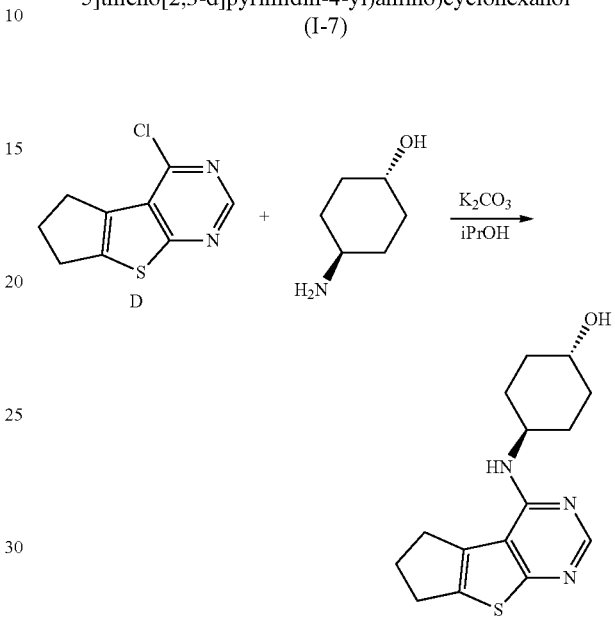

To a solution of compound D (100 mg, 0.48 mmol) and trans-4-aminocyclohexanol (110 mg, 0.95 mmol, 2.0 eq) in 5 mL of iPrOH was added K$_2$CO$_3$ (132 mg, 0.95 mmol, 2.0 eq). The reaction was heated at reflux overnight and cooled down. The mixture was poured into water (50 mL) and extracted with EtOAc (50 mL×3). The combined organics were dried over anhydrous Na$_2$SO$_4$ and filtered. The filtrate was concentrated and the residue was purified by column chromatography in silica gel (DCM/MeOH=50:1-20:1) to give the product as white solid (30 mg, 21%). $^1$H NMR (400 MHz, DMSO-d$_6$) δ 1.23-1.31 (m, 2H), 1.44-1.53 (m, 2H), 1.85-1.92 (m, 4H), 2.40-2.45 (m, 2H), 2.90-2.94 (m, 2H), 3.05-3.08 (m, 2H), 3.41-3.45 (m, 1H), 4.01-4.01 (m, 1H), 4.60 (d, J=4.0 Hz, 1H), 5.95 (d, J=8.0 Hz, 1H), 8.26 (s, 1H). MS: m/z 290.0 (M+H)+.

Example 12

Synthesis of trans-N$^1$-(6,7-dihydro-5H-cyclopenta[4,5]thieno[2,3-d]pyrimidin-4-yl)cyclohexane-1,4-diamine (I-10)

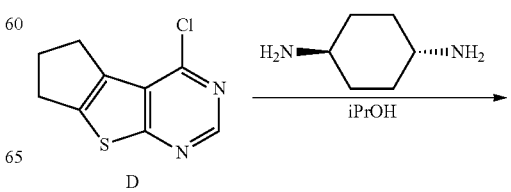

-continued

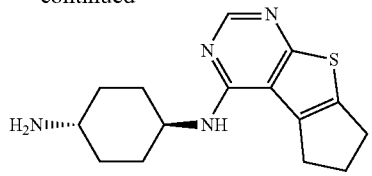

Compound I-10 was synthesized in a manner consistent with Example 8. Isolated a white solid in 87% yield. ¹H NMR (400 MHz, DMSO-$d_6$) δ 1.16-1.23 (m, 2H), 1.44-1.53 (m, 2H), 1.80-1.92 (m, 4H), 2.40-2.43 (m, 2H), 2.58-2.63 (m, 1H), 2.92 (t, J=7.2 Hz, 2H), 3.06 (t, J=7.2 Hz, 2H), 4.00-4.04 (m, 1H), 5.97 (d, J=8.0 Hz, 1H), 8.26 (s, 1H). MS: m/z 289.1 (M+H)⁺.

Example 13

Synthesis of N-(trans-4-((6,7-dihydro-5H-cyclopenta[4,5]thieno[2,3-d]pyrimidin-4-yl)amino)cyclohexyl)acetamide (I-11)

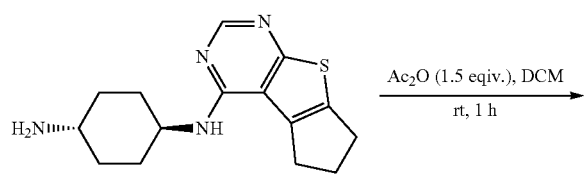

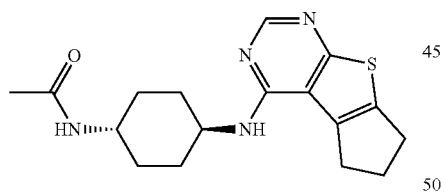

To a solution of compound I-10 (80 mg, 0.278 mmol, 1.0 eq) in dichloromethane (10 mL) was added Ac₂O (42 mg, 0.427 mmol, 1.5 eq) and the reaction mixture was stirred at room temperature for 1 h. Water (2 mL) was added and extracted with EA (10 mL×3). The combined organic layers were concentrated under reduced pressure. The resulting residue was recrystallized with MeOH/water to give compound I-11 (67 mg, 73%) as white solid. ¹H NMR (400 MHz, DMSO-$d_6$) δ 1.22-1.32 (m, 2H), 1.47-1.57 (m, 2H), 1.78 (s, 3H), 1.82-1.85 (m, 2H), 1.92-1.95 (m, 2H), 2.40-2.46 (m, 2H), 2.93 (t, J=7.6 Hz, 2H), 3.08 (t, J=7.6 Hz, 2H), 3.50-3.54 (m, 1H), 4.03-4.05 (m, 1H), 6.02 (d, J=8.0 Hz, 1H), 7.78 (d, J=7.6 Hz, 1H), 8.26 (s, 1H). MS: m/z 331.2 (M+H)⁺.

Example 14

Synthesis of 3-((6,7-dihydro-5H-cyclopenta[4,5]thieno[2,3-d]pyrimidin-4-yl)amino)cyclohexanol (I-15)

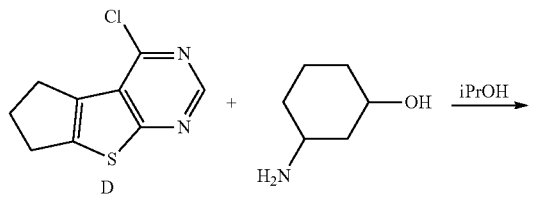

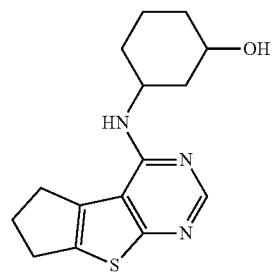

Compound I-15 was synthesized in a manner consistent with Example 8. Isolated a white solid in 15% yield. A mixture of cis and trans. ¹H NMR (400 MHz, DMSO-$d_6$) δ 1.31-1.78 (m, 7H), 1.91-1.95 (m, 1H), 2.40-2.47 (m, 2H), 2.91-2.95 (m, 2H), 3.03-3.11 (m, 2H), 3.77 (s, 0.5H, cis), 3.97 (s, 0.5H, trans), 4.27-4.29 (m, 1H, cis and trans), 4.46-4.53 (m, 0.5H, trans), 5.00-5.07 (m, 0.5H, cis), 5.88 (d, J=8.0 Hz, 0.5H, trans), 6.87 (s, 0.5H, cis), 8.24 (s, 0.5H, cis), 8.25 (s, 0.5H, trans). MS: m/z 290.0 (M+H)⁺.

Example 15

Synthesis of cis-3-((6,7-dihydro-5H-cyclopenta[4,5]thieno[2,3-d]pyrimidin-4-yl)amino)cyclohexanol (I-21)

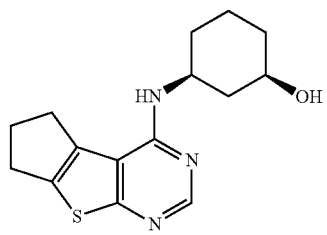 [SMILES: O[C@@H]1CCC[C@H](Nc2ncnc3sc4c(c23)CCC4)C1]

Compound I-21 was separated from compound I-15 by preparative HPLC as white solid. ¹H NMR (400 MHz, DMSO-$d_6$) δ 1.32-1.41 (m, 2H), 1.55-1.77 (m, 5H), 1.92-1.95 (m, 1H), 2.40-2.47 (m, 2H), 2.91-2.95 (m, 2H), 3.02-3.06 (m, 2H), 3.77 (s, 1H), 4.26-4.29 (m, 1H), 5.03 (s, 1H), 6.87 (s, 1H), 8.24 (s, 1H). MS: m/z 290.0 (M+H)⁺.

Example 16

Synthesis of trans-3-((6,7-dihydro-5H-cyclopenta[4,5]thieno[2,3-d]pyrimidin-4-yl)amino)cyclohexanol (I-22)

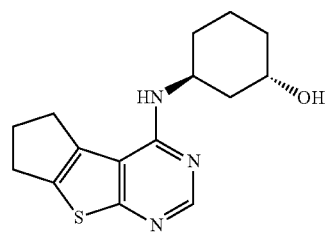 [SMILES: O[C@H]1CCC[C@H](Nc2ncnc3sc4c(c23)CCC4)C1]

Compound I-22 was separated from compound I-15 by preparative HPLC as white solid. ¹H NMR (400 MHz, DMSO-d₆) δ 1.41-1.52 (m, 4H), 1.68-1.74 (m, 2H), 1.78-1.84 (m, 2H), 2.41-2.45 (m, 2H), 2.91-2.95 (m, 2H), 3.05-3.10 (m, 2H), 3.97 (s, 1H), 4.48 (d, J=3.2 Hz, 1H), 4.51 (s, 1H), 5.87 (d, J=8.0 Hz, 1H), 8.25 (s, 1H). MS: m/z 290.0 (M+H)⁺.

Example 17

Synthesis of trans-4-((5,6-dimethylthieno[2,3-d]pyrimidin-4-yl)amino)cyclohexanol (I-19)

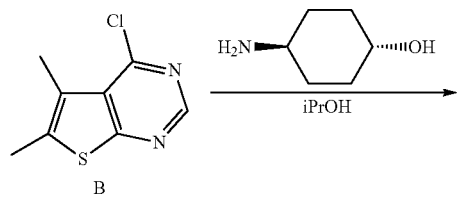

Compound I-19 was synthesized in a manner consistent with Example 8. Isolated a white solid in 71% yield. ¹H NMR (400 MHz, DMSO-d₆) δ 1.26-1.32 (m, 2H), 1.43-1.48 (m, 2H), 1.86 (d, J=10.0 Hz, 2H), 1.95 (d, J=10.2 Hz, 2H), 2.38 (s, 3H), 2.44 (s, 3H), 3.31-3.44 (m, 1H), 4.01-4.03 (m, 1H), 4.60 (d, J=0.8 Hz, 1H), 6.01 (d, J=8.0 Hz, 1H), 8.25 (s, 1H). MS: m/z 278.0 (M+H)⁺.

Example 18

Synthesis of 3-((5,6-dimethylthieno[2,3-d]pyrimidin-4-yl)amino)cyclohexanol

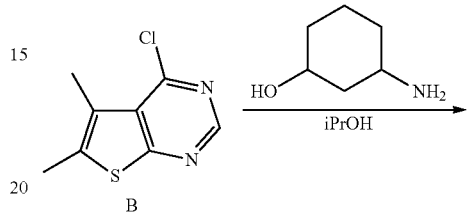

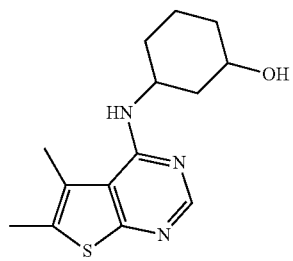

3-((5,6-dimethylthieno[2,3-d]pyrimidin-4-yl)amino)cyclohexanol was synthesized in a manner consistent with Example 8. Isolated a white solid in 73% yield. A mixture of cis and trans. ¹H NMR (400 MHz, CDCl₃) δ 1.30-0.14 (m, 1H), 1.51-1.65 (m, 3H), 1.75-1.89 (m, 3H), 1.90-2.10 (m, 1H), 2.23-2.33 (m, 1H), 2.37 (s, 3H), 2.38 (s, 3H), 4.04 (d, J=3.2 Hz, 1H), 4.40 (s, 0.5H), 4.54 (m, 0.5H), 5.30 (d, J=7.6 Hz, 1H), 8.27 (s, 0.5H), 8.29 (s, 0.5H). MS: m/z 278.0 (M+H)⁺.

Example 19

Synthesis of trans-N¹-(5,6-dimethylthieno[2,3-d]pyrimidin-4-yl)-N⁴-methylcyclohexane-1,4-diamine (I-44)

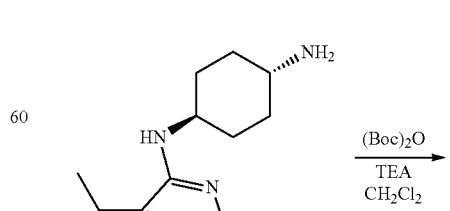

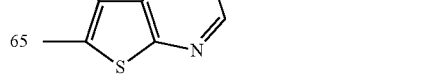

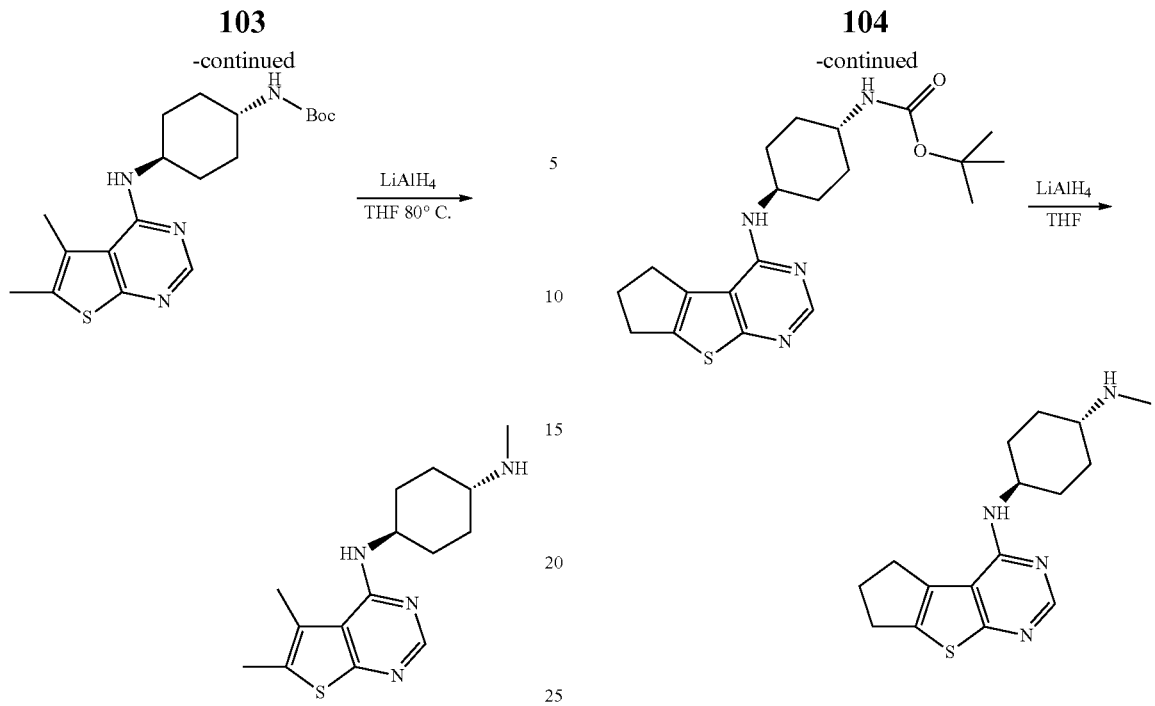

A mixture of I-57 (150 mg, 0.54 mmol, 1.0 eq), (Boc)₂O (129 mg, 0.59 mmol, 1.1 eq) and TEA (71 mg, 0.81 mmol, 1.5 eq) in CH₂Cl₂ (10 mL) was stirred at rt for 2 hours. The solvent was removed under vacuum and the residue (160 mg, 90%) was used to the next step without further purification.

To a mixture of LiAlH₄ (160 mg, 2.1 mmol, 5.0 eq) in THF (5 mL) was added a solution of tert-butyl trans-4-(5,6-dimethylthieno[2,3-d]pyrimidin-4-ylamino)cyclohexylcarbamate (160 mg, 0.42 mmol, 1.0 eq) in THF (5 mL). The mixture was stirred at 80° C. for 2 hours. The reaction was quenched with a mixture of THF/H₂O and filtered. The cake was washed with CH₂Cl₂. The filtrate was concentrated and the residue was purified by column chromatography (CH₂Cl₂/MeOH/Et₃N=20:1:0.5) on silica gel to give desired product compound I-44 as a white solid (72 mg, 60%). ¹H NMR (400 MHz, CDCl₃) δ 1.18-1.25 (m, 4H), 1.47 (br s, 2H), 1.95-1.98 (m, 2H), 2.16-2.18 (m, 2H), 2.34 (s, 3H), 2.38 (s, 3H), 2.39 (s, 3H), 4.02-4.08 (m, 1H), 5.23 (m, 1H), 8.23 (s, 1H). MS: m/z 291.2 (M+H)⁺.

Example 20

Synthesis of trans-N¹-(6,7-dihydro-5H-cyclopenta[4,5]thieno[2,3-d]pyrimidin-4-yl)-N⁴-methylcyclohexane-1,4-diamine (I-34)

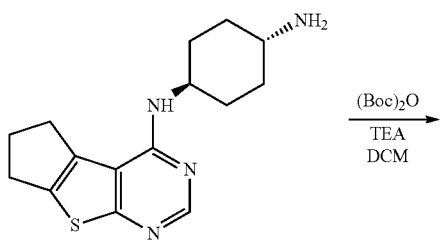

Compound I-34 was synthesized in a manner consistent with Example 19. Isolated a white solid in 9% yield. ¹H NMR (400 MHz, DMSO-d₆) δ 1.06-1.14 (m, 2H), 1.21-1.29 (m, 2H), 1.42-1.52 (m, 2H), 1.92-1.94 (m, 4H), 2.23 (s, 3H), 2.38-2.45 (m, 2H), 2.93 (t, J=7.6 Hz, 2H), 3.07 (t, J=7.2 Hz, 2H), 4.02-4.06 (m, 1H), 5.98 (d, J=8.0 Hz, 1 H), 8.25 (s, 1H). MS: m/z 303.2 (M+H)⁺.

Example 21

Synthesis of 3-((6-methyl-5,6,7,8-tetrahydrobenzo[4,5]thieno[2,3-d]pyrimidin-4-yl)amino)cyclohexanol (I-35)

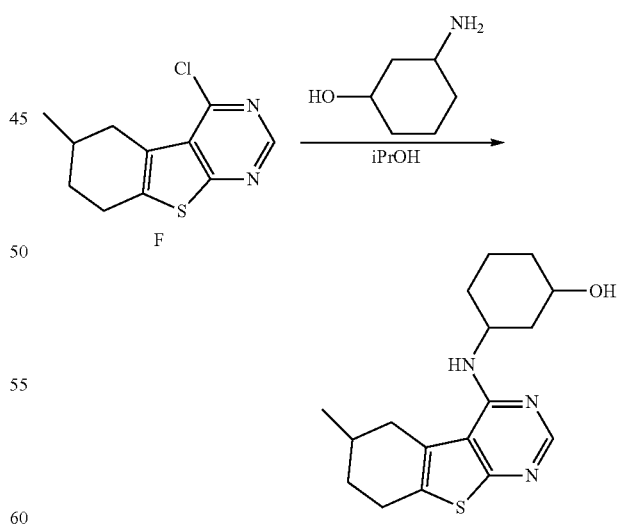

Compound I-35 was synthesized in a manner consistent with Example 8. Isolated a brown solid in 7% yield. A mixture of cis and trans. ¹H NMR (400 MHz, DMSO-d₆) δ 1.09 (d, J=6.4 Hz, 3H), 1.31-1.34 (m, 1H), 1.41-1.46 (m, 2H), 1.62-1.80 (m, 4H), 1.88-1.95 (m, 3H), 2.48-2.59 (m, 2H), 2.79 (s, 2H), 3.03-3.12 (m, 1H), 3.80 (s, 0.5H), 3.96 (s, 0.5H), 4.30 (s, 0.5H), 4.49 (m, 1H), 5.03 (s, 0.5H), 5.80-5.82 (m, 0.5H), 6.92 (s, 0.5H), 8.22 (s, 0.5H), 8.24 (s, 0.5H). MS: m/z 318.0 (M+H)⁺.

Example 22

Synthesis of trans-4-((6-methyl-5,6,7,8-tetrahydrobenzo[4,5]thieno[2,3-d]pyrimidin-4-yl)amino)cyclohexanol (I-37)

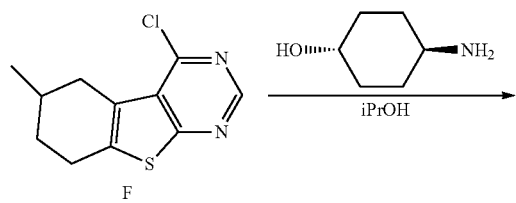

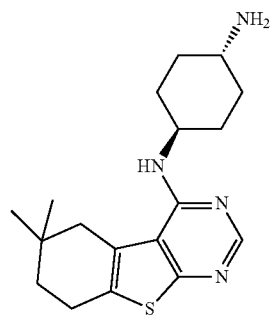

Compound I-37 was synthesized in a manner consistent with Example 11. Isolated a brown solid in 25% yield. ¹H NMR (400 MHz, DMSO-d₆) δ 1.09 (d, J=6.4 Hz, 3H), 1.10-1.28 (m, 2H), 1.44-1.51 (m, 3H), 1.85-1.95 (m, 6H), 2.48-2.51 (m, 1H), 2.79-2.80 (m, 2H), 3.05 (dd, J=4.8, 15.6 Hz, 1H), 3.41-3.46 (m, 1H), 4.58 (d, J=4.8 Hz, 1H), 5.85 (d, J=8.0 Hz, 1H), 8.25 (s, 1H). MS: m/z 318.1 (M+H)⁺.

Example 23

Synthesis of trans-N¹-(6,6-dimethyl-5,6,7,8-tetrahydrobenzo[4,5]thieno[2,3-d]pyrimidin-4-yl)cyclohexane-1,4-diamine (I-38)

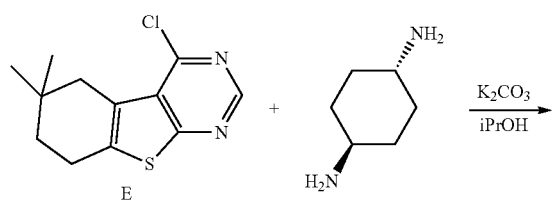

To a solution of compound E (506 mg, 2.0 mmol) and cyclohexane-1,4-diamine (273 mg, 2.4 mmol, 1.2 eq) in 10 mL of iPrOH was added K₂CO₃ (828 mg, 6.0 mmol, 3 eq). The reaction was heated at 100° C. overnight and cooled down. The mixture was poured into water (10 mL). The precipitate was collected by filtration and purified by column chromatography on silica gel (DCM/MeOH=100:5) to give the product as white solid (400 mg, 60%). ¹H NMR (400 MHz, CDCl₃) δ1.01 (s, 6H), 1.21-2.16 (m, 4H), 1.41 (br s, 2H), 1.56-1.59 (m, 2H), 1.87-1.90 (m, 2H), 2.13-2.16 (m, 2H), 2.54-2.56 (m, 2H), 2.68 (m, 1H), 2.73-2.76 (m, 2H), 4.01-4.04 (m, 1H), 5.00 (d, J=8.0 Hz, 1H), 8.29 (s, 1H). MS: m/z 331.1 (M+H)⁺.

Example 24

Synthesis of trans-N¹-(7-ethyl-5,6,7,8-tetrahydrobenzo[4,5]thieno[2,3-d]pyrimidin-4-yl)cyclohexane-1,4-diamine (I-39)

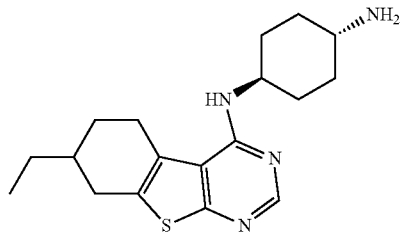

Compound I-39 was synthesized in a manner consistent with Example 8. Isolated a white solid in 70% yield. ¹H NMR (400 MHz, DMSO-d₆) δ 0.96 (t, J=7.2 Hz, 3H), 1.17-1.46 (m, 4H), 1.67 (m, 4H), 1.83-1.96 (m, 3H), 2.10-2.14 (m, 4H), 2.35-2.40 (m, 1H), 2.60-2.65 (m, 1H), 2.81-2.87 (m, 3H), 4.00-4.02 (m, 1H), 5.88 (d, J=8.0 Hz, 1H), 8.30 (s, 1H). MS: m/z 331.1 (M+H)⁺.

Example 25

Synthesis of trans-N$^1$-(6,6-dimethyl-5,6,7,8-tetrahydrobenzo[4,5]thieno[2,3-d]pyrimidin-4-yl)-N$^4$,N$^4$-dimethylcyclohexane-1,4-diamine (I-40)

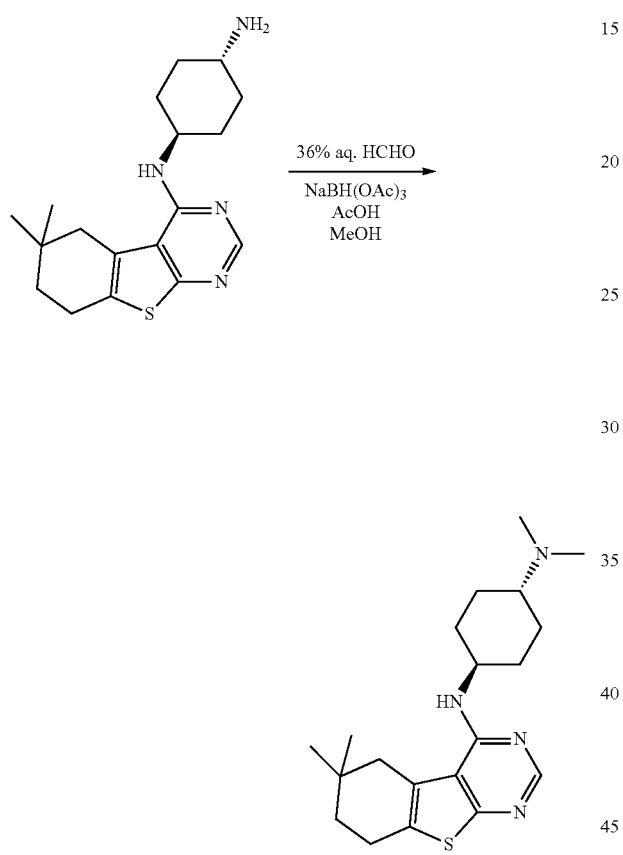

36% aq. HCHO (46 mg, 0.552 mmol, 2.0 eq) was added to a solution of compound I-38 (91 mg, 0.276 mmol) in 5 mL of MeOH, followed by AcOH (83 mg, 1.38 mmol, 5 eq). The reaction was stirred for 10 minutes and NaBH(OAc)₃ (233 mg, 1.10 mmol, 4 eq) was added. The resulting mixture was stirred for additional 2 h. The reaction was poured into 30 mL of water and extracted with dichloromethane (3×30 mL). The combined organics were dried over anhydrous Na₂SO₄ and filtered. The filtrate was concentrated and the residue was purified by column chromatography in silica gel (DCM/MeOH=100:5) to give the product as white solid (80 mg, 80%). ¹H NMR (400 MHz, CDCl₃) δ 1.01 (s, 6H), 1.20-1.24 (m, 2H), 1.42-1.46 (m, 2H), 1.57-1.60 (m, 2H), 1.93-1.96 (m, 2H), 2.02-2.23 (m, 3H), 2.32 (s, 6H), 2.55 (s, 2H), 2.73-2.76 (m, 2H), 4.03-4.05 (m, 1H), 5.00 (d, J=8.0 Hz, 1H), 8.29 (s, 1H). MS: m/z 359.1 (M+H)⁺.

Example 26

Synthesis of trans-N$^1$-(6,6-dimethyl-5,6,7,8-tetrahydrobenzo[4,5]thieno[2,3-d]pyrimidin-4-yl)-N$^4$-methylcyclohexane-1,4-diamine (I-41)

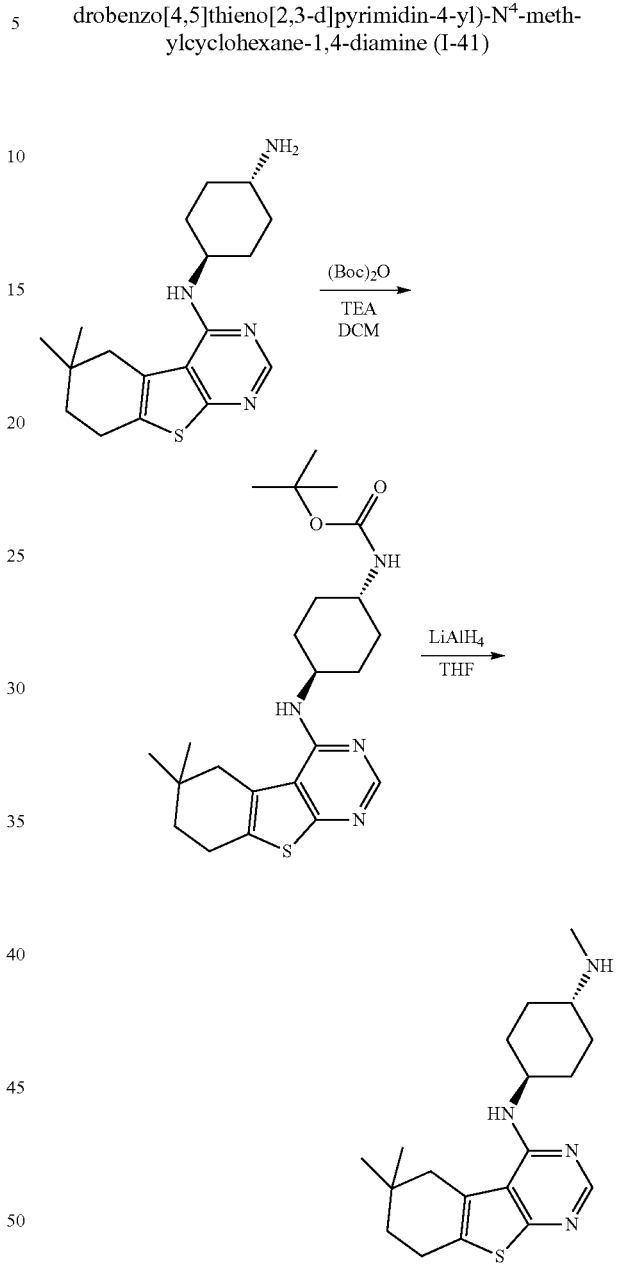

Into a mixture of compound I-38 (160 mg, 0.48 mmol) and (Boc)₂O (105 mg, 0.48 mmol) in 5 mL of dichloromethane was added TEA (97 mg, 0.96 mmol, 2 eq) at room temperature. The reaction was stirred at room temperature overnight. The reaction mixture was concentrated and the residue was purified by column chromatography on silica gel (DCM/MeOH=100:5) to give tert-butyl trans-4-(6,6-dimethyl-5,6,7,8-tetrahydrobenzo[4,5]thieno[2,3-d]pyrimidin-4-ylamino)cyclohexanylcarbamate as white solid (210 mg, quantitive). MS: m/z 431.1 (M+H)⁺.

To a solution of tert-butyl trans-4-(6,6-dimethyl-5,6,7,8-tetrahydrobenzo[4,5]thieno[2,3-d]pyrimidin-4-ylamino)cyclohexanylcarbamate (210 mg, 0.49 mmol) in 10 mL of THF was added LiAlH$_4$ (88 mg, 2.44 mmol, 5.0 eq) carefully at 0° C. The resulting mixture was heated at reflux for 2 h and cooled down. The reaction was cooled to 0° C. and quenched with a mixture of THF/H$_2$O. Extracted with EtOAc (3×20 mL) and the combined organics were dried over anhydrous Na$_2$SO$_4$ and filtered. The filtrate was concentrated and the residue was purified by column chromatography in silica gel (DCM/MeOH/NH$_4$OH=100:8:1) to give the product as white solid (140 mg, 80%). $^1$H NMR (400 MHz, CDCl$_3$) δ 1.01 (s, 6H), 1.18-1.30 (m, 4H), 1.58 (t, J=6.4 Hz, 2H), 1.96 (br s, 1H), 1.98-2.01 (m, 2H), 2.17-2.19 (m, 2H), 2.38-2.40 (m, 1H), 2.41 (s, 3H), 2.56 (s, 2H), 2.73-2.76 (m, 2H), 4.07-4.10 (m, 1H), 5.01 (d, J=7.2 Hz, 1H), 8.29 (s, 1H). MS: m/z 345.1 (M+H).

Example 27

Synthesis of trans-4-((6,6-dimethyl-5,6,7,8-tetrahydrobenzo[4,5]thieno[2,3-d]pyrimidin-4-yl)amino)cyclohexanol (I-43)

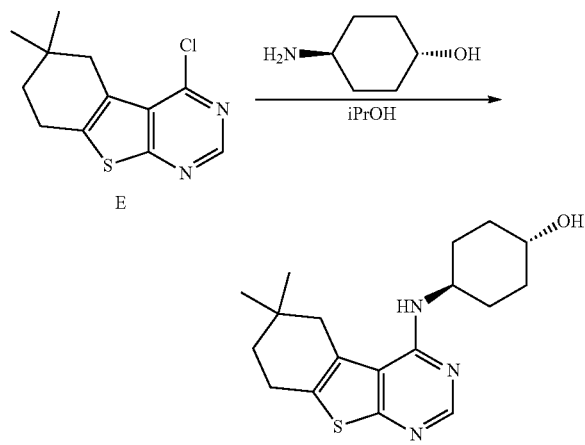

Compound I-43 was synthesized in a manner consistent with Example 8. Isolated a white solid in 70% yield. $^1$H NMR (400 MHz, CDCl$_3$) δ 1.02 (s, 6H), 1.23-1.29 (m, 2H), 1.46-1.52 (m, 2H), 1.58 (t, J=6.8 Hz, 2H), 1.85-1.95 (m, 4H), 2.73-2.78 (m, 4H), 3.39-3.42 (m, 1H), 4.01-4.08 (m, 1H), 4.59 (d, J=4.4 Hz, 1H), 5.85 (d, J=7.6 Hz, 1H), 8.25 (s, 1H). MS: m/z 332.2 (M+H)$^+$.

Example 28

Synthesis of trans-N$^1$,N$^1$-dimethyl-N$^4$-(5,6,7,8-tetrahydrobenzo[4,5]thieno[2,3-d]pyrimidin-4-yl)cyclohexane-1,4-diamine (I-50)

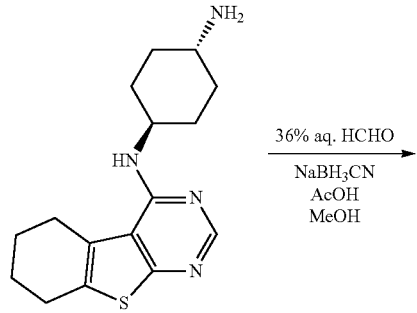

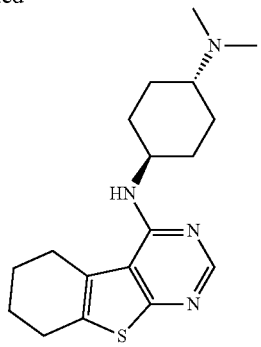

36% aq. HCHO (58 mg, 0.696 mmol, 2.2 eq) was added to a solution of compound I-49 (100 mg, 0.316 mmol) in 5 mL of MeOH, followed by AcOH (95 mg, 1.58 mmol, 5 eq). The reaction was stirred for 10 minutes and NaBH$_3$CN (44 mg, 1.10 mmol, 4 eq) was added. The resulting mixture was stirred for additional 6 h. The reaction was poured into 50 mL of water and extracted with dichloromethane (3×50 mL). The combined organics were dried over anhydrous Na$_2$SO$_4$ and filtered. The filtrate was concentrated and the residue was purified by column chromatography in silica gel (DCM/MeOH=20:1~15:1) to give the product as white solid (15 mg, 15%). $^1$H NMR (400 MHz, CDCl$_3$) δ 1.15-1.22 (m, 2H), 1.36-1.43 (m, 2H), 1.80-1.91 (m, 6H), 2.18-2.23 (m, 3H), 2.24 (s, 6H), 2.72-2.75 (m, 2H), 2.81-2.84 (m, 2H), 4.01-4.04 (m, 1H), 5.03 (d, J=7.2 Hz, 1H), 8.29 (s, 1H). MS: m/z 331.1 (M+H)$^+$.

Example 29

Synthesis of trans-N$^1$-(5,6-dimethylthieno[2,3-d]pyrimidin-4-yl)-N$^4$,N$^4$-dimethylcyclohexane-1,4-diamine (I-42)

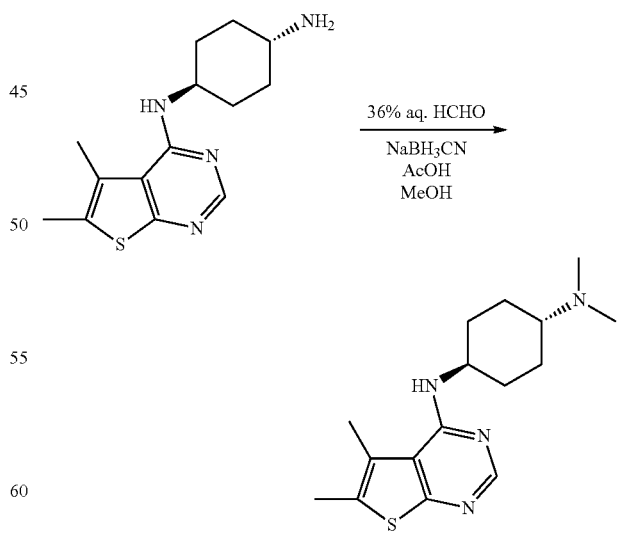

Compound I-42 was synthesized in a manner consistent with Example 28. Isolated a white solid in 60% yield. $^1$H NMR (400 MHz, CDCl$_3$) δ 1.16-1.23 (m, 2H), 1.39-1.43 (m, 2H), 1.90 (m, 2H), 2.19-2.20 (m, 3H), 2.17 (s, 6H), 2.34 (s, 3H), 2.37 (s, 3H), 4.02-4.04 (m, 1H), 5.18 (d, J=6.8 Hz, 1H), 8.29 (s, 1H). MS: m/z 305.2 (M+H)⁺.

Example 30

Synthesis of trans-4-(((R)-6-methyl-5,6,7,8-tetrahydrobenzo[4,5]thieno[2,3-d]pyrimidin-4-yl)amino)cyclohexanol (I-47)

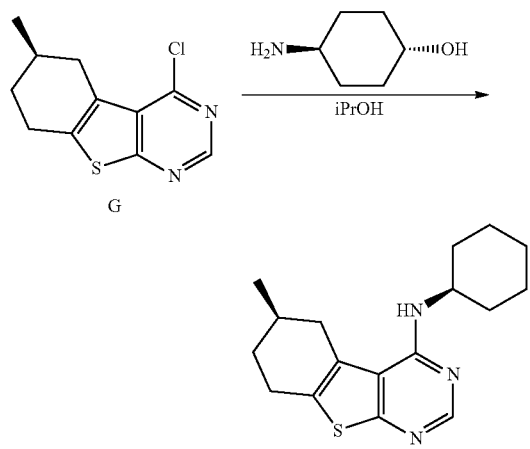

Compound I-47 was synthesized in a manner consistent with Example 8. Isolated a white solid in 79% yield. ¹H NMR (400 MHz, CDCl₃) δ 1.10 (t, J=6.6 Hz, 3H), 1.20-1.27 (m, 2H), 1.40-1.51 (m, 4H), 1.88-1.99 (m, 4H), 2.10-2.18 (m, 2H), 2.35-2.40 (m, 1H), 2.75-2.78 (m, 2H), 2.87 (m, 1H), 3.63-3.65 (m, 1H), 4.03-4.08 (m, 1H), 5.03 (d, J=7.7 Hz, 1H), 8.30 (s, 1H). MS: m/z 318.2 (M+H)⁺.

Example 31

Synthesis of trans-N¹-((R)-6-methyl-5,6,7,8-tetrahydrobenzo[4,5]thieno[2,3-d]pyrimidin-4-yl)cyclohexane-1,4-diamine (I-48)

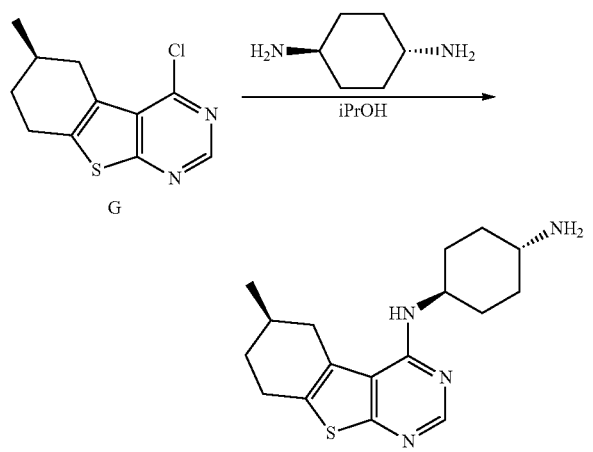

Compound I-48 was synthesized in a manner consistent with Example 8. Isolated a white solid in 76% yield. ¹H NMR (400 MHz, CDCl₃) δ 1.06 (t, J=6.6 Hz, 3H), 1.19-1.29 (m, 4H), 1.43-1.45 (m, 1H), 1.64 (m, 1H), 1.78-1.80 (m, 2H), 1.91-1.93 (m, 4H), 2.10-2.13 (m, 2H), 2.35-2.43 (m, 1H), 2.88 (d, 1H), 3.63-3.65 (m, 1H), 4.03-4.08 (m, 1H), 5.02 (d, J=8.0 Hz, 1H), 8.30 (s, 1H). MS: m/z 317.1 (M+H)⁺.

Example 32

Synthesis of trans-N¹-(5,6,7,8-tetrahydrobenzo[4,5]thieno[2,3-d]pyrimidin-4-yl)cyclohexane-1,4-diamine (I-49)

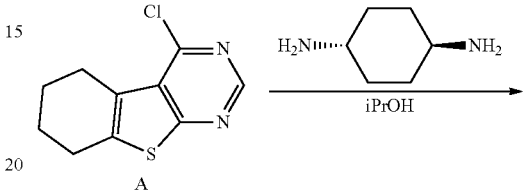

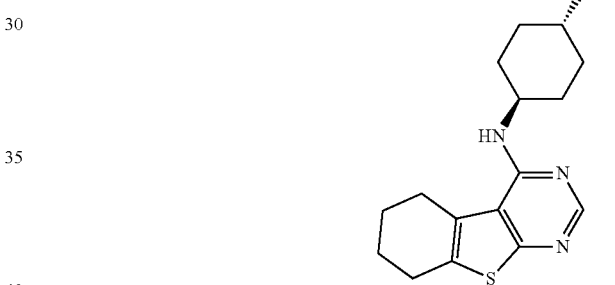

Compound I-49 was synthesized in a manner consistent with Example 11. Isolated a light yellow solid in 82% yield. ¹H NMR (400 MHz, CDCl₃) δ 1.18-1.29 (m, 4H), 1.40 (br s, 2H), 1.80-1.88 (m, 6H), 2.11-2.15 (m, 2H), 2.63-2.66 (m, 1H), 2.72-2.75 (m, 2H), 2.81-2.84 (m, 2H), 4.04-4.07 (m, 1H), 5.02 (d, J=7.2 Hz, 1H), 8.29 (s, 1H). MS: m/z 303.0 (M+H)⁺.

Example 33

Synthesis of trans-N¹-(6-methyl-5,6,7,8-tetrahydrobenzo[4,5]thieno[2,3-d]pyrimidin-4-yl)cyclohexane-1,4-diamine (I-51)

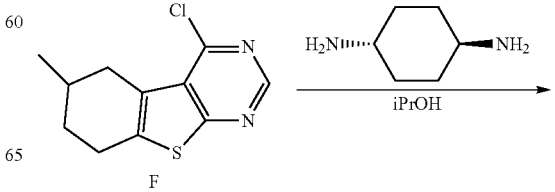

113
-continued

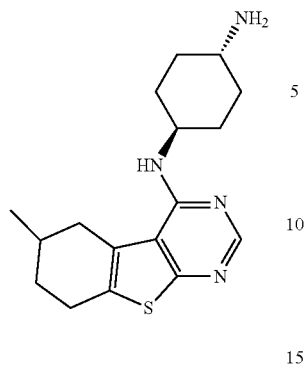

Compound I-51 was synthesized in a manner consistent with Example 11. Isolated a light yellow solid in 80% yield. $^1$H NMR (400 MHz, CDCl$_3$) δ 1.08 (d, J=6.8 Hz, 3H), 1.19-1.30 (m, 3H), 1.41-1.45 (m, 4H), 1.87-1.91 (m, 4H), 2.11-2.16 (m, 2H), 2.35-2.41 (m, 1H), 2.66-2.70 (m, 1H), 2.74-2.77 (m, 2H), 2.88 (dd, J=4.8, 14.8 Hz, 1H), 4.03-4.08 (m, 1H), 5.02 (d, J=7.6 Hz, 1H), 8.29 (s, 1H). MS: m/z 317.1 (M+H)$^+$.

Example 34

Synthesis of trans-N$^1$-methyl-N4-(6-methyl-5,6,7,8-tetrahydrobenzo[4,5]thieno[2,3-d]pyrimidin-4-yl)cyclohexane-1,4-diamine (I-52)

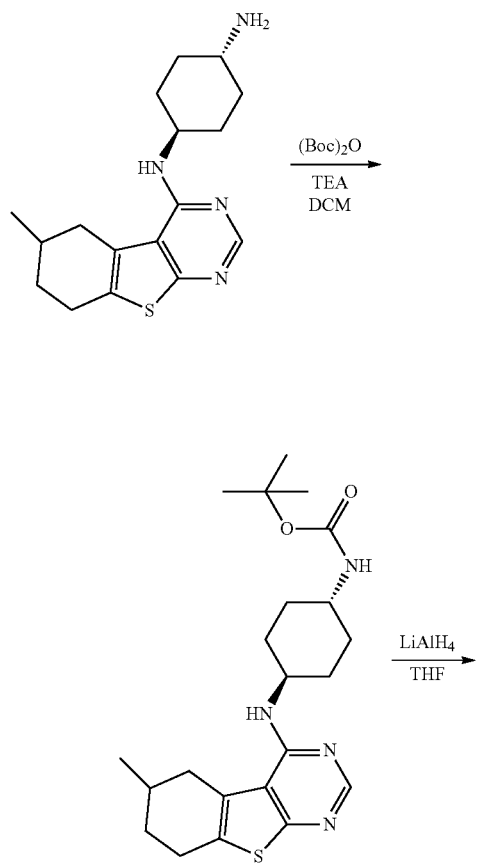

114
-continued

Compound I-52 was synthesized in a manner consistent with Example 19. Isolated a brown solid in 20% yield. $^1$H NMR (400 MHz, CDCl$_3$) δ 1.08 (d, J=6.4 Hz, 3H), 1.18-1.25 (m, 4H), 1.41-1.47 (m, 2H), 1.88-1.98 (m, 4H), 2.17 (s, 2H), 2.31-2.41 (m, 2H), 2.39 (s, 3H), 2.75-2.87 (m, 2H), 2.90 (dd, J=5.2, 15.2 Hz, 1H), 4.06-4.09 (m, 1H), 5.04 (d, J=7.6 Hz, 1H), 8.29 (s, 1H). MS: m/z 331.2 (M+H)$^+$.

Example 35

Synthesis of trans-N$^1$-methyl-N4-(5,6,7,8-tetrahydrobenzo[4,5]thieno[2,3-d]pyrimidin-4-yl)cyclohexane-1,4-diamine (I-53)

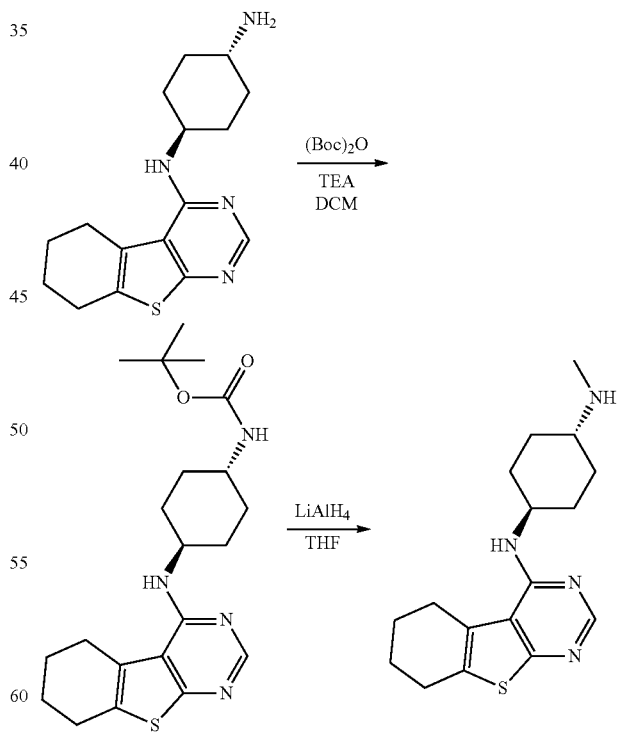

Compound I-53 was synthesized in a manner consistent with Example 19. Isolated a brown solid in 15% yield. $^1$H NMR (400 MHz, CDCl$_3$) δ 1.16-1.25 (m, 4H), 1.63 (br s, 1H), 1.80-1.87 (m, 4H), 1.95-1.98 (m, 2H), 2.14-2.17 (m, 2H), 2.30-2.38 (m, 1H), 2.39 (s, 3H), 2.72-2.75 (m, 2H), 2.82-2.85 (m, 2H), 4.01-4.12 (m, 1H), 5.04 (d, J=7.6 Hz, 1H), 8.29 (s, 1H). MS: m/z 317.1 (M+H)+.

Example 36

Synthesis of trans-$N^1$,$N^1$-dimethyl-$N^4$-(6-methyl-5,6,7,8-tetrahydrobenzo[4,5]thieno[2,3-d]pyrimidin-4-yl)cyclohexane-1,4-diamine (I-54)

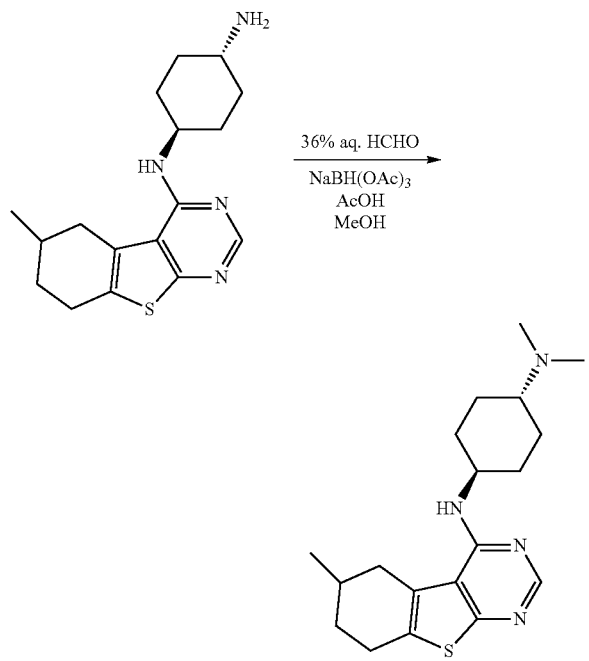

Compound I-54 was synthesized in a manner consistent with Example 28. Isolated a white solid in 10% yield. $^1$H NMR (400 MHz, CDCl$_3$) δ 1.09 (d, J=6.4 Hz, 3H), 1.22-1.29 (m, 2H), 1.42-1.57 (m, 3H), 1.89-1.93 (m, 2H), 2.06-2.11 (m, 2H), 2.25-2.27 (m, 2H), 2.41-2.45 (m, 1H), 2.45 (s, 6H), 2.59-2.63 (m, 1H), 2.75-2.78 (m, 2H), 2.88 (dd, J=4.4, 14.8 Hz, 1H), 4.05-4.09 (m, 1H), 5.02 (d, J=6.8 Hz, 1H), 8.29 (s, 1H). MS: m/z 345.1 (M+H)+.

Example 37 trans-$N^1$-(7-ethyl-5,6,7,8-tetrahydrobenzo[4,5]thieno[2,3-d]pyrimidin-4-yl)-$N^4$,$N^4$-dimethylcyclohexane-1,4-diamine (I-55)

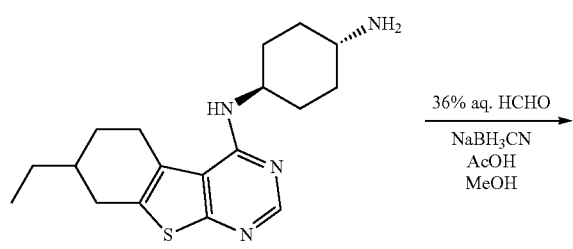

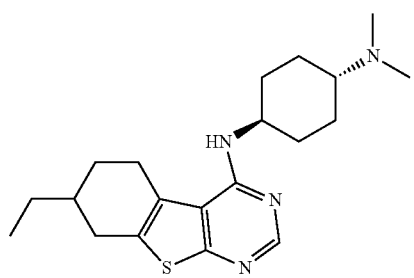

Compound I-55 was synthesized in a manner consistent with Example 29. Isolated a white solid in 65% yield. $^1$H NMR (400 MHz, CDCl$_3$) δ 0.96 (t, J=7.2 Hz, 3H), 1.16-1.32 (m, 3H), 1.38-1.51 (m, 5H), 1.66 (t, J=2.8 Hz, 1H), 1.87-1.90 (m, 2H), 1.97 (m, 1H), 2.16-2.20 (m, 2H), 2.21 (s, 6H), 2.32-3.38 (m, 1H), 2.81-2.87 (m, 3H), 4.00-4.04 (m, 1H), 5.04 (d, J=8.0 Hz, 1H), 8.29 (s, 1H). MS: m/z 359.2 (M+H)+.

Example 38

Synthesis of trans-$N^1$,$N^1$-dimethyl-$N^4$-((R)-6-methyl-5,6,7,8-tetrahydrobenzo[4,5]thieno[2,3-d]pyrimidin-4-yl)cyclohexane-1,4-diamine (I-56)

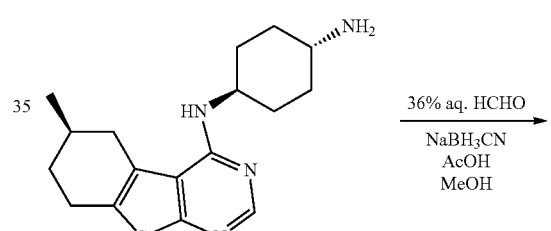

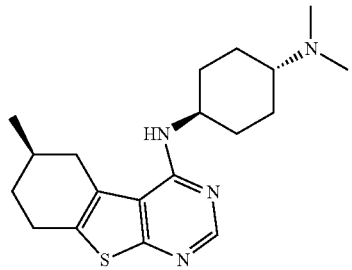

Compound I-56 was synthesized in a manner consistent with Example 28. Isolated a white solid in 60% yield. $^1$H NMR (400 MHz, CDCl$_3$) δ 1.07 (d, J=6.8 Hz, 3H), 1.18-1.25 (m, 4H), 1.39-1.46 (m, 3H), 1.89-1.91 (m, 4H), 2.18-2.20 (m, 1H), 2.21 (s, 6H) 2.38-3.41 (m, 1H), 2.77 (m, 2H), 2.86-2.91 (m, 1H), 4.02-4.04 (m, 1H), 5.03 (d, J=7.6 Hz, 1H), 8.28 (s, 1H). MS: m/z 345.2 (M+H)+.

Example 39

Synthesis of trans-$N^1$-(5,6-dimethylthieno[2,3-d]pyrimidin-4-yl)cyclohexane-1,4-diamine (I-57)

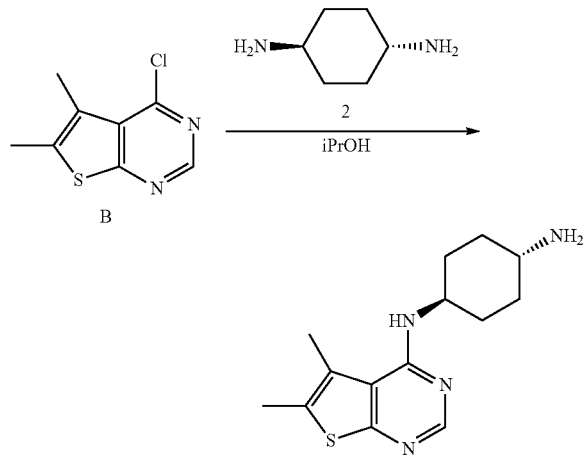

Compound I-57 was synthesized in a manner consistent with Example 8. Isolated a white solid in 60% yield. $^1$H NMR (400 MHz, CDCl$_3$) δ 1.18-1.25 (m, 4H), 1.29-1.39 (m, 2H), 1.87 (d, J=10.8 Hz, 2H), 2.14 (d, J=10.8 Hz, 2H), 2.34 (s, 3H), 2.37 (s, 3H), 2.66-2.67 (m, 1H), 4.05-4.07 (m, 1H), 5.18 (d, J=7.2 Hz, 1H), 8.29 (s, 1H). MS: m/z 277.1 (M+H)$^+$.

Example 40

Synthesis of trans-N1-(7-ethyl-5,6,7,8-tetrahydrobenzo[4,5]thieno[2,3-d]pyrimidin-4-yl)-N4-methylcyclohexane-1,4-diamine (I-58)

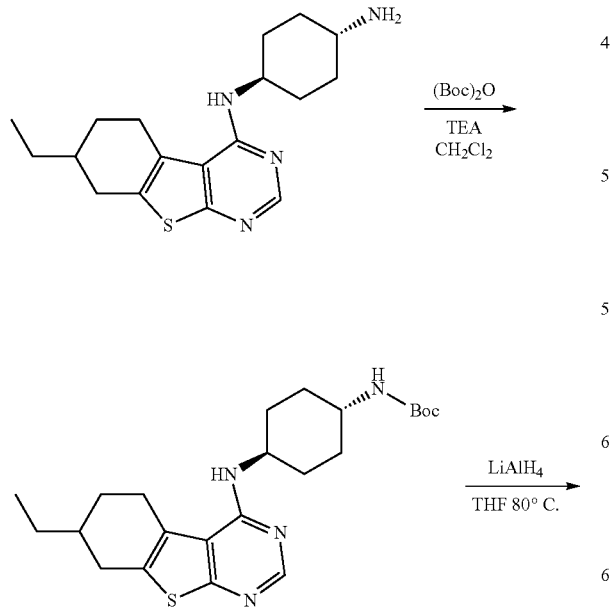

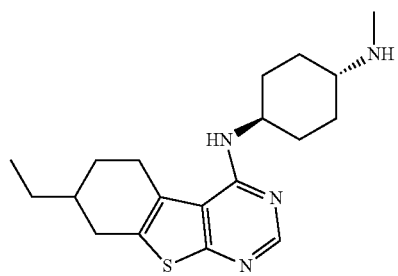

Compound I-57 was synthesized in a manner consistent with Example 19. Isolated a white solid in 60% yield. $^1$H NMR (400 MHz, CDCl$_3$) δ 0.91 (t, J=7.2 Hz, 3H), 1.18-1.25 (m, 4H), 1.35-1.39 (m, 3H), 1.61-1.76 (m, 1H), 1.94-1.97 (m, 3H), 2.12-2.17 (m, 3H), 2.26-2.41 (m, 5H), 2.78-2.96 (m, 3H), 4.01-4.16 (m, 1H), 5.04 (d, J=8.0 Hz, 1H), 8.28 (s, 1H). MS: m/z 345.2 (M+H)$^+$.

Example 41

Synthesis of trans-4-((6,7-dihydro-5H-cyclopenta[4,5]thieno[2,3-d]pyrimidin-4-yl)oxy)cyclohexanamine (I-61)

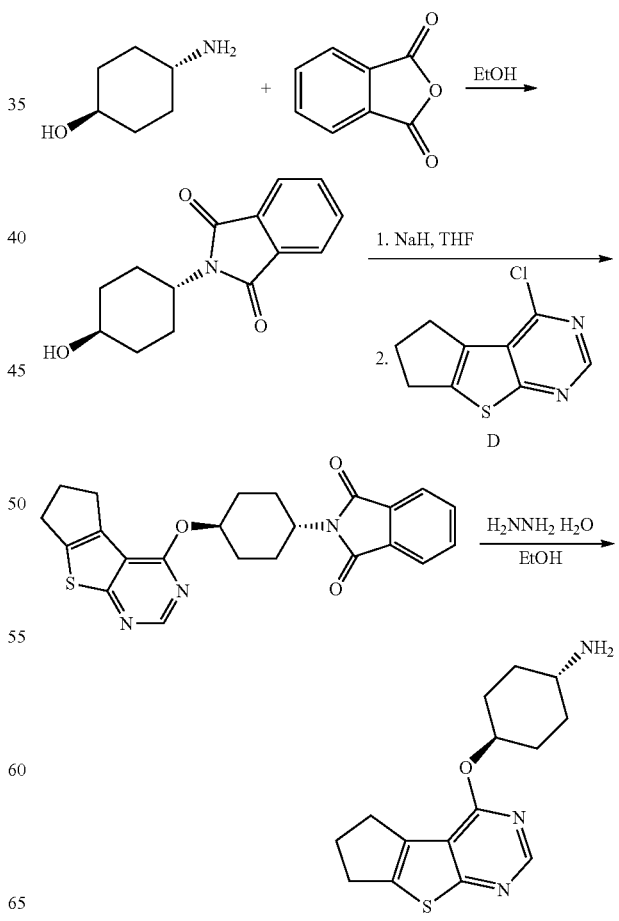

Synthesis of 2-(4-hydroxycyclohexyl)isoindoline-1,3-dione

A mixture of 4-aminocyclohexanol (3.9 g, 34 mmol) and isobenzofuran-1,3-dione (4.9 g, 34 mmol, 1.0 eq) in 100 mL of EtOH was heated at reflux for 2 days. EtOH was removed and the residue was purified by column chromatography on silica gel (eluent with DCM) to give 2-(4-hydroxycyclohexyl)isoindoline-1,3-dione as white solid (5.0 g, 59%). MS: m/z 246.0 (M+H)$^+$.

Synthesis of 2-(trans-4-((6,7-dihydro-5H-cyclopenta[4,5]thieno[2,3-d]pyrimidin-4-yl)hydroxycyclohexyl)isoindoline-1,3-dione To a solution of 2-(4-hydroxycyclohexyl)isoindoline-1,3-dione (837 mg, 3.42 mmol, 1.2 eq) in 20 mL of THF was added NaH (137 mg, 3.42 mmol, 60% in oil, 1.2 eq) in one portion at room temperature. The resulting mixture was heated at reflux for 2 hours and cooled down. Compound D (600 mg, 2.85 mmol, 1.0 eq) was added to the mixture as solid in one portion. The reaction was stirred for additional 30 minutes at room temperature. The reaction was quenched with water carefully and extracted with EtOAc (50 mL×3). The combined organics was dried over anhydrous $Na_2SO_4$ and filtered. The filtrate was concentrated and the residue was purified by column chromatography in silica gel (eluent with DCM) to give 2-(trans-4-((6,7-dihydro-5H-cyclopenta[4,5]thieno[2,3-d]pyrimidin-4-yl)hydroxycyclohexyl)isoindoline-1,3-dione as white solid (1.16 g, 77%). MS: m/z 420.1 (M+H)$^+$.

Synthesis of Compound I-61

To a solution of 2-(trans-4-((6,7-dihydro-5H-cyclopenta[4,5]thieno[2,3-d]pyrimidin-4-yl)hydroxycyclohexyl)isoindoline-1,3-dione (1.16 g, 2.63 mmol, 1.0 eq) in 10 mL of EtOH was added hydrazine hydrate (776 mg, 13.2 mmol, 5.0 eq) at room temperature. The reaction was heated at reflux for 4 h and cooled down. EtOH was removed and the residue was purified by column chromatography on silica gel (DCM/MeOH/NH$_4$OH=100:5:1~100:10:1) to give I-61 as white solid (600 mg, 79%). $^1$H NMR (400 MHz, CDCl$_2$) δ 1.26-1.37 (m, 2H), 1.36 (br s, 2H), 1.50-1.53 (m, 2H), 1.88-1.92 (m, 2H), 2.12-2.16 (m, 2H), 2.39-2.45 (m, 2H), 2.74-2.80 (m, 1H), 2.92-2.96 (m, 4H), 5.15-5.18 (m, 1H), 8.42 (s, 1H). MS: m/z 290.1 (M+H)$^+$.

Example 42

Synthesis of 2-((trans-4-((6,7-dihydro-5H-cyclopenta[4,5]thieno[2,3-d]pyrimidin-4-yl)amino)cyclohexyl)amino)acetic acid (I-65)

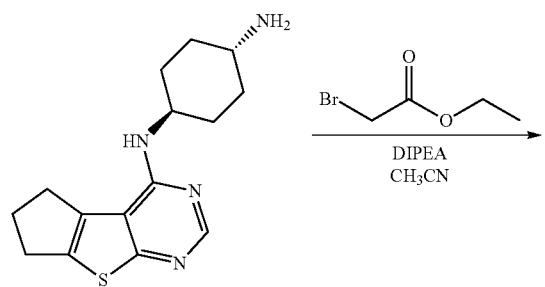

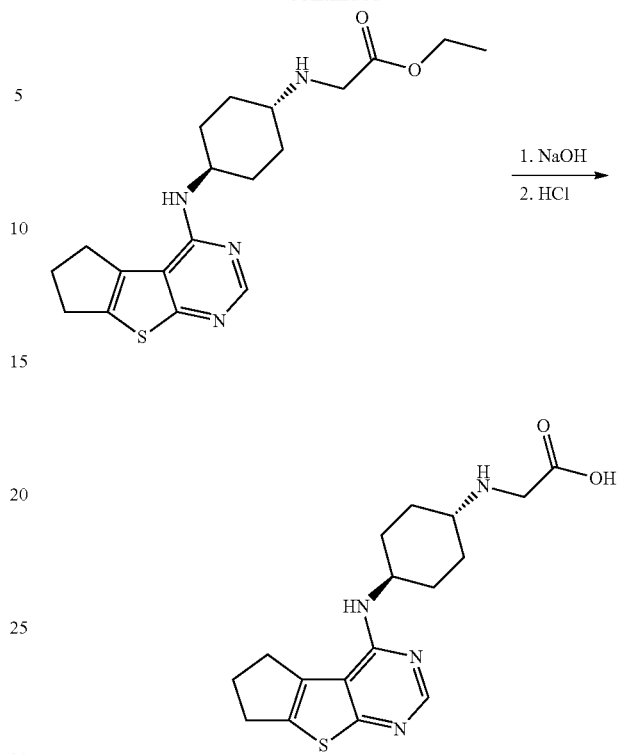

Synthesis of Ethyl 2-((trans-4-((6,7-dihydro-5H-cyclopenta[4,5]thieno[2,3-d]pyrimidin-4-yl)amino)cyclohexyl)amino)acetate To a solution of I-10 (150 mg, 0.52 mmol) in CH$_3$CN (15 mL) was added DIPEA (70 mg, 0.52 mmol, 1 eq). Then ethyl 2-bromoacetate (87 mg, 0.52 mmol, 1 eq) in 5 mL of CH$_3$CN was added dropwise at room temperature over 15 minutes. The reaction was stirred at room temperature overnight and CH$_3$CN was removed. The residue was separated between dichloromethane (20 mL) and water (20 mL). The aqueous layer was extracted with dichloromethane twice. The combined organics were dried over anhydrous Na$_2$SO$_4$ and filtered. The filtrate was concentrated and the residue was purified by column chromatography in silica gel (DCM/MeOH=100:1~50:1) to give ethyl 2-((trans-4-((6,7-dihydro-5H-cyclopenta[4,5]thieno[2,3-d]pyrimidin-4-yl)amino)cyclohexyl)amino)acetate as white solid (80 mg, 40%).

Synthesis of Compound I-65

To a solution of ethyl 2-((trans-4-((6,7-dihydro-5H-cyclopenta[4,5]thieno[2,3-d]pyrimidin-4-yl)amino)cyclohexyl)amino)acetate (80 mg, 0.21 mmol) in 5 mL of MeOH was added NaOH (34 mg, 0.85 mmol, 4 eq) in 5 mL of water. The reaction was stirred at room temperature for 1.5 h and MeOH was removed. The aqueous solution was adjusted to pH=5 with 1N HCl. The precipitate was collected by filtration and washed with water, dried in vacuo to give the product compound I-65 as HCl salt (30 mg, 85%). $^1$H NMR (400 MHz, DMSO-d$_6$) δ 1.50-1.55 (m, 4H), 2.01 (br s, 2H), 2.13 (br s, 2H), 2.40-2.44 (m, 2H), 2.92-2.95 (m, 2H), 3.06-3.10 (m, 3H), 3.93 (br s, 2H), 4.06 (br s, 1H), 6.15 (d, J=8.0 Hz, 1H), 8.28 (s, 1H), 9.14 (br s, 2H), 13.80 (br s, 1H). MS: m/z 347.2 (M+H)⁺.

Example 43

Synthesis of trans-4-((6,7-dihydro-5H-cyclopenta[4,5]thieno[2,3-d]pyrimidin-4-yl)oxy)-N-methylcyclohexanamine (I-66)

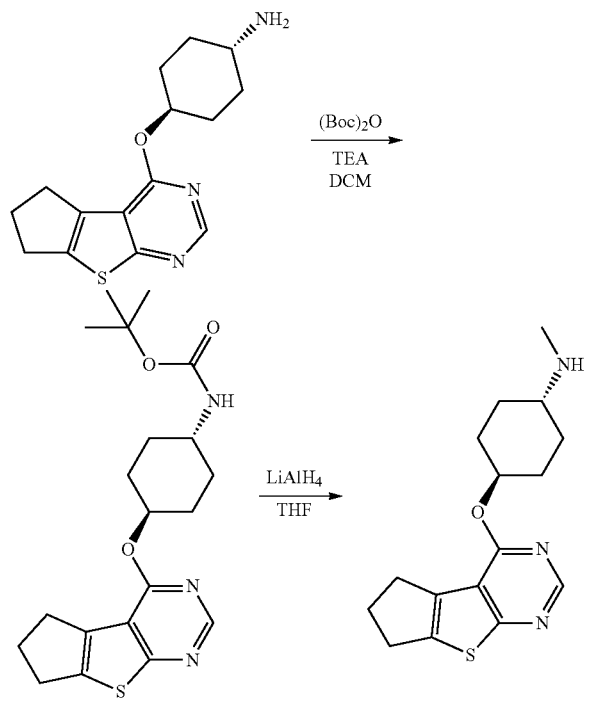

Compound I-66 was synthesized in a manner consistent with Example 19. Isolated a brown solid in 55% yield. ¹H NMR (400 MHz, CDCl₃) δ 1.27-1.31 (m, 2H), 1.49-1.52 (m, 2H), 1.97-2.01 (m, 2H), 2.14-2.18 (m, 3H), 2.39-2.46 (m, 3H), 2.43 (s, 3H), 2.92-2.96 (m, 4H), 5.16-5.20 (m, 1H), 8.42 (s, 1H). MS: m/z 304.2 (M+H)⁺.

Example 44

Synthesis of trans-4-((6,7-dihydro-5H-cyclopenta[4,5]thieno[2,3-d]pyrimidin-4-yl)oxy)-N,N-dimethylcyclohexanamine (I-67)

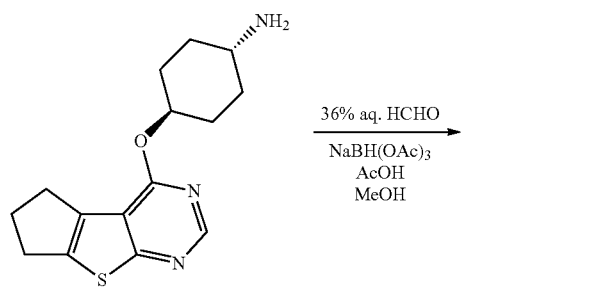

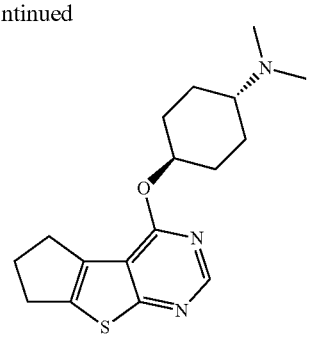

Compound I-67 was synthesized in a manner consistent with Example 28. Isolated a white solid in 55% yield. ¹H NMR (400 MHz, CDCl₃) δ 1.54-1.68 (m, 4H), 2.15-2.18 (m, 2H), 2.38-2.45 (m, 4H), 2.70 (s, 6H), 2.91-2.94 (m, 4H), 3.01-3.08 (m, 1H), 5.12-5.17 (m, 1H), 8.40 (s, 1H). MS: m/z 318.2 (M+H)⁺.

Example 45

Synthesis of 2-((trans-4-((6,7-dihydro-5H-cyclopenta[4,5]thieno[2,3-d]pyrimidin-4-yl)oxy)cyclohexyl)amino)acetic acid (I-68)

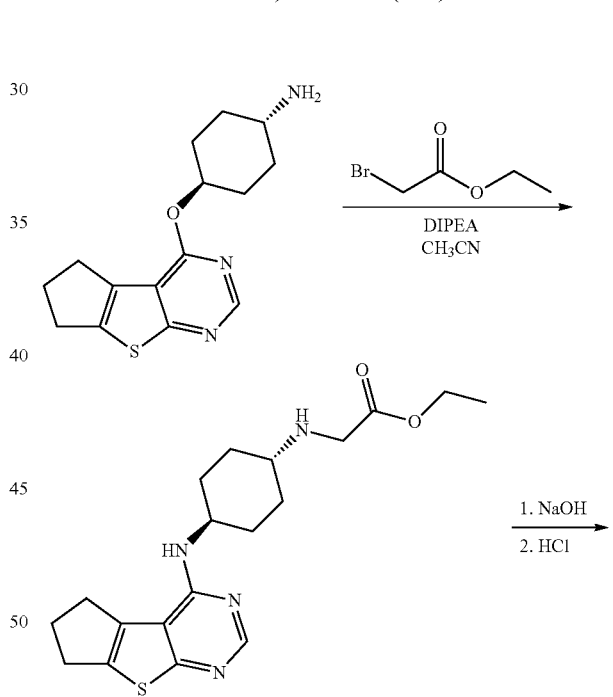

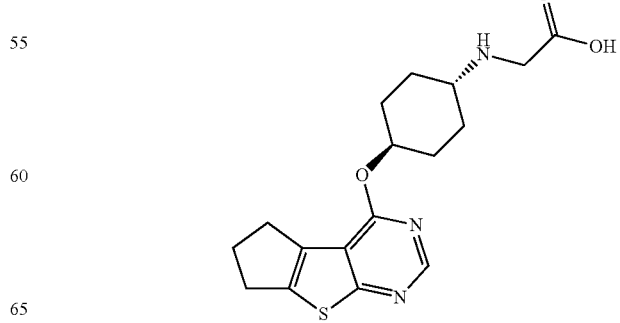

Compound I-68 was synthesized in a manner consistent with Example 43. Isolated the hydrochloride salt as a white solid in 80% yield. $^1$H NMR (400 MHz, DMSO-$d_6$) δ 1.46-1.63 (m, 4H), 2.14-2.24 (m, 4H), 2.38-2.46 (m, 2H), 2.92-3.00 (m, 4H), 3.14 (m, 1H), 3.81 (br s, 2H), 5.14 (s, 1H), 8.55 (s, 1H), 9.12 (br s, 1H). MS: m/z 370.2 (M+Na)$^+$.

Example 46

Synthesis of trans-N$^1$-(6,7-dihydro-5H-cyclopenta[4,5]thieno[2,3-d]pyrimidin-4-yl)-N$^4$-ethylcyclohexane-1,4-diamine (I-71)

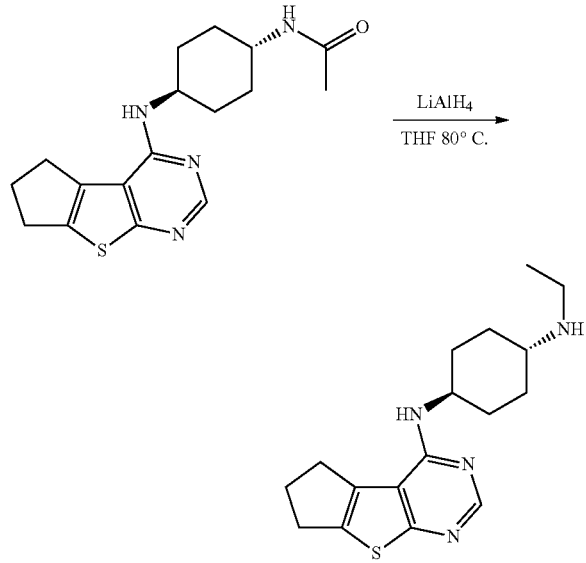

The mixture of LiAlH$_4$ (85 mg, 1.6 mmol, 8.0 eq) in THF (5 mL) was stirred at room temperature for 10 minutes, compound I-11 (70 mg, 0.21 mmol, 1.0 eq) in THF (5 mL) was added to the mixture. The mixture was stirred at 80° C. for 2 hours. The reaction was quenched with a mixture of THF/H$_2$O and filtered. The cake was washed with CH$_2$Cl$_2$. The filtrate was concentrated and the residue was purified by column chromatography (CH$_2$Cl$_2$/MeOH/Et$_3$N=20:1:0.5) on silica gel to give desired product compound I-71 as a white solid (41 mg, 61%). $^1$H NMR (400 MHz, CDCl$_3$) δ 1.06-1.23 (m, 5H), 1.28-1.42 (m, 2H), 1.63 (d, J=5.2 Hz, 1H), 2.01-2.05 (m, 2H), 2.16-2.19 (d, J=10.6 Hz, 2H), 2.45-2.51 (m, 2H), 2.68-2.72 (m, 2H), 2.91-2.96 (m, 4H), 3.63 (m, 1H), 4.06-4.08 (m, 1H), 4.78 (d, J=8.0 Hz, 1H), 8.31 (s, 1H). MS: m/z 317.2 (M+H)$^+$.

Example 47

Synthesis of trans-N$^1$-(6,7-dihydro-5H-cyclopenta[4,5]thieno[2,3-d]pyrimidin-4-yl)-N$^4$,N$^4$-diethylcyclohexane-1,4-diamine (I-72)

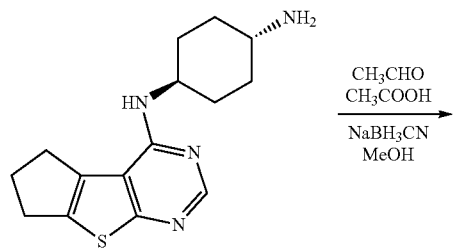

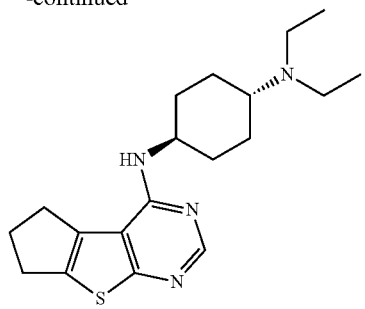

The mixture of compound I-10 (80 mg, 0.28 mmol, 1.0 eq), CH$_3$CHO (102 mg, 0.84 mmol, 3.0 eq), CH$_3$COOH (83 mg, 1.4 mmol, 5.0 eq), NaBH$_3$CN (236 mg, 1.1 mmol, 4 eq) in methanol (10 mL) was stirred at rt for 6.5 hours. The mixture was poured into sat.NaHCO$_3$, extracted with CH$_2$Cl$_2$. The organics layers were dried over Na$_2$SO$_4$, and concentrated, the residue was purified bycolumn chromatography on silica gel (CH$_2$Cl$_2$/MeOH/Et$_3$N=30:1:1) to give desired product compound I-72 as a white solid (57 mg, 60%). $^1$H NMR (400 MHz, CDCl$_3$) δ 0.92-1.33 (m, 8H), 1.48-1.54 (m, 5H), 1.90 (m, 1H), 2.18 (d, J=8.0 Hz, 2H), 2.43-2.45 (m, 2H), 2.47-2.63 (m, 3H), 2.93 (m, 4H), 4.02 (m, 1H), 4.77 (d, J=8.0 Hz, 1H), 8.30 (s, 1H). MS: m/z 345.1 (M+H)$^+$.

Example 48

Synthesis of trans-N$^1$-(6,7-dihydro-5H-cyclopenta[4,5]thieno[2,3-d]pyrimidin-4-yl)-N$^4$-ethyl-N$^4$-methyl-cyclohexane-1,4-diamine (I-73)

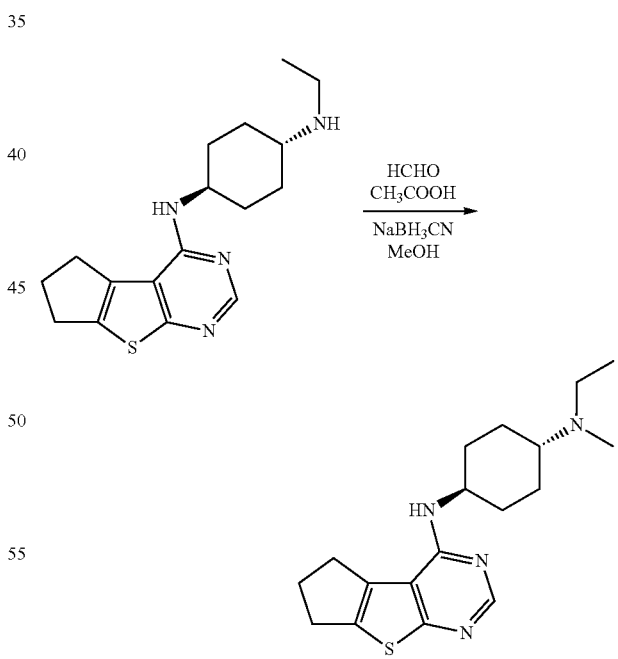

The mixture of compound I-71 (90 mg, 0.28 mmol, 1.0 eq), HCHO (17 mg, 36%, 0.56 mmol, 2 eq), CH$_3$COOH (34 mg, 0.56 mmol, 2.0 eq), NaBH$_3$CN (151 mg, 0.71 mmol, 2.5 eq) in methanol (10 mL) was stirred at rt for 6.5 hours. The mixture was poured into sat. aq. NaHCO$_3$, extracted with CH$_2$Cl$_2$, dried over Na$_2$SO$_4$, and concentrated, the residue was purified by column chromatography on silica gel ($CH_2Cl_2$/MeOH/$Et_3N$=30:1:1) to give desired product compound I-73 as white solid (48 mg, 51%). $^1H$ NMR (400 MHz, $CDCl_3$) δ 1.05 (t, J=8.0 Hz, 3H), 1.17-1.24 (m, 2H), 1.43-1.54 (m, 4H), 1.88 (d, J=9.6 Hz, 2H), 2.10-2.24 (m, 5H), 2.43-2.51 (m, 3H), 2.91-2.96 (m, 4H), 3.99-4.02 (m, 1H), 4.78 (d, J=8.0 Hz, 1H), 8.30 (s, 1H). MS: m/z 331.2 $(M+H)^+$.

Example 49

Synthesis of trans-$N^1$-(6,7-dihydro-5H-cyclopenta[4,5]thieno[2,3-d]pyrimidin-4-yl)-$N^4$,$N^4$-dimethylcyclohexane-1,4-diamine (I-12)

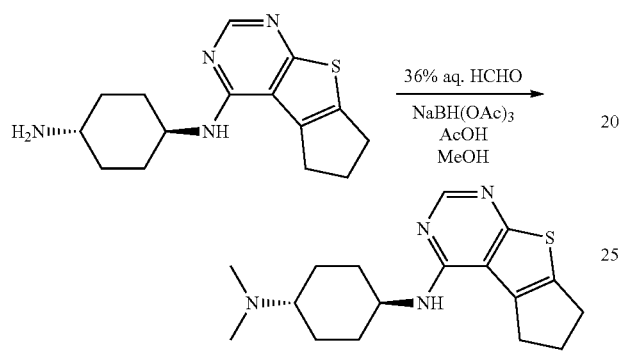

Compound I-12 was synthesized in a manner consistent with Example 25. Isolated a pale solid in 68% yield. $^1H$ NMR (400 MHz, DMSO-$d_6$) δ 1.27-1.30 (m, 2H), 1.44-1.48 (m, 2H), 1.81-1.84 (m, 2H), 1.97-1.99 (m, 2H), 2.17 (s, 6H), 2.40-2.43 (m, 2H), 2.92 (t, J=7.2 Hz, 2H), 3.07 (t, J=7.2 Hz, 2H), 4.00-4.02 (m, 2H), 5.99 (d, J=8.0 Hz, 1H), 8.25 (s, 1H). MS: m/z 317.2 $(M+H)^+$.

Example 50

Synthesis of Additional Compounds

Other compounds of the present invention were prepared using methods known in the art and those described above in Examples 1-49. Characterization data for such compounds is set forth below in Table 2 which provides LC/MS data. Compound numbers in Table 2 correspond to compound numbers recited in Table 1, supra.

TABLE 2

| Compound # | Structure | LC/MS |
|---|---|---|
| I-6 | | m/z 304.0 $(M + H)^+$ |
| I-8 | 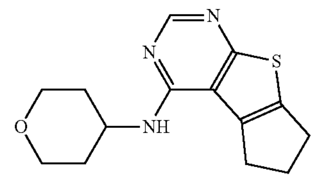 [SMILES: c1nc(NC2CCOCC2)c2c3c(sc2n1)CCC3] | m/z 276.1 $(M + H)^+$ |
| I-9 | 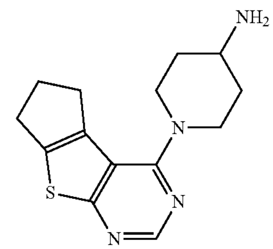 [SMILES: NC1CCN(c2ncnc3sc4c(c23)CCC4)CC1] | m/z 275.0 $(M + H)^+$ |
| I-13 | 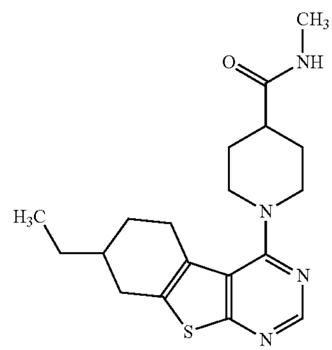 [SMILES: CCC1CCc2c(sc3ncnc(N4CCC(C(=O)NC)CC4)c23)C1] | m/z 359.1 $(M + H)^+$ |
| I-14 | 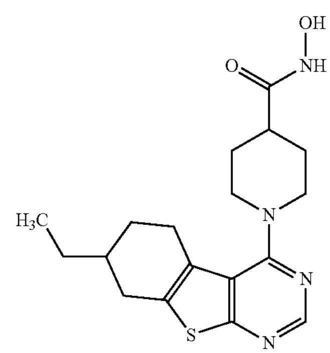 [SMILES: CCC1CCc2c(sc3ncnc(N4CCC(C(=O)NO)CC4)c23)C1] | m/z 361.0 $(M + H)^+$ |
| I-16 | 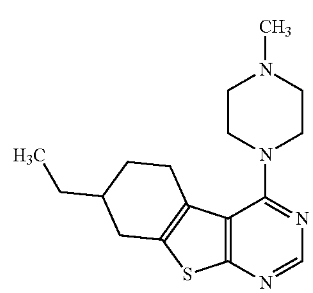 [SMILES: CCC1CCc2c(sc3ncnc(N4CCN(C)CC4)c23)C1] | m/z 317.1 $(M + H)^+$ |

TABLE 2-continued
Characterization Data
| Compound # | Structure | LC/MS |
|---|---|---|
| I-17 | 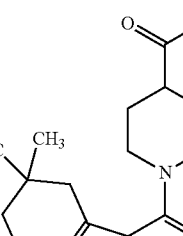 | m/z 345.2 (M + H)+ |
| I-18 | 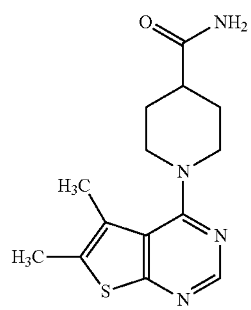 [SMILES: Cc1sc2ncnc(N3CCC(C(N)=O)CC3)c2c1C] | m/z 291.1 (M + H)+ |
| I-20 | 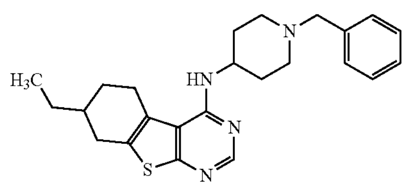 [SMILES: CCC1CCc2c(sc3ncnc(NC4CCN(Cc5ccccc5)CC4)c23)C1] | m/z 407.1 (M + H)+ |
| I-36 | 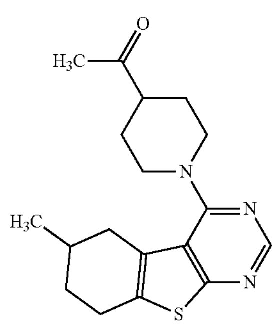 [SMILES: CC(=O)C1CCN(c2ncnc3sc4c(c23)CC(C)CC4)CC1] | m/z 331.1 (M + H)+ |
| I-45 | 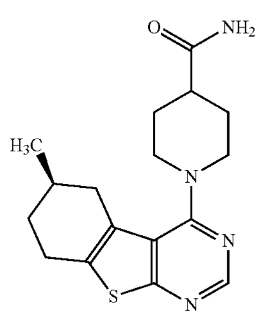 [SMILES: C[C@@H]1CCc2sc3ncnc(N4CCC(C(N)=O)CC4)c3c2C1] | m/z 331.0 (M + H)+ |
TABLE 2-continued
Characterization Data
| Compound # | Structure | LC/MS |
|---|---|---|
| I-46 | 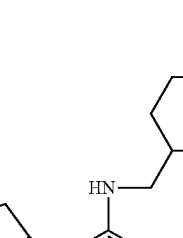 | m/z 345.2 (M + H)+ |
| I-59 | 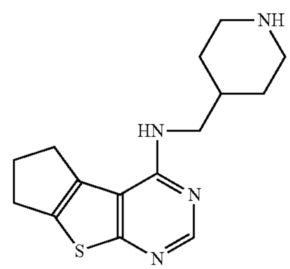 [SMILES: c1nc(NCC2CCNCC2)c2c3c(sc2n1)CCC3] | m/z 289.2 (M + H)+ |
| I-60 | 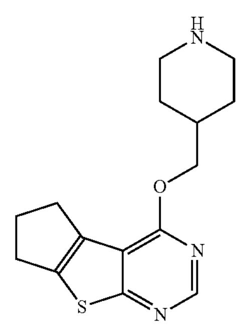 [SMILES: c1nc(OCC2CCNCC2)c2c3c(sc2n1)CCC3] | m/z 290.0 (M + H)+ |
| I-62 | 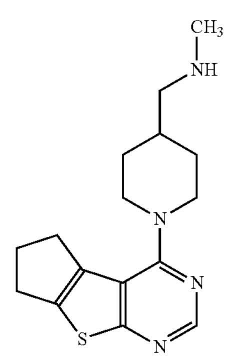 [SMILES: CNCC1CCN(c2ncnc3sc4c(c23)CCC4)CC1] | m/z 303.2 (M + H)+ |

TABLE 2-continued

Characterization Data

| Compound # | Structure | LC/MS |
|---|---|---|
| I-63 | (structure: 4-aminomethyl-piperidinyl cyclopenta-thieno-pyrimidine) | m/z 289.2 (M + H)+ |
| I-64 | (structure: 1-methylpiperidin-4-ylmethoxy cyclopenta-thieno-pyrimidine) | m/z 304.0 (M + H)+ |
| I-69 | (structure: N,N-dimethylaminomethyl-piperidinyl cyclopenta-thieno-pyrimidine) | m/z 317.2 (M + H)+ |

Example 51

Synthesis of 1-N-(2-methoxyethyl)-1-N-methyl-4-N-[7-thia-9,11-diazatricyclo[6.4.0.0^[2,6]]dodeca-1(8),2(6),9,11-tetraen-12-yl]cyclohexane-1,4-diamine (I-169)

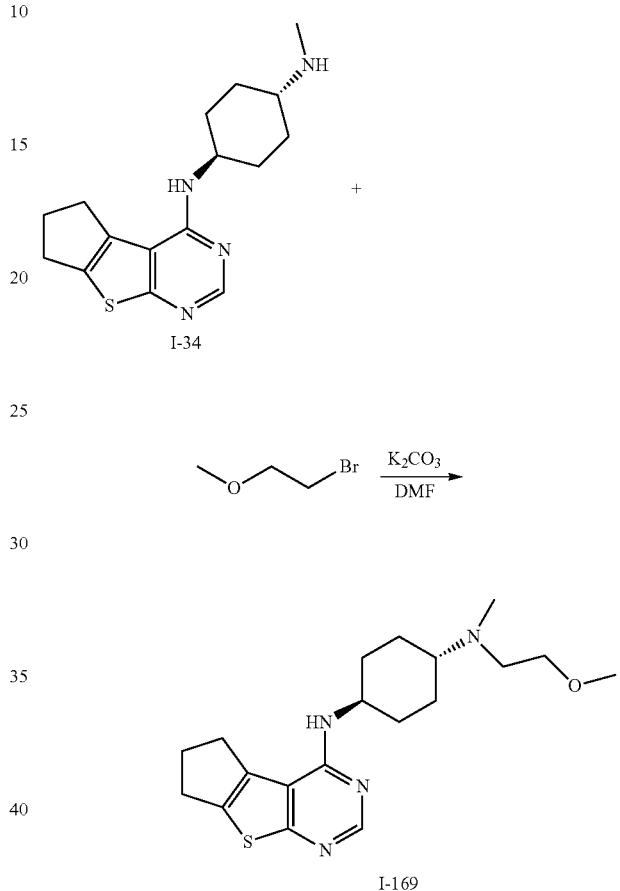

A mixture of I-34 (500 mg, 1.65 mmol, 1.00 equiv), 1-bromo-2-methoxyethane (276 mg, 1.99 mmol, 1.20 equiv) and potassium carbonate (275 mg, 1.99 mmol, 1.20 equiv) in N,N-dimethylformamide (10 g, 136.82 mmol, 82.76 equiv) was stirred for 48 h at room temperature and diluted with 200 mL of water. The resulting solution was extracted with 3×200 mL of ethyl acetate and the organic layers combined. The resulting mixture was washed with 3×300 mL of brine. The mixture was dried over anhydrous sodium sulfate and concentrated under vacuum. The residue was purified by preparative HPLC (2#-Gilson Gx 281(HPLC-09)) under the following conditions: column: Atlantis T3, 5 um, 19*150 mm; mobile phase: water (with 0.05% trifluoroacetic acid) and acetonitrile (10.0% acetonitrile up to 20.0% in 1 min, up to 30.0% in 5 min, up to 43.0% in 7 min, hold 100.0% in 2 min); detector: UV 220 nm. Purification afforded 8.5 mg (1%) of Compound I-169 as an off-white solid. $^1$H NMR (400 MHz, CDCl$_3$, ppm) δ 8.38-8.36 (1H, d), 4.84-4.82 (1H, d), 4.16-4.11 (1H, m), 3.86-3.82 (2H, t), 3.37 (3H, s), 3.30-3.23 (1H, m), 3.15-3.12 (2H, t), 3.02-2.98 (4H, t), 2.69 (3H, s), 2.59-2.50 (2H, m), 2.37-2.25 (4H, m), 1.72-1.60 (2H, q), 1.39 (2H, q). MS: m/z 361 (M+H)+.

Example 52

Synthesis of 1-N-methyl-1-N-(2-phenylethyl)-4-N-[7-thia-9,11-diazatricyclo[6.4.0.0^[2,6]]dodeca-1(8),2(6),9,11-tetraen-12-yl]cyclohexane-1,4-diamine (I-168)

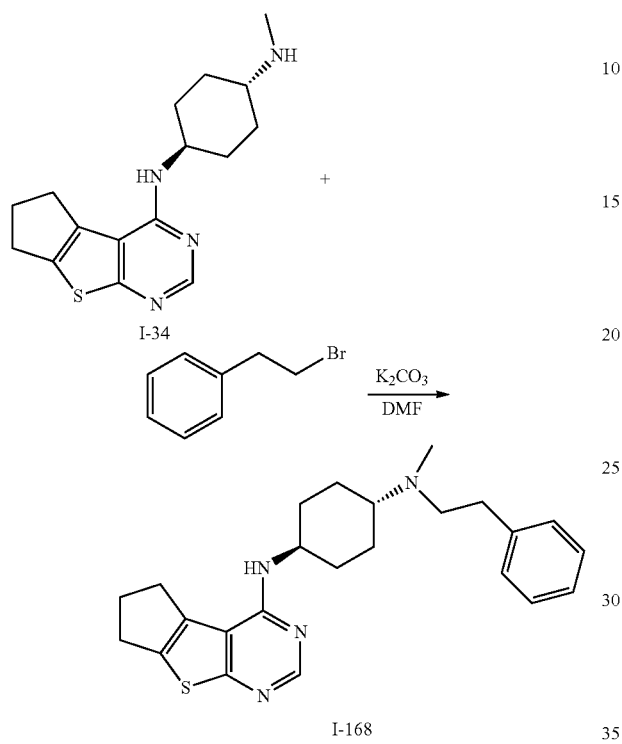

Compound I-168 was synthesized in a manner consistent with Example 51 above from Compound I-34 and (2-bromoethyl)benzene. Isolated a white solid in 12% yield. $^1$H NMR (400 MHz, CDCl$_3$, ppm) δ 8.39 (1H, s), 7.35-7.29 (2H, m), 7.25-7.23 (3H, m), 4.88-4.85 (1H, d), 4.13-4.07 (1H, m), 3.03-3.02 (4H, m), 2.80-2.78 (4H, m), 2.61-2.51 (3H, m), 2.42 (3H, s), 2.30-2.06 (2H, m), 1.97-1.93 (2H, m), 1.62-1.50 (2H, q), 1.32-1.21 (2H, q). MS: m/z 407 (M+H)$^+$.

Example 53

Synthesis of 1-N-[(2-chloro-6-fluorophenyl)methyl]-1-N-methyl-4-N-[7-thia-9,11-diazatricyclo[6.4.0.0^[2,6]]dodeca-1(8),2(6),9,11-tetraen-12-yl]cyclohexane-1,4-diamine (I-99)

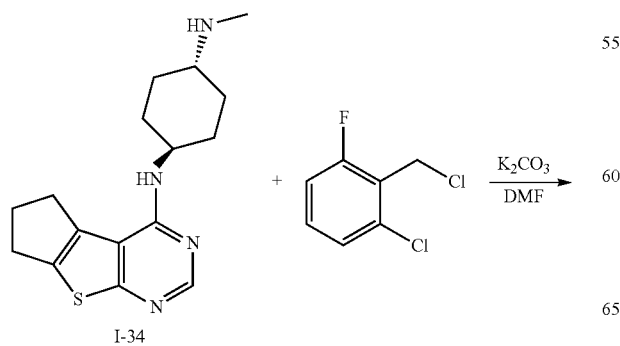

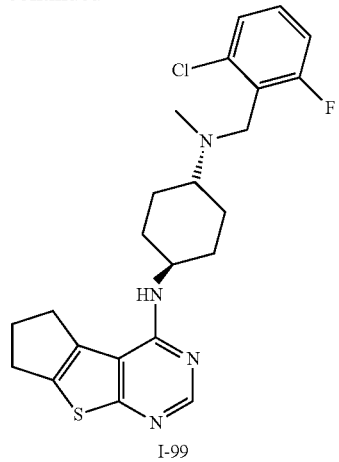

Compound I-99 was synthesized in a manner consistent with Example 51 above from Compound I-34 and 1-chloro-2-(chloromethyl)-3-fluorobenzene. Isolated a white solid in 13% yield. $^1$H NMR (400 MHz, CDCl$_3$, ppm) δ 8.39 (1H, s), 7.28-7.23 (2H, m), 7.02-7.01 (1H, m), 4.89-4.86 (1H, d), 4.17-4.12 (1H, m), 3.80 (2H, s), 3.06-2.99 (4H, m), 2.69 (1H, br), 2.61-2.51 (2H, m), 2.34-2.31 (5H, m). 2.08 (2H, m), 1.73-1.65 (2H, q), 1.36-1.25 (2H, q). MS: m/z 445 (M+H)$^+$.

Example 54

Synthesis of 1-N-methyl-1-N-(pyridin-3-ylmethyl)-4-N-[7-thia-9,11-diazatricyclo[6.4.0.0^[2,6]]dodeca-1(12),2(6),8,10-tetraen-12-yl]cyclohexane-1,4-diamine (I-163)

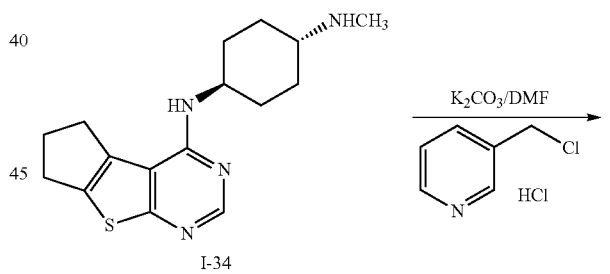

Compound I-163 was synthesized in a manner consistent with Example 51 above from Compound I-34 and 3-(chloromethyl)pyridine hydrochloride. Isolated a yellow solid in 5% yield. $^1$H NMR (400 MHz, CDCl$_3$, ppm) δ 8.54-8.56 (2H, d), 8.39 (1H, s), 7.72 (1H, s), 7.28 (1H, s), 4.85-4.87 (1H, d), 4.11-4.16 (1H, m), 3.65-3.74 (1H, m), 3.01-3.03 (4H, m), 2.52-2.59 (3H, m), 2.28-2.36 (5H, m), 1.99-2.12 (2H, m), 1.47-1.65 (2H, m), 1.22-1.30 (2H, q). MS: m/z 394 (M+H)+.

Example 55

Synthesis of [3-([methyl[4-([7-thia-9,11-diazatricyclo[6.4.0.0^[2,6]]dodeca-1(8),2(6),9,11-tetraen-12-yl]amino)cyclohexyl]amino]methyl)phenyl]methanol (I-165)

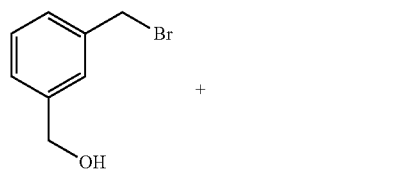

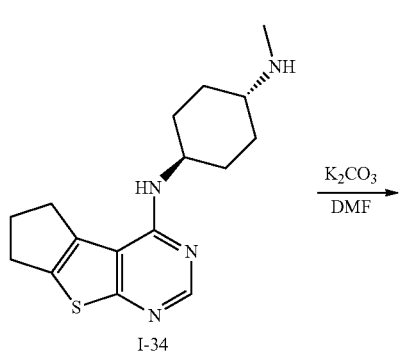

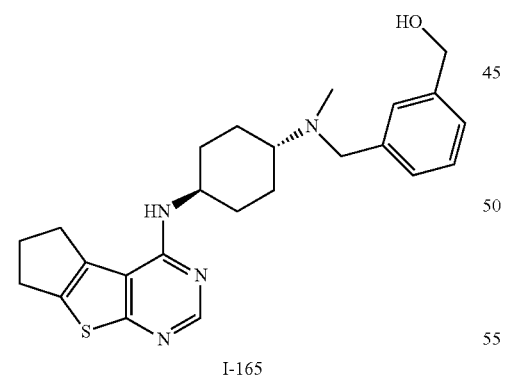

Compound I-165 was synthesized in a manner consistent with Example 51 above from Compound I-34 and [3-(bromomethyl)phenyl]methanol. Isolated a white solid in 4% yield. $^1$H NMR (400 MHz, CDCl$_3$, ppm) δ 8.37 (1H, s), 7.40 (1H, s), 7.35-7.28 (3H, m), 4.85-4.83 (1H, d), 4.71-4.70 (2H, d), 4.11-4.06 (1H, m), 3.65 (2H, s), 2.99 (4H, m), 2.61-2.50 (3H, m), 2.27 (5H, m), 2.03-2.00 (2H, m), 1.80 (1H, m), 1.70-1.57 (3H, q), 1.28-1.20 (2H, q) MS: m/z 423 (M+H)+.

Example 56

Synthesis of 3-([methyl[4-([7-thia-9,11-diazatricyclo[6.4.0.0^[2,6]]dodeca-1(8),2(6),9,11-tetraen-12-yl]amino)cyclohexyl]amino]methyl)benzoic acid (I-167)

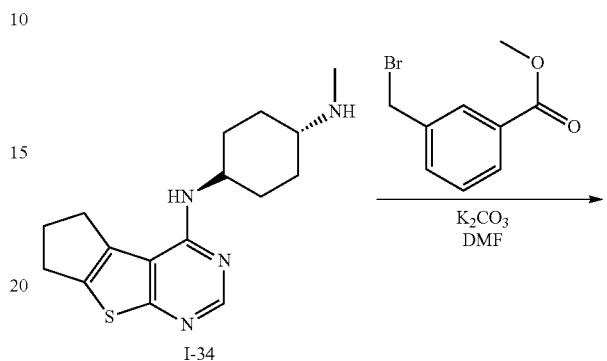

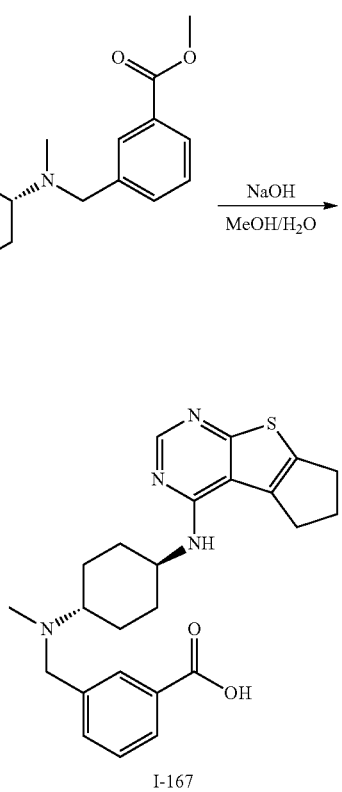

Synthesis of methyl 3-([methyl[4-([7-thia-9,11-diazatricyclo[6.4.0.0^[2,6]]dodeca-1(8),2(6),9,11-tetraen-12-yl]amino)cyclohexyl]amino]methyl)benzoate Methyl 3-([methyl[4-([7-thia-9,11-diazatricyclo[6.4.0.0^[2,6]]dodeca-1(8),2(6),9,11-tetraen-12-yl]amino)cyclohexyl]amino]methyl)benzoate was synthesized in a manner consistent with Example 51 above from Compound I-34 and methyl 3-(bromomethyl)benzoate. Isolated a white solid in 67% yield. MS: m/z 451 (M+H)+.

135

Synthesis of Compound I-167

To a 100-mL round-bottom flask was added methyl 3-([methyl[4-([7-thia-9,11-diazatricyclo[6.4.0.0^[2,6]]dodeca-1(8),2(6),9,11-tetraen-12-yl]amino)cyclohexyl]amino]methyl)benzoate (1.5 g, 3.33 mmol, 1.00 equiv), sodium hydroxide (267 mg, 6.67 mmol, 2.00 equiv), water (2 mL) and methanol (30 mL). The resulting solution was stirred for 2 h at 50° C. in an oil bath. The resulting mixture was concentrated under vacuum. The pH value of the solution was adjusted to 2 with hydrogen chloride (6 mol/L). The resulting mixture was concentrated under vacuum. The crude product was purified by preparative HPLC (2#-Waters 2767-2 (HPLC-08)) under the following conditions: column: Xbridge Prep Phenyl, 5 um, 19*150 mm; mobile phase: water (with 50 mmol $NH_4HCO_3$) and $CH_3CN$ (10.0% CH3CN up to 33.0% in 2 min, up to 53.0% in 8 min, up to 100.0% in 1 min, down to 10.0% in 1 min); detector: UV 220 nm. This procedure afforded 50.8 mg (3%) of Compound I-167 as a white solid. 1HNMR (300 MHz, $CD_3OD$) δ 8.27 (1H, s), 8.05 (2H, m), 7.57-7.52 (2H, m), 4.32 (2H, s), 4.22 (1H, m), 3.34 (1H, m), 3.10 (2H, m), 3.03 (1H, m), 2.74 (3H, s), 2.58 (2H, m), 2.32-2.22 (4H, m). 1.88-1.84 (2H, m), 1.60-1.56 (2H, m). MS: m/z 437 (M+H)+.

Example 57

Synthesis of 4-([methyl[4-([7-thia-9,11-diazatricyclo[6.4.0.0^[2,6]]dodeca-1(8),2(6),9,11-tetraen-12-yl]amino)cyclohexyl]amino]methyl)benzamide (I-164)

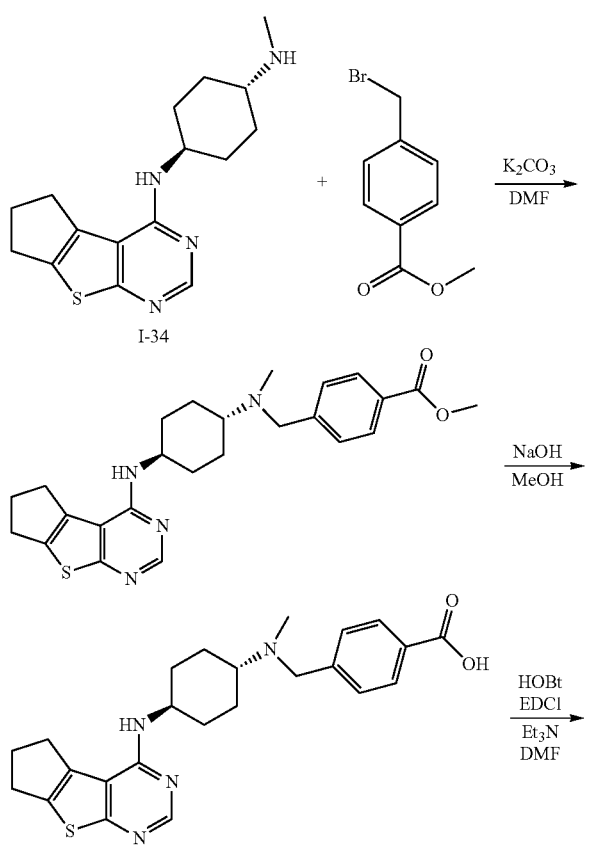

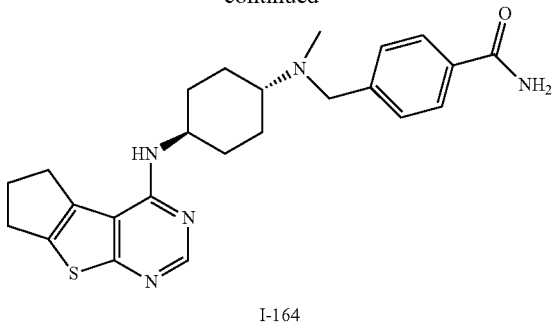

I-164

Synthesis of methyl 4-([methyl[4-([7-thia-9,11-diazatricyclo[6.4.0.0^[2,6]]dodeca-1(8),2(6),9,11-tetraen-12-yl]amino)cyclohexyl]amino]methyl)benzoate Methyl 4-([methyl[4-([7-thia-9,11-diazatricyclo[6.4.0.0^[2,6]]dodeca-1(8),2(6),9,11-tetraen-12-yl]amino)cyclohexyl]amino]methyl)benzoate was synthesized in a manner consistent with Example 51 above from Compound I-34 and methyl 4-(bromomethyl)benzoate. Isolated a yellow solid in 57% yield. MS: m/z 451 (M+H)+.

Synthesis of 4-([methyl[4-([7-thia-9,11-diazatricyclo[6.4.0.0^[2,6]]dodeca-1(8),2(6),9,11-tetraen-12-yl]amino)cyclohexyl]amino]methyl)benzoic acid A mixture of methyl 4-([methyl[4-([7-thia-9,11-diazatricyclo[6.4.0.0^[2,6]]dodeca-1(8),2(6),9,11-tetraen-12-yl]amino)cyclohexyl]amino]methyl)benzoate (500 mg, 1.11 mmol, 1.00 equiv), methanol (20 mL), sodium hydroxide (89 mg, 2.23 mmol, 2.00 equiv) and water (2 mL) was stirred for 2 h at 50° C. in an oil bath. The resulting mixture was concentrated under vacuum. The pH value of the solution was adjusted to 1 with hydrogen chloride (12 mol/L). The resulting mixture was concentrated under vacuum to yield 1 g of crude 4-([methyl[4-([7-thia-9,11-diazatricyclo[6.4.0.0^[2,6]]dodeca-1(8),2(6),9,11-tetraen-12-yl]amino)cyclohexyl]amino]methyl)benzoic acid as a yellow solid. The crude product was used in the next step without further purification. MS: m/z 437 (M+H)+.

Synthesis of Compound I-164

A mixture of 4-([methyl[4-([7-thia-9,11-diazatricyclo[6.4.0.0^[2,6]]dodeca-1(8),2(6),9,11-tetraen-12-yl]amino)cyclohexyl]amino]methyl)benzoic acid (1.0 g, 2.29 mmol, 1.00 equiv), ammonium chloride (146 mg, 2.73 mmol, 1.20 equiv), EDCI (875 mg, 4.56 mmol, 2.00 equiv), 1H-1,2,3-benzotriazol-1-ol (371 mg, 2.75 mmol, 1.20 equiv) and triethylamine (694 mg, 6.86 mmol, 3.00 equiv) in N,N-dimethylformamide (20 mL) was stirred overnight at room temperature. The resulting solution was diluted with 150 mL of water. The solids were collected by filtration and purified by preparative HPLC (2#-Waters 2767-2(HPLC-08)) under the following conditions: column: Xbridge Prep Phenyl, 5 um, 19*150 mm; mobile phase: water (with 50 mmol ammonium bicarbonate) and acetonitrile (10.0% acetonitrile up to 33.0% in 2 min, up to 53.0% in 8 min, up to 100.0% in 1 min, down to 10.0% in 1 min); detector: UV 220 nm. This procedure afforded 97.4 mg (10%) of Compound I-164 as a white solid. $^1$H NMR (400 MHz, $CDCl_3$) δ 8.37 (1H, s), 7.78-7.76

(2H, d), 7.52-7.44 (2H, t), 6.07 (1H, br), 5.59 (1H, br), 4.85-4.83 (1H, d), 4.11-4.06 (1H, m), 3.66 (2H, s), 3.0-2.99 (4H, m). 2.57-2.49 (3H, m), 2.25-2.16 (5H, m), 1.98-1.95 (2H, m), 1.64-1.56 (2H, m), 1.27-1.21 (2H, m). MS: m/z 436 (M+H)$^+$.

Example 58

Synthesis of 4-([methyl[4-([7-thia-9,11-diazatricyclo[6.4.0.0ˆ[2,6]]dodeca-1(8),2(6),9,11-tetraen-12-yl]amino)cyclohexyl]amino]methyl)benzamide (I-105)

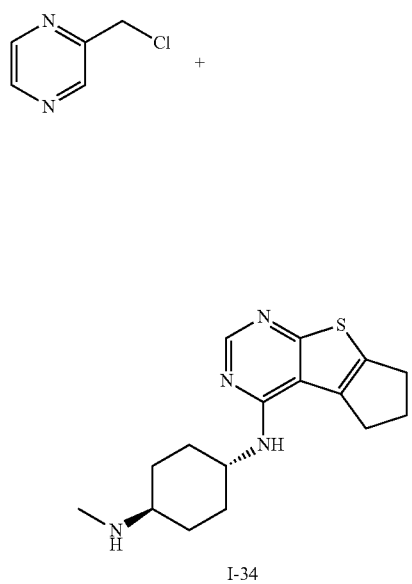

Compound I-105 was prepared in a manner consistent with Example 51 above from I-34 and 2-(chloromethyl)pyrazine. Isolated a light yellow solid (62%). $^1$H NMR (300 MHz, CD$_3$OD) δ 8.37 (d, 1H), 8.58 (t, 1H), 8.51 (d, 1H), 8.23 (s, 1H), 4.15-4.05 (m, 1H), 3.86 (s, 2H), 3.34-2.97 (m, 4H), 2.65-2.50 (m, 3H), 2.33 (s, 3H), 2.19 (d, 2H), 2.03 (d, 2H), 1.67-1.59 (m, 4H). MS: m/z 395 (M+H)$^+$.

Example 59

Synthesis of 1-N-methyl-1-N-[2-(pyridin-2-yl)ethyl]-4-N-[7-thia-9,11-diazatricyclo[6.4.0.0ˆ[2,6]]dodeca-1(8),2(6),9,11-tetraen-12-yl]cyclohexane-1,4-diamine (I-106)

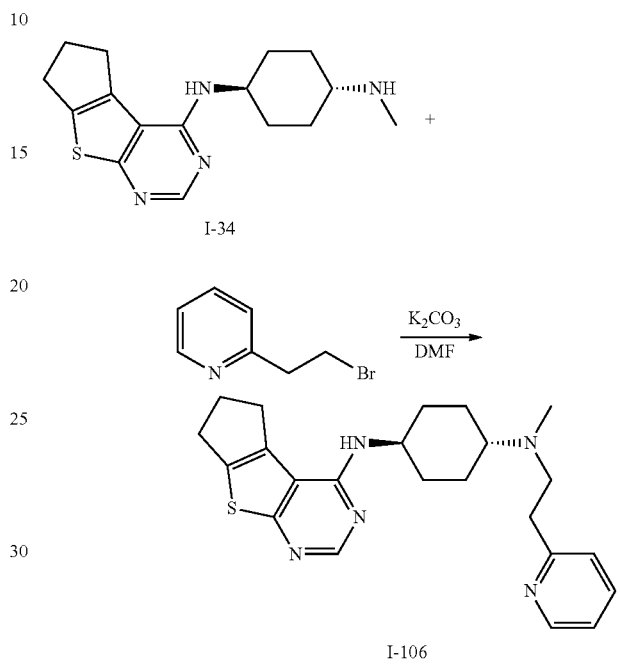

Compound I-106 was prepared from Compound I-34 and 2-(2-bromoethyl)pyridine in a manner consistent with Example 51 above. Isolated a light yellow oil (9%). $^1$H NMR (300 MHz, CD$_3$OD) δ 8.47-8.45 (1H, m), 8.21 (1H, s), 7.80-7.74 (1H, m), 7.38-7.35 (1H, m), 7.29-7.25 (1H, m), 4.07-4.04 (1H, m), 3.07-2.85 (8H, m), 2.61-2.44 (3H, m), 2.39 (3H, s), 2.22-2.14 (2H, m), 1.96-1.94 (2H, m), 1.55-1.45 (4H, m). MS: m/z 408 (M+H)$^+$.

Example 60

Synthesis of 3-[methyl[4-([7-thia-9,11-diazatricyclo[6.4.0.0ˆ[2,6]]dodeca-1(8),2(6),9,11-tetraen-12-yl]amino)cyclohexyl]amino]propanoic acid (I-108)

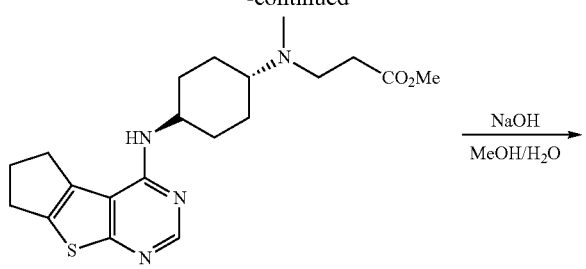

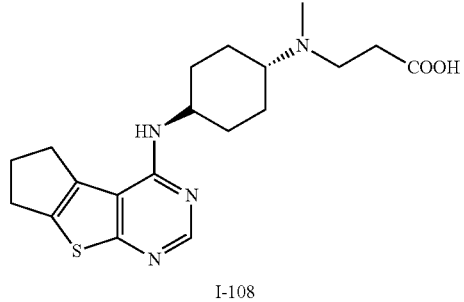

I-108

Synthesis of methyl 3-[methyl[4-([7-thia-9,11-diazatricyclo[6.4.0.0^[2,6]]dodeca-1(8),2(6),9,11-tetraen-12-yl]amino)cyclohexyl]amino]propanoate To a 50-mL round-bottom flask was added Compound I-34 (400 mg, 1.32 mmol, 1.00 equiv) and methyl prop-2-enoate (227 mg, 2.64 mmol, 2.00 equiv) in methanol (10 mL). The resulting solution was heated to reflux overnight in an oil bath. The resulting mixture was concentrated under vacuum to yield 500 mg (crude) of methyl 3-[methyl[4-([7-thia-9,11-diazatricyclo[6.4.0.0^[2,6]]dodeca-1(8),2(6),9,11-tetraen-12-yl]amino)cyclohexyl]amino]propanoate as a yellow oil. MS: m/z 389 (M+H)$^+$.

Synthesis of Compound I-108

A mixture of methyl 3-[methyl[4-([7-thia-9,11-diazatricyclo[6.4.0.0^[2,6]]dodeca-1(8),2(6),9,11-tetraen-12-yl]amino)cyclohexyl]amino]propanoate (500 mg, 1.29 mmol, 1.00 equiv), sodium hydroxide (103.2 mg, 2.58 mmol, 2.00 equiv), water (2 mL) and methanol (20 mL) was stirred overnight at 50° C. in an oil bath. The resulting mixture was concentrated under vacuum. The pH value of the residue was adjusted to 1-2 with hydrogen chloride (6 mol/L). The resulting mixture was concentrated under vacuum. The residue was purified by preparative HPLC (2#-Waters 2767-2(HPLC-08)) under the following conditions: column: Xbridge Prep Phenyl, 5 um, 19*150 mm; mobile phase: water (with 50 mmol ammonium bicarbonate) and acetonitrile (10.0% acetonitrile up to 33.0% in 2 min, up to 53.0% in 8 min, up to 100.0% in 1 min, down to 10.0% in 1 min); detector: UV 220 nm. This procedure afforded 33.2 mg (7%) of Compound I-108 as a gray solid. $^1$H NMR (400 MHz, CDCl$_3$) δ 8.36 (1H, s), 4.85-4.82 (1H, d), 4.17-4.07 (1H, m), 3.03-2.99 (4H, m), 2.93-2.89 (2H, t), 2.84-2.76 (1H, t), 2.59-2.50 (4H, m), 2.45 (3H, s), 2.36-2.32 (2H, d), 2.23-2.22 (2H, d), 2.01-1.97 (2H, q). 1.71-1.60 (2H, q). MS: m/z 375 (M+H)$^+$.

Example 61

Synthesis of 3-[methyl[4-([7-thia-9,11-diazatricyclo[6.4.0.0^[2,6]]dodeca-1(8),2(6),9,11-tetraen-12-yl]amino)cyclohexyl]amino]propanamide (I-109)

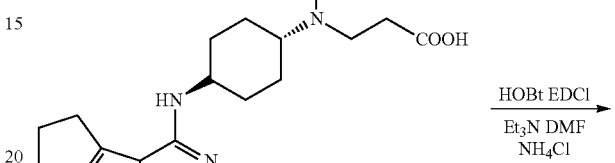

I-108

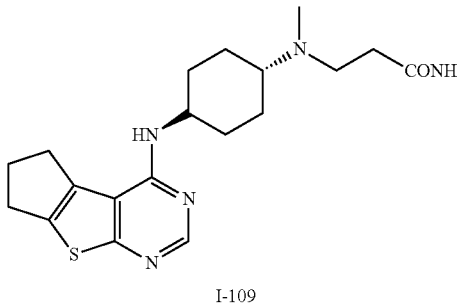

I-109

Synthesis of Compound I-YY

A mixture of Compound I-108 (280 mg, 0.75 mmol, 1.00 equiv), ammonium chloride (47.7 mg, 0.89 mmol, 1.20 equiv), HOBt (121.5 mg, 0.90 mmol, 1.20 equiv), EDCI (286.5 mg, 1.49 mmol, 2.00 equiv) and triethylamine (227.2 mg, 2.25 mmol, 3.00 equiv) in N,N-dimethylformamide (20 mL) was stirred overnight at room temperature. The resulting solution was diluted with 100 mL of water. The resulting solution was extracted with 3×200 mL of dichloromethane and the organic layers combined and dried over anhydrous sodium sulfate and concentrated under vacuum. The residue was purified by preparative HPLC (2#-Waters 2767-2 (HPLC-08)) under the following conditions: column: Xbridge Prep Phenyl, 5 um, 19*150 mm; mobile phase: water (with 50 mmol ammonium bicarbonate) and acetonitrile (10.0% acetonitrile up to 33.0% in 2 min, up to 53.0% in 8 min, up to 100.0% in 1 min, down to 10.0% in 1 min); detector: UV 220 nm. This procedure afforded 32.7 mg (11%) of Compound I-109 as a white solid. $^1$H NMR (300 MHz, CDCl$_3$) δ 8.36 (1H, s), 8.16-8.11 (1H, d), 5.28 (1H, s), 4.85-4.82 (1H, d), 4.14-4.06 (1H, m), 3.01-3.00 (4H, m), 2.79-2.77

(2H, m), 2.64-2.49 (3H, m), 2.45-2.43 (2H, m), 2.31-2.26 (5H, m), 1.91-1.87 (2H, m). 1.65-1.53 (2H, q), 1.35-1.19 (2H, q). MS: m/z 374 (M+H)+.

Example 62

Synthesis of 1-N-[2-(2-chlorophenyl)ethyl]-1-N-methyl-4-N-[7-thia-9,11-diazatricyclo[6.4.0.0^[2,6]]dodeca-1(12),2(6),8,10-tetraen-12-yl]cyclohexane-1,4-diamine (I-112)

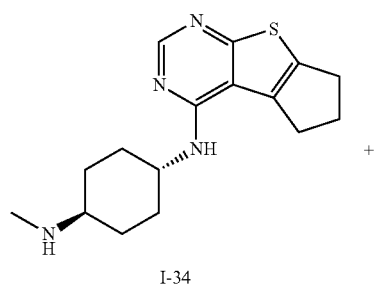

I-34

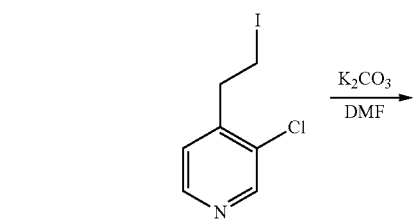

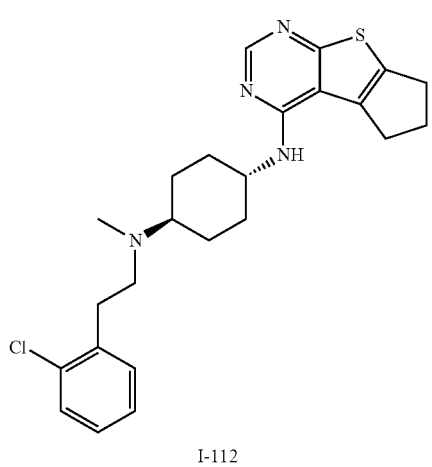

I-112

Compound I-112 was synthesized from Compound I-34 and 1-chloro-2-(2-iodoethyl)benzene in a manner consistent with Example 51 above. Isolated as a colorless oil (7%). $^1$H NMR (300 MHz, CDOD) δ 8.38 (s, 1H), 7.49-7.45 (m, 2H), 7.36-7.33 (m, 2H), 4.25 (s, 1H), 3.56-3.44 (m, 3H), 3.33-3.32 (m, 2H), 3.14-3.11 (m, 2H), 3.06-3.04 (m, 2H), 3.00 (s, 3H), 2.63-2.54 (m, 2H), 2.30 (d, 2H), 2.21 (d, 2H), 1.95-1.59 (m, 4H). MS: m/z 441 (M+H)+.

Example 63

Synthesis of 2-[methyl[4-([7-thia-9,11-diazatricyclo[6.4.0.0^[2,6]]dodeca-1(8),2(6),9,11-tetraen-12-yl]amino)cyclohexyl]amino]-N-phenylacetamide (I-114)

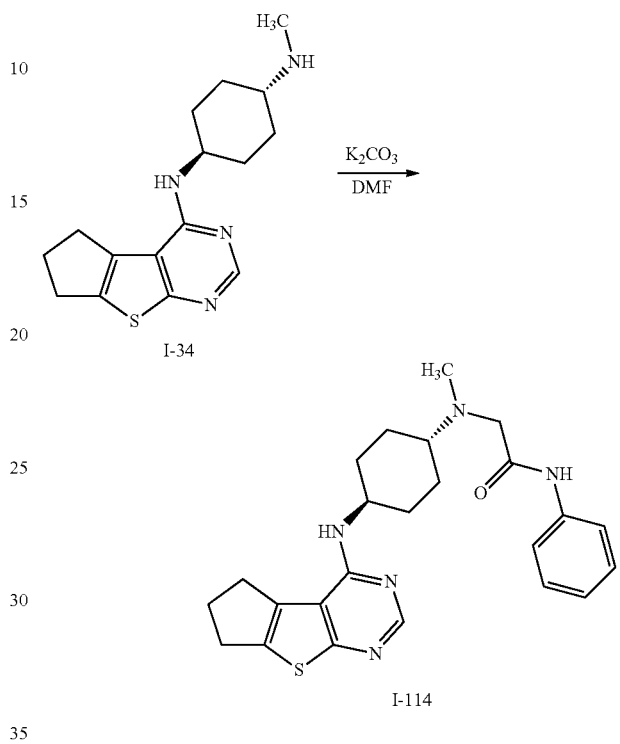

Compound I-114 was synthesized from Compound I-34 and 2-chloro-N-phenylacetamide in a manner consistent with Example 51 above. Isolated a white solid (12%). $^1$H NMR (300 MHz, CDCl$_3$) δ 9.03 (1H, s), 8.37 (1H, s), 7.57-7.60 (2H, d), 7.31-7.36 (2H, t), 7.08-7.13 (1H, t), 4.82-4.84 (1H, d), 4.07-4.12 (1H, m), 3.20 (2H, m), 2.99 (4H, m), 2.49-2.58 (3H, m), 2.41 (3H, s), 2.26-2.30 (2H, d), 1.93-2.00 (2H, d), 1.51-1.62 (2H, m), 1.21-1.32 (2H, q). MS: m/z 435 (M+H)+.

Example 64

Synthesis of 1-N-(furan-2-ylmethyl)-1-N-methyl-4-N-[7-thia-9,11-diazatricyclo[6.4.0.0^[2,6]]dodeca-1(8),2(6),9,11-tetraen-12-yl]cyclohexane-1,4-diamine (I-101)

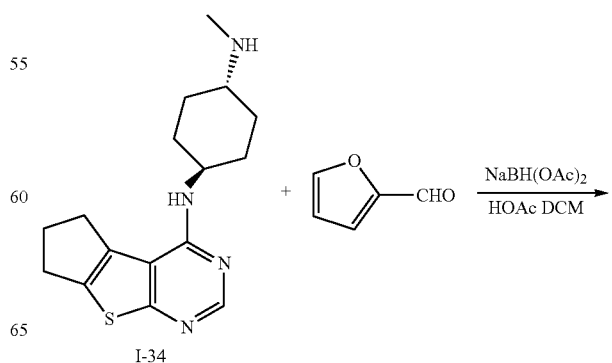

-continued

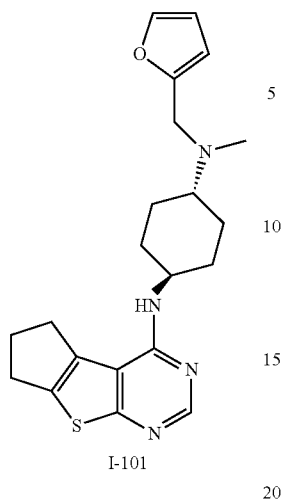

I-101

To a 50-mL round-bottom flask was added I-34 (350 mg, 1.16 mmol, 1.00 equiv), furan-2-carbaldehyde (134 mg, 1.39 mmol, 1.20 equiv), NaBH(OAc)$_3$ (1.3 g, 6.13 mmol, 5.00 equiv), acetic acid (2 mL), 4 A molecular sieves (1 g) and dichloromethane (20 mL). The resulting solution was stirred for 48 h at 45° C. in an oil bath. The solids were filtered off. The filtrate was concentrated under vacuum. The residue was purified by preparative HPLC (2#-Waters 2767-2(HPLC-08)) under the following conditions: column: Xbridge Prep Phenyl, 5 um, 19*150 mm; mobile phase: water (with 50 mmol NH$_4$HCO$_3$) and CH$_3$CN (10.0% CH$_3$CN up to 33.0% in 2 min, up to 53.0% in 8 min, up to 100.0% in 1 min, down to 10.0% in 1 min); detector: UV 220 nm. This procedure afforded 51.1 mg (12%) of Compound I-101 as a white solid. $^1$H NMR (300 MHz, CDCl$_3$) δ 8.39 (1H, s), 7.62 (1H, s), 6.36-6.35 (1H, m), 6.28 (1H, s), 4.86-4.84 (1H, d), 4.18-4.05 (1H, m), 3.74 (2H, s), 3.03-2.99 (4H, m), 2.60-2.50 (3H, m), 2.35-2.27 (5H, m), 2.05-2.01 (2H, m), 1.65-1.47 (2H, m), 1.32-1.27 (2H, m). MS: m/z 383 (M+H)$^+$.

Example 65

Synthesis of 1-N-[(3-chloropyridin-4-yl)methyl]-1-N-methyl-4-N-[7-thia-9,11-diazatricyclo[6.4.0.0^[2,6]]dodeca-1(8),2(6),9,11-tetraen-12-yl]cyclohexane-1,4-diamine (I-100)

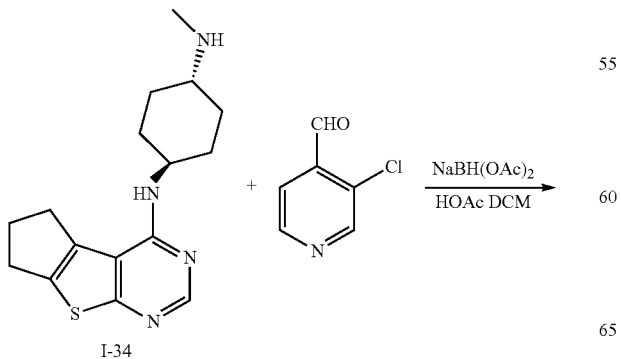

-continued

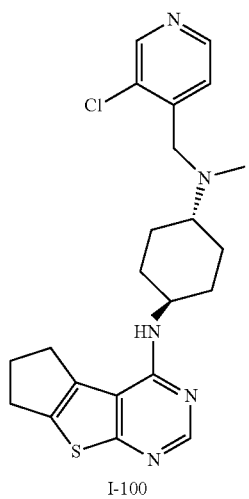

I-100

Compound I-100 was synthesized from Compound I-34 and 3-chloropyridine-4-carbaldehyde in a manner consistent with Example 64 above. Isolated a white solid (22%). $^1$H NMR (400 MHz, CDCl$_3$) δ 8.53 (1H, s), 8.47-8.45 (1H, d), 8.38 (1H, s), 7.54-7.52 (1H, d), 4.87-4.85 (1H, d), 4.18-4.05 (1H, m), 3.72 (2H, s), 3.02-2.98 (4H, m), 2.59-2.50 (3H, m), 2.30-2.27 (5H, m), 2.00-1.96 (2H, d). 1.69-1.55 (2H, q), 1.35-1.20 (2H, q). MS: m/z 428 (M+H)$^+$.

Example 66

Synthesis of 1-N-[(3-fluoropyridin-2-yl)methyl]-1-N-methyl-4-N-[7-thia-9,11-diazatricyclo[6.4.0.0^[2,6]]dodeca-1(12),2(6),8,10-tetraen-12-yl]cyclohexane-1,4-diamine (I-104)

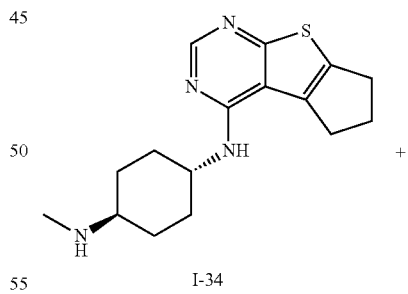

I-34

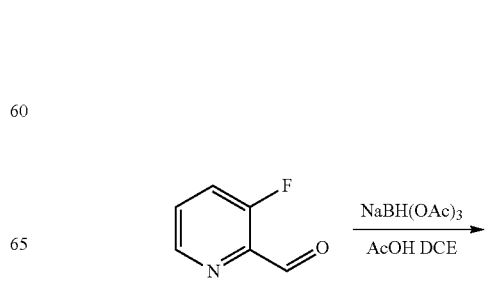

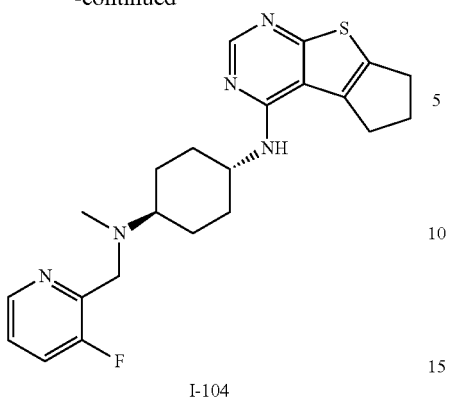

I-104

A mixture of I-34 (60 mg, 0.19 mmol, 1.00 equiv, 95%), 3-fluoropyridine-2-carbaldehyde (40 mg, 0.30 mmol, 1.61 equiv) and AcOH (20 mg, 0.33 mmol, 1.77 equiv) in DCE (2 mL) was stirred for 4 hours at room temperature. Then NaBH(OAc)$_3$ (212 mg, 1.00 mmol, 5.31 equiv) was added. The resulting solution was stirred for 20 h at room temperature. The reaction was diluted with 30 mL of ethyl acetate and then washed with 1×50 mL of water and 1×50 mL of brine. The organic solution was concentrated under vacuum. The residue was loaded onto a silica gel column with ethyl acetate/petroleum ether (0:1-1:1) and purified to afford 35 mg (45%) of Compound I-104 as a white solid. $^1$H NMR (400 MHz, CDCl$_3$) δ 8.38 (s, 1H), 8.23 (s, 1H), 7.65-7.58 (m, 1H), 7.46-7.39 (m, 1H), 4.13-4.06 (m, 1H), 3.85 (d, 2H), 3.33 (t, 2H), 3.10-2.96 (m, 2H), 2.67-2.50 (m, 3H), 2.33 (s, 3H), 2.20 (d, 2H), 2.05 (d, 2H), 1.67-1.40 (m, 4H). MS: m/z 412 (M+H)$^+$.

Example 67

Synthesis of 1-N-[(3-fluoropyridin-4-yl)methyl]-1-N-methyl-4-N-[7-thia-9,11-diazatricyclo[6.4.0.0ˆ[2,6]]dodeca-1(12),2(6),8,10-tetraen-12-yl]cyclohexane-1,4-diamine (I-111)

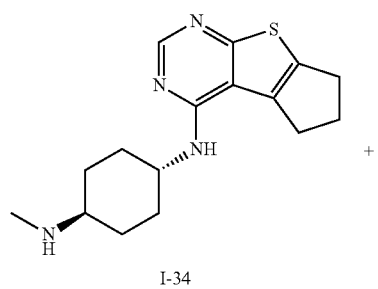

I-34

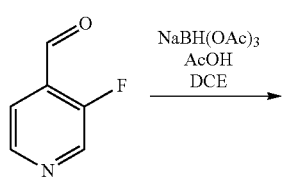

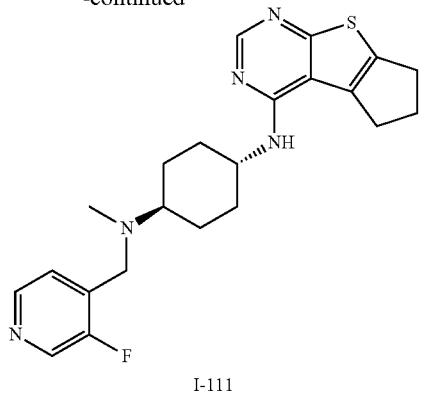

I-111

Compound I-111 was synthesized from Compound I-34 and 3-fluoropyridine-4-carbaldehyde in a manner consistent with Example 66 above. Isolated a white solid (42%). $^1$H NMR (300 MHz, CD$_3$OD): δ 8.41 (m, 2H), 8.24 (s, 1H), 7.61 (t, 1H), 4.14-4.07 (m, 1H), 3.79 (s, 2H), 3.12-2.98 (m, 4H), 2.65-2.57 (m, 3H), 2.32 (s, 3H), 2.20 (d, 2H), 2.02 (d, 2H), 1.67-1.55 (m, 4H). MS: m/z 412 (M+H)$^+$.

Example 68

Synthesis of 1-N-(2-phenylethyl)-4-N-[7-thia-9,11-diazatricyclo[6.4.0.0ˆ[2,6]]dodeca-1(12),2(6),8,10-tetraen-12-yl]cyclohexane-1,4-diamine (I-115)

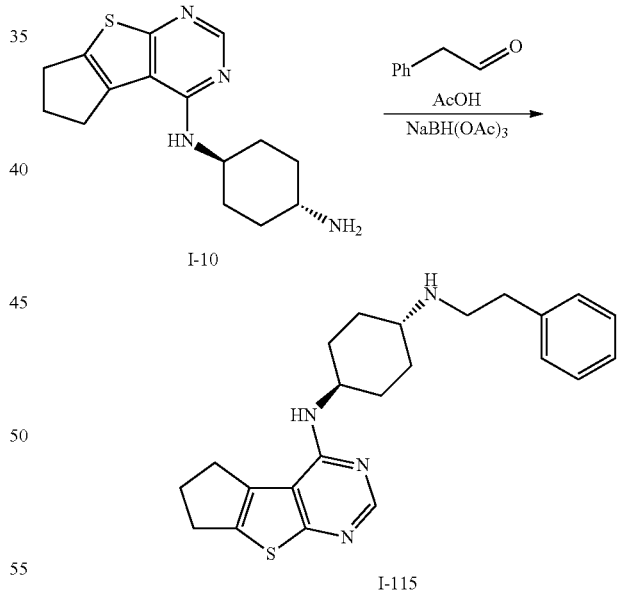

I-115

To a 50-mL round-bottom flask was added Compound I-10 (200 mg, 0.68 mmol, 1.00 equiv, 98%), dichloromethane (4 mL), 2-phenylacetaldehyde (100 mg, 0.82 mmol, 1.20 equiv), AcOH (0.05 mL, 98%), and NaBH(OAc)$_3$ (800 mg, 3.70 mmol, 5.44 equiv, 98%). The resulting solution was stirred overnight at 35° C. in an oil bath. The reaction was then quenched by the addition of 100 mL of water/ice. The solution was extracted with 3×30 mL of ethyl acetate and the organic layers combined. The combined organic layers were washed with 3×20 mL of water. The mixture was dried over anhydrous sodium sulfate and concentrated under vacuum. The residue was purified by flash preparative HPLC to yield 13.4 mg (5%) of Compound I-115 as a white solid. Isolated a white solid (5%). $^1$H NMR (300 MHz, CDCl$_3$): δ 8.36 (1H, s), 7.30-7.33 (2H, d, J=9 Hz), 7.26-7.30 (3H, t, J=6 Hz), 4.82-4.85 (1H, d), 4.09-4.13 (1H, m), 2.96-3.00 (4H, m), 2.90-2.95 (2H, m), 2.79-2.83 (2H, t), 2.50-2.58 (3H, m), 2.18-2.21 (2H, t), 1.97-2.00 (2H, d), 1.32-1.50 (4H, m). MS: m/z 393 (M+H)$^+$.

Example 69

Synthesis of 2-(3-chlorophenyl)-N-methyl-N-[4-([7-thia-9,11-diazatricyclo[6.4.0.0ˆ[2,6]]dodeca-1(8),2(6),9,11-tetraen-12-yl]amino)cyclohexyl]acetamide (I-102)

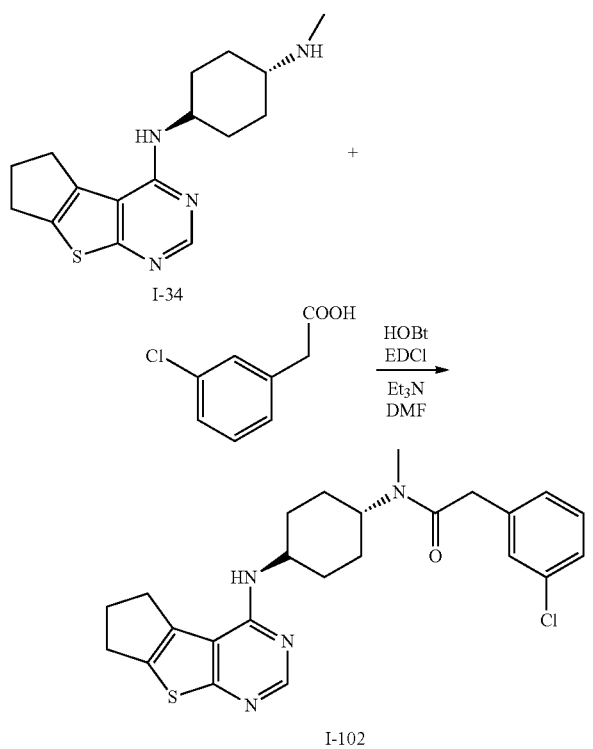

To a 50-mL round-bottom flask was added Compound I-34 (500 mg, 1.65 mmol, 1.00 equiv), 2-(3-chlorophenyl)acetic acid (342 mg, 2.00 mmol, 1.20 equiv), EDCI (478 mg, 2.49 mmol, 1.50 equiv), 1H-1,2,3-benzotriazol-1-ol (270 mg, 2.00 mmol, 1.20 equiv), triethylamine (503 mg, 4.97 mmol, 3.00 equiv), and N,N-dimethylformamide (10 mL). The resulting solution was stirred overnight at room temperature. The reaction was then diluted with 150 mL of water and extracted with 3×200 mL of ethyl acetate. The organic layers were combined and washed with 3×300 mL of brine, dried over anhydrous sodium sulfate and concentrated under vacuum. The residue was loaded onto a silica gel column with dichloromethane/methanol (50/1) to give 26.3 mg (3%) of Compound I-102 as a white solid. $^1$H NMR (300 MHz, CDCl$_3$): δ 8.36 (1H, s), 7.26-7.14 (4H, m), 4.86-4.83 (1H, d), 4.62-4.54 (1H, m), 4.10-4.05 (1H, m), 3.75-3.69 (2H, m), 3.01-2.99 (4H, m), 2.85 (3H, s), 2.59-2.52 (2H, m). 2.26-2.22 (2H, m), 1.72-1.58 (4H, m), 1.45-1.19 (2H, m). MS: m/z 455 (M+H)$^+$.

Example 70

Synthesis of N-methyl-2-(pyridin-2-yl)-N-[4-([7-thia-9,11-diazatricyclo[6.4.0.0ˆ[2,6]]dodeca-1(8),2(6),9,11-tetraen-12-yl]amino)cyclohexyl]acetamide (I-103)

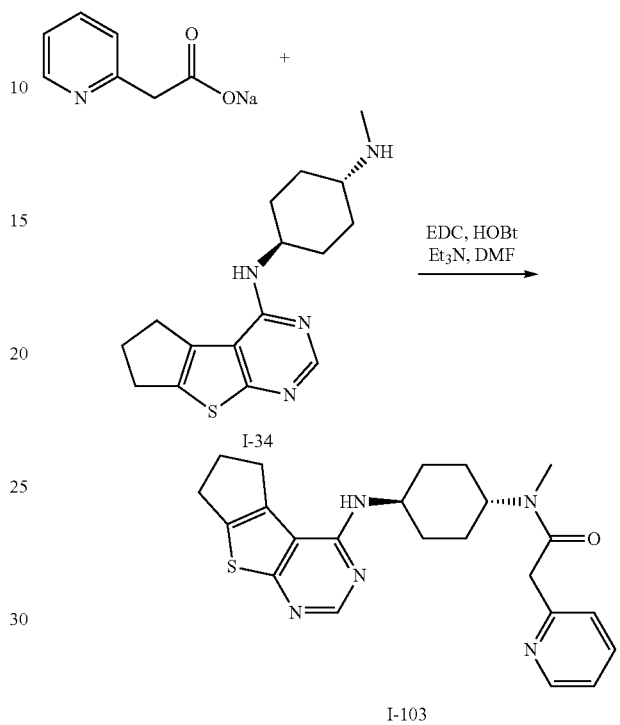

A mixture of sodium 2-(pyridin-2-yl)acetate (126 mg, 0.79 mmol, 1.20 equiv), Compound I-34 (200 mg, 0.66 mmol, 1.00 equiv), EDC (308 mg, 1.98 mmol, 3.00 equiv), HOBt (107 mg), and triethylamine (201 mg, 1.99 mmol, 3.01 equiv) in N,N-dimethylformamide (20 mL) was stirred for 5 h at 50° C. in an oil bath. The solids were filtered off. The filtrate was concentrated under vacuum to yield 24.5 mg (9%) of Compound I-103 as an off-white foam. $^1$H NMR (300 MHz, CD$_3$OD) δ 8.50-8.48 (1H, m), 8.23 (1H, s), 7.84-7.79 (1H, m), 7.43-7.30 (2H, m), 4.49 (1H, m), 4.12-3.97 (3H, m), 3.12-2.94 (6H, m), 2.88 (3H, s), 2.60-2.53 (2H, m), 2.20-2.12 (2H, m), 1.86-1.31 (6H, m). MS: m/z 455 (M+H)$^+$.

Example 71

Synthesis of 1-N-[2-(3-chlorophenyl)ethyl]-1-N-methyl-4-N-[7-thia-9,11-diazatricyclo[6.4.0.0ˆ[2,6]]dodeca-1(8),2(6),9,11-tetraen-12-yl]cyclohexane-1,4-diamine (I-107)

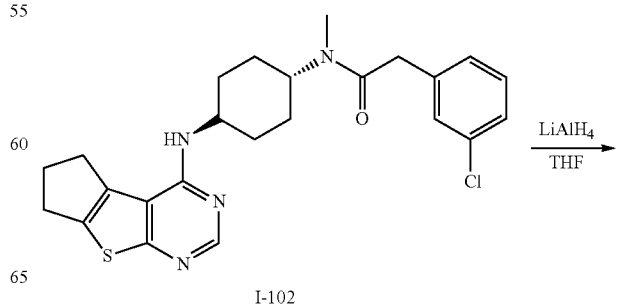

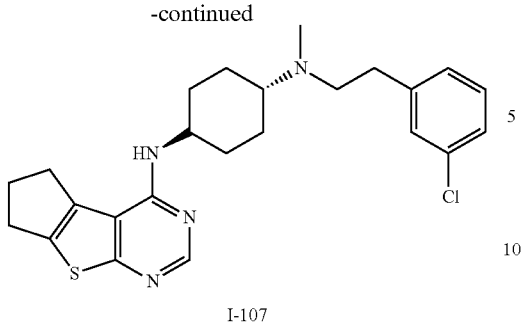

I-107

A solution of Compound I-102 (364 mg, 0.80 mmol, 1.00 equiv) in tetrahydrofuran (30 mL) was added dropwise into a solution of lithium aluminium tetrahydride (152 mg, 4.01 mmol, 5.00 equiv) in tetrahydrofuran (20 mL) with stirring at 0-5° C. The resulting solution was stirred for 5 h at 80° C. in an oil bath. The reaction was then quenched by the addition of 5 mL of water. The solids were filtered off. The filtrate was extracted with 3×100 mL of dichloromethane and the organic layers combined and dried over anhydrous sodium sulfate and concentrated under vacuum. The residue was purified by preparative HPLC (2#-Waters 2767-2(HPLC-08)) under the following conditions: column: Xbridge Prep Phenyl, 5 um, 19*150 mm; mobile phase: Water (50 mM ammonium bicarbonate) and acetonitrile (10.0% acetonitrile up to 33.0% in 2 min, up to 53.0% in 8 min, up to 100.0% in 1 min, down to 10.0% in 1 min); detector, UV 220 nm, to yield 20.3 mg (6%) of Compound I-107 as an off-white solid. $^1$H NMR (400 MHz, CDCl$_3$) δ 8.36 (1H, s), 7.26-7.07 (4H, m), 4.85-4.83 (1H, d), 4.12-4.02 (1H, m), 3.00-2.97 (4H, m), 2.76-2.70 (4H, m), 2.58-2.49 (3H, m), 2.37 (3H, s). 2.27-2.23 (2H, d), 1.94-1.89 (2H, d), 1.71-1.47 (2H, q), 1.29-1.25 (2H, q). MS: m/z 441 (M+H)$^+$.

Example 72

Synthesis of 1-N,1-N-dimethyl-4-N-[7-thia-9,11-diazatricyclo[6.4.0.0^[2,6]]dodeca-1(12),2(6),8,10-tetraen-12-yl]cyclohexane-1,4-diamine (I-12)

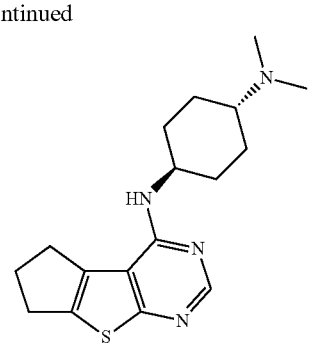

I-12

A mixture of Compound I-10 (1.97 g, 6.83 mmol, 1.00 equiv) and formaldehyde (2.05 g, 68.24 mmol, 9.99 equiv) in formic acid (20 mL) was heated to reflux for 16 hr. The reaction mixture was cooled with a water/ice bath. The pH value of the solution was adjusted to 12 with sodium hydroxide (2N). The solids were collected by filtration. The crude product was purified by re-crystallization from ethanol to give 984.4 mg (53%) of Compound I-12 as a yellow solid, m. p.=97-98° C. $^1$H NMR (400 MHz, CDCl$_3$) δ 8.36 (1H, s), 7.26-7.07 (4H, m), 4.85-4.83 (1H, d), 4.12-4.02 (1H, m), 3.00-2.97 (4H, m), 2.76-2.70 (4H, m), 2.58-2.49 (3H, m), 2.37 (3H, s), 2.27-2.23 (2H, d), 1.94-1.89 (2H, d), 1.71-1.47 (2H, q), 1.29-1.25 (2H, q). MS: m/z 317 (M+H)$^+$.

Example 73

Synthesis of 1-N-benzyl-1-N-ethyl-4-N-[7-thia-9,11-diazatricyclo[6.4.0.0[2,6]]dodeca-1(8),2(6),9,11-tetraen-12-yl]cyclohexane-1,4-diamine (I-120)

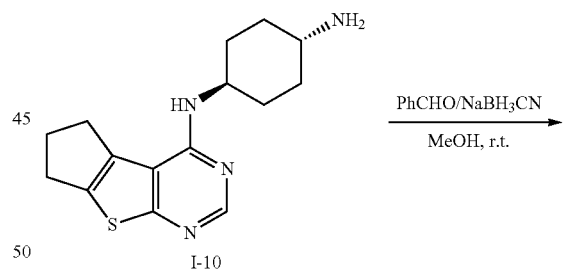

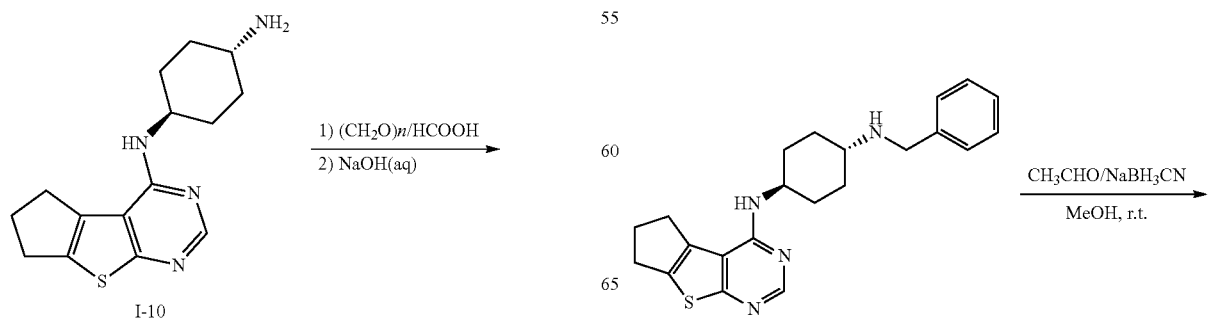

-continued

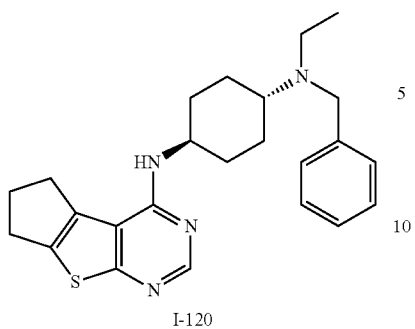

I-120

Synthesis of 1-N-benzyl-4-N-[7-thia-9,11-diazatricyclo[6.4.0.0[2,6]]dodeca-1(8),2(6),9,11-tetraen-12-yl] cyclohexane-1,4-diamine To a solution of Compound I-10 (800 mg, 2.77 mmol, 1.00 equiv) in methanol (20 mL) was added benzaldehyde (300 mg, 2.83 mmol, 1.00 equiv) and catalytic amounts of AcOH (1-2 drops). The resulting solution was stirred for 1 h at room temperature. Then NaCNBH$_3$ (247 mg, 1.40 equiv) was added and the reaction mixture was stirred overnight at ambient temperature. The resulting solution was diluted with EtOAc and washed with brine. The organic layer was dried over anhydrous sodium sulfate and concentrated under vacuum. The desired product (870 mg, 83%) was obtained as a gray solid.

Synthesis of Compound I-120

To a 25-mL round-bottom flask was added a solution of 1-N-benzyl-4-N-[7-thia-9,11-diazatricyclo[6.4.0.0[2,6]]dodeca-1(8),2(6),9,11-tetraen-12-yl]cyclohexane-1,4-diamine (100 mg, 0.26 mmol, 1.00 equiv) in methanol (4 mL). Then acetaldehyde (23 mg, 0.52 mmol, 2.00 equiv) and HOAc (1-2 drops) were added and the reaction was stirred for 0.5 h at room temperature. NaBH$_3$CN (33 mg, 525.48 mmol, 2.00 equiv) was added and stirring was continued overnight at room temperature. The reaction mixture was diluted with EtOAc and washed with brine. The organic phase was dried over anhydrous sodium sulfate and concentrated in vacuo. The crude product (100 mg) was purified by preparative HPLC under the following conditions: column, C18; mobile phase: water:acetonitrile=50:50 to 0:100 in 15 min; UV detection at 254 nm. Compound I-120 (50 mg, 47%) was obtained as a white solid. $^1$H NMR: (400 MHz, d$_6$-DMSO) δ 8.24 (s, 1H), 7.28-7.35 (m, 4H), 7.20-7.22 (d, 1H, J=6.8 Hz), 5.93-5.95 (d, 1H, J=8.0 Hz), 4.05 (s, 1H), 3.60 (s, 2H), 3.04 (t, 2H, J=7.2 Hz), 2.92 (t, 2H, J=7.2 Hz), 2.41 (t, 2H, J=7.2 Hz), 1.97 (s, 2H), 1.79 (s, 2H), 1.43 (t, 4H, J=8.4 Hz), 0.97 (t, 3H, J=6.8 Hz). MS: m/z 407 (M+H)$^+$.

Example 74

Synthesis of (1s,4s)-N1-(6,7-dihydro-5H-cyclopenta[4,5]thieno[2,3-d]pyrimidin-4-yl)cyclohexane-1,4-diamine (I-154)

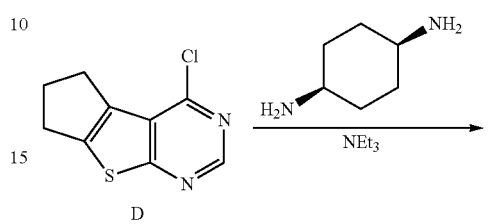

D

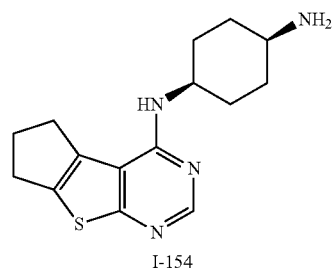

I-154

A mixture of intermediate D (500 mg, 2.37 mmol, 1.00 equiv), cis-cyclohexane-1,4-diamine (675 mg, 5.91 mmol, 2.49 equiv) and triethylamine (718 mg, 7.10 mmol, 2.99 equiv) in N,N-dimethylformamide (8 mL) was stirred for 14 h at 30° C. The reaction was then quenched by the addition of 50 mL of water. The solids were collected by filtration and dried in an oven under reduced pressure, then loaded onto a silica gel column with dichloromethane/methanol (15/1~5/1) to give 285.7 mg (42%) of Compound I-154 as a white solid. $^1$H NMR: (400 MHz, CDCl$_3$) δ 8.39 (1H, s), 5.22 (1H, br), 4.37 (1H, s), 3.02-3.06 (4H, m), 2.55-2.58 (2H, m), 1.80-1.88 (6H, m), 1.27-1.45 (2H, m). MS: m/z 289 (M+H)$^+$.

Example 75

Synthesis of (1s,4s)-1-N,1-N-dimethyl-4-N-[7-thia-9,11-diazatricyclo[6.4.0.0^[2,6]]dodeca-1(8),2(6),9,11-tetraen-12-yl]cyclohexane-1,4-diamine (I-155)

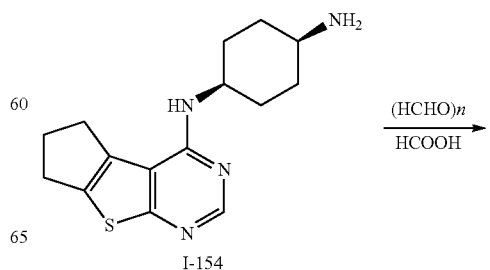

I-154

-continued

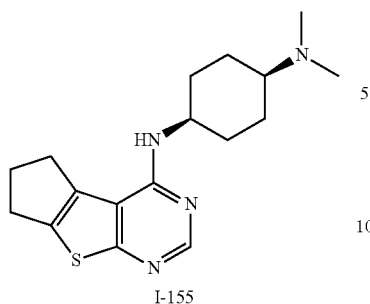

I-155

A mixture of Compound I-154 (500 mg, 1.73 mmol, 1.00 equiv), polyoxymethylene (520 mg, 17.31 mmol, 9.98 equiv) and formic acid (10 mL, 88%) was heated to reflux for 14 hrs. The reaction was then quenched by the addition of 80 mL of water. The solids were collected by filtration and applied onto a silica gel column with dichloromethane/methanol (15/1~5/1) to give 233.8 mg (43%) of Compound I-155 as a white solid. $^1$H NMR: (400 MHz, CDCl$_3$) δ 8.38 (1H, s), 5.24-5.26 (1H, br), 4.40 (1H, s), 2.90-3.08 (4H, dt), 2.54-2.60 (2H, m), 2.36 (6H, s), 2.24 (1H, m), 1.80-1.93 (2H, m), 1.57-1.75 (6H, m). MS: m/z 317 (M+H)$^+$.

Example 76

Synthesis of (1r,4r)-4-((6,7-dihydro-5H-cyclopenta[4,5]thieno[2,3-d]pyrimidin-4-yl)amino)-N,N,N-trimethylcyclohexanaminium iodide (I-139)

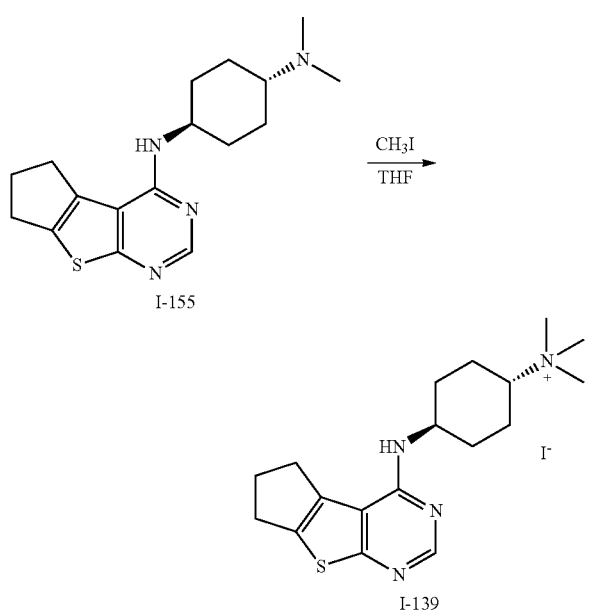

A mixture of I-155 (30 mg, 0.095 mmol, 1.0 eq), CH$_3$I (25 mg, 1.9 mmol, 2.0 eq) in THF (10 ml) was stirred at rt for 2 h. The solvent was removed under vacuum to give the product I-139 as a buff solid (34 mg, 92%). $^1$H NMR: (400 MHz, CDCl$_3$) δ 1.58-1.61 (m, 4H), 1.66-1.75 (m, 2H), 2.38-2.41 (m, 2H), 2.52-2.59 (m, 2H), 2.97-3.05 (m, 4H), 3.41 (s, 9H), 4.19-4.23 (m, 1H), 4.50-4.55 (m, 1H), 4.91 (d, J=7.6 Hz, 1H), 8.35 (s, 1H). MS: m/z 331.2 (M+H)$^+$.

Example 77

Synthesis of (1s,4s)-1-N-methyl-4-N-[7-thia-9,11-diazatricyclo[6.4.0.0^[2,6]]dodeca-1(12),2(6),8,10-tetraen-12-yl]cyclohexane-1,4-diamine (I-156)

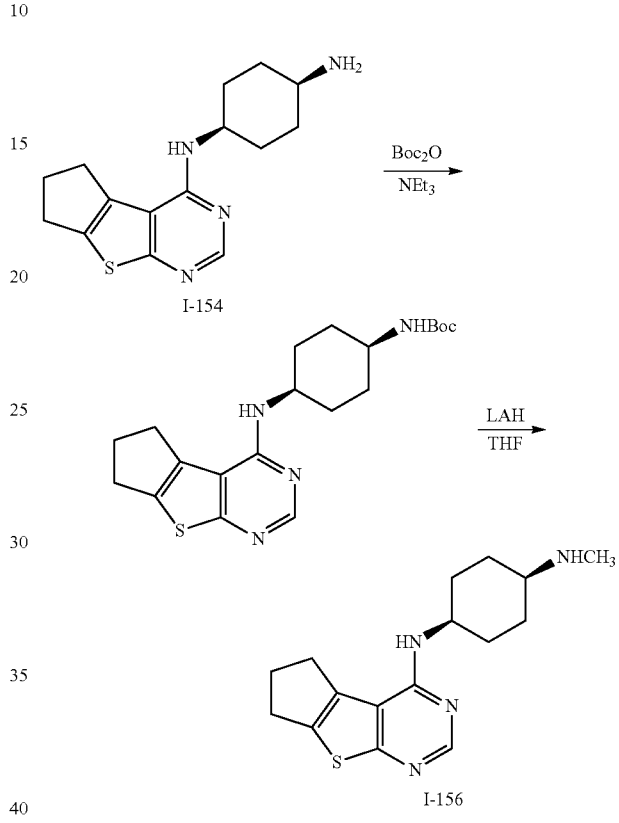

Synthesis of (1s,4s)-tert-butyl N-[4-([7-thia-9,11-diazatricyclo[6.4.0.0^[2,6]]dodeca-1(12),2(6),8,10-tetraen-12-yl]amino)cyclohexyl]carbamate A mixture of I-154 (460 mg, 1.59 mmol, 1.00 equiv), di-tert-butyl dicarbonate (383 mg, 1.75 mmol, 1.10 equiv), triethylamine (242 mg, 2.39 mmol, 1.50 equiv) in dichloromethane (8 mL) was stirred for 12 h at room temperature. The reaction was monitored by TLC (petroleum ether/ethyl acetate=2/1). The reaction was then quenched by the addition of 10 mL of water and the organic phase was combined. The mixture was dried over anhydrous sodium sulfate and concentrated under vacuum to yield 520 mg (84%) of tert-butyl N-[4-([7-thia-9,11-diazatricyclo[6.4.0.0^ [2,6]]dodeca-1(12),2(6),8,10-tetraen-12-yl]amino)cyclohexyl]carbamate as a yellow solid.

Synthesis of Compound I-156

A solution of tert-butyl N-[4-([7-thia-9,11-diazatricyclo[6.4.0.0^ [2,6]]dodeca-1(12),2(6),8,10-tetraen-12-yl]amino)cyclohexyl]carbamate (600 mg, 1.54 mmol, 1.00 equiv) in tetrahydrofuran (15 mL) was added to a solution of lithium aluminium tetrahydride (117 mg, 3.45 mmol, 2.23 equiv) in tetrahydrofuran (5 mL) dropwise with stirring. The resulting solution was heated to reflux for 1 hr. The reaction was then quenched by the addition of 20 mL of water. The resulting solution was extracted with 2×20 mL of ethyl acetate and the organic layers combined and concentrated under vacuum. The residue was purified by preparative HPLC under the following conditions (2#-Waters 2767-2(HPLC-08)): Column: Xbridge Prep $C_{18}$, 5 um, 19*150 mm; mobile phase: water with 50 mmol ammonium bicarbonate and acetonitrile (5.0% acetonitrile up to 29.0% in 13 min, up to 100.0% in 1 min, down to 5.0% in 1 min); detector: UV 220 nm. Purification gave 105.7 mg (23%) of Compound I-156 as a white solid. $^1$H NMR: (400 MHz, $CD_3OD$) δ 8.26 (1H, s), 4.34 (1H, s), 3.17-3.19 (2H, t), 3.02-3.05 (2H, t), 2.81-2.83 (1H, m), 2.56-2.64 (2H, m), 2.54 (3H, s), 1.79-1.97 (6H, m), 1.67 (2H, m). MS: m/z 303 (M+H)$^+$.

Example 78

Synthesis of (1r,4r)-N1-benzyl-N4-(6,7-dihydro-5H-cyclopenta[4,5]thieno[2,3-d]pyrimidin-4-yl)-N1-methylcyclohexane-1,4-diamine (I-151)

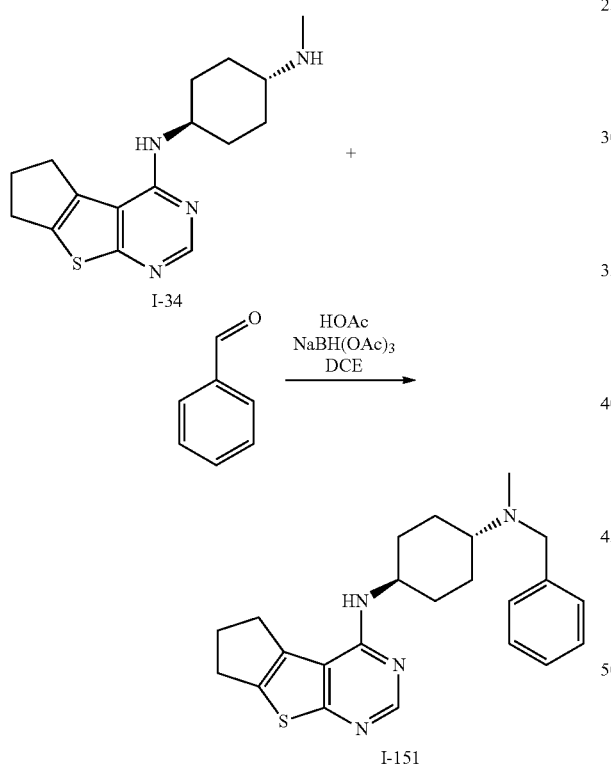

To a mixture of I-34 (100 mg, 0.33 mmol, 1.0 eq) and benzaldehyde (42 mg, 0.40 mmol, 1.2 eq) in 5 mL of DCE was added HOAc (40 mg, 0.66 mmol, 2.0 eq) at rt. The mixture was stirred at rt for 1 h and NaBH(OAc)$_3$ (168 mg, 0.8 mmol, 2.4 eq) was added. The resulting mixture was stirred overnight and poured into 50 mL of sat. aq. NaHCO$_3$ and extracted with DCM (50 mL*3). The combined organics was dried and concentrated. The crude product was purified by column on silica gel (DCM/MeOH/ammonia=100:5:1) to give Compound I-151 as a white solid (80 mg, 62%). $^1$H NMR: (400 MHz, DMSO-d$_6$) δ 1.42-1.47 (m, 4H), 1.83 (m, 2H), 1.99 (m, 2H), 2.14 (s, 3H), 2.39-2.49 (m, 3H), 2.90-2.93 (m, 2H), 3.05-3.07 (m, 2H), 3.56 (s, 2H), 4.05 (m, 2H), 5.98 (d, J=6.4 Hz, 1H), 7.21-7.31 (m, 5H), 8.25 (s, 1H). MS: m/z 393.3 (M+H)$^+$.

Example 79

Synthesis of 1-(3-((6,7-dihydro-5H-cyclopenta[4,5]thieno[2,3-d]pyrimidin-4-yl)oxy)cyclobutyl)-N,N-dimethylmethanamine (I-141)

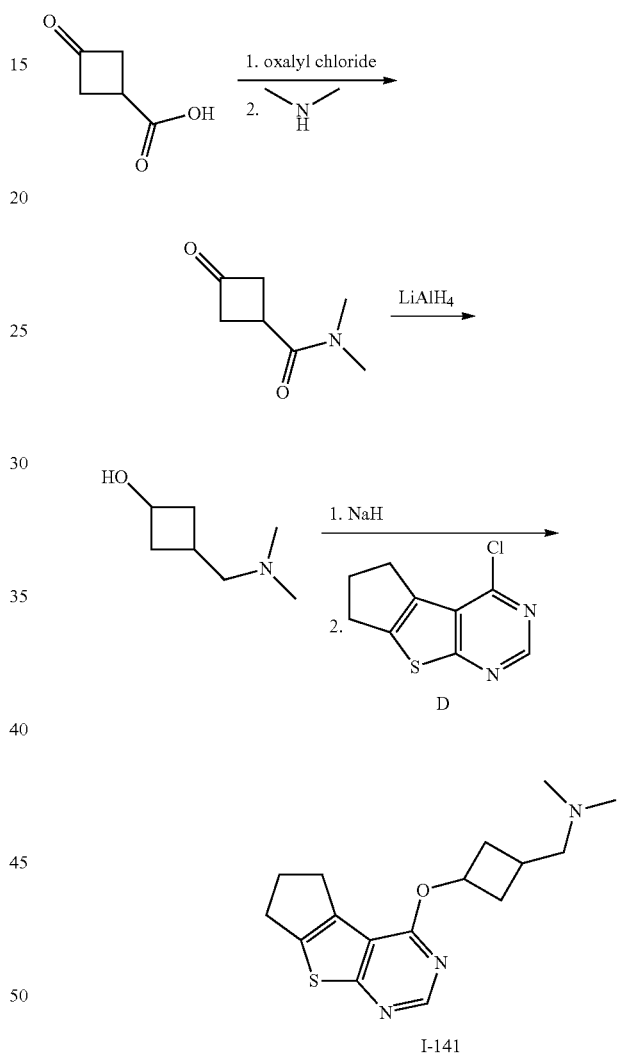

Synthesis of N,N-dimethyl-3-oxocyclobutanecarboxamide

To a solution of 3-oxocyclobutanecarboxylic acid (1 g, 8.77 mmol) in 10 mL of DCM was added one drop of DMF, followed by oxalyl chloride (1.11 g, 8.77 mmol) carefully. The resulting mixture was stirred at rt overnight and concentrated. The residue was dissolved in 5 mL of THF and dimethyl amine gas was bubbled into the solution for 10 min. The precipitate was filtered off and the filtrate was concentrated to give the desired product as a yellow oil (990 mg, 80%). MS: m/z 142.2 (M+H)$^+$.

Synthesis of 3-((dimethylamino)methyl)cyclobutanol

To a solution of N,N-dimethyl-3-oxocyclobutanecarboxamide (700 mg, 5 mmol) in 20 mL of THF was added LAH (370 mg, 10 mmol, 2 eq) at 0° C. The mixture was heated at reflux for 2 h and cooled down. The reaction was quenched with 1 mL of water carefully and filtered. The filtrated was concentrated to afford the desired product as a brown oil (370 mg, 56%), which was used in the next step without further purification. MS: m/z 130.0 (M+H)$^+$.

Synthesis of Compound I-141

To a solution of 3-((dimethylamino)methyl)cyclobutanol (155 mg, 1.2 mmol) in 5 mL of THF was added NaH (50 mg, 60%, 1.2 mmol). The reaction was heated at reflux for 2 h and cooled down. Intermediate D (210 mg, 1.0 mmol) was added to the reaction mixture in one portion and the reaction was stirred for an additional 30 min. 50 mL of water was added and the mixture was extracted with DCM (50 mL×3). The combined organics were dried and concentrated. The residue was purified by column chromatography on silica gel (DCM/MeOH=20:1) to afford Compound I-141 as a white solid (200 mg, 69%). $^1$H NMR: (400 MHz, CDCl$_3$) δ 1.85-1.88 (m, 2H), 2.17-2.20 (m, 1H), 2.29 (s, 6H), 2.45-2.53 (m, 4H), 2.75-2.78 (m, 2H), 2.99-3.06 (m, 4H), 5.28-5.32 (m, 1H), 8.48 (s, 1H). MS: m/z 304.0 (M+H)$^+$.

Example 80

Synthesis of (1r,4r)-4-(((6,7-dihydro-5H-cyclopenta[4,5]thieno[2,3-d]pyrimidin-4-yl)oxy)methyl)-N,N-dimethylcyclohexanamine (I-148)

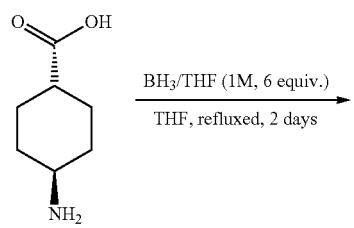

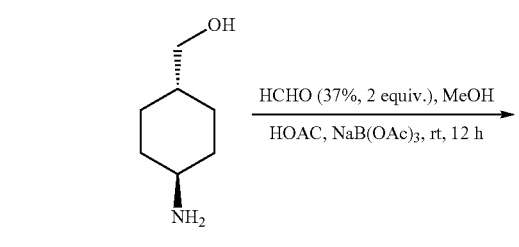

((1r,4r)-4-(dimethylamino)cyclohexyl)methanol

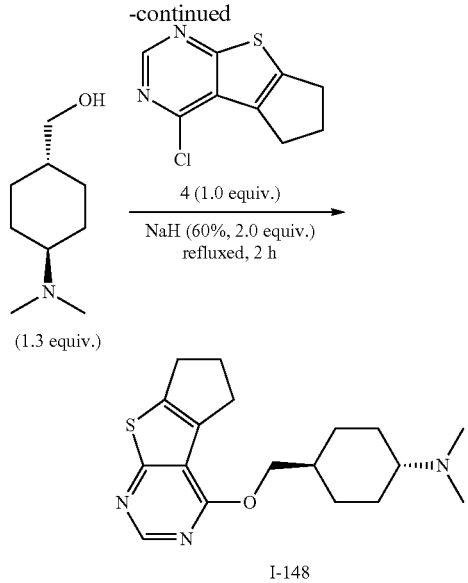

Synthesis of ((1r,4r)-4-aminocyclohexyl)methanol

To a solution of (1r,4r)-4-aminocyclohexanecarboxylic acid (860 mg, 6.0 mmol, 1.0 eq) in THF (10 mL) was added dropwise BH$_3$/THF (1.0 mol/L in THF, 30 mL, 5.0 equiv.) at 0° C. The reaction was allowed to warm to room temperature. The reaction was heated at reflux for 48 hours. The reaction was quenched with AcOH and concentrated in vacuo to get crude ((1r,4r)-4-aminocyclohexyl)methanol (600 mg, 78%) which was used to the next step without further purification. MS: m/z 130.1 (M+H)$^+$.

Synthesis of ((1r,4r)-4-(dimethylamino)cyclohexyl)methanol

A formaldehyde solution (36 percent, 835 mg, 9.3 mmol, 2.0 eq), acetic acid (2032 mg, 23.25 mmol, 5.0 eq) and NaBH(OAc)$_3$ (1949 mg, 9.3 mmol, 2.0 eq) were added to a solution of ((1r,4r)-4-aminocyclohexyl)methanol (600 mg, 4.65 mmol, 1.0 eq) in methanol (5 ml), and the resulting mixture was stirred at room temperature for 12 hours. The reaction mixture was poured into a saturated aqueous sodium hydrogencarbonate solution and then extracted with ethyl acetate (3×600 mL). The organic layer was concentrated under reduced pressure to afford ((1r,4r)-4-(dimethylamino)cyclohexyl)methanol (600 mg, 82%). MS: m/z 158.1 (M+H)$^+$.

Synthesis of Compound I-148

((1r,4r)-4-(dimethylamino)cyclohexyl)methanol (401 mg, 1.91 mmol, 1.0 eq) was added to a mixture of D (300 mg, 1.91 mmol, 1.0 equiv.) and NaH (91 mg, 60%, 2.29 mmol, 1.2 equiv.) in anhydrous DMF (10 mL) at rt portionwise. This mixture was heated to reflux for 2 hours. After cooling to rt, this mixture was poured into water (30 mL) and stirred for 30 min then filtered. The resulting solid was crystallized with MeOH/water to afford Compound I-148 (141 mg, 29%). $^1$H NMR: (400 MHz, CDCl$_3$) δ 1.12-1.30 (m, 4H), 1.76-1.80 (m, 1H), 1.97-1.99 (m, 4H), 2.19-2.22 (m, 1H), 2.31 (s, 6H), 2.47-2.54 (m, 2H), 3.01-3.06 (m, 4H), 4.30 (d, J=6.4 Hz, 2H), 8.50 (s, 1H). MS: m/z 332.2 (M+H)$^+$.

Example 81

Synthesis of Intermediate H

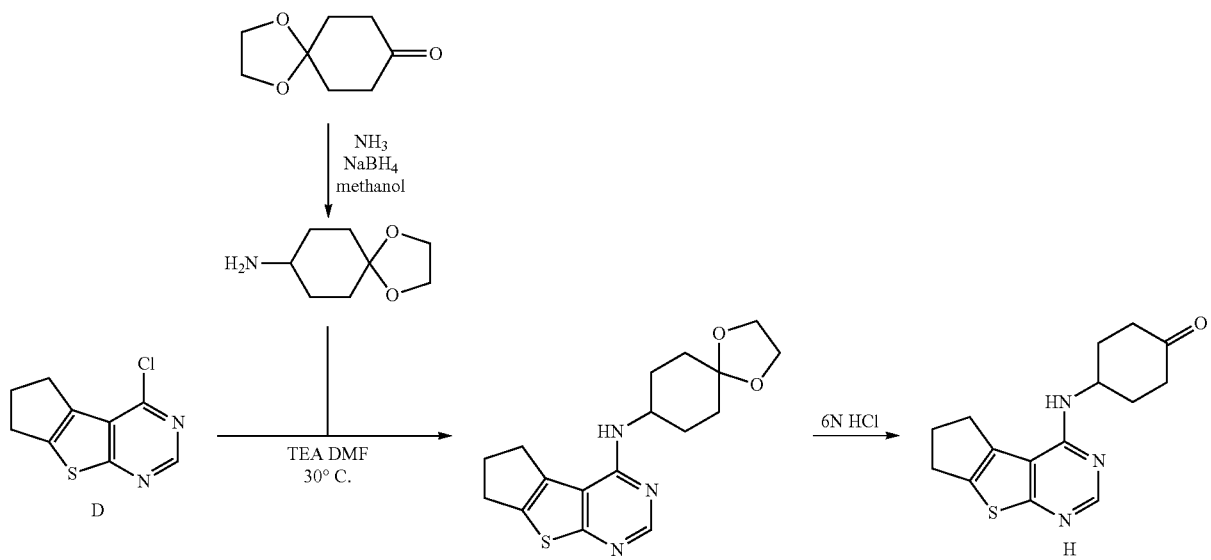

Synthesis of 1,4-dioxaspiro[4.5]decan-8-amine

Ammonia gas was bubbled into a solution of 1,4-dioxaspiro[4.5]decan-8-one (31.2 g, 199.77 mmol, 1.00 equiv) in methanol (300 mL). The resulting solution was stirred for 8 hrs at 0-10° C. This was followed by the addition of sodium borohydride (11.4 g, 301.35 mmol, 1.51 equiv) in several batches at 0-10° C. The resulting solution was stirred for 1 h at room temperature. The resulting solution was diluted with 50 mL of water. The resulting solution was extracted with 4×300 mL of dichloromethane and the organic layers combined. The resulting mixture was washed with 2×100 mL of brine. The mixture was dried over anhydrous sodium sulfate and concentrated under vacuum to yield 20 g (64%) of 1,4-dioxaspiro[4.5]decan-8-amine as colorless oil.

Synthesis of N-(1,4-dioxaspiro[4.5]decan-8-yl)-6,7-dihydro-5H-cyclopenta[4,5]thieno[2,3-d]pyrimidin-4-amine A mixture of intermediate D (12.28 g, 78.2 mmol, 6.00 equiv) and triethylamine (3.36 g, 33.2 mmol, 2.50 equiv) in N,N-dimethylformamide (30 mL) was stirred overnight at room temperature. The reaction was then quenched by the addition of 150 mL of water and ice mixture. The solids were collected by filtration to yield 3.5 g (79%) of the desired product as a gray solid. $^1$H NMR: (400 MHz, CDCl$_3$) δ 8.40 (1H, s), 5.0 (1H, s), 4.28-4.29 (1H, d), 4.39-4.40 (4H, d), 3.00-3.03 (4H, t), 2.54-2.60 (2H, m), 2.13-2.16 (2H, m), 1.79-1.87 (5H, m), 1.68-1.79 (3H, m). MS: m/z 332 (M+H)$^+$.

Synthesis of Intermediate H

A solution of N-[1,4-dioxaspiro[4.5]decan-8-yl]-7-thia-9,11-diazatricyclo[6.4.0.0^[2,6]]dodeca-1(8),2(6),9,11-tetraen-12-amine (3.5 g, 10.56 mmol, 1.00 equiv) in tetrahydrofuran/6N hydrogen chloride (35/35 mL) was stirred overnight at 60° C. The resulting mixture was concentrated under vacuum and cooled to 0° C. The pH value of the solution was adjusted to 10~11 with sodium hydroxide (3 N). This resulted in 2.2 g (72%) of intermediate H as an off-white solid. $^1$H NMR: (400 MHz, CDCl$_3$) δ 8.41 (1H, s), 4.96-4.98 (1H, d), 4.61-4.78 (3H, m), 3.00-3.05 (4H, m), 2.44-2.64 (8H, m), 1.75-1.86 (6H, m). MS: m/z 288 (M+H)$^+$.

Example 82

Synthesis of N-[4-(azetidin-1-yl)cyclohexyl]-7-thia-9,11-diazatricyclo[6.4.0.0^[2,6]]dodeca-1(8),2(6),9,11-tetraen-12-amine (I-158)

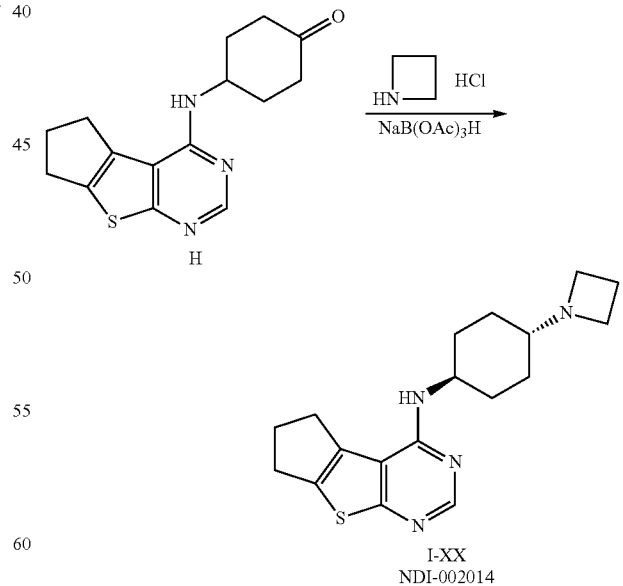

I-XX
NDI-002014

A mixture of H (800 mg, 2.78 mmol, 1.00 equiv), azetidine hydrochloride (300 mg, 3.2 mmol, 1.20 equiv), 1-[acetyl(sodio)boranyl]ethan-1-one acetic acid dihydrate (900 mg, 4.17 mmol, 1.50 equiv) in dichloromethane (10 mL) was stirred overnight at room temperature. The reaction was then quenched by the addition of 50 mL of water. The resulting solution was extracted with 3×50 mL of ethyl acetate and the organic layers combined. The resulting mixture was washed with 3×100 mL of brine. The mixture was dried over anhydrous sodium sulfate and concentrated under vacuum. The residue was purified by preparative HPLC (2#-Waters 2767-2(HPLC-08)) under the following conditions: column: SunFire Prep $C_{18}$, 19*150 mm 5 um; mobile phase: water (0.05% trifluoroacetic acid) and acetonitrile (10.0% acetonitrile up to 17.0% in 2 min, up to 21.0% in 10 min, up to 100.0% in 2 min, down to 10.0% in 2 min); detector: UV 220 nm. This resulted in 15 mg (2%) of Compound I-158 as a white solid. $^1$H NMR: (400 MHz, CDCl$_3$) δ 8.39 (1H, s), 4.83-4.85 (1H, d), 4.13 (1H, s), 3.47-3.61 (4H, br), 3.01-3.02 (4H, d), 2.52-2.59 (2H, m), 2.26-2.29 (4H, d), 1.93 (2H, s), 1.37-1.41 (2H, m), 1.20-1.28 (2H, q). MS: m/z 329 (M+H)$^+$.

Example 83

Synthesis of N-((1r,4r)-4-morpholinocyclohexyl)-6,7-dihydro-5H-cyclopenta[4,5]thieno[2,3-d]pyrimidin-4-amine. (I-149)

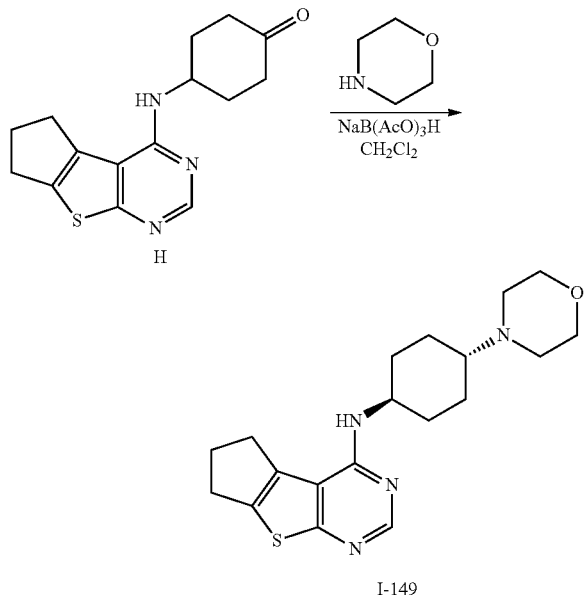

A mixture of intermediate H (1.0 g, 3.48 mmol, 1.00 equiv), acetic acid (2 mL), 1-[acetyl(sodio)boranyl]ethan-1-one acetic acid dihydrate (1.5 g, 6.95 mmol, 2.00 equiv) and morpholine (500 mg, 5.74 mmol, 1.65 equiv) in dichloromethane (10 mL) was stirred overnight at room temperature. The reaction was then quenched by the addition of 50 mL of water. The pH value of the solution was adjusted to 10 with sodium hydroxide (3 N) at 0-5° C. The resulting solution was extracted with 3×50 mL of ethyl acetate and the organic layers combined. The resulting mixture was washed with 3×50 mL of brine. The mixture was dried over anhydrous sodium sulfate and concentrated under vacuum. The residue was purified by preparative HPLC (2#-Waters 2767-2 (HPLC-08)) under the following conditions: column: SunFire Prep $C_{18}$, 19*150 mm 5 um; mobile phase: water (0.05% trifluoroacetic acid) and acetonitrile (10.0% acetonitrile up to 25.0% in 15 min, up to 100.0% in 2 min, down to 10.0% in 2 min); detector: UV 220 nm. Purification afforded 160 mg (13%) of Compound I-149 as a white solid. $^1$H NMR: (400 MHz, CDCl$_3$) δ 8.39 (1H, s), 4.86-4.88 (1H, d), 4.09-4.13 (1H, m), 3.76 (4H, s), 2.99-3.04 (4H, q), 2.52-2.61 (6H, m), 2.28-2.31 (3H, d), 2.00-2.03 (2H, d), 1.60 (4H, s), 1.50-1.53 (2H, d), 1.22-1.31 (2H, q). MS: m/z 359 (M+H)$^+$.

Example 84

Synthesis of 1-N-(propan-2-yl)-4-N-[7-thia-9,11-diazatricyclo[6.4.0.0˙[2,6]]dodeca-1(8),2(6),9,11-tetraen-12-yl]cyclohexane-1,4-diamine (I-157)

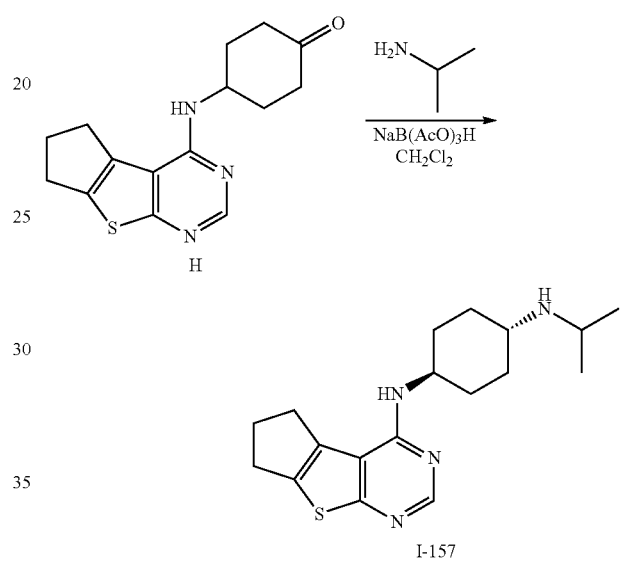

Compound I-157 was synthesized in a manner consistent with Example 85. Isolated a white solid (15%). $^1$H NMR: (400 MHz, CDCl$_3$) δ 8.38 (1H, s), 4.85-4.87 (1H, d), 4.12-4.14 (1H, m), 2.99-3.04 (5H, m), 2.52-2.62 (3H, m), 2.22-2.24 (2H, d), 2.03-2.06 (2H, d), 1.37-1.52 (4H, m), 1.09-1.10 (6H, d). MS: m/z 331 (M+H)$^+$.

Example 85

Synthesis of Intermediate I

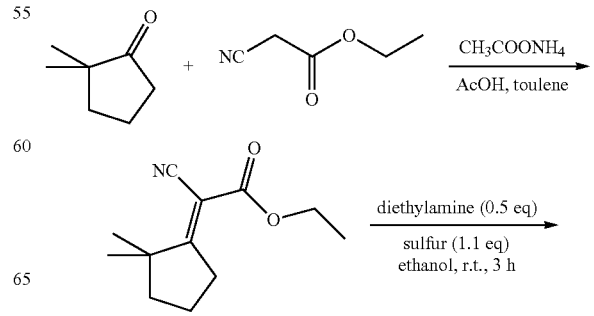

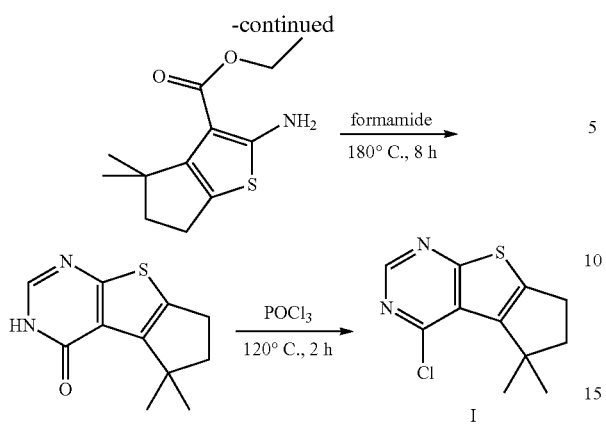

Synthesis of (E)-ethyl 2-cyano-2-(2,2-dimethylcyclopentylidene)acetate 2,2-dimethylcyclopentanone (5 g, 44.6 mmol, 1 equiv.) was dissolved in toluene (100 mL). Then, ethyl 2-cyanoacetate (5.04 g, 44.6 mmol, 1 equiv.), ammonium acetate (2.4 g, 31.2 mmol, 0.7 equiv.) and acetic acid (2.8 mL) were added in the mixture at room temperature. The mixture was refluxed for 20 hours. 10% NaCl solution (100 mL) was added in the mixture. Then, the organic layer was washed by water (50 mL) and brine (50 mL), dried by sodium sulfate and filtered. The organic layer was concentrated and the residue was purified by column chromatography to give (E)-ethyl 2-cyano-2-(2,2-dimethylcyclopentylidene)acetate (2.47 g, 32%) as a colorless oil. MS: m/z 208 (M+H)$^+$.

Synthesis of ethyl 2-amino-4,4-dimethyl-5,6-dihydro-4H-cyclopenta[b]thiophene-3-carboxylate Diethylamine (433 mg, 5.93 mmol, 0.5 equiv.) was added in the solution of (E)-ethyl 2-cyano-2-(2,2-dimethylcyclopentylidene)acetate (2.47 g, 11.87 mmol, 1 equiv.) and sulfur (418 mg, 13.06 mmol, 1.1 equiv.) in ethanol (120 mL) slowly at 50° C. The mixture was stirred for 2 hours at 50° C. The mixture was filtered, and the filtration was concentrated and the residue purified by column chromatography (hexane:ethyl acetate=20:1) to give ethyl 2-amino-4,4-dimethyl-5,6-dihydro-4H-cyclopenta[b]thiophene-3-carboxylate (2.34 g, 83%) as a yellow solid. MS: m/z 240 (M+H)$^+$.

Synthesis of 5,5-dimethyl-6,7-dihydro-3H-cyclopenta[4,5]thieno[2,3-d]pyrimidin-4(5H)-one Ethyl 2-amino-4,4-dimethyl-5,6-dihydro-4H-cyclopenta[b]thiophene-3-carboxylate (2.3 g, 9.9 mmol, 1 equiv.) was dissolved in formamide (12 mL). The mixture was stirred for 1 hour at 180° C. Then water (50 mL) was added and the product extracted with ethyl acetate (50 mL*3). The organic layer was washed with water (100 mL*2) and brine (100 mL), dried by sodium sulfate and filtered. The organic layer was concentrated and the residue purified by column chromatography (hexane:ethyl acetate=6:5) to give the desired product (1.57 g, 75%) as a yellow solid. MS: m/z 221 (M+H)$^+$.

Synthesis of Compound I 5,5-dimethyl-6,7-dihydro-3H-cyclopenta[4,5]thieno[2,3-d]pyrimidin-4(5H)-one (1.5 g, 6.8 mmol, 1 equiv.) was dissolved in phosphoryl trichloride (40 mL). The mixture was stirred for 2 hours at 120° C. The solution was added to water (150 mL) slowly, and extracted with ethyl acetate (60 mL*3). Then the organic layer was washed by brine (100 mL) and dried with sodium sulfate. The organic layer was concentrated and the residue purified by column chromatography (hexane:ethyl acetate=20:1) and the desired product (1.3 g, 83%) was obtained as a yellow solid. MS: m/z 239 (M+H)$^+$.

Example 86

Synthesis of (1r,4r)-N1-(5,5-dimethyl-6,7-dihydro-5H-cyclopenta[4,5]thieno[2,3-d]pyrimidin-4-yl)-N4,N4-dimethylcyclohexane-1,4-diamine (I-170)

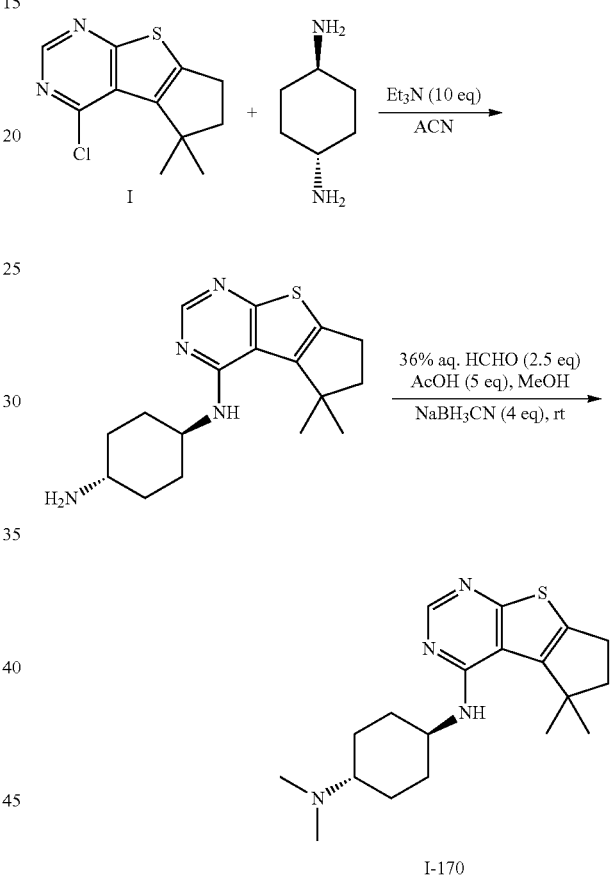

Synthesis of (1r,4r)-N1-(5,5-dimethyl-6,7-dihydro-5H-cyclopenta[4,5]thieno[2,3-d]pyrimidin-4-yl)cyclohexane-1,4-diamine Intermediate I (238 mg, 1 mmol, 1 equiv.) and trans-1,4-diaminocyclohexane (1.1 g, 10 mmol, 10 equiv.) were dissolved in acetonitrile (15 mL). Then triethylamine (1 g, 10 mmol, 10 equiv.) was added to the mixture. The mixture was stirred for 20 hours at 50° C. Then the mixture was concentrated and the residue was purified by reverse phase chromatography on a Biotage instrument. The desired product (154 mg, 48%) was obtained as a yellow solid. MS: m/z 317 (M+H)$^+$.

Synthesis of Compound I-170

(1r,4r)-N1-(5,5-dimethyl-6,7-dihydro-5H-cyclopenta[4,5]thieno[2,3-d]pyrimidin-4-yl)cyclohexane-1,4-diamine (140 mg, 0.44 mmol, 1 equiv.) was dissolved in methanol (5 mL). 36% aq. formaldehyde (92 mg, 1.1 mmol, 2.5 equiv.) and acetic acid (133 mg, 2.2 mmol, 5 equiv.) were added to the solution. The mixture was stirred for 10 minutes at room temperature, and then sodium cyanoborohydride (377 mg, 1.77 mmol, 4 equiv.) was added to the mixture. The latter was stirred for 20 hours at room temperature. Then the solution was added to water (50 mL) slowly, and extracted with ethyl acetate (50 mL*3). The organic layer was washed with brine (100 mL), and dried with sodium sulfate. The organic layer was concentrated and purified by preparative HPLC. The desired product I-170 (31 mg, 20%) was obtained as a white solid. $^1$H NMR: (400 MHz, CDCl$_3$) δ 8.36 (s, 1 H), 5.04 (d, 1 H), 4.17-2.24 (m, 1 H), 3.22 (t, 1 H), 2.97 (t, 2 H), 2.78 (m, 6 H), 2.40 (d, 2 H), 2.33-2.37 (m, 4 H), 1.73 (dd, 2 H), 1.44 (s, 6 H), 1.25-1.42 (m, 2 H). MS: m/z 345 (M+H)$^+$.

Example 87

Synthesis of (1r,4r)-4-((5,5-dimethyl-6,7-dihydro-5H-cyclopenta[4,5]thieno[2,3-d]pyrimidin-4-yl)oxy)-N,N-dimethylcyclohexanamine (I-171)

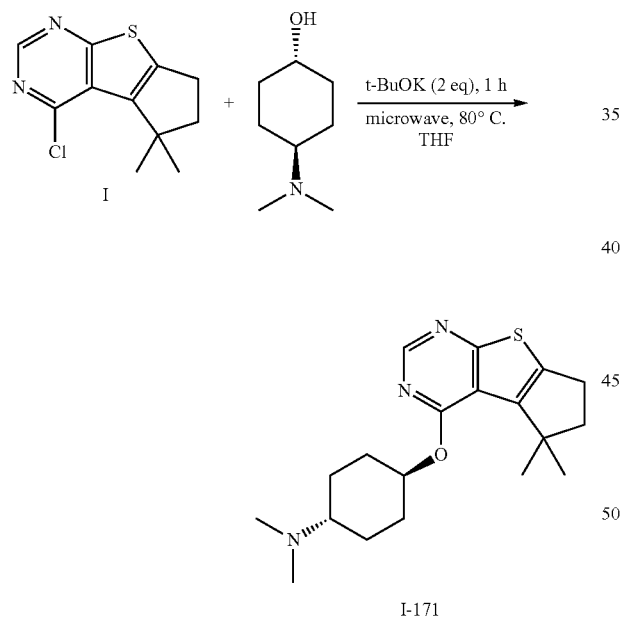

I-171

To a suspension of (1r,4r)-4-(dimethylamino)cyclohexanol (600 mg, 4.2 mmol, 1 equiv) in THF (10 mL) was added compound 1 (250 mg, 1.05 mmol) and t-BuOK (235 mg, 2.1 mmol). The suspension was heated to 80° C. in a sealed tube for 1 h in a microwave. The suspension was poured into water (10 mL) and then extracted by EtOAc (10 mL*3). The residue was purified by preparative HPLC to give a white solid product (30 mg, 10%). $^1$H NMR: (500 MHz, CDCl$_3$) δ 8.52 (1H, s), 8.47 (1H, 2), 5.31-5.29 (1H, m), 3.04-2.99 (3H, m), 2.63 (6H, s), 2.44 (2H, s), 2.33-2.30 (2H, t), 2.22 (2H, s), 1.68-1.64 (4H, m), 1.38 (6H, s). MS: m/z 346 (M+H)$^+$.

Example 88

Synthesis of (1r,4r)-N-benzyl-4-((6,7-dihydro-5H-cyclopenta[4,5]thieno[2,3-d]pyrimidin-4-yl)oxy)-N-ethylcyclohexanamine (I-117)

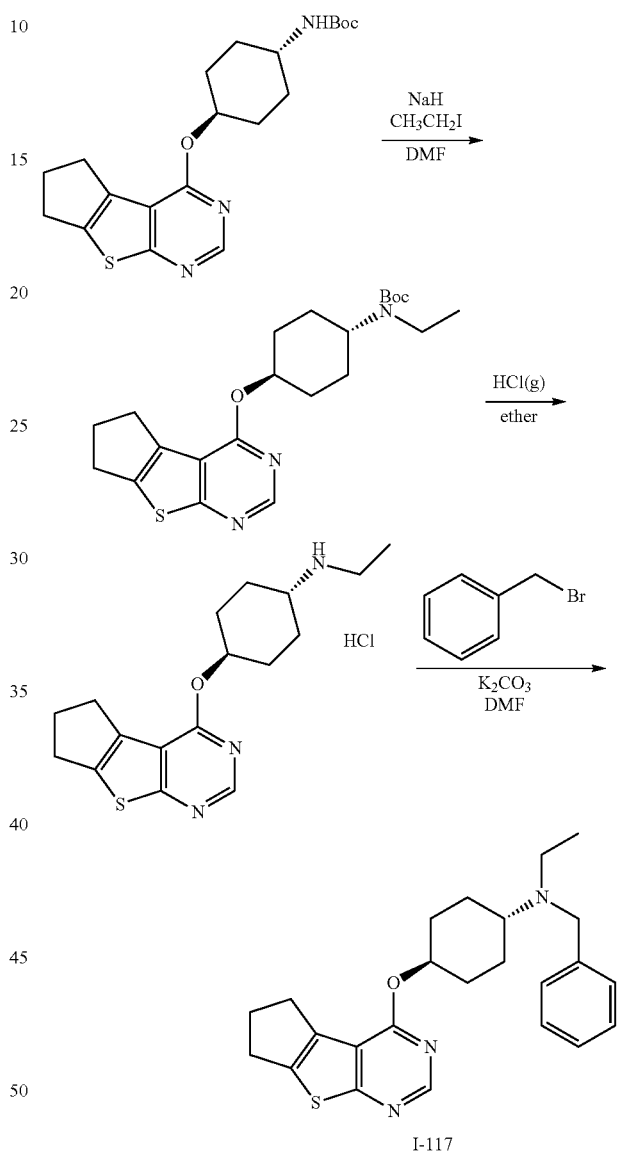

I-117

Synthesis of tert-butyl ((1r,4r)-4-((6,7-dihydro-5H-cyclopenta[4,5]thieno[2,3-d]pyrimidin-4-yl)oxy) cyclohexyl)(ethyl)carbamate To a 50-mL round-bottom flask was added a solution of tert-butyl N-(4-[7-thia-9,11-diazatricyclo[6.4.0.0ˆ[2,6]] dodeca-1(8),2(6),9,11-tetraen-12-yloxy]cyclohexyl)carbamate (prepared as in Example 19; 350 mg, 0.90 mmol, 1.00 equiv) in N,N-dimethylformamide (10 mL). This was followed by the addition of sodium hydride (108 mg, 4.50 mmol, 5.01 equiv) at 0-5° C. To this solution was added iodoethane (842.4 mg, 5.40 mmol, 6.01 equiv) dropwise with stirring at 0-5° C. The resulting solution was stirred overnight at room temperature. The reaction was then quenched by the addition of 10 mL of water. The resulting solution was extracted with 3×100 mL of ethyl acetate and the organic layers combined. The resulting mixture was washed with 3×200 mL of brine. The mixture was dried over anhydrous sodium sulfate and concentrated under vacuum. This resulted in 300 mg (80%) of tert-butyl 4-[7-thia-9,11-diazatricyclo[6.4.0.0ˆ[2,6]]dodeca-1(8),2(6),9,11-tetraen-12-yloxy]cyclohexyl N-ethylcarbamate as yellow oil.

Synthesis of N-ethyl-4-[7-thia-9,11-diazatricyclo [6.4.0.0ˆ[2,6]]dodeca-1(8),2(6),9,11-tetraen-12-yloxy]cyclohexan-1-amine hydrochloride To a 100-mL round-bottom flask was added tert-butyl N-ethyl-N-(4-[7-thia-9,11-diazatricyclo[6.4.0.0ˆ[2,6]]dodeca-1(8),2(6),9,11-tetraen-12-yloxy]cyclohexyl)carbamate (300 mg, 0.72 mmol, 1.00 equiv) and ether (20 mL). Hydrogen chloride (g) was introduced at 0-5° C. The resulting solution was stirred for 5 h at 0-5° C. in a water/ice bath. The resulting mixture was concentrated under vacuum. This resulted in 240 mg (94%) of N-ethyl-4-[7-thia-9,11-diazatricyclo[6.4.0.0ˆ[2,6]]dodeca-1(8),2(6),9,11-tetraen-12-yloxy] cyclohexan-1-amine hydrochloride as a light yellow solid.

Synthesis of Compound I-117

To a 50-mL round-bottom flask was added N-ethyl-4-[7-thia-9,11-diazatricyclo[6.4.0.0ˆ[2,6]]dodeca-1(8),2(6),9,11-tetraen-12-yloxy]cyclohexan-1-amine hydrochloride (200 mg, 0.57 mmol, 1.00 equiv), (bromomethyl)benzene (116 mg, 0.68 mmol, 1.20 equiv) and potassium carbonate (312 mg, 2.26 mmol, 4.00 equiv) in N,N-dimethylformamide (10 mL). The resulting solution was stirred overnight at 40° C. in an oil bath. The resulting solution was diluted with 100 mL of an ice-water mixture. The resulting solution was extracted with 3×100 mL of ethyl acetate and the organic layers combined. The resulting mixture was washed with 3×200 mL of brine. The mixture was dried over anhydrous sodium sulfate and concentrated under vacuum. The residue was purified by preparative HPLC (2#-Waters 2767-2(HPLC-08)) under the following conditions: column: Xbridge Prep Phenyl, 5 um, 19*150 mm; mobile phase: water (50 mM ammonium bicarbonate) and acetonitrile (10.0% acetonitrile up to 30.0% in 2 min, up to 50.0% in 8 min, up to 100.0% in 1 min, down to 10.0% in 1 min); detector: UV 254 nm. This resulted in 34.5 mg (15%) of N-benzyl-N-ethyl-4-[7-thia-9,11-diazatricyclo[6.4.0.0ˆ[2,6]]dodeca-1(8),2(6),9,11-tetraen-12-yloxy]cyclohexan-1-amine as a white solid. $^1$H NMR: (400 MHz, CDCl$_3$) δ 8.50 (1H, s), 7.62-7.22 (5H, m), 5.24-5.15 (1H, m), 3.66 (2H, s), 3.03-2.99 (4H, t), 2.67-2.43 (5H, m), 2.29-2.21 (2H, m), 1.97-1.94 (2H, m), 1.64-1.44 (4H, m), 1.06 (3H, t). MS: m/z 408 (M+H)$^+$.

Example 89

Synthesis of Intermediate J

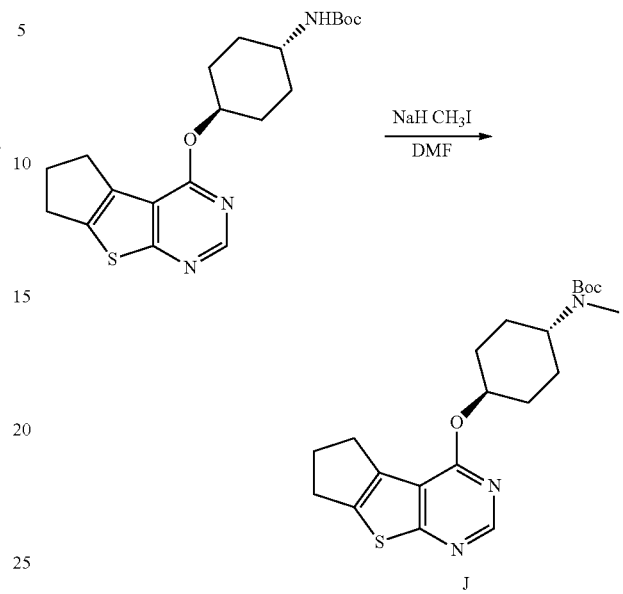

To a 50-mL round-bottom flask was added a solution of tert-butyl N-(4-[7-thia-9,11-diazatricyclo[6.4.0.0ˆ[2,6]]dodeca-1(8),2(6),9,11-tetraen-12-yloxy]cyclohexyl)carbamate (350 mg, 0.90 mmol, 1.00 equiv) in N,N-dimethylformamide (10 mL). This was followed by the addition of sodium hydride (108 mg, 4.50 mmol, 5.01 equiv) at 0-5° C. To this was added iodomethane (766.8 mg, 5.40 mmol, 6.01 equiv) dropwise with stirring at 0-5° C. The resulting solution was stirred overnight at room temperature. The reaction was then quenched by the addition of 10 mL of water. The resulting solution was extracted with 3×100 mL of ethyl acetate and the organic layers combined. The resulting mixture was washed with 3×100 mL of brine. The mixture was dried over anhydrous sodium sulfate and concentrated under vacuum. This resulted in 300 mg (83%) of intermediate J as a yellow oil.

Example 90

Synthesis of N-methyl-N-(3-phenylpropyl)-4-[7-thia-9,11-diazatricyclo[6.4.0.0ˆ[2,6]]dodeca-1(8),2 (6),9,11-tetraen-12-yloxy]cyclohexan-1-amine (I-116)

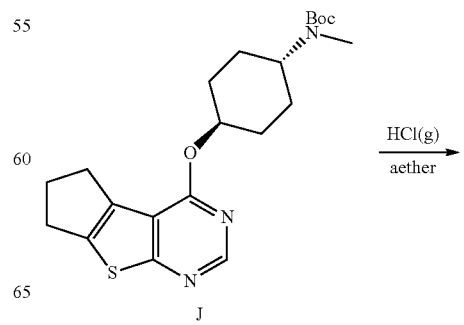

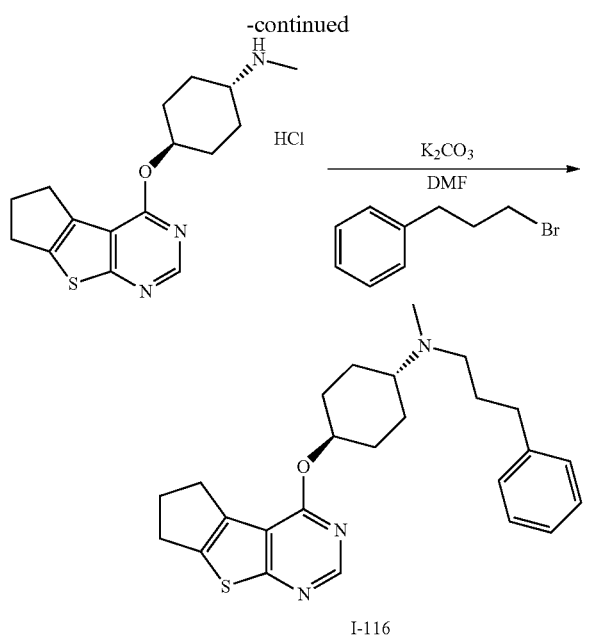

Synthesis of (1r,4r)-4-((6,7-dihydro-5H-cyclopenta[4,5]thieno[2,3-d]pyrimidin-4-yl)oxy)-N-methylcyclohexanamine hydrochloride To a 100-mL round-bottom flask was added a solution of intermediate J (300 mg, 0.74 mmol, 1.00 equiv) in ether (20 mL). To the above hydrogen chloride (g) was introduced in at 0-5° C. The resulting solution was stirred for 5 h at 0-5° C. in a water/ice bath. The resulting mixture was concentrated under vacuum. This resulted in 250 mg (crude) of N-methyl-4-[7-thia-9,11-diazatricyclo[6.4.0.0^[2,6]]dodeca-1(8),2(6),9,11-tetraen-12-yloxy]cyclohexan-1-amine hydrochloride as a light yellow solid.

Synthesis of Compound I-116

To a 50-mL round-bottom flask was added (3-bromopropyl)benzene (200 mg, 1.00 mmol, 1.00 equiv), N-methyl-4-[7-thia-9,11-diazatricyclo[6.4.0.0^[2,6]]dodeca-1(8),2(6),9,11-tetraen-12-yloxy]cyclohexan-1-amine hydrochloride (141.3 mg, 0.42 mmol, 1.20 equiv), potassium carbonate (326 mg, 2.36 mmol, 4.00 equiv) and N,N-dimethylformamide (10 mL). The resulting solution was stirred for 3 days at 40° C. in an oil bath. The resulting solution was diluted with 100 mL of an ice/water mixture. The resulting solution was extracted with 3×100 mL of ethyl acetate and the organic layers combined. The resulting mixture was washed with 3×200 mL of brine. The mixture was dried over anhydrous sodium sulfate and concentrated under vacuum. The crude product was purified by preparative HPLC (2#-Waters 2767-2(HPLC-08)) under the following conditions: column: SunFire Prep C18, 19*150 mm 5 um; mobile phase: water (0.05% sodium bicarbonate) and acetonitrile (5.0% acetonitrile up to 12.0% in 2 min, up to 20.0% in 10 min, up to 100.0% in 1 min, down to 5.0% in 1 min); detector: UV 254 nm. Purification afforded 48.1 mg (11%) of Compound I-116 as a colorless oil. $^1$H NMR: (400 MHz, CDCl$_3$) δ 8.48 (1H, s), 7.31-7.15 (5H, m), 5.18-5.14 (1H, m), 3.02-2.97 (4H, t), 2.66-2.61 (2H, t), 2.52-2.42 (5H, m), 2.05 (3H, s), 1.90-1.75 (5H, m), 1.58-1.42 (4H, m). 1.30-1.24 (1H, m). MS: m/z 422 (M+H)$^+$.

Example 91

Synthesis of N-methyl-N-(2-phenylethyl)-4-[7-thia-9,11-diazatricyclo[6.4.0.0[2,6]]dodeca-1(8),2(6),9,11-tetraen-12-yloxy]cyclohexan-1-amine (I-121)

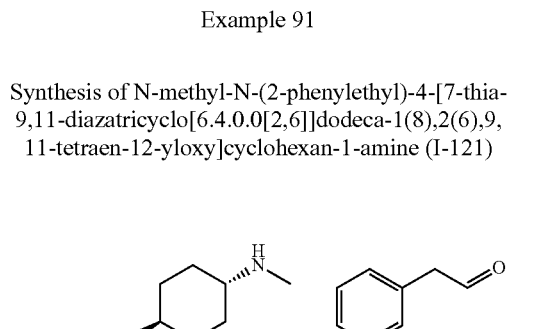

To a 25-mL round-bottom flask was added a solution of Compound I-66 (60 mg, 0.20 mmol, 1.00 equiv) in methanol (5 mL), phenylacetaldehyde (47.5 mg, 0.40 mmol, 2.00 equiv), acetic acid (1-2 drops) and NaBH$_3$CN (24.5 mg, 0.39 mmol, 2.00 equiv) at room temperature. The resulting mixture was stirred overnight at ambient temperature. After completion of the reaction, the resulting mixture was concentrated under vacuum. The crude product (100 mg) was purified by preparative HPLC (Pre-HPLC-001(SHIMADZU)) under the following conditions: column: SunFire Prep C18, 19*150 mm 5 um; mobile phase: water (0.05% NH$_4$HCO$_3$) and CH$_3$CN (7.0% CH$_3$CN up to 47.0% in 22 min); UV detection at 254 nm. The resulting Compound I-121 (30 mg, 37%) was obtained as an off-white semi-solid. $^1$H NMR: (400 MHz, CDCl$_3$) δ 8.49 (s, 1H), 7.28-7.33 (m, 2H), 7.22 (t, 3H, J=7.2 Hz), 5.19 (t, 1H, J=4.0 Hz), 3.00-3.03 (m, 4H), 2.73-2.82 (m, 4H), 2.61 (s, 1H), 2.45-2.52 (m, 2H), 2.41 (s, 1H), 2.29 (s, 2H), 1.96 (s, 2H), 1.52-1.60 (m, 4H). MS: m/z 408 (M+H)$^+$.

Example 92

Synthesis of Intermediate K

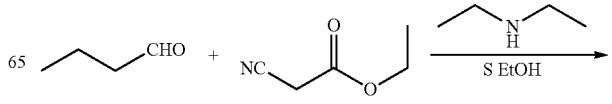

171

-continued

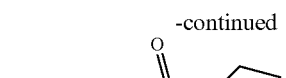
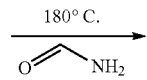

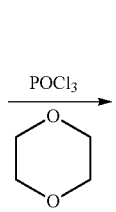

K

Synthesis of ethyl 2-amino-5-ethylthiophene-3-carboxylate

Diethylamine (21 g, 287.13 mmol, 1.00 equiv) was added to a mixture of butanal (20.16 g, 279.59 mmol, 1.00 equiv), ethyl 2-isocyanoacetate (31.64 g, 280 mmol, 1.00 equiv) and S (8.9 g, 1.00 equiv) in ethanol (100 mL) dropwise with stirring. The resulting solution was stirred for 3 h at room temperature. The reaction was then quenched by the addition of 400 mL of water and ice mixture. The solids were collected by filtration and dried in an oven under reduced pressure to yield 36 g (65%) of ethyl 2-amino-5-ethylthiophene-3-carboxylate as a yellow solid. MS: m/z 200 (M+H)$^+$.

Synthesis of 6-ethylthieno[2,3-d]pyrimidin-4-ol

A solution of ethyl 2-amino-5-ethylthiophene-3-carboxylate (5 g, 25.09 mmol, 1.00 equiv) in formamide (60 mL) was stirred for 4 h at 180° C. in an oil bath. The reaction mixture was cooled and diluted with 200 mL of water. The solids were collected by filtration and dried in an oven under reduced pressure to give 2.6 g (57%) of 6-ethylthieno[2,3-d]pyrimidin-4-ol as a black solid. MS: m/z 181 (M+H)$^+$.

Synthesis of Intermediate K

Phosphoryl trichloride (2.3 mL, 3.00 equiv) was added to a solution of 6-ethylthieno[2,3-d]pyrimidin-4-ol (1.5 g, 8.32 mmol, 1.00 equiv) in dioxane (15 mL) dropwise with stirring at room temperature. The resulting solution was stirred overnight at 110° C. in an oil bath. The resulting solution was cooled and quenched by the addition of 100 mL of water and ice mixture. The resulting solution was extracted with 3×100 mL of ethyl acetate and the organic layers combined. The resulting mixture was washed with 3×200 mL of brine. The mixture was dried over anhydrous sodium sulfate and concentrated under vacuum. The residue was applied onto a silica gel column with ethyl acetate/petroleum ether (1/10) to yield

172

700 mg (42%) of 4-chloro-6-ethylthieno[2,3-d]pyrimidine as a yellow solid. MS: m/z 199 (M+H)$^+$.

Example 93

Synthesis of 1-(6-ethylthieno[2,3-d]pyrimidin-4-yl)-N,N-dimethylpiperidin-4-amine dihydrochloride (I-172)

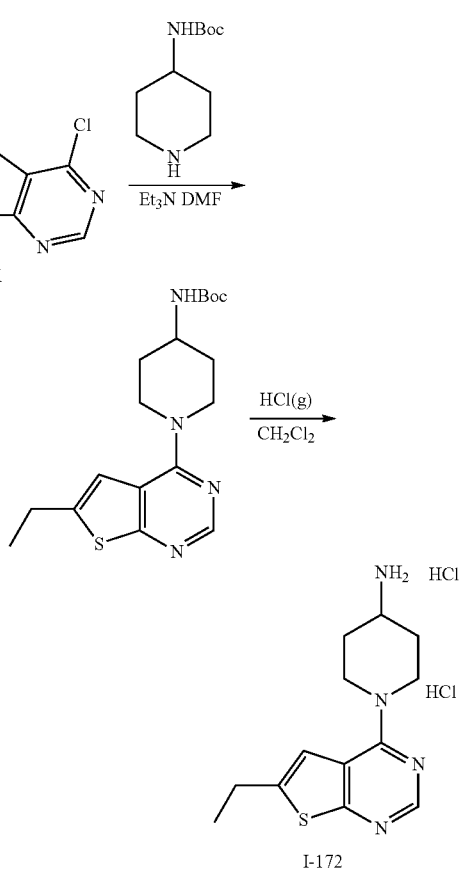

Synthesis of tert-butyl N-(1-[6-ethylthieno[2,3-d]pyrimidin-4-yl]piperidin-4-yl)carbamate A mixture of intermediate K (507 mg, 2.53 mmol, 1.00 equiv), tert-butyl N-(piperidin-4-yl)carbamate (2.56 g, 12.78 mmol, 5.00 equiv) and triethylamine (776 mg, 7.67 mmol, 3.00 equiv) in N,N-dimethylformamide (10 mL) was stirred overnight at room temperature. The resulting solution was diluted with 100 mL of water. The resulting solution was extracted with 3×150 mL of ethyl acetate and the organic layers combined and dried over anhydrous sodium sulfate and concentrated under vacuum to yield 900 mg (98%) of tert-butyl N-(1-[6-ethylthieno[2,3-d]pyrimidin-4-yl]piperidin-4-yl)carbamate as a yellow solid. MS: m/z 363 (M+H)$^+$.

Synthesis of 1-[6-ethylthieno[2,3-d]pyrimidin-4-yl]piperidin-4-amine dihydrochloride (I-172)

Excess hydrogen chloride gas was bubbled into a solution of tert-butyl N-(1-[6-ethylthieno[2,3-d]pyrimidin-4-yl]piperidin-4-yl)carbamate (1 g, 2.76 mmol, 1.00 equiv) in dichloromethane (20 mL). The resulting solution was stirred for 2 h at 0° C. in a water/ice bath. The resulting mixture was concentrated under vacuum to give 650 mg (70%) of 1-[6-ethylthieno[2,3-d]pyrimidin-4-yl]piperidin-4-amine dihydrochloride as a yellow solid. $^1$H NMR: (400 MHz, CDCl$_3$) δ 8.61 (1H, s), 7.45 (1H, s), 5.70 (1H, s), 4.68-4.65 (2H, d), 3.43-3.37 (3H, t), 2.96-2.91 (2H, q), 2.16-2.13 (2H, d), 1.70-1.64 (2H, t), 1.29-1.26 (3H, t). MS: m/z 263 (M−2HCl+H)$^+$.

Example 94

Synthesis of 1-(6-ethylthieno[2,3-d]pyrimidin-4-yl)-N,N-dimethylpiperidin-4-amine dihydrochloride (I-173)

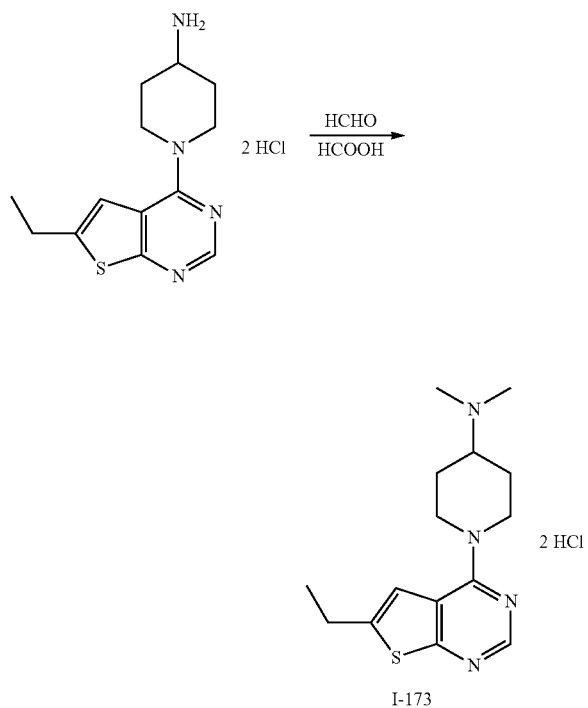

To a 100-mL round-bottom flask was added Compound I-172 (440 mg, 1.31 mmol, 1.00 equiv), formaldehyde (380 mg, 12.66 mmol, 10.0 equiv) and formic acid (20 mL). The resulting solution was heated to reflux for 14 hr. The reaction mixture was cooled with a water/ice bath. The pH value of the solution was adjusted to 10 with sodium hydroxide (aq). The solids were collected by filtration. The crude product (500 mg) was purified by preparative HPLC (2#-Waters 2767-2 (HPLC-08)) under the following conditions: column: SunFire Prep C18, 19*150 mm 5 um; mobile phase: water (50 mM ammonium bicarbonate) and acetonitrile (10.0% acetonitrile up to 15.0% in 2 min, up to 37.0% in 8 min, up to 100.0% in 1 min, down to 10.0% in 1 min); detector: UV 220 nm. The product was treated with HCl (aq) to give 119.3 mg (25%) of Compound I-173 as a yellow solid. $^1$H NMR: (400 MHz, CD$_3$OD) δ 8.58 (1H, s), 7.43 (1H, s), 4.98-5.02 (2H, d), 3.59-3.65 (1H, t), 3.37-3.44 (2H, t), 2.93-2.98 (2H, q), 2.82 (6H, s), 2.25-2.28 (2H, d), 1.80-1.88 (2H, q), 1.28-1.33 (3H, t). MS: m/z 291 (M−2HCl+H)$^+$.

Example 95

Synthesis of Intermediate L

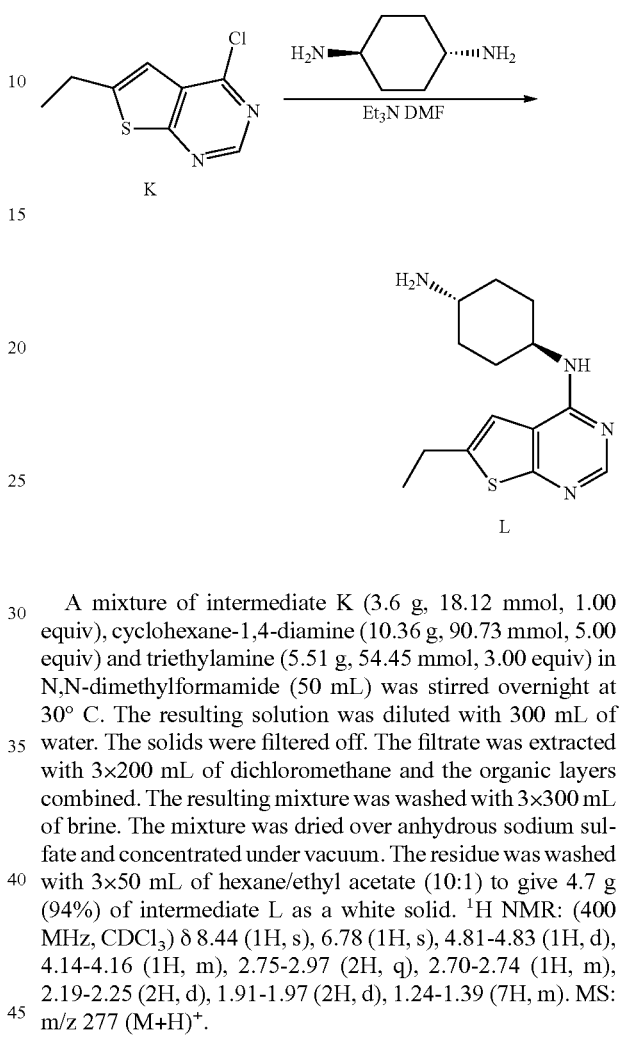

A mixture of intermediate K (3.6 g, 18.12 mmol, 1.00 equiv), cyclohexane-1,4-diamine (10.36 g, 90.73 mmol, 5.00 equiv) and triethylamine (5.51 g, 54.45 mmol, 3.00 equiv) in N,N-dimethylformamide (50 mL) was stirred overnight at 30° C. The resulting solution was diluted with 300 mL of water. The solids were filtered off. The filtrate was extracted with 3×200 mL of dichloromethane and the organic layers combined. The resulting mixture was washed with 3×300 mL of brine. The mixture was dried over anhydrous sodium sulfate and concentrated under vacuum. The residue was washed with 3×50 mL of hexane/ethyl acetate (10:1) to give 4.7 g (94%) of intermediate L as a white solid. $^1$H NMR: (400 MHz, CDCl$_3$) δ 8.44 (1H, s), 6.78 (1H, s), 4.81-4.83 (1H, d), 4.14-4.16 (1H, m), 2.75-2.97 (2H, q), 2.70-2.74 (1H, m), 2.19-2.25 (2H, d), 1.91-1.97 (2H, d), 1.24-1.39 (7H, m). MS: m/z 277 (M+H)$^+$.

Example 96

Synthesis of 4-N-[6-ethylthieno[2,3-d]pyrimidin-4-yl]-1-N,1-N-dimethylcyclohexane-1,4-diamine (I-174)

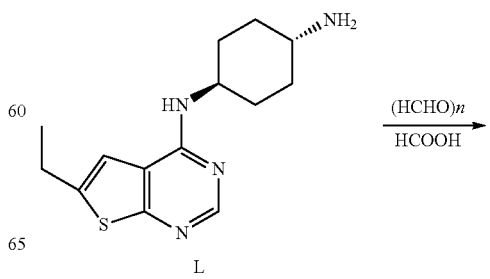

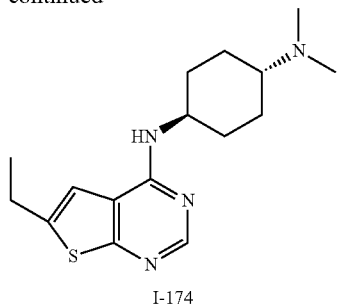

I-174

A solution of intermediate L (828 mg, 3.00 mmol, 1.00 equiv) and paraformaldehyde (900 mg, 30.00 mmol, 10.00 equiv) in formic acid (10 mL) was stirred at 110° C. overnight. The reaction mixture was quenched with 100 mL of an ice/water mixture. The pH value of the solution was adjusted to 12 with 2 M aqueous sodium hydroxide solution. The solid was collected by filtration and the residue purified on a silica gel column, eluting with dichloromethane/methanol (5:1) to give 263 mg (29%) of Compound I-174 as a yellow solid. $^1$H NMR: (400 MHz, CDCl$_3$) δ 8.45 (1H, s), 6.80 (1H, s), 4.89-4.87 (1H, d), 4.18-4.09 (1H, m), 2.97-2.89 (2H, q), 2.34-2.25 (9H, m), 2.17-2.01 (2H, d), 1.54-1.45 (2H, q), 1.44-1.34 (5H, m). MS: m/z 305 (M+H)$^+$.

Example 97

Synthesis of 1-N-ethyl-1-N-[6-ethylthieno[2,3-d]pyrimidin-4-yl]-4-N,4-N-dimethylcyclohexane-1,4-diamine (I-175)

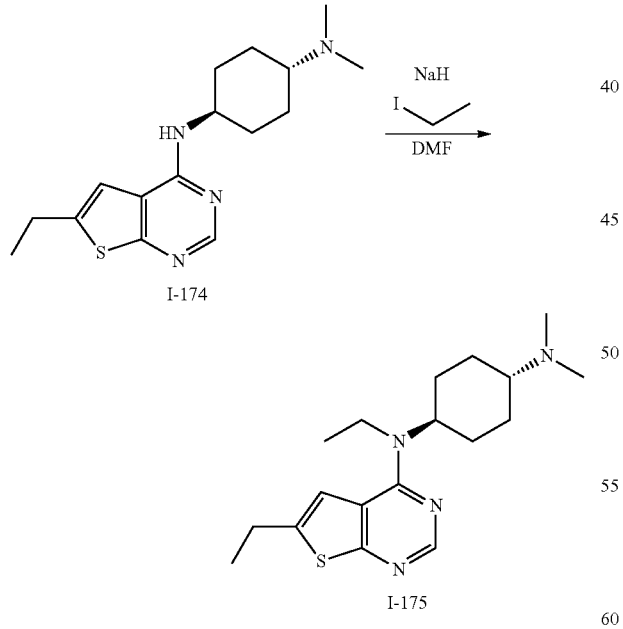

Into a 100-mL 3-necked round-bottom flask purged and maintained with an inert atmosphere of nitrogen, was placed a solution of I-174 (1.0 g, 3.28 mmol, 1.00 equiv) in N,N-dimethylformamide (10 mL). This was followed by the addition of sodium hydride (660 mg, 27.50 mmol, 8.37 equiv), in portions at 0° C. in 2 min. The resulting solution was stirred for 2 h at 10° C. To this was added iodoethane (770 mg, 4.94 mmol, 1.50 equiv) dropwise with stirring at 10° C. in 5 min. The resulting solution was allowed to react, with stirring, for an additional 1 h at 10° C. The reaction was then quenched by the addition of 100 mL of water. The resulting solution was extracted with 3×50 mL of ethyl acetate and the organic layers combined. The resulting mixture was washed with 3×50 mL of brine. The mixture was dried over anhydrous sodium sulfate and concentrated under vacuum. The crude product was purified by preparative HPLC (2#-Gilson Gx 281(HPLC-09)) under the following conditions: column: Xbridge Prep C18, 5 um, 19*150 mm; mobile phase: water (50 mmol NH$_4$HCO$_3$) and CH$_3$CN (10.0% CH$_3$CN up to 17.0% in 1 min, up to 35.0% in 10 min, hold 100.0% in 2 min); detector: UV 220 nm. This resulted in 400 mg (37%) of Compound I-175 as a white solid. $^1$H NMR: (400 MHz, CDCl$_3$) δ 8.39 (1H, s), 6.95 (1H, s), 4.61-4.67 (1H, t), 3.63-3.68 (2H, q), 2.87-2.93 (2H, q), 2.33 (6H, s), 2.23-2.29 (1H, t), 2.04-2.07 (2H, d), 1.94-1.97 (2H, d), 1.65-1.74 (2H, q), 1.41-1.50 (2H, q), 1.32-1.38 (6H, m).
MS: m/z 333 (M+H)$^+$.

Example 98

Synthesis of 1-N-[6-ethylthieno[2,3-d]pyrimidin-4-yl]-4-N-methylcyclohexane-1,4-diamine (I-176)

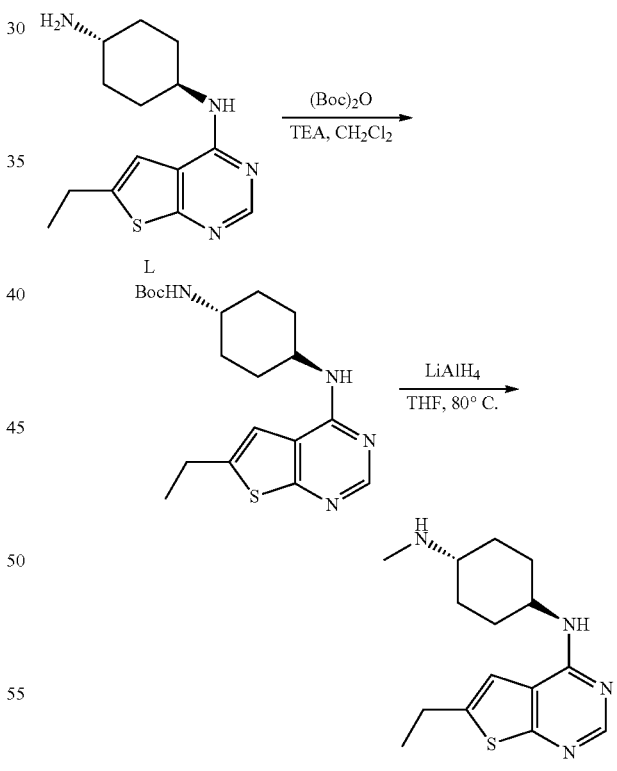

Synthesis of tert-butyl N-[4-([6-ethylthieno[2,3-d]pyrimidin-4-yl]amino)cyclohexyl]carbamate A mixture of intermediate L (1.5 g, 5.43 mmol, 1.00 equiv), di-tert-butyl dicarbonate (1.3 g, 5.96 mmol, 1.10 equiv) and triethylamine (820 mg, 8.12 mmol, 1.50 equiv) in dichloromethane (30 mL) was stirred for 3 h at room temperature. The resulting mixture was concentrated under vacuum to give 2 g (crude) of tert-butyl N-[4-([6-ethylthieno[2,3-d]pyrimidin-4-yl]amino)cyclohexyl]carbamate as a yellow solid. MS: m/z 377 (M+H)+.

Synthesis of Compound I-176

To a 250-mL 3-necked round-bottom flask was added a solution of tert-butyl N-[4-([6-ethylthieno[2,3-d]pyrimidin-4-yl]amino)cyclohexyl]carbamate (2.1 g, 5.58 mmol, 1.00 equiv) in tetrahydrofuran (40 mL) was added to a solution of lithium aluminium tetrahydride (1.06 g, 27.89 mmol, 5.00 equiv) in tetrahydrofuran (60 mL) dropwise with stirring at room temperature. The resulting solution was stirred for 2 h at 80° C. in an oil bath. The reaction was then quenched by the addition of 20 mL of tetrahydrofuran and water mixture. The solids were filtered off. The filtrate was extracted with 3×100 mL of dichloromethane and the organic layers combined and dried over anhydrous sodium sulfate and concentrated under vacuum. The crude product was purified by preparative HPLC (2#-Waters 2767-2(HPLC-08)) under the following conditions: column: Xbridge Prep C$_{18}$, 5 um, 19*150 mm; mobile phase: water (50 mM ammonium bicarbonate) and acetonitrile (10% acetonitrile up to 35% in 10 min, up to 100% in 1 min, down to 10% in 1 min); detector: UV 220 nm. Purification afforded 398.4 mg (25%) of Compound I-176 as a yellow solid. $^1$H NMR: (400 MHz, CDCl$_3$) δ 8.45 (1H, s), 6.790 (1H, s), 4.805-4.825 (1H, d), 4.170 (1H, m), 2.857-2.954 (2H, q), 2.490 (3H, s), 2.416-2.441 (1H, m), 2.237-2.258 (2H, d), 2.067-2.090 (2H, d),1.265-1.406 (7H, m).

MS: m/z 291 (M+H)+.

Example 99

Synthesis of 1-[6-ethylthieno[2,3-d]pyrimidin-4-yl]piperidine-4-carboxamide (I-177)

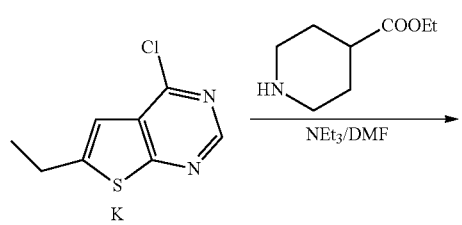

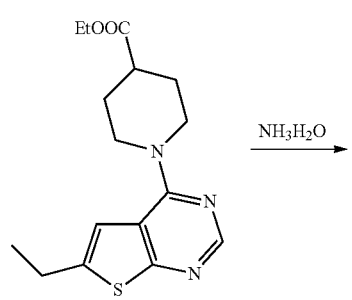

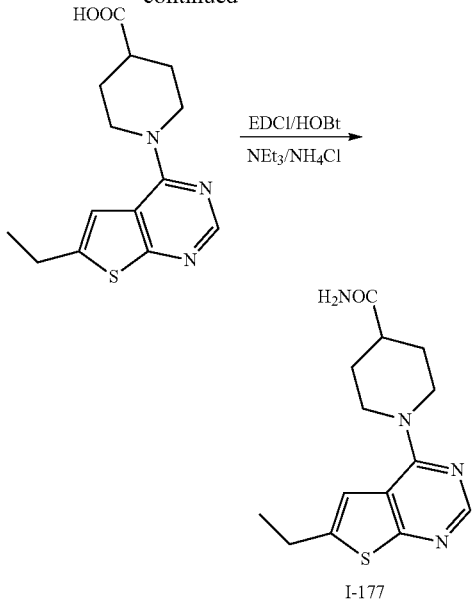

Synthesis of ethyl 1-[6-ethylthieno[2,3-d]pyrimidin-4-yl]piperidine-4-carboxylate A mixture of intermediate K (1 g, 5.03 mmol, 1.00 equiv), ethyl piperidine-4-carboxylate (828 mg, 5.27 mmol, 1.05 equiv) and triethylamine (1 g, 9.88 mmol, 1.96 equiv) in N,N-dimethylformamide (15 mL) was stirred for 13 h at room temperature. The reaction was then quenched by the addition of 20 mL of water. The resulting solution was extracted with 2×25 mL of ethyl acetate and the organic layers combined. The resulting mixture was washed with 1×50 mL of brine. The resulting mixture was dried and concentrated under vacuum to yield 1.4 g (87%) of ethyl 1-[6-ethylthieno[2,3-d]pyrimidin-4-yl]piperidine-4-carboxylate as a yellow oil.

Synthesis of ethyl 1-[6-ethylthieno[2,3-d]pyrimidin-4-yl]piperidine-4-carboxylate A solution of ethyl 1-[6-ethylthieno[2,3-d]pyrimidin-4-yl]piperidine-4-carboxylate (1.4 g, 4.38 mmol, 1.00 equiv) in ammonium hydroxide (50 mL) was heated to reflux for 12 hrs. The reaction mixture was cooled. The resulting mixture was concentrated under vacuum and dissolved in 20 ml of aqueous hydrogen chloride (12 N) and concentrated again to give 950 mg (crude) of 1-[6-ethylthieno[2,3-d]pyrimidin-4-yl]piperidine-4-carboxylic acid as a yellow solid.

Synthesis of Compound I-177

A mixture of 1-[6-ethylthieno[2,3-d]pyrimidin-4-yl]piperidine-4-carboxylic acid (950 mg, 3.26 mmol, 1.00 equiv), 1H-1,2,3-benzotriazol-1-ol (586 mg, 4.34 mmol, 1.33 equiv), N-(3-dimethylaminopropyl)-N'-ethylcarbodiimide hydrochloride (834 mg, 4.34 mmol, 1.33 equiv), amine hydrochloride (307 mg, 5.74 mmol, 1.76 equiv) and triethylamine (876 mg, 8.66 mmol, 2.66 equiv) in N,N-dimethylformamide (15 mL) was stirred for 12 h at 30° C. The reaction was then quenched by the addition of 30 mL of water. The resulting solution was extracted with 2×20 mL of ethyl acetate and the organic layers combined. The resulting mixture was washed with 1×50 mL of brine. The resulting mixture was concentrated under vacuum. The crude product was purified by preparative HPLC (2#-Waters 2767-2(HPLC-08)) under the following conditions: column: Xbridge Prep $C_{18}$, 5 um, 19*150 mm; mobile phase: water with 50 mmol ammonium bicarbonate and acetonitrile (10.0% acetonitrile up to 22.0% in 2 min, up to 32.0% in 10 min, up to 100.0% in 1 min, down to 10.0% in 1 min); detector: UV 220 nm. Purification afforded 167.4 mg (18%) of Compound I-177 as a white solid. $^1$H NMR: (400 MHz, CDCl$_3$) δ 8.45 (1H, s), 6.95 (1H, s), 5.48-5.53 (1H, d), 4.54-4.57 (2H, d), 3.18-3.24 (2H, t), 2.89-2.92 (2H, q), 2.49-2.55 (1H, m), 2.03-2.05 (2H, m), 1.84-1.94 (2H, m), 1.35-1.38 (3H, t). MS: m/z 291 (M+H)$^+$.

Example 100

Synthesis of (1-[6-ethylthieno[2,3-d]pyrimidin-4-yl]piperidin-4-yl)methanamine hydrochloride (I-178)

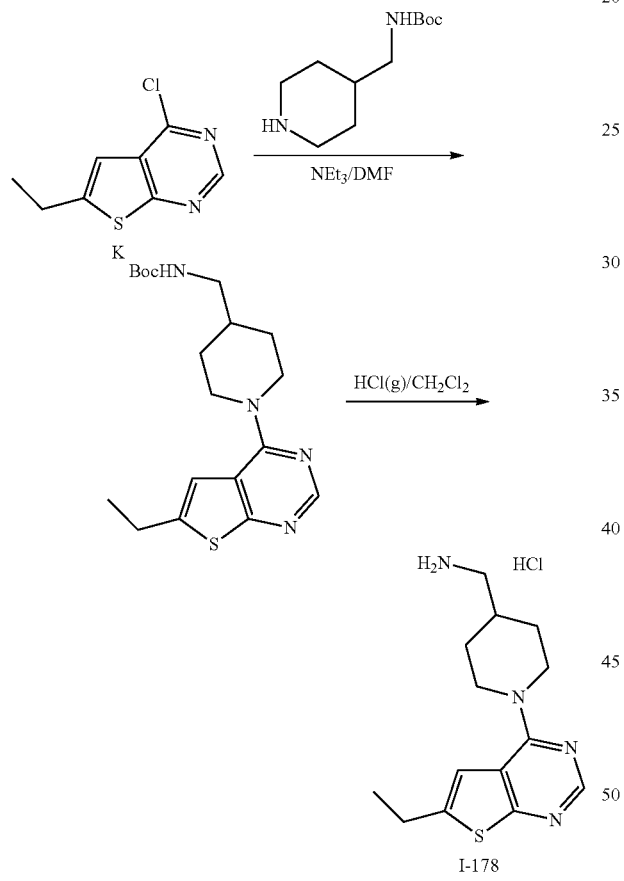

Synthesis of tert-butyl N-[(1-[6-ethylthieno[2,3-d]pyrimidin-4-yl]piperidin-4-yl)methyl]carbamate A mixture of intermediate K (2 g, 10.07 mmol, 1.00 equiv), tert-butyl N-(piperidin-4-ylmethyl)carbamate (2.25 g, 10.50 mmol, 1.04 equiv) and triethylamine (2 g, 19.76 mmol, 1.96 equiv) in N,N-dimethylformamide (30 mL) was stirred for 10 hours at 30° C. The reaction was then quenched by the addition of 50 mL of water. The resulting solution was extracted with 2×20 mL of ethyl acetate and the organic layers combined. The resulting mixture was washed with 1×50 mL of brine. The resulting mixture was dried and concentrated under vacuum to yield 3.4 g (90%) of tert-butyl N-[(1-[6-ethylthieno[2,3-d]pyrimidin-4-yl]piperidin-4-yl)methyl]carbamate as a yellow solid.

Synthesis of (1-[6-ethylthieno[2,3-d]pyrimidin-4-yl]piperidin-4-yl)methanamine hydrochloride (I-178).

Excess hydrogen chloride gas was bubbled into a solution of tert-butyl N-[(1-[6-ethylthieno[2,3-d]pyrimidin-4-yl]piperidin-4-yl)methyl]carbamate (3.4 g, 9.03 mmol, 1.00 equiv) in dichloromethane (30 mL). The resulting solution was stirred for 2 h at room temperature. The product was precipitated and collected by filtration. The solid was dried in an oven under reduced pressure to give 2.5 g (88%) of Compound I-178 as a yellow solid. $^1$H NMR: (400 MHz, CD$_3$OD) δ 8.59 (1H, s), 7.46 (1H, s), 4.90-4.95 (2H, d), 3.44-3.50 (2H, t), 3.02-3.07 (2H, q), 2.94-2.95 (2H, d), 2.16-2.21 (1H, m), 2.06-2.09 (2H, d), 1.49-1.55 (2H, q), 1.39-1.43 (3H, t). MS: m/z 277 (M+H)$^+$.

Example 101

Synthesis of [(1-[6-ethylthieno[2,3-d]pyrimidin-4-yl]piperidin-4-yl)methyl]dimethylamine hydrochloride (I-179)

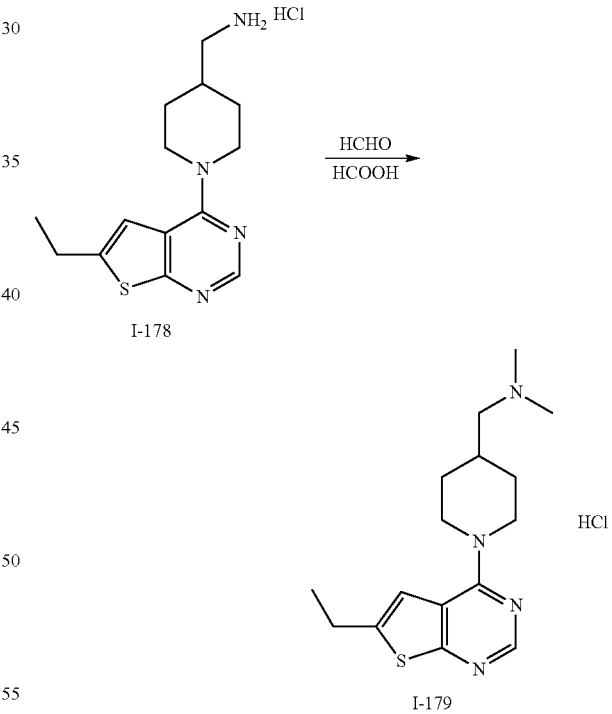

A mixture of Compound I-178 (500 mg, 1.60 mmol, 1.00 equiv) and formaldehyde (480 mg, 15.99 mmol, 10.00 equiv) in formic acid (10 ml, 88%) was heated to reflux for 12 hrs. The reaction mixture was cooled and concentrated under vacuum. The pH value of the solution was adjusted to 11 with sodium hydroxide (6N). The resulting solution was extracted with 3×30 mL of dichloromethane and the organic layers combined, dried and concentrated under vacuum. The residue was treated with HCl (aq) and concentrated again to give 108.2 mg (20%) of Compound I-179 as a white solid. $^1$H NMR: (400 MHz, D$_2$O) δ 8.36 (1H, s), 7.25 (1H, s), 4.63-4.66 (2H, d), 3.36-3.42 (2H, t), 3.04-3.06 (2H, d), 2.87-2.91 (2H, m), 2.85 (6H, s), 2.29-2.33 (1H, m), 1.92-1.96 (2H, d), 1.37-1.47 (2H, q), 1.23-1.27 (3H, t). MS: m/z 305 (M+H)$^+$.

Example 102

Synthesis of 2-[[4-(dimethylamino)cyclohexyl]([6-ethylthieno[2,3-d]pyrimidin-4-yl])amino]ethan-1-ol (I-180)

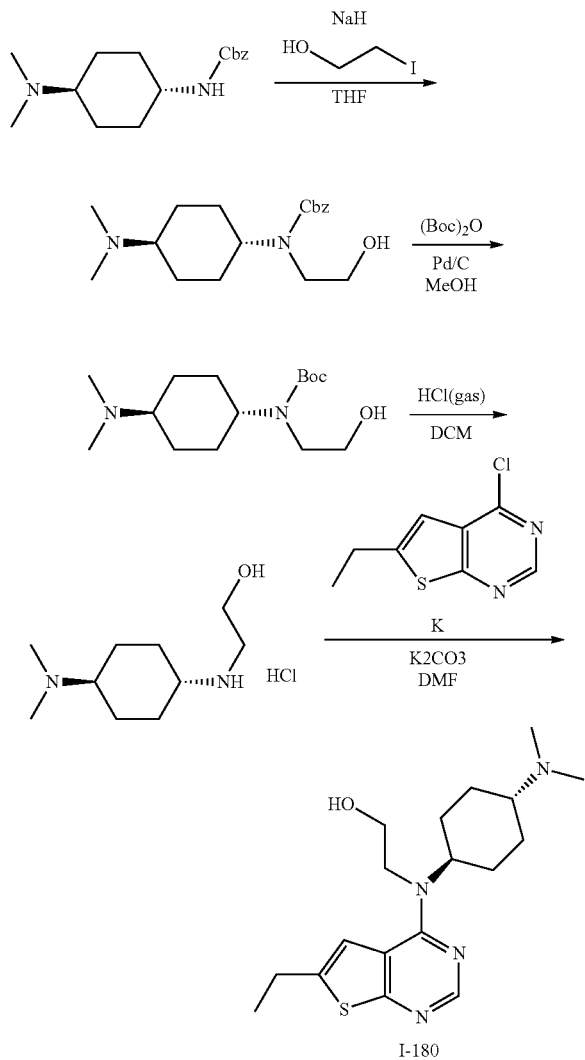

Synthesis of benzyl N-[4-(dimethylamino)cyclohexyl]-N-(2-hydroxyethyl)carbamate

To a 100-mL 3-necked round-bottom flask purged and maintained with an inert atmosphere of nitrogen was added a solution of benzyl N-[4-(dimethylamino)cyclohexyl]carbamate (2 g, 7.24 mmol, 1.00 equiv) in tetrahydrofuran (20 mL). This was followed by the addition of a solution of sodium hydride (320 mg 60% W/W, 7.971 mmol, 1.1 equiv) in tetrahydrofuran (10 mL) dropwise with stirring at 0-5° C. The resulting solution was stirred for 2 h at room temperature. To this was added 2-iodoethan-1-ol (2.5 g, 14.54 mmol, 2.01 equiv) dropwise with stirring at 0-5° C. The resulting solution was allowed to react, with stirring, for an additional 4 days at room temperature. The reaction was then quenched by the addition of 10 mL of water and concentrated under vacuum. The residue was washed with a solution of dichloromethane/methanol (10:1, 20 mL×4) and the organic layers combined, dried and concentrated to give 3.5 g (crude) of benzyl N-[4-(dimethylamino)cyclohexyl]-N-(2-hydroxyethyl)carbamate as a yellow oil. MS: m/z 321 (M+H)$^+$.

Synthesis of tert-butyl N-[4-(dimethylamino)cyclohexyl]-N-(2-hydroxyethyl)carbamate To a 100-mL round-bottom flask was added benzyl N-[4-(dimethylamino)cyclohexyl]-N-(2-hydroxyethyl)carbamate (3.5 g, 10.92 mmol, 1.00 equiv), methanol (50 mL), 10% palladium on carbon (1.0 g) and di-tert-butyl dicarbonate (2.4 g, 11.00 mmol, 1.01 equiv). The resulting solution was stirred overnight at room temperature. The solids were filtered off. The filtrate was concentrated under vacuum and then washed with 4×10 mL of ethyl acetate. The combined organic layers were concentrated under vacuum to yield 3.0 g (96%) of tert-butyl N-[4-(dimethylamino)cyclohexyl]-N-(2-hydroxyethyl)carbamate as a yellow oil. MS: m/z 287 (M+H)$^+$.

Synthesis of 2-[[4-(dimethylamino)cyclohexyl]amino]ethan-1-ol hydrochloride

To a 100-mL round-bottom flask was added a solution of tert-butyl N-[4-(dimethylamino)cyclohexyl]-N-(2-hydroxyethyl)carbamate (3.0 g, 10.47 mmol, 1.00 equiv) in dichloromethane (50 mL). To this solution was added hydrogen chloride (gas). The resulting solution was stirred for 3 h at 0-10° C. The resulting mixture was concentrated under vacuum to give 2.0 g (86%) of 2-[[4-(dimethylamino)cyclohexyl]amino]ethan-1-ol hydrochloride as a yellow oil. MS: m/z 187 (M+H)$^+$.

Synthesis of Compound I-180

To a 100-mL round-bottom flask was added a solution of intermediate D (500 mg, 2.71 mmol, 1.00 equiv) in N,N-dimethylformamide (10 mL), potassium carbonate (1.52 g, 10.92 mmol, 4.03 equiv) and 2-[4-(dimethylamino)cyclohexyl]aminoethan-1-ol hydrochloride (0.67 g, 3.016 mmol 1.2 eq). The resulting solution was stirred overnight at 50° C. and then quenched by the addition of 50 mL of water. The resulting mixture was concentrated under vacuum. The residue was purified by preparative HPLC (2#-Waters 2767-2 (HPLC-08)) under the following conditions: column: Xbridge Shield RP 18, 5 um, 19*150 mm; mobile phase: water (50 mmol NH$_4$HCO$_3$) and CH$_3$CN (10.0% CH$_3$CN up to 16.0% in 2 min, up to 30.0% in 10 min, up to 100.0% in 1 min, down to 10.0% in 1 min); detector: UV 220 nm. Purification afforded 66.5 mg (7%) of 2-[[4-(dimethylamino)cyclohexyl]([6-ethylthieno[2,3-d]pyrimidin-4-yl])amino]ethan-1-ol as a white solid. $^1$H NMR: (400 MHz, CD$_3$OD) δ 8.27 (1H, s), 7.24 (1H, s), 4.15-4.22 (1H, t), 4.04 (2H, s), 3.55-3.70 (3H, m), 3.18 (6H, s),2.91-2.99 (2H, dd), 2.31-2.40 (4H, t),1.80-1.91 (2H, m), 1.53-1.65 (2H, m),1.39-1.42 (3H, t). MS: m/z 349 (M+H)$^+$.

Example 103

Synthesis of 1-N,1-N-dimethyl-4-N-[6-(propan-2-yl)thieno[2,3-d]pyrimidin-4-yl]cyclohexane-1,4-diamine (I-181)

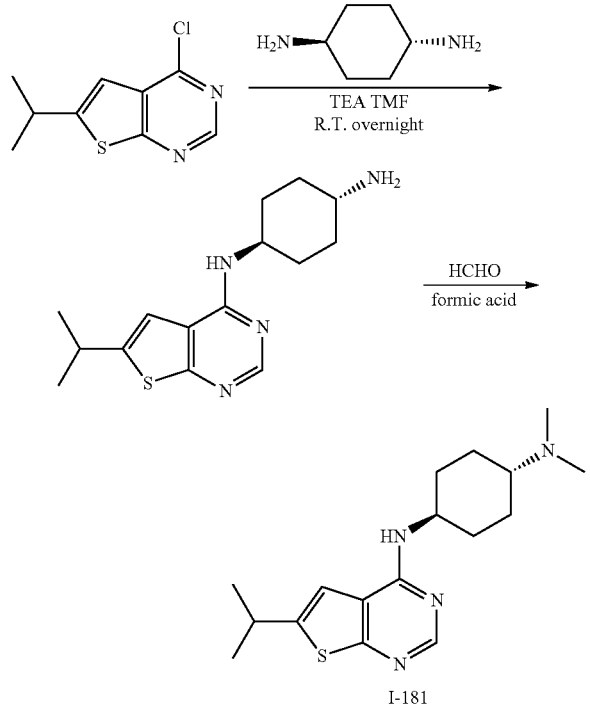

Synthesis of 1-N-[6-(propan-2-yl)thieno[2,3-d]pyrimidin-4-yl]cyclohexane-1,4-diamine To a 100-mL round-bottom flask was added a solution of commercially available 4-chloro-6-(propan-2-yl)thieno[2,3-d]pyrimidine (3 g, 14.10 mmol, 1.00 equiv) in N,N-dimethylformamide (30 mL), TEA (4.3 g, 42.49 mmol, 3.01 equiv), and cyclohexane-1,4-diamine (9.6 g, 84.07 mmol, 5.96 equiv). The resulting solution was stirred overnight at room temperature. The reaction was then quenched by the addition of 100 mL of water. The resulting solution was extracted with 3×100 mL of ethyl acetate and the organic layers combined. The resulting mixture was washed with 3×100 mL of brine. The mixture was dried over anhydrous sodium sulfate and concentrated under vacuum. This resulted in 3.5 g (85%) of 1-N-[6-(propan-2-yl)thieno[2,3-d]pyrimidin-4-yl]cyclohexane-1,4-diamine as a yellow oil.

Synthesis of Compound I-181

To a 100-mL round-bottom flask was added 1-N-[6-(propan-2-yl)thieno[2,3-d]pyrimidin-4-yl]cyclohexane-1,4-diamine (3.5 g, 12.05 mmol, 1.00 equiv), formic acid (35 mL) and polyoxymethylene (3.6 g, 112.35 mmol, 9.32 equiv). The resulting solution was heated to reflux overnight. The resulting mixture was concentrated under vacuum. The resulting solution was diluted with 100 mL of water. The pH value of the solution was adjusted to 10 with 3N sodium hydroxide at 0-5° C. The solids were collected by filtration. The crude product was purified by re-crystallization from MeCN. This resulted in 3.4 g (89%) of Compound I-181 as a white solid. $^1$H NMR: (400 MHz, CDCl$_3$) δ 8.45 (1H, s), 6.79 (1H, s), 4.82-4.84 (1H, d), 4.10-4.17 (1H, m), 3.19-3.25 (1H, m), 2.26-2.36 (9H, m), 2.00-2.03 (2H, d), 1.46-1.55 (2H, q), 1.39-1.41 (6H, d), 1.26-1.39 (2H, q). MS: m/z 319 (M+H)$^+$.

Example 104

Synthesis of N,N-dimethyl-4-[[6-(propan-2-yl)thieno[2,3-d]pyrimidin-4-yl]oxy]cyclohexan-1-amine (I-182)

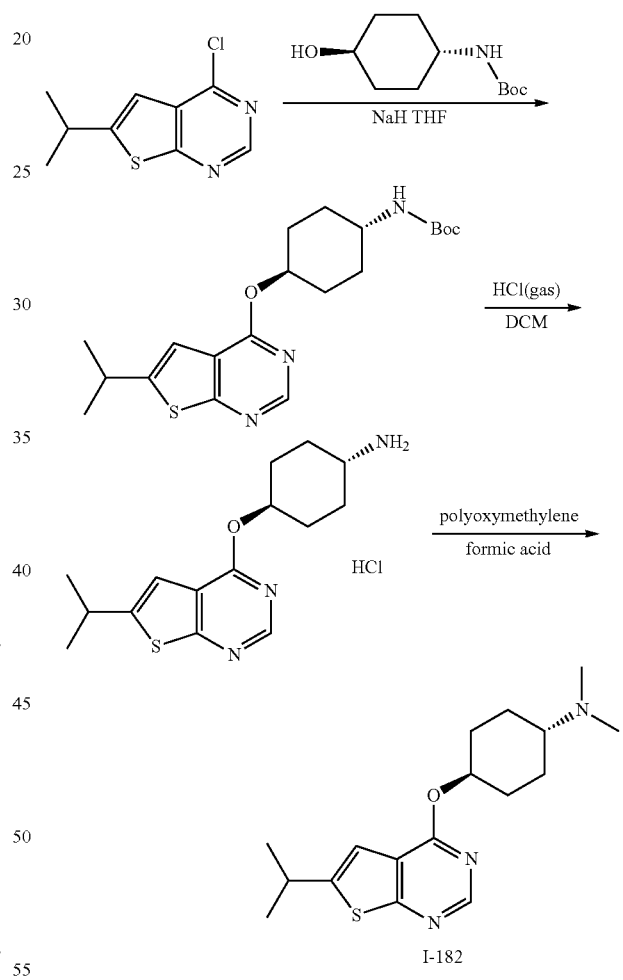

Synthesis of tert-butyl N-(4-[[6-(propan-2-yl)thieno[2,3-d]pyrimidin-4-yl]oxy]cyclohexyl)carbamate To a 100-mL 3-necked round-bottom flask purged and maintained with an inert atmosphere of nitrogen was placed a solution of tert-butyl N-(4-hydroxycyclohexyl)carbamate (3.3 g, 15.33 mmol, 1.10 equiv) in tetrahydrofuran (20 mL). This was followed by the addition of sodium hydride (800 mg, 33.33 mmol, 2.36 equiv) in portions at 0-5° C. The resulting solution was stirred for 2.5 h at room temperature.

To this was added a solution of commercially available 4-chloro-6-(propan-2-yl)thieno[2,3-d]pyrimidine (3.0 g, 14.10 mmol, 1.00 equiv) in tetrahydrofuran (10 mL) at 5-10° C. The resulting solution was stirred overnight at room temperature. The reaction mixture was cooled to 5-10° C. with a water/ice bath. The reaction was then quenched by the addition of 100 mL of water. The resulting mixture was concentrated under vacuum. The solids were collected by filtration. This resulted in 4.8 g (87%) of tert-butyl N-(4-[[6-(propan-2-yl)thieno[2,3-d]pyrimidin-4-yl]oxy]cyclohexyl)carbamate as a yellow solid. MS: m/z 392 (M+H)+.

Synthesis of 4-[[6-(propan-2-yl)thieno[2,3-d]pyrimidin-4-yl]oxy]cyclohexan-1-amine To a 100-mL round-bottom flask was added a solution of tert-butyl N-(4-[[6-(propan-2-yl)thieno[2,3-d]pyrimidin-4-yl]oxy]cyclohexyl)carbamate (4.8 g, 12.26 mmol, 1.00 equiv) in dichloromethane (100 mL). Hydrogen chloride was bubbled through the solution. The resulting solution was stirred for 5 h at 0-10° C. The resulting mixture was concentrated under vacuum. This resulted in 3.6 g (90%) of 4-[[6-(propan-2-yl)thieno[2,3-d]pyrimidin-4-yl]oxy]cyclohexan-1-amine hydrochloride as a yellow solid. MS: m/z 292 (M+H)+.

Synthesis of Compound I-182

A 100-mL round-bottom flask was charged with 4-[[6-(propan-2-yl)thieno[2,3-d]pyrimidin-4-yl]oxy]cyclohexan-1-amine hydrochloride (1.0 g, 3.05 mmol, 1.00 equiv), formic acid (20 mL) and polyoxymethylene (0.9 g). The resulting solution was stirred overnight at 110° C. The resulting mixture was concentrated under vacuum. The resulting solution was diluted with 100 mL of water. The pH value of the solution was adjusted to 10 with 3N sodium hydroxide. The resulting solution was extracted with 3×100 mL of ethyl acetate and the organic layers combined. The resulting mixture was washed with 3×100 mL of brine. The mixture was dried over anhydrous sodium sulfate and concentrated under vacuum. The crude product was purified by preparative HPLC (2#-Waters 2767-2(HPLC-08)) under the following conditions: column: Xbridge Prep C18, 5 um, 19*150 mm; mobile phase: water (50 mM NH4HCO3) and CH3CN (10.0% CH3CN up to 35.0% in 2 min, up to 58.0% in 8 min, up to 100.0% in 1 min, down to 10.0% in 1 min); detector: UV 220 nm. This resulted in 114.6 mg (12%) of Compound I-182 as a white solid. $^1$H NMR: (400 MHz, CDCl3) δ 8.53 (1H, s), 7.01-7.01 (1H, d), 5.19-5.25 (1H, m), 3.19-3.26 (1H, m), 2.40 (7H, s), 2.29-2.32 (2H, d), 2.06-2.08 (2H, d), 1.42-1.63 (4H, m), 1.39-1.40 (6H, d). MS: m/z 320 (M+H)+.

Example 105

Synthesis of 1-N,1-N-dimethyl-4-N-[5-(pyridin-2-yl)thieno[2,3-d]pyrimidin-4-yl]cyclohexane-1,4-diamine (I-183)

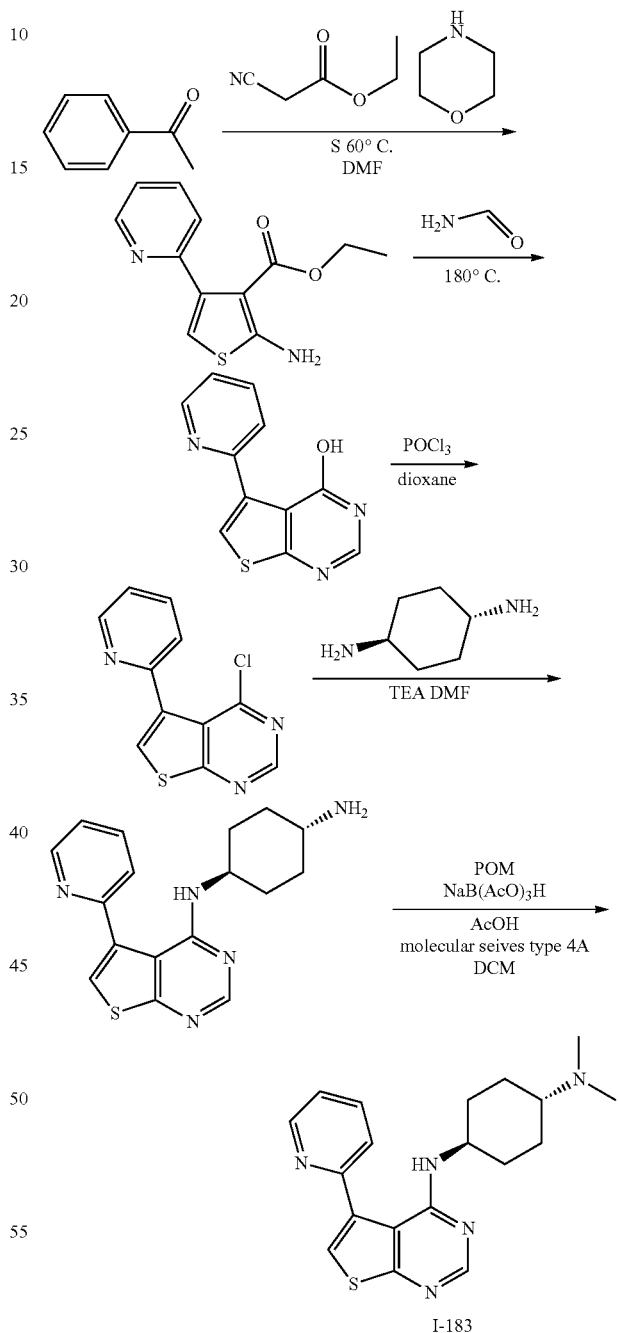

I-183

Synthesis of ethyl 2-amino-4-(pyridin-2-yl)thiophene-3-carboxylate

A 500-mL round-bottom flask purged and maintained with an inert atmosphere of nitrogen was charged with 1-(pyridin- 2-yl)ethan-1-one (24.2 g, 199.77 mmol, 1.00 equiv), N,N-dimethylformamide (400 mL), ethyl 2-cyanoacetate (45.2 g, 399.59 mmol, 2.00 equiv), morpholine (34.2 g, 392.56 mmol, 1.97 equiv), and S (16 g, 500.00 mmol, 2.50 equiv). The resulting solution was stirred overnight at 60° C. The resulting solution was allowed to react, with stirring, for an additional 4 h at 60° C. The reaction mixture was cooled to room temperature with a water bath. The reaction was then quenched by the addition of 1 L of water. The resulting solution was extracted with 5×1 L of ethyl acetate and the organic layers combined. The resulting mixture was washed with 2×1 L of brine. The mixture was dried over anhydrous sodium sulfate and concentrated under vacuum. The residue was applied onto a silica gel column with ethyl acetate/petroleum ether (1:7-1:1). Purification resulted in 14 g (28%) of ethyl 2-amino-4-(pyridin-2-yl)thiophene-3-carboxylate as a brown solid. MS: m/z 249 (M+H)$^+$.

Synthesis of
5-(pyridin-2-yl)thieno[2,3-d]pyrimidin-4-ol

A 250-mL 3-necked round-bottom flask purged and maintained with an inert atmosphere of nitrogen was charged with ethyl 2-amino-4-(pyridin-2-yl)thiophene-3-carboxylate (10 g, 40.27 mmol, 1.00 equiv) and formamide (100 mL). The resulting solution was stirred for 4 h at 180° C. The reaction mixture was cooled to 20° C. with a water/ice bath. The reaction was then quenched by the addition of 200 mL of water. The resulting solution was extracted with 5×100 mL of ethyl acetate and the organic layers combined. The resulting mixture was washed with 1×100 mL of brine. The organic layers combined was dried over anhydrous sodium sulfate and concentrated under vacuum. The residue was applied onto a silica gel column with DCM/methanol (30:1l0:1). Purification resulted in 4 g (43%) of 5-(pyridin-2-yl)thieno[2,3-d]pyrimidin-4-ol as a yellow solid. MS: m/z 249 (M+H)$^+$.

Synthesis of
2-[4-chlorothieno[2,3-d]pyrimidin-5-yl]pyridine

A 100-mL round-bottom flask was charged with 5-(pyridin-2-yl)thieno[2,3-d]pyrimidin-4-ol (2 g, 8.72 mmol, 1.00 equiv) and dioxane (30 mL). This was followed by the addition of phosphoroyl trichloride (4.0 g, 26.09 mmol, 2.99 equiv), in portions at room temperature. The resulting solution was stirred overnight at 110° C. The resulting mixture was concentrated under vacuum. The residue was then quenched by the addition of 50 mL of water/ice. The pH value of the solution was adjusted to 8 with saturated aqueous sodium bicarbonate. The solids were collected by filtration and dried under vacuum. This resulted in 1.0 g (46%) of 2-[4-chlorothieno[2,3-d]pyrimidin-5-yl]pyridine as a gray solid. MS: m/z 248 (M+H)$^+$.

Synthesis of 1-N-[5-(pyridin-2-yl)thieno[2,3-d]pyrimidin-4-yl]cyclohexane-1,4-diamine A 100-mL round-bottom flask was charged with 2-[4-chlorothieno[2,3-d]pyrimidin-5-yl]pyridine (1.0 g, 4.04 mmol, 1.00 equiv), N,N-dimethylformamide (10 mL), TEA (1.2 g, 11.86 mmol, 2.94 equiv) and cyclohexane-1,4-diamine (2.8 g, 24.52 mmol, 6.07 equiv). The resulting solution was stirred overnight at room temperature. The reaction was then quenched by the addition of 50 mL of water. The resulting solution was extracted with 4×50 mL of ethyl acetate and the organic layers combined. The resulting mixture was washed with 4×50 mL of brine. The mixture was dried over anhydrous sodium sulfate and concentrated under vacuum. This resulted in 0.9 g (69%) of 1-N-[5-(pyridin-2-yl)thieno[2,3-d]pyrimidin-4-yl]cyclohexane-1,4-diamine as yellow oil. MS: m/z 326 (M+H)$^+$.

Synthesis of Compound I-183

A 250-mL round-bottom flask was charged with 1-N-[5-(pyridin-2-yl)thieno[2,3-d]pyrimidin-4-yl]cyclohexane-1,4-diamine (900 mg, 2.77 mmol, 1.00 equiv), dichloromethane (50 mL), POM (1 g, 33.33 mmol, 12.05 equiv), sodium triacetoxyborohydride (11.7 g, 54.17 mmol, 19.59 equiv), molecular seives type 4 A (3 g) and acetic acid (10 mL). The resulting solution was stirred overnight at 50° C. The solids were filtered off. The filtrate was diluted with 100 mL of dichloromethane. The resulting mixture was washed with 1×50 mL of brine. The mixture was dried over anhydrous sodium sulfate and concentrated under vacuum. The residue was applied onto a silica gel column with dichloromethane/methanol (10/1). This resulted in 17 mg (2%) of 1-N,1-N-dimethyl-4-N-[5-(pyridin-2-yl)thieno[2,3-d]pyrimidin-4-yl]cyclohexane-1,4-diamine as a yellow solid. $^1$H NMR: (400 MHz, CDCl$_3$) δ 10.58-10.60 (1H, d), 8.55-8.56 (1H, d), 8.41 (1H, s), 7.79-7.87 (2H, m), 7.56 (1H, s), 7.32-7.35 (1H, m), 4.04-4.08 (1H, m), 2.51 (6H, s), 2.37-2.39 (3H, d), 2.13 (2H, s), 1.50-1.63 (2H, q), 1.25-1.38 (2H, q). MS: m/z 354 (M+H)$^+$.

Example 106

Synthesis of 4-N-[6-cyclopropylthieno[2,3-d]pyrimidin-4-yl]-1-N,1-N-dimethylcyclohexane-1,4-diamine (I-184)

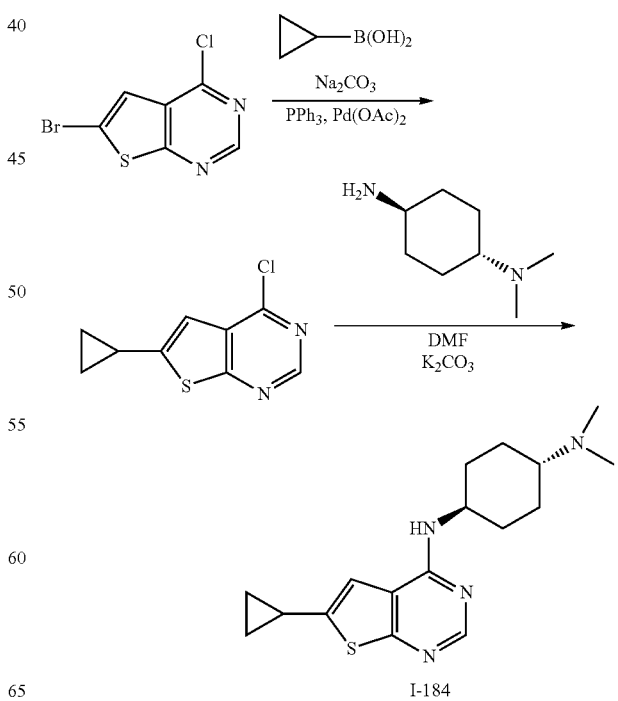

I-184

Synthesis of 4-chloro-6-cyclopropylthieno[2,3-d]pyrimidine

A 100-mL 3-necked round-bottom flask purged and maintained with an inert atmosphere of nitrogen was charged with commercially available 6-bromo-4-chlorothieno[2,3-d]pyrimidine (1.5 g, 6.01 mmol, 1.00 equiv), cyclopropylboronic acid (1.2 g, 13.97 mmol, 2.30 equiv), sodium carbonate (2.16 g, 20.38 mmol, 3.40 equiv), PPh$_3$ (552 mg, 2.10 mmol, 0.35 equiv), Pd(OAc)$_2$ (162 mg, 0.72 mmol, 0.12 equiv), water (7.5 mL) and methylbenzene (22.5 mL). The resulting solution was stirred overnight at 110° C. in an oil bath. The resulting solution was diluted with 50 mL of water. The resulting solution was extracted with 3×100 mL of dichloromethane and the organic layers combined. The resulting mixture was washed with 3×200 mL of brine. The mixture was dried over anhydrous sodium sulfate and concentrated under vacuum. The residue was applied onto a silica gel column with ethyl acetate/petroleum ether (1:15-1:5). This resulted in 400 mg (32%) of 4-chloro-6-cyclopropylthieno[2,3-d]pyrimidine as a yellow solid.

Synthesis of Compound I-184

A 50-mL round-bottom flask was charged with 4-chloro-6-cyclopropylthieno[2,3-d]pyrimidine (400 mg, 1.90 mmol, 1.00 equiv), 1-N,1-N-dimethylcyclohexane-1,4-diamine (324 mg, 2.28 mmol, 1.20 equiv) and potassium carbonate (393 mg, 2.84 mmol, 1.50 equiv) in N,N-dimethylformamide (10 mL). The resulting solution was stirred for 48 h at 45° C. in an oil bath. The resulting solution was diluted with 150 mL of water. The resulting solution was extracted with 3×200 mL of dichloromethane and the organic layers combined. The resulting mixture was washed with 3×300 mL of brine. The mixture was dried over anhydrous sodium sulfate and concentrated under vacuum. The residue was purified by preparative HPLC (2#-Waters 2767-2(HPLC-08)) under the following conditions: column: Xbridge Prep Phenyl, 5 um, 19*150 mm; mobile phase: water (50 mM NH$_4$HCO$_3$) and CH$_3$CN (10.0% CH$_3$CN up to 33.0% in 2 min, up to 53.0% in 8 min, up to 100.0% in 1 min, down to 10.0% in 1 min); detector: UV 220 nm. This resulted in 43.3 mg (7%) of Compound I-184 as a white solid. $^1$H NMR: (400 MHz, CDCl$_3$) δ 8.41 (1H, s), 6.73 (1H, s), 4.77-4.75 (2H, d), 4.15-4.05 (1H, m), 2.35 (6H, s), 2.31-2.27 (2H, d), 2.17-2.07 (1H, m), 2.01-1.96 (2H, d), 1.56-1.42 (2H, m). 1.34-1.21 (3H, m), 1.11-1.04 (2H, m), 0.78-0.85 (2H, m). MS: m/z 317 (M+H)$^+$.

Example 107

Synthesis of 4-N-[5-(1-benzofuran-2-yl)thieno[2,3-d]pyrimidin-4-yl]-1-N,1-N-dimethylcyclohexane-1,4-diamine (I-185)

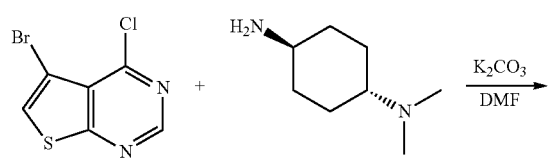

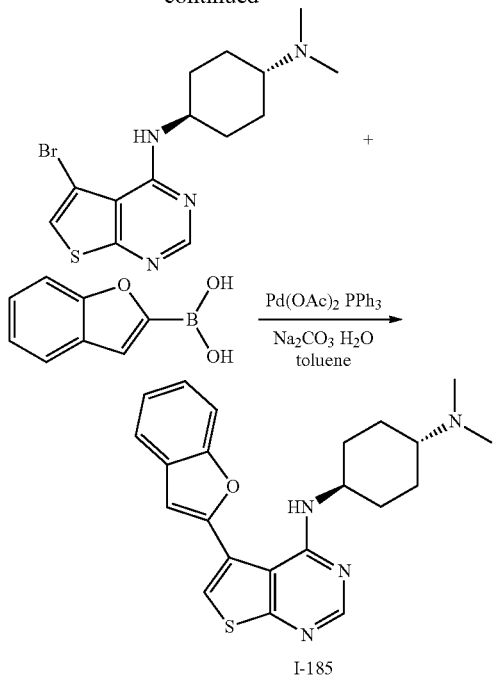

Synthesis of 4-N-[5-bromothieno[2,3-d]pyrimidin-4-yl]-1-N,1-N-dimethylcyclohexane-1,4-diamine A 50-mL round-bottom flask was charged with commercially available 5-bromo-4-chlorothieno[2,3-d]pyrimidine (300 mg, 1.20 mmol, 1.00 equiv), 1-N,1-N-dimethylcyclohexane-1,4-diamine (205 mg, 1.44 mmol, 1.20 equiv), potassium carbonate (497 mg, 3.60 mmol, 3.00 equiv) in N,N-dimethylformamide (10 mL). The resulting solution was stirred overnight at room temperature. The resulting solution was diluted with 100 mL of water. The resulting solution was extracted with 3×100 mL of ethyl acetate and the organic layers combined. The resulting mixture was washed with 3×200 mL of brine. The mixture was dried over anhydrous sodium sulfate and concentrated under vacuum. This resulted in 250 mg (59%) of 4-N-[5-bromothieno[2,3-d]pyrimidin-4-yl]-1-N,1-N-dimethylcyclohexane-1,4-diamine as a yellow oil.

Synthesis of Compound I-185

A 100-mL round-bottom flask was charged with 4-N-[5-bromothieno[2,3-d]pyrimidin-4-yl]-1-N,1-N-dimethylcyclohexane-1,4-diamine (100 mg, 0.28 mmol, 1.00 equiv), (1-benzofuran-2-yl)boronic acid (106 mg, 0.65 mmol, 2.30 equiv), sodium carbonate (102 mg, 0.96 mmol, 3.40 equiv), triphenylphosphane (26.2 mg, 0.10 mmol, 0.35 equiv), (acetyloxy)palladio acetate (7.6 mg, 0.03 mmol, 0.12 equiv), toluene (7.5 mL), and water (2.5 mL). The resulting solution was stirred overnight at 110° C. in an oil bath. The reaction mixture was cooled to room temperature. The resulting solution was diluted with 50 mL of water. The resulting solution was extracted with 3×100 mL of dichloromethane and the organic layers combined. The resulting mixture was washed with 3×200 mL of brine. The mixture was dried over anhydrous sodium sulfate and concentrated under vacuum. The crude product was purified by preparative HPLC (2#-Waters 2767-2(HPLC-08)) under the following conditions: column:

Xbridge Shield RP 18, 5 um, 19*150 mm; mobile phase: water (50 mmol NH$_4$HCO$_3$) and CH$_3$CN (10.0% CH$_3$CN up to 20% in 2 min, up to 50% in 10 min, up to 100.0% in 1 min, down to 10.0% in 1 min); detector: UV 254 nm. This resulted in 23 mg (21%) of Compound I-185 as a white solid. $^1$H NMR: (400 MHz, CDCl$_3$) δ 8.50 (1H, s), 7.68-7.65 (1H, d), 7.55-7.52 (2H, d), 7.43-7.32 (2H, m), 6.98 (1H, s), 6.61-6.59 (1H, d), 4.13-4.08 (1H, m), 2.30-2.20 (7H, m), 2.20-2.25 (2H, d), 1.96-1.91 (2H, d), 1.55-1.39 (2H, q), 1.13-1.07 (2H, q). MS: m/z 393 (M+H)$^+$.

Example 108

Synthesis of Intermediate M

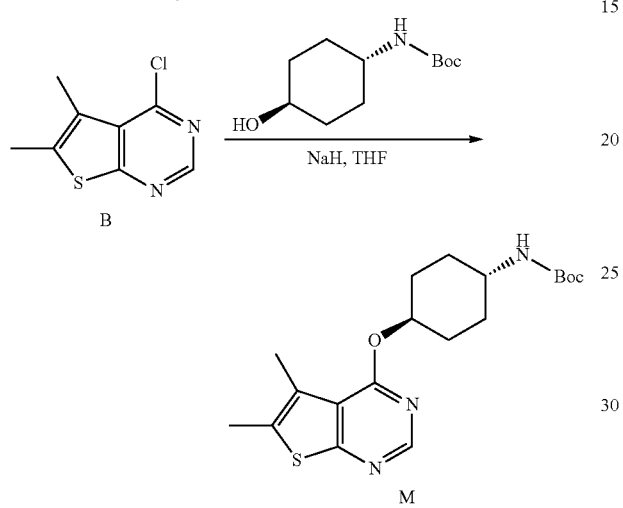

Sodium hydride (200 mg, 8.33 mmol, 3.04 equiv) was added into a solution of tert-butyl N-(4-hydroxycyclohexyl)carbamate (590 mg, 2.74 mmol, 1.00 equiv) in tetrahydrofuran (10 mL) in several batches at 0° C. and the reaction mixture was stirred for 30 min at room temperature. To this was added a solution of B (500 mg, 2.52 mmol, 0.92 equiv) in tetrahydrofuran (5 mL) dropwise with stirring at room temperature. The resulting solution was stirred for 5 h at 30° C. in an oil bath and then quenched by the addition of 5 mL of water. The resulting solution was diluted with 50 mL of water, extracted with 2×50 mL of ethyl acetate and the organic layers combined. The resulting mixture was washed with 2×50 mL of brine, dried over anhydrous sodium sulfate and concentrated under vacuum to give 0.9 g (87%) of intermediate M as a white solid.

Example 109

Synthesis of 4-([5,6-dimethylthieno[2,3-d]pyrimidin-4-yl]oxy)cyclohexan-1-amine dihydrochloride (I-186)

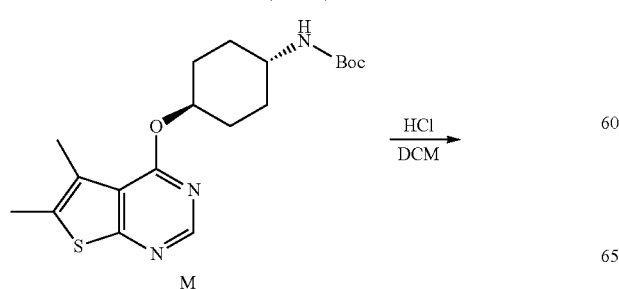

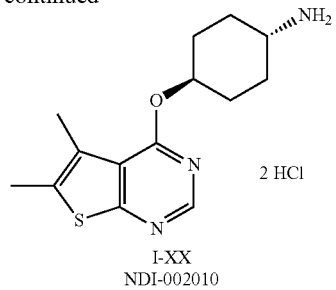

I-XX
NDI-002010

Excess hydrogen chloride (gas) was bubbled into a solution of M (900 mg, 2.38 mmol, 1.00 equiv) in dichloromethane (15 mL). The resulting solution was stirred for 2 h at 0° C. and then concentrated under vacuum. The crude product was purified by re-crystallization from ethanol to yield 500 mg (59%) of Compound I-186 as a white solid. $^1$H NMR: (400 MHz, CD$_3$OD) δ 8.97-9.00 (1H, m), 5.49-5.56 (2H, m), 2.57 (3H, s), 2.53 (3H, s), 2.42-2.44 (2H, m), 2.21-2.24 (2H, m), 1.65-1.89 (4H, m) MS: m/z 278 (M−2HCl+H)$^+$.

Example 110

Synthesis of 4-([5,6-dimethylthieno[2,3-d]pyrimidin-4-yl]oxy)-N,N-dimethylcyclohexan-1-amine (I-187)

A mixture of I-186 (350 mg, 1.12 mmol, 1.00 equiv), formic acid (10 mL) and polyformaldehyde (0.34 g) was heated to reflux overnight in an oil bath. The resulting mixture was concentrated under vacuum. The pH value of the residue was adjusted to 12 with aqueous sodium hydroxide (2 mol/L). The crude product was precipitated and collected by filtration. The crude product was purified by preparative HPLC (2#-Waters 2767-2(HPLC-08)) under the following conditions: column: Xbridge Prep C18, 5 um, 19*150 mm; mobile phase: water (50 mM ammonium bicarbonate) and acetonitrile (10.0% acetonitrile up to 66.0% in 8 min, up to 100.0% in 1 min, down to 10.0% in 1 min); detector: UV 220 nm. This procedure afforded 0.15 g (44%) of Compound I-187 as a white solid. $^1$H NMR: (400 MHz, CD$_3$OD) δ 8.48 (1H, s), 5.19-5.25 (1H, m), 2.29-2.43 (15H, m), 2.01-2.03 (2H, m), 1.47-1.62 (4H, m). MS: m/z 306 (M+H)⁺.

Example 111

Synthesis of 4-([5,6-dimethylthieno[2,3-d]pyrimidin-4-yl]oxy)-N-methylcyclohexan-1-amine (I-188)

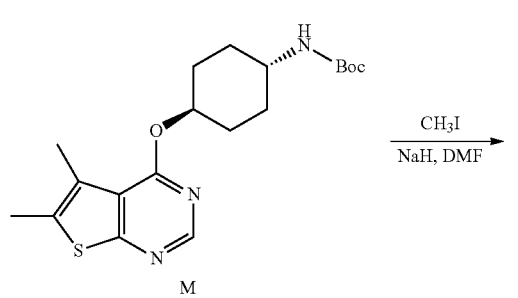

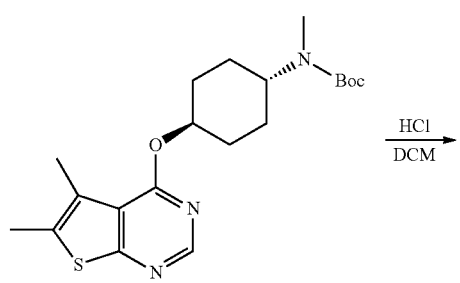

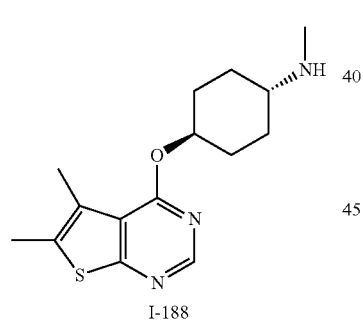

I-188

Synthesis of tert-butyl N-[4-([5,6-dimethylthieno[2,3-d]pyrimidin-4-yl]oxy)cyclohexyl]-N-methylcarbamate Sodium hydride (220 mg, 9.17 mmol, 3.46 equiv) was added to a solution of tert-butyl N-[4-([5,6-dimethylthieno[2,3-d]pyrimidin-4-yl]oxy)cyclohexyl]carbamate (1.0 g, 2.65 mmol, 1.00 equiv) in N,N-dimethylformamide (15 mL) in several batches at 0° C. and the reaction mixture was stirred for 30 min. To this reaction mixture was added iodomethane (450 mg, 3.17 mmol, 1.20 equiv) dropwise at room temperature. The reaction mixture was stirred for 1 h at 30° C. and then quenched by the addition of 5 mL of water. The resulting solution was diluted with 50 mL of water, extracted with 2×50 mL of ethyl acetate and the organic layers combined. The resulting mixture was washed with 2×50 mL of brine. The mixture was dried over anhydrous sodium sulfate and concentrated under vacuum to give 0.6 g (58%) of tert-butyl N-[4-([5,6-dimethylthieno[2,3-d]pyrimidin-4-yl]oxy)cyclohexyl]-N-methylcarbamate as a brown solid.

Synthesis of Compound I-188

Excess hydrogen chloride gas was bubbled into a solution of tert-butyl N-[4-([5,6-dimethylthieno[2,3-d]pyrimidin-4-yl]oxy)cyclohexyl]-N-methylcarbamate (600 mg, 1.53 mmol, 1.00 equiv) in dichloromethane (10 mL) and the resulting solution was stirred for 2 h at 0° C. The solids were collected by filtration and purified by preparative HPLC (2#-Waters 2767-2(HPLC-08)) under the following conditions: column: SunFire Prep C₁₈, 19*150 mm 5 um; mobile phase: water (50 mmol ammonium acid carbonate) and acetonitrile (10.0% acetonitrile up to 15.0% in 3 min, up to 36.0% in 10 min, up to 100.0% in 1 min, down to 10.0% in 1 min); detector: UV 220 nm. This procedure afforded 300 mg (64%) of Compound I-188 as a white solid. ¹H NMR: (400 MHz, CDCl₃) δ 8.48 (1H, s), 5.26-5.53 (1H, m), 2.42-2.53 (10H, m), 2.23-2.27 (2H, m), 2.04-2.07 (2H, m), 1.79 (1H, m), 1.54-1.64 (2H, m), 1.30-1.39 (2H, m) MS: m/z 292 (M+H)⁺.

Examples 112-113

Removed.

Example 114

Synthesis of N-methyl-4-[7-thia-9,11-diazatricyclo[6.4.0.0^[2,6]]dodeca-1(12),2(6),8,10-tetraen-12-yloxy]cycloheptan-1-amine (I-113)

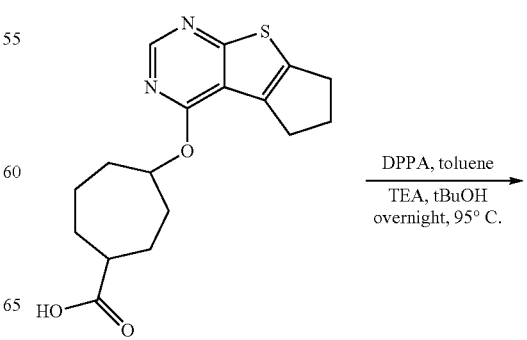

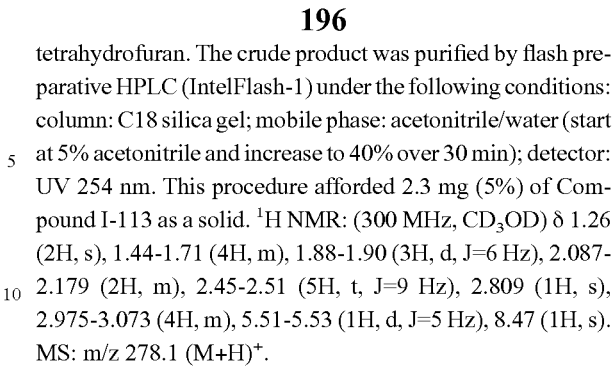

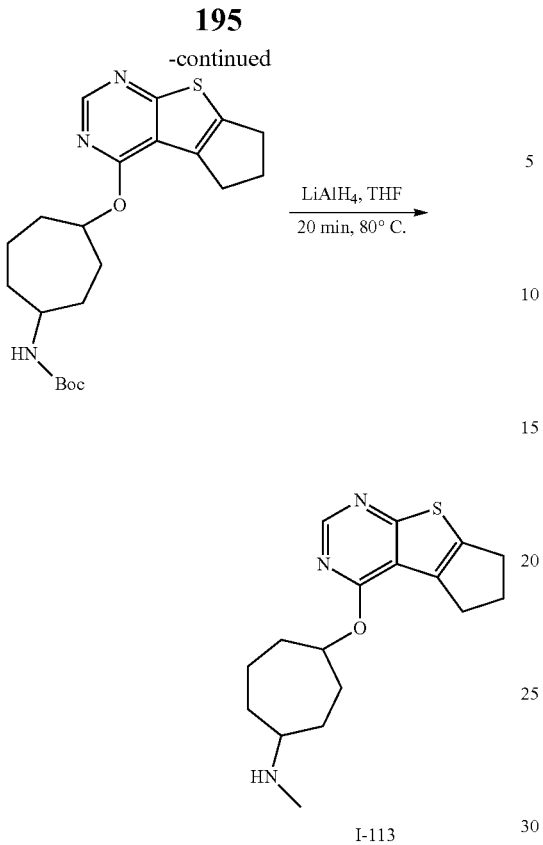

Synthesis of tert-butyl (4-((6,7-dihydro-5H-cyclopenta[4,5]thieno[2,3-d]pyrimidin-4-yl)oxy)cycloheptyl)carbamate A 50-mL 3-necked round-bottom flask was charged with a solution of 4-[7-thia-9,11-diazatricyclo[6.4.0.0^[2,6]]dodeca-1(12),2(6),8,10-tetraen-12-yloxy]cycloheptane-1-carboxylic acid (150 mg, 0.41 mmol, 1.00 equiv, 90%) in toluene (15 mL), DPPA (188 mg, 0.67 mmol, 1.65 equiv) and TEA (138 mg, 1.42 mmol, 3.50 equiv, 98%). The resulting solution was stirred at 30° C. for 1 hour. To this solution was added tert-butanol (2 mL, 98%). The resulting solution was stirred overnight at 95° C. in an oil bath. The resulting mixture was concentrated under vacuum. The residue was applied onto a silica gel column with ethyl acetate/petroleum ether (1/5). This resulted in 50 mg (30%) of tert-butyl N-(4-[7-thia-9,11-diazatricyclo[6.4.0.0^[2,6]]dodeca-1(12),2(6),8,10-tetraen-12-yloxy]cycloheptyl)carbamate as a yellow oil.

Synthesis of Compound I-113

A 10-mL round-bottom flask was charged with tert-butyl N-(4-[7-thia-9,11-diazatricyclo[6.4.0.0^[2,6]]dodeca-1(12),2(6),8,10-tetraen-12-yloxy]cycloheptyl)carbamate (60 mg, 0.15 mmol, 1.00 equiv, 98%), tetrahydrofuran (3 mL), and lithium aluminium tetrahydride (28.2 mg, 0.73 mmol, 4.99 equiv). The resulting solution was stirred for 20 min at 80° C. in an oil bath. The reaction was then quenched by the addition of 1 mL of water. The residue was dissolved in 5 mL of tetrahydrofuran. The crude product was purified by flash preparative HPLC (IntelFlash-1) under the following conditions: column: C18 silica gel; mobile phase: acetonitrile/water (start at 5% acetonitrile and increase to 40% over 30 min); detector: UV 254 nm. This procedure afforded 2.3 mg (5%) of Compound I-113 as a solid. $^1$H NMR: (300 MHz, CD$_3$OD) δ 1.26 (2H, s), 1.44-1.71 (4H, m), 1.88-1.90 (3H, d, J=6 Hz), 2.087-2.179 (2H, m), 2.45-2.51 (5H, t, J=9 Hz), 2.809 (1H, s), 2.975-3.073 (4H, m), 5.51-5.53 (1H, d, J=5 Hz), 8.47 (1H, s). MS: m/z 278.1 (M+H)$^+$.

Example 115

Synthesis of 4-N-[5-bromo-6-ethylthieno[2,3-d]pyrimidin-4-yl]-1-N,1-N-dimethylcyclohexane-1,4-diamine (I-190)

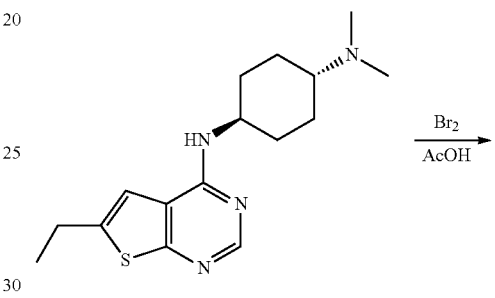

Into a 250-mL round-bottom flask, was placed a solution of 4-N-[6-ethylthieno[2,3-d]pyrimidin-4-yl]-1-N,1-N-dimethylcyclohexane-1,4-diamine (4.0 g, 13.14 mmol, 1.00 equiv) in AcOH (40 mL), dibromane (4.2 g, 26.28 mmol, 2.00 equiv). The resulting solution was stirred overnight at 70° C. The resulting mixture was concentrated under vacuum. The residue was diluted with 50 mL of water. The pH value of the solution was adjusted to 8.0 with saturated sodium carbonate. The resulting solution was extracted with 4×50 mL of chloroform and the organic layers combined and dried over anhydrous sodium sulfate and concentrated under vacuum. This resulted in 3.0 g (60%) of 4-N-[5-bromo-6-ethylthieno[2,3-d]pyrimidin-4-yl]-1-N,1-N-dimethylcyclohexane-1,4-diamine as a yellow solid. MS (ES, m/z): 383 [M+H]$^+$ $^1$H-NMR (400 MHz, DMSO-d6, ppm): δ 8.36 (1H, s), 6.75-6.77 (1H, d), 4.01-4.07 (1H, m), 2.81-2.88 (2H, q), 2.27 (7H, s), 2.09-2.11 (2H, d), 1.86 (2H, d), 1.32-1.40 (4H, q),1.21-1.26 (3H, t).

Example 116

4-N-[6-ethyl-5-(pyridin-2-yl)thieno[2,3-d]pyrimidin-4-yl]-1-N,1-N-dimethylcyclohexane-1,4-diamine (I-191)

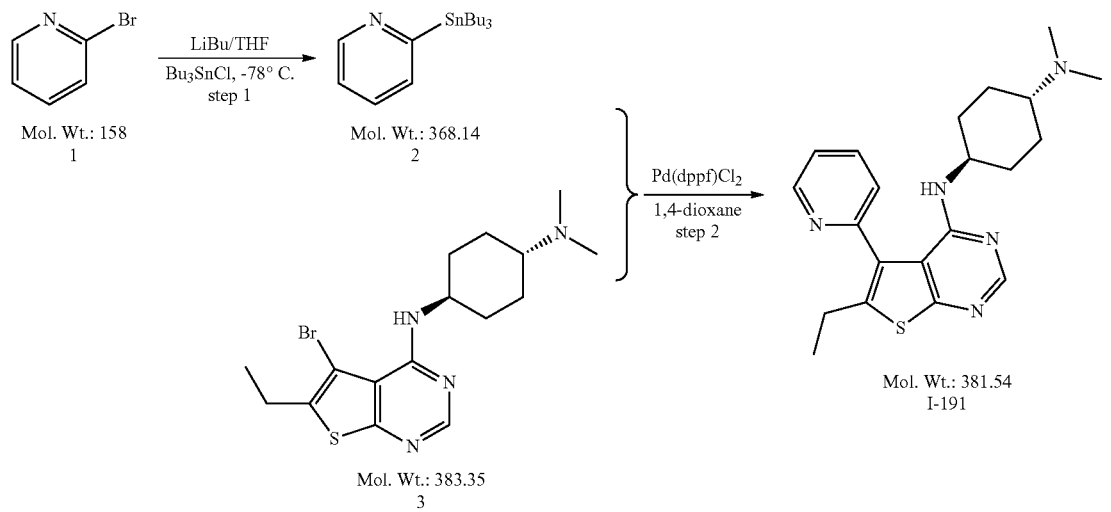

Synthesis of 2-(tributylstannyl)pyridine

To a solution of 2-bromopyridine (5 g, 31.65 mmol, 1.00 equiv) in freshly distilled THF (50 mL) was added n-BuLi (15.3 mL, 3.80 mmol, 1.20 equiv) dropwise at −78° C. under $N_2$. After stirring for 30 min at this temperature, tributyl (chloro)stannane (12.5 g, 38.40 mmol, 1.21 equiv) was added via a syringe at −78° C. and stirred for additional 1 h. Then the reaction mixture was warmed to room temperature and stirred for another 2 h. The reaction was quenched by the addition of 50 mL of $NH_4Cl$ (sat), extracted with 3×100 mL of ethyl acetate, washed with brine, dried over anhydrous sodium sulfate and concentrated under vacuum. The residue was purified on a silica gel column with ethyl acetate/petroleum ether (1/20) to give 2-(tributylstannyl)pyridine (1.0 g) as a pale yellow oil.

Synthesis of Compound I-191

Into a 25 ml sealed tube containing a solution of 4-N-[5-bromo-6-ethylthieno[2,3-d]pyrimidin-4-yl]-1-N,1-N-dimethylcyclohexane-1,4-diamine (100 mg, 0.26 mmol, 1.00 equiv) in dioxane (5 mL) was added 2-(tributylstannyl)pyridine (96 mg, 0.26 mmol, 1.00 equiv) and $Pd(dppf)Cl_2$ (30 mg, 0.04 mmol, 0.16 equiv) at room temperature under nitrogen. The sealed tube was heated with stirring overnight at 100° C. The reaction mixture was cooled to room temperature and diluted with 20 mL of $H_2O$, extracted with 3×50 mL of ethyl acetate, washed with brine, dried over sodium sulfate and concentrated under vacuum. The crude product (80 mg) was purified by Prep-HPLC with the following conditions (SHIMADZU): Column, SunFire Prep C18, 19*150 mm 5 um; mobile phase, water with 0.05% $NH_4HCO_3$ and $CH_3CN$ (6.0% $CH_3CN$ up to 49.0% in 27 min); Flow rate, 20 mL/min; UV detection at 254/220 nm. The product-containing fractions were collected and partially evaporated to remove water and $CH_3CN$ under reduced pressure. The residue was lyophilized overnight to give the corresponding 4-N-[6-ethyl-5-(pyridin-2-yl)thieno[2,3-d]pyrimidin-4-yl]-1-N,1-N-dimethylcyclohexane-1,4-diamine (12 mg) as a light yellow oil. MS (ES, m/z): 382 [M+H]$^+$. $^1$H NMR (400 MHz, CDCl$_3$): δ 8.75-8.41 (d, 1H), 7.90 (s, 1H), 7.89-7.84 (m, 1H), 7.46-7.38 (m, 2H), 6.73-6.71 (d, 1H), 3.95-3.89 (m, 1H), 2.89-2.81 (dd, 2, H), 2.29 (s, 6H), 2.25-2.04 (m, 3H), 1.90-1.86 (m, 2 H), 1.47-1.38 (m, 2H), 1.32-1.27 (m, 3H), 1.05-1.92 (m, 2H).

Example 117

4-[[4-(dimethylamino)cyclohexyl]oxy]-6-ethyl-N-(3-fluoropyridin-4-yl)thieno[2,3-d]pyrimidine-5-carboxamide (I-192)

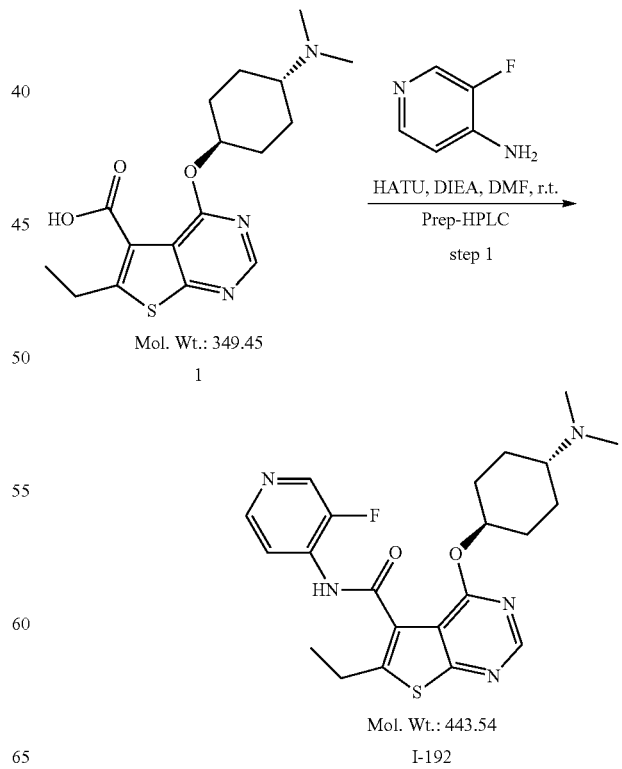

To a solution of 4-[[4-(dimethylamino)cyclohexyl]oxy]-6-ethylthieno[2,3-d]pyrimidine-5-carboxylic acid (100 mg, 0.29 mmol, 1.00 equiv) in distilled DMF (5 mL) was added HATU (217 mg, 0.57 mmol, 2.00 equiv), DIEA (110.9 mg, 0.86 mmol, 3.00 equiv) and 3-fluoropyridin-4-amine (32 mg, 0.29 mmol, 1.00 equiv) under nitrogen. The resulting solution was stirred for 1 h at room temperature. After evaporation under reduced pressure, the crude product (120 mg) was purified by Prep-HPLC with the following conditions (Waters): Column, SunFire Prep C18, 19*150 mm 5 um; mobile phase, water with 0.05% $NH_4HCO_3$ and $CH_3CN$ (7.0% $CH_3CN$ up to 48.0% in 10 min); Flow rate, 20 mL/min; UV detection at 254/220 nm. The product-containing fractions were collected and partially evaporated to remove water and $CH_3CN$ under reduced pressure. The residue was lyophilized overnight to give the corresponding 4-[[4-(dimethylamino)cyclohexyl]oxy]-6-ethyl-N-(3-fluoropyridin-4-yl)thieno[2,3-d]pyrimidine-5-carboxamide (40 mg) as a white solid. MS (ES, m/z): 444 [M+H]$^+$. $^1$H NMR: (400 MHz, $CD_3OD$): 8.55-8.59 (2H, m), 8.50 (1H, d), 8.40 (1H, d), 5.19-5.24 (1H, m), 3.07 (2H, q), 2.28 (6H, s), 2.10-2.19 (3H, m), 1.89-1.92 (2H, m), 1.27-1.43 (5H, m), 1.22-1.25 (2H, m).

Example 119

4-N-[5-(1-benzofuran-2-yl)-6-ethylthieno[2,3-d]pyrimidin-4-yl]-1-N,1-N-dimethylcyclohexane-1,4-diamine (I-193)

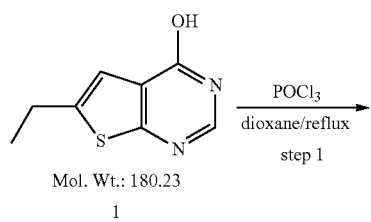

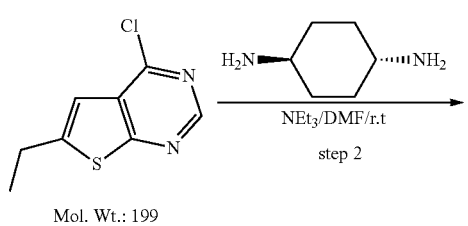

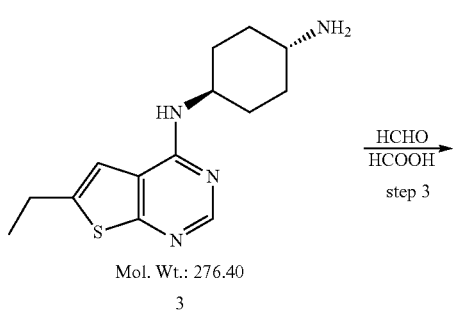

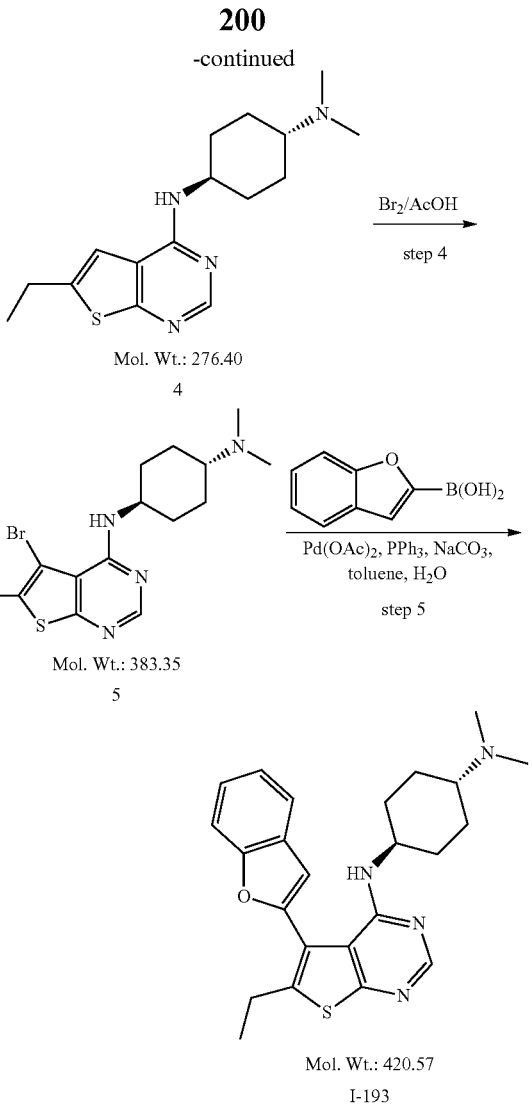

Synthesis of 4-chloro-6-ethylthieno[2,3-d]pyrimidine

To a solution of 6-ethylthieno[2,3-d]pyrimidin-4-ol (10 g, 55.49 mmol, 1.00 equiv) in 1,2-dioxane (100 mL) was added $POC_3$ (30 mL) and heated to reflux for 4 hr. After completion of the reaction, the reaction mixture was concentrated under vacuum and then quenched with water/ice. The resulting solution was extracted with 3×200 mL of ethyl acetate. The combined organic layers were washed with brine, dried over anhydrous sodium sulfate and concentrated under vacuum. The residue was purified on a silica gel column with ethyl acetate/petroleum ether (1/10) to give 7 g (64%) of 4-chloro-6-ethylthieno[2,3-d]pyrimidine as a yellow solid. MS (ES, m/z): 382 (M+H$^+$).

Synthesis of 1-N-[6-ethylthieno[2,3-d]pyrimidin-4-yl]cyclohexane-1,4-diamine

Into a 50-mL round-bottom flask, was placed 4-chloro-6-ethylthieno[2,3-d]pyrimidine (200 mg, 1.01 mmol, 1.00 equiv), cyclohexane-1,4-diamine (600 mg, 5.25 mmol, 5.22 equiv) in anhydrous N,N-dimethylformamide (5 mL) at room temperature. Then triethylamine (300 mg, 2.96 mmol, 2.95 equiv) was added via syringe and the resulting solution was stirred overnight at ambient temperature. After completion of the reaction, the resulting solution was diluted H₂O, extracted with 3×30 mL of ethyl acetate. The combined organic layers were washed with brine, dried over anhydrous sodium sulfate and concentrated under vacuum. This desired 1-N-[6-ethylthieno[2,3-d]pyrimidin-4-yl]cyclohexane-1,4-diamine (0.3 g, crude) was obtained as a off-white solid which was used for next step without further purification.

Synthesis of 4-N-[6-ethylthieno[2,3-d]pyrimidin-4-yl]-1-N,1-N-dimethylcyclohexane-1,4-diamine A solution of 1-N-[6-ethylthieno[2,3-d]pyrimidin-4-yl]cyclohexane-1,4-diamine (700 mg, 2.53 mmol, 1.00 equiv) and HCHO (30%, 760 mg, 25.33 mmol, 10.00 equiv) in HCOOH (7 mL) was heated to reflux overnight. The reaction mixture was cooled to room temperature and the pH value of the solution was adjusted to 9 with sodium carbonate (sat.), extracted with 3×30 mL of ethyl acetate. The combined organic layers were washed with brine, dried over anhydrous sodium sulfate and concentrated under vacuum to give the resulted 4-N-[6-ethylthieno[2,3-d]pyrimidin-4-yl]-1-N,1-N-dimethylcyclohexane-1,4-diamine (0.4 g, 52%) as a white solid.

Synthesis 4-N-[5-bromo-6-ethylthieno[2,3-d]pyrimidin-4-yl]-1-N,1-N-dimethylcyclohexane-1,4-diamine Into a 250-mL round-bottom flask containing a solution of 4-N-[6-ethylthieno[2,3-d]pyrimidin-4-yl]-1-N,1-N-dimethylcyclohexane-1,4-diamine (2 g, 6.57 mmol, 1.00 equiv) in AcOH (40 mL) was added Br₂ (2.1 g, 13.14 mmol, 2.00 equiv) at room temperature. The resulting solution was stirred overnight at 70° C. The resulting mixture was concentrated under vacuum. The pH value of the solution was adjusted to 9 with sodium carbonate (sat.) and extracted with 3×200 mL of ethyl acetate. The combined organic layers were washed with 300 mL of brine, dried over anhydrous sodium sulfate and concentrated under vacuum to give the resulted 4-N-[5-bromo-6-ethylthieno[2,3-d]pyrimidin-4-yl]-1-N,1-N-dimethylcyclohexane-1,4-diamine (0.9 g, crude) as a brown solid.

Synthesis of Compound (I-193)

A solution of 4-N-[5-bromo-6-ethylthieno[2,3-d]pyrimidin-4-yl]-1-N,1-N-dimethylcyclohexane-1,4-diamine (1 g, 2.61 mmol, 1.00 equiv) in toluene/H₂O (30/10 mL) was added 1-benzofuran-2-yl)boronic acid (970 mg, 5.99 mmol, 2.30 equiv), Pd(OAc)₂ (70 mg, 0.31 mmol, 0.12 equiv), PPh₃ (240 mg, 0.92 mmol, 0.35 equiv) and sodium carbonate (940 mg, 8.87 mmol, 3.40 equiv) subsequently under nitrogen. The resulting solution was heated to reflux for 4 hr and cooled to room temperature. The resulting solution was diluted with 50 mL of H₂O and extracted with 3×80 mL of ethyl acetate. The combined organic layers were washed with brine, dried over anhydrous sodium sulfate and concentrated under vacuum. The crude product (500 mg) was purified by Prep-HPLC with the following conditions (SHIMADZU): Column, SunFire Prep C18, 19*150 mm 5 um; mobile phase, water with 0.05% TFA and CH₃CN (10% CH₃CN up to 30% in 14 min); Flow rate, 20 mL/min; UV detection at 254/220 nm. The product-containing fractions were collected and partially evaporated to remove water and CH₃CN under reduced pressure. The residue was neutralized with 2 M aqueous NaOH solution and extracted with DCM, dried over Na₂SO₄ and concentrated under reduced pressure to give the corresponding 4-N-[5-(1-benzofuran-2-yl)-6-ethylthieno[2,3-d]pyrimidin-4-yl]-1-N,1-N-dimethylcyclohexane-1,4-diamine (130 mg) as yellow semi-solid. MS (ES, m/z): 421 [M+H]⁺. ¹H NMR (300 Hz, CDCl₃): δ 8.45 (s, 1H), 7.71-7.68 (d, 1H), 7.57-7.54 (d, 1H), 7.45-7.36 (m, 2H), 6.85 (s, 1H), 5.44-5.42 (d, 1H), 4.03-3.93 (m, 1H) 2.99-2.91 (dd, 2H), 2.30 (s, 6H) 2.23-2.10 (m, 4H), 2.02-1.85 (m, 3H), 1.46-1.31 (m, 5H), 0.92-0.89 (dd, 2H).

Example 120

4-[[5-(1-benzofuran-2-yl)thieno[2,3-d]pyrimidin-4-yl]oxy]-N,N-dimethylcyclohexan-1-amine (I-194)

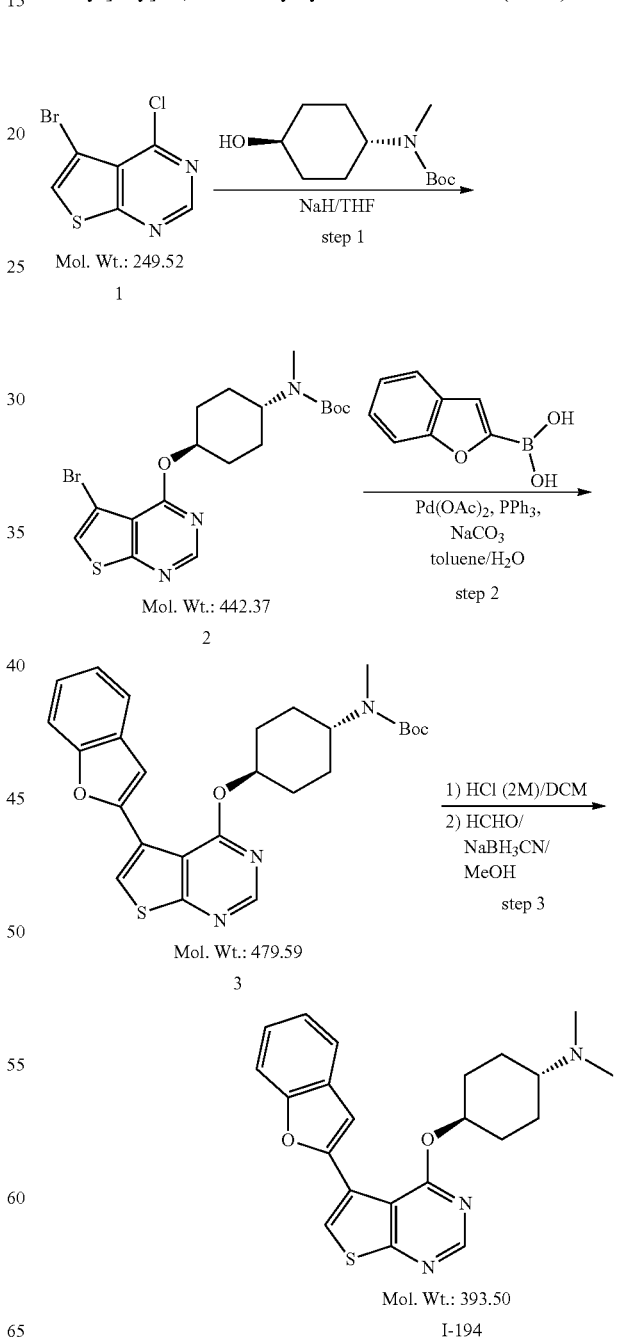

Synthesis of tert-butyl ((1r,4r)-4-((5-bromothieno[2,3-d]pyrimidin-4-yl)oxy)cyclohexyl)(methyl)carbamate Sodium hydride (72 mg, 1.80 mmol, 2.99 equiv, 60% dispersion in mineral oil) was treated with tert-butyl N-(4-hydroxycyclohexyl)-N-methylcarbamate (165 mg, 0.72 mmol, 1.20 equiv) in 10 mL of anhydrous THF at room temperature for 30 min under nitrogen. A solution of 5-bromo-4-chlorothieno[2,3-d]pyrimidine (150 mg, 0.60 mmol, 1.00 equiv) in THF (3 mL) was added and the resulting mixture was stirred for 4 h at 60° C. The reaction was then quenched by the addition of 20 mL of H$_2$O, extracted with 3×20 mL of ethyl acetate, washed with brine, dried over sodium sulfate and concentrated under vacuum. The residue was applied onto a silica gel column with ethyl acetate/PE (1/5) to give 160 mg (60%) of the desired product as a colorless oil.

Synthesis of tert-butyl ((1r,4r)-4-((5-(benzofuran-2-yl)thieno[2,3-d]pyrimidin-4-yl)oxy)cyclohexyl)(methyl)carbamate

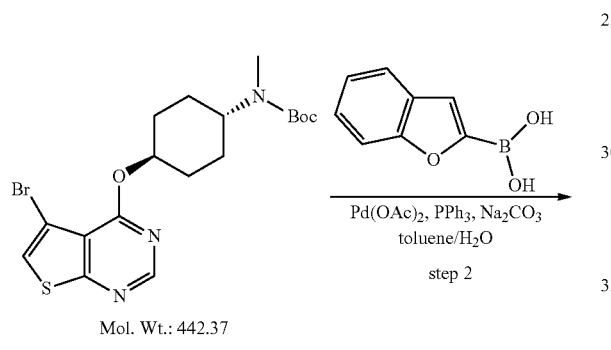

Mol. Wt.: 442.37
2

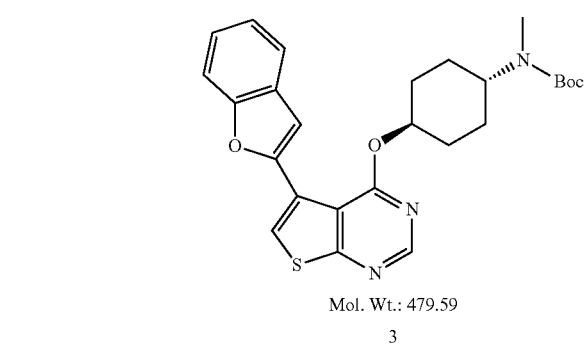

Mol. Wt.: 479.59
3

Into a 80 ml sealed tube and maintained with an inert atmosphere of nitrogen, a mixture of tert-butyl N-[4-([5-bromothieno[2,3-d]pyrimidin-4-yl]oxy)cyclohexyl]-N-methylcarbamate (130 mg, 0.29 mmol, 1.00 equiv) (12/4 mL), (1-benzofuran-2-yl)boronic acid (109 mg, 0.67 mmol, 2.29 equiv), Pd(OAc)$_2$ (8 mg, 0.04 mmol, 0.12 equiv), PPh$_3$ (27 mg, 0.10 mmol, 0.35 equiv) and sodium carbonate (106 mg, 1.00 mmol, 3.40 equiv) in a mixed toluene/H$_2$O was heated to reflux overnight under nitrogen. The reaction mixture was cooled to room temperature and diluted with water, extracted with 3×50 mL of ethyl acetate. The organic layer was washed with brine, dried over sodium sulfate and concentrated under vacuum. The residue was purified on a silica gel column with ethyl acetate/PE (1/5) to give 180 mg (crude) of the desired compound as yellow oil.

Synthesis of Compound I-194

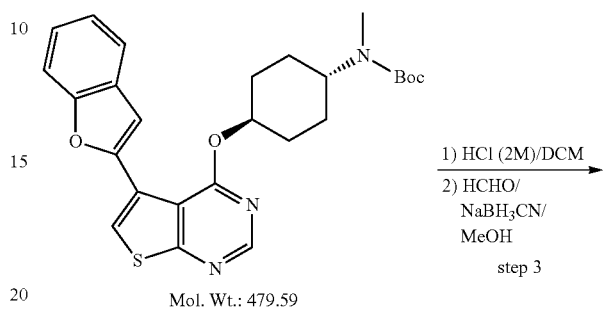

Mol. Wt.: 479.59
3

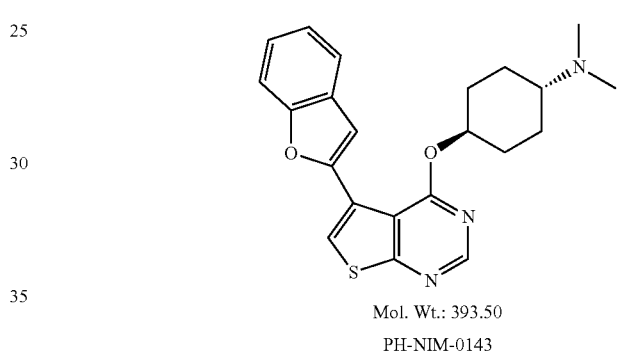

Mol. Wt.: 393.50
PH-NIM-0143

A solution of tert-butyl N-(4-[[5-(1-benzofuran-2-yl)thieno[2,3-d]pyrimidin-4-yl]oxy]cyclohexyl)-N-methylcarbamate (60 mg, 0.13 mmol, 1.00 equiv) in dichloromethane (5 mL) was added hydrochloric acid (1 mL, 12 M) at 0° C. and stirred for 1 h at room temperature. The pH value of the solution was adjusted to 9 with sodium carbonate (sat.) and extracted with 3×20 mL of dichloromethane. The organic layer was washed with brine, dried over anhydrous sodium sulfate and concentrated under vacuum to give 40 mg (84%) of 4-[[5-(1-benzofuran-2-yl)thieno[2,3-d]pyrimidin-4-yl]oxy]-N-methylcyclohexan-1-amine as colorless oil which was used directly for next step. To a solution of 4-[[5-(1-benzofuran-2-yl)thieno[2,3-d]pyrimidin-4-yl]oxy]-N-methylcyclohexan-1-amine (40 mg, 0.11 mmol, 1.00 equiv) in methanol (2 mL) was added HCHO (37%, 0.07 mL, 1.06 mmol) and stirred for 1 h at room temperature. Then NaBH$_3$CN (20 mg, 0.32 mmol, 3.01 equiv) was added and stirred for additional 1 h at room temperature. The reaction was then quenched by the addition of 20 mL of NH$_4$Cl (sat.) and extracted with 3×20 mL of ethyl acetate. The combined organic layers were dried over sodium sulfate and concentrated under vacuum. The crude product (60 mg) was recrystallized from ethyl acetate to give 15 mg (36%) of pure 4-[[5-(1-benzofuran-2-yl)thieno[2,3-d]pyrimidin-4-yl]oxy]-N,N-dimethylcyclohexan-1-amine as a white solid. MS (ES, m/z): 394 [M+H]$^+$. $^1$H NMR (300 MHz, CD$_3$OD): δ 8.66 (s, 1H), 8.08 (s, 1H), 7.68-7.65 (d, 1H), 7.56-7.54 (d, 1H), 7.38-

7.25 (m, 3H), 5.45-5.42 (m, 1H), 3.33 (s, 1H), 2.90 (s, 6H), 2.53-2.50 (d, 2H), 2.23-2.20 (d, 2H), 1.82-1.66 (m, 4 H).

Example 121

4-N-[5-(1-benzofuran-2-yl)-6-methylthieno[2,3-d]pyrimidin-4-yl]-1-N,1-N-dimethylcyclohexane-1,4-diamine (I-195)

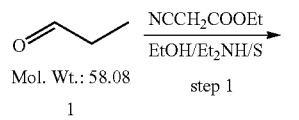

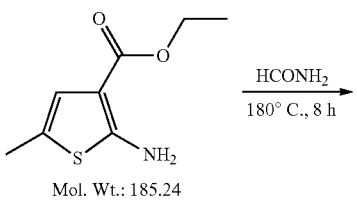

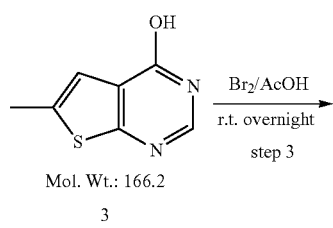

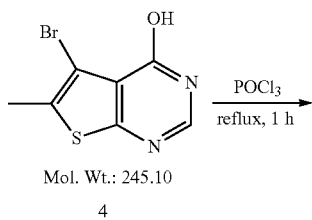

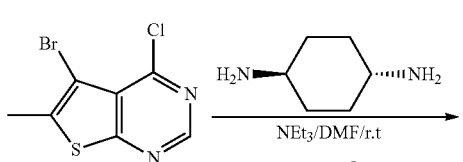

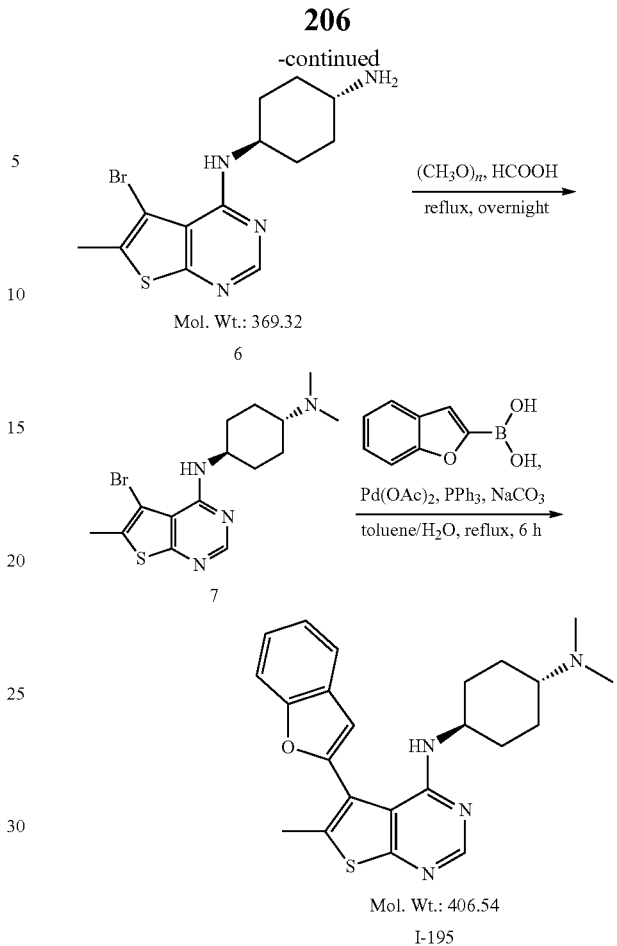

Synthesis of ethyl 2-amino-5-methylthiophene-3-carboxylate

A solution of ethyl 2-cyanoacetate (23.38 g, 206.90 mmol, 1.20 equiv), propanal (10 g, 172.41 mmol, 1.00 equiv), diethylamine (15.10 g, 206.90 mmol, 1.20 equiv), S (6.62 g, 206.90 mmol, 1.20 equiv) in ethanol (200 mL) was stirred overnight at room temperature under nitrogen. The resulting mixture was concentrated under vacuum. The residue was diluted with 200 mL of EtOAc and the solids were filtered out. The filtrate was washed with brine, dried over anhydrous sodium sulfate. After concentrated in vacuo, the residue was purified on a silica gel column with ethyl acetate/petroleum ether (1:5) to give the resulted ethyl 2-amino-5-methylthiophene-3-carboxylate (12.03 g, 38%) as a yellow solid. MS (ES, m/z): 186 [M+H$^+$].

Synthesis of 6-methylthieno[2,3-d]pyrimidin-4-ol

Into a 25-mL round-bottom flask placed ethyl 2-amino-5-methylthiophene-3-carboxylate (500 mg, 2.70 mmol, 1.00 equiv) in 10 mL of formamide was stirred for 8 h at 180° C. in an oil bath. After completion of the reaction, the reaction mixture was cooled down to room temperature and then quenched with water/ice, extracted with 3×50 mL of ethyl acetate. The combined organic layers were washed with brine, dried over anhydrous sodium sulfate and concentrated under vacuum. The residue was purified on a silica gel column with ethyl acetate/petroleum ether (2:1) to provide the resulted 6-methylthieno[2,3-d]pyrimidin-4-ol (114 mg, 25%) as a yellow solid. MS (ES, m/z): 167 [M+H⁺].

Synthesis of 5-bromo-6-methylthieno[2,3-d]pyrimidin-4-ol

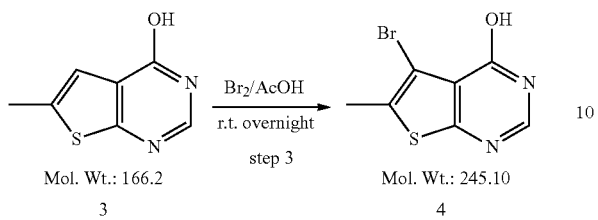

A solution of 6-methylthieno[2,3-d]pyrimidin-4-ol (95 mg, 0.57 mmol, 1.00 equiv) in acetic acid (2 mL) was added Br₂ (181 mg, 1.13 mmol, 2.00 equiv) and the resulting solution was stirred overnight at room temperature under nitrogen. After finished of the reaction, the reaction was then quenched with saturated aqueous NaHSO₃ and extracted with 3×50 mL of ethyl acetate. The combined organic layers were washed with brine, dried over anhydrous sodium sulfate and concentrated under vacuum to give the resulted 5-bromo-6-methylthieno[2,3-d]pyrimidin-4-ol (111 mg, 79%) as a yellow solid.

Synthesis of 5-bromo-4-chloro-6-methylthieno[2,3-d]pyrimidine

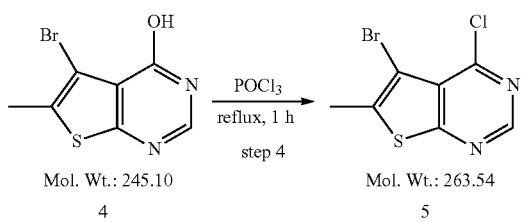

To a 25-mL round-bottom flask containing 5-bromo-6-methylthieno[2,3-d]pyrimidin-4-ol (100 mg, 0.41 mmol, 1.00 equiv) in POC₃ (10 mL) was stirred for 1 h at 110° C. in an oil bath. The resulting mixture was concentrated under vacuum. The residue was then quenched with saturated aqueous sodium carbonate, extracted with ethyl acetate, washed with brine and dried over anhydrous sodium sulfate. After concentrated under vacuum, this resulted 5-bromo-4-chloro-6-methylthieno[2,3-d]pyrimidine (79 mg, 73%) as a yellow solid.

Synthesis of 1-N-[5-bromo-6-methylthieno[2,3-d]pyrimidin-4-yl]cyclohexane-1,4-diamine

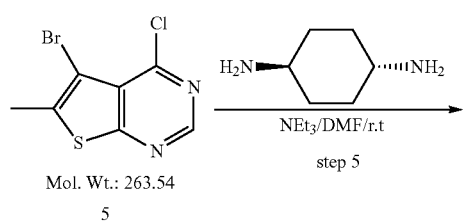

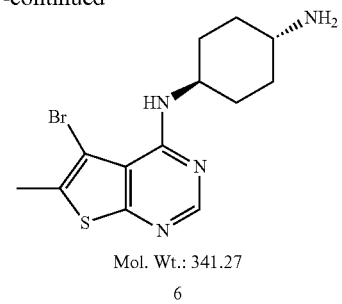

A solution of 5-bromo-4-chloro-6-methylthieno[2,3-d]pyrimidine (79 mg, 0.30 mmol, 1.00 equiv) in anhydrous DMF (5 mL) was added cyclohexane-1,4-diamine (171 mg, 1.50 mmol, 5.00 equiv) and triethylamine (91 mg, 0.90 mmol, 3.00 equiv) successively at room temperature. The resulting solution was stirred overnight at ambient temperature and then quenched with water. The resulting solution was extracted with 3×20 mL of ethyl acetate. The combined organic layers were washed with brine, dried over anhydrous sodium sulfate and concentrated under vacuum to provide the resulted 1-N-[5-bromo-6-methylthieno[2,3-d]pyrimidin-4-yl]cyclohexane-1,4-diamine (90 mg, 88%) as a yellow solid.

Synthesis of 4-N-[5-bromo-6-methylthieno[2,3-d]pyrimidin-4-yl]-1-N,1-N-dimethylcyclohexane-1,4-diamine

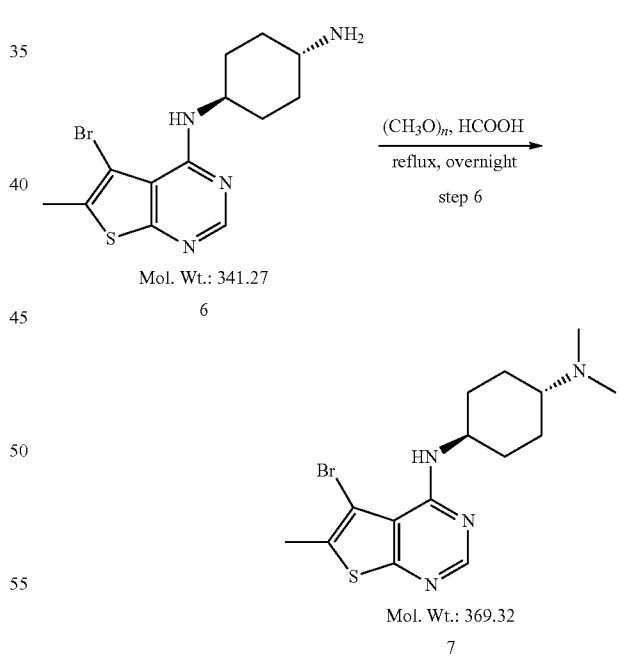

Into a 50-mL round-bottom flask placed 1-N-[5-bromo-6-methylthieno[2,3-d]pyrimidin-4-yl]cyclohexane-1,4-diamine (90 mg, 0.26 mmol, 1.00 equiv) was added (CH₃O)n (90 mg, 3 mmol, 10.00 equiv) and HCOOH (3 mL) at room temperature. The resulting solution was stirred overnight at 110° C. in an oil bath. The reaction was then quenched by the addition of 5 mL of sodium carbonate (sat.) and extracted with 3×50 mL of ethyl acetate. The combined organic layers were washed with brine, dried over anhydrous sodium sulfate and concentrated under vacuum to give the resulted 4-N-[5-bromo-6-methylthieno[2,3-d]pyrimidin-4-yl]-1-N,1-N-dimethylcyclohexane-1,4-diamine (78 mg, 80%) as a yellow solid.

Synthesis of I-195

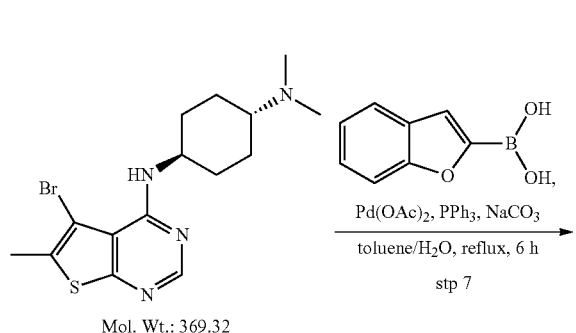

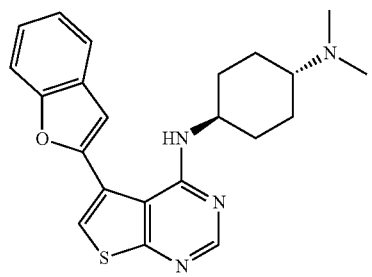

A solution of 4-N-[5-bromo-6-methylthieno[2,3-d]pyrimidin-4-yl]-1-N,1-N-dimethylcyclohexane-1,4-diamine (300 mg, 0.81 mmol, 1.00 equiv) in anhydrous toluene (6 mL) was added (1-benzofuran-2-yl)boronic acid (292 mg, 1.80 mmol, 2.30 equiv), sodium carbonate (286 mg, 2.70 mmol, 3.40 equiv), PPh$_3$ (79 mg, 0.30 mmol, 0.35 equiv), Pd(OAc)$_2$ (22 mg, 0.10 mmol, 0.12 equiv) and water (2 mL) at room temperature under nitrogen. The resulting mixture was stirred for 6 h at 100° C. in an oil bath. After cooled to room temperature, the reaction was then quenched water and extracted with 3×50 mL of ethyl acetate. The combined organic layers were washed with brine, dried over anhydrous sodium sulfate and concentrated under vacuum. The residue was applied onto a silica gel column with dichloromethane/methanol (8:1) to give the desired 4-N-[5-(1-benzofuran-2-yl)-6-methylthieno[2,3-d]pyrimidin-4-yl]-1-N,1-N-dimethylcyclohexane-1,4-diamine (120 mg, 36%) as a off-white solid. MS (ES, m/z): 407 [M+H$^+$]. $^1$H NMR (300 MHz, CDCl$_3$) δ 8.46 (s, 1H), 7.71 (d, 1H), 7.57 (m, 2H), 6.86 (s, 1H), 5.62 (d, 1H), 4.00 (m, 1H), 2.59 (s, 3H), 2.33 (s, 6H), 2.13 (m, 3H), 1.94 (m, 2H), 1.44 (dd, 2H), 0.98 (dd, 2H).

Example 122

2-(4-(6,7-dihydro-5H-cyclopenta[4,5]thieno[2,3-d]pyrimidin-4-yl)piperazin-1-yl)-N,N-dimethylethanamine. (I-150)

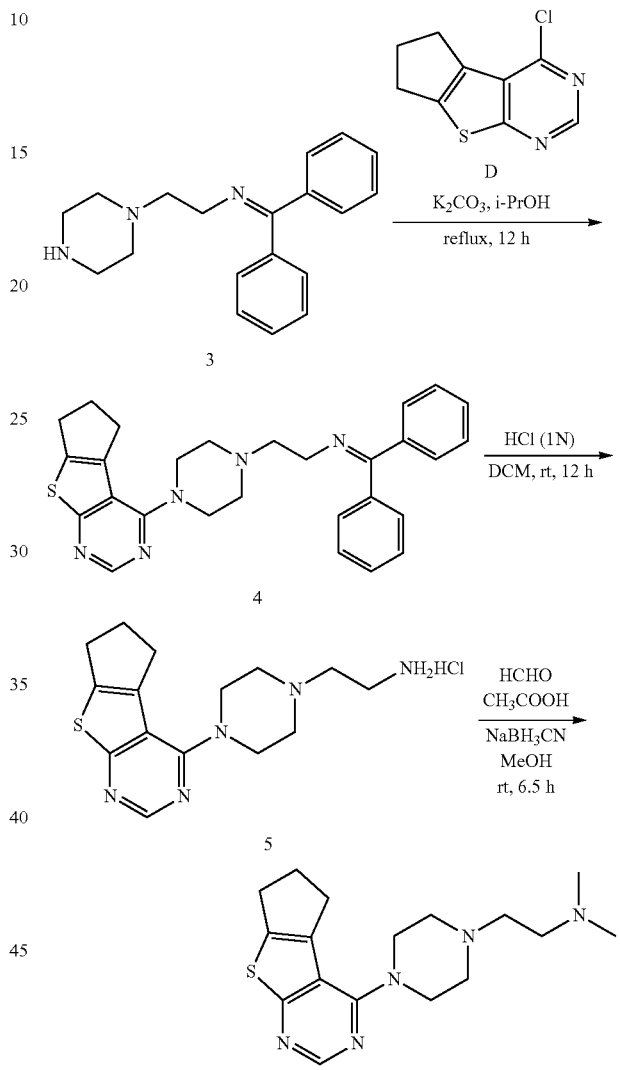

Synthesis of 2-(4-(6,7-dihydro-5H-cyclopenta[4,5]thieno[2,3-d]pyrimidin-4-yl)piperazin-1-yl)-N-(diphenylmethylene)ethanamine A mixture of Intermediate D (100 mg, 0.3 mmol, 1.0 eq), 3 (93 mg, 0.3 mmol, 1.0 eq) and K$_2$CO$_3$ (124 mg, 0.9 mmol 3.0 eq) in i-PrOH (10 mL) was stirred at reflux for 12 hours. The solvent was removed and water (10 mL) was added. The aqueous phase was extracted with CH$_2$Cl$_2$ (3×10 mL). The combined organic phases were washed (brine), dried (Na$_2$SO$_4$), filtered and concentrated. The residue was purified by column chromatography on silica gel (CH$_2$Cl$_2$/MeOH/Et$_3$N=30:2:1) to give 4 (100 mg, 44%) as a white solid. LC/MS calcd. for C$_{28}$H$_{29}$N$_5$S: 467.2. Found: 468.1.

Synthesis of compound 2-(4-(6,7-dihydro-5H-cyclopenta[4,5]thieno[2,3-d]pyrimidin-4-yl)piperazin-1-yl)ethanamine hydrochloride A solution of 4 (100 mg, 1.7 mmol, 1.0 eq) in DCM (20 mL) was added HCl (1N, 2 mL). The reaction mixture was stirred at rt for 12 h. The solvent was removed to give crude 5 (80 mg) which was used to the next step without further purification.

Synthesis of I-150

A mixture of 5 (50 mg, 0.15 mmol, 1.0 eq), HCHO (25 mg, 37%, 0.3 mmol, 2.0 eq), CH$_3$COOH (45 mg, 0.75 mmol, 5.0 eq) and NaBH$_3$CN (22 mg, 0.34 mmol, 2.2 eq) in methanol (10 mL) was stirred at rt for 6.5 h. The mixture was diluted with sat. aq. NaHCO$_3$ (50 mL) and extracted with CH$_2$Cl$_2$ (40 mL×2). The combined organics were dried and concentrated. The residue was purified by column chromatography on silica gel (CH$_2$Cl$_2$/MeOH/Et$_3$N=30:1:1) to give 2-(4-(6,7-dihydro-5H-cyclopenta[4,5]thieno[2,3-d]pyrimidin-4-yl)piperazin-1-yl)-N,N-dimethylethanamine as a white solid (25 mg, 51%). $^1$H NMR (400 MHz, CDCl$_3$) δ 2.31 (s, 6H), 2.37-2.41 (m, 2H), 2.54-2.59 (m, 8H), 2.91-2.98 (m, 4H), 3.53-3.56 (m, 4H), 8.38 (s, 1H). LC/MS calcd. for C$_{17}$H$_{25}$N$_5$S: 331.18. Found: 332.1.

Example 123

N-(2-(piperazin-1-yl)ethyl)-6,7-dihydro-5H-cyclopenta[4,5]thieno[2,3-d]pyrimidin-4-amine. (I-147)

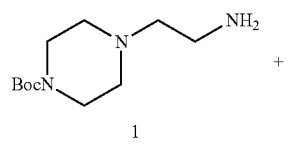

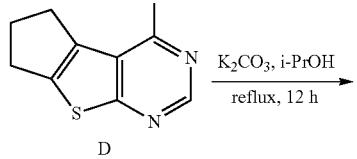

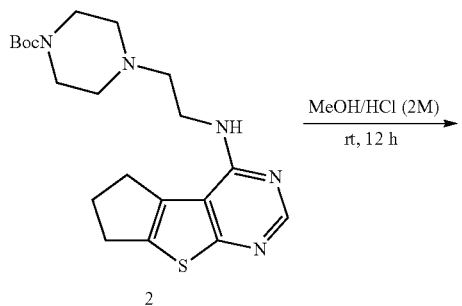

Synthesis of tert-butyl 4-(2-((6,7-dihydro-5H-cyclopenta[4,5]thieno[2,3-d]pyrimidin-4-yl)amino)ethyl)piperazine-1-carboxylate A mixture of compound D (189 mg, 0.9 mmol, 1 eq) and compound 1 (200 mg, 0.9 mmol, 1 eq) in 5 ml, of isopropanol was added K$_2$CO$_3$ (248 mg, 1.8 mmol, 2 eq). The reaction mixture was heated at reflux overnight. The mixture was poured into 30 mL of water and extracted with DCM (20 mL×3). The combined organic layer was washed with brine, dried over anhydrous Na$_2$SO$_4$ and concentrated. The residue was purified by column chromatography on silica gel (DCM/MeOH=20/1) to give tert-butyl 4-(2-((6,7-dihydro-5H-cyclopenta[4,5]thieno[2,3-d]pyrimidin-4-yl)amino)ethyl)piperazine-1-carboxylate as white solid (100 mg, 25%).

Synthesis of Compound I-147

A mixture of Compound 2 (100 mg, 0.25 mmol, 1 eq) in MeOH/HCl (2N, 3 ml) was stirred at rt for 12 h. The solvent was removed under vacuum and the residue was purified by Prep-HPLC to give N-(2-(piperazin-1-yl)ethyl)-6,7-dihydro-5H-cyclopenta[4,5]thieno[2,3-d]pyrimidin-4-amine as a yellow solid (62 mg, 82%). $^1$H NMR (400 MHz, D$_2$O) δ 2.25-2.29 (m, 2H), 2.72-2.79 (m, 4H), 3.26-3.34 (m, 11H), 3.80 (t, J=6.0 Hz, 1H), 8.24 (s, 1H). LC/MS calcd for C$_{15}$H$_{21}$N$_5$S: 303.15. Found: 304.1.

Example 123

4-(2-(piperazin-1-yl)ethoxy)-6,7-dihydro-5H-cyclopenta[4,5]thieno[2,3-d]pyrimidine. (I-140)

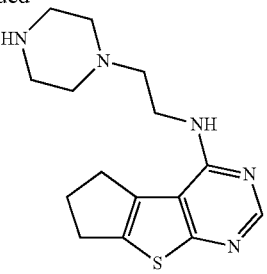

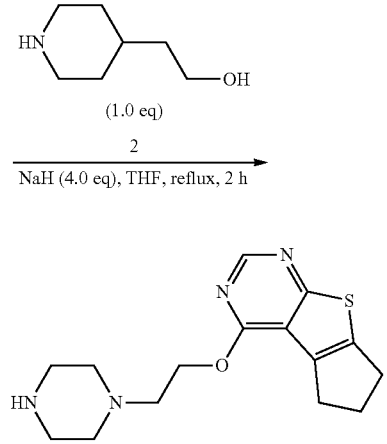

Into a solution of compound 2 (58 mg, 04 mmol) in 5 mL of THF was added NaH (72 mg, 60%, 1.2 mmol). The reaction was heated at reflux for 2 h and cooled down. Compound D (100 mg, 04 mmol) was added to the reaction mixture in one portion and the reaction was stirred for additional 30 min. 50 mL of water was added and the mixture was extracted with DCM (50 mL×3). The combined organics were dried and concentrated. The residue was purified by column chromatography on silica gel (DCM/MeOH=20:1) to afford 4-(2-(piperazin-1-yl)ethoxy)-6,7-dihydro-5H-cyclopenta[4,5]thieno[2,3-d]pyrimidine as white solid (84 mg, 62%). $^1$H NMR (400 MHz, CDCl$_3$) δ 2.47-2.51 (m, 2H), 2.66-2.68 (m, 4H), 2.87 (t, J=5.2 Hz, 2H), 2.97-3.03 (m, 8H), 4.64 (t, J=4.4 Hz, 2H), 8.51 (s, 1H). LC/MS: calcd. for $C_{15}H_{20}N_4OS$: 304.14. Found: 305.0.

Example 124

1r,4r)-N1-(6,7-dihydro-5H-cyclopenta[4,5]thieno[2,3-d]pyrimidin-4-yl)cyclohexane-1,4-diamine. (I-10)

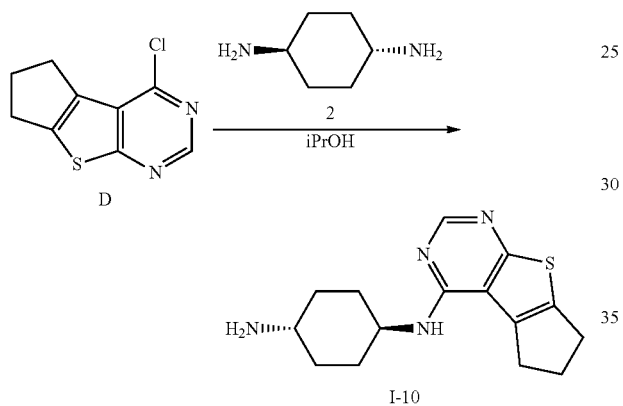

Using a synthesis procedure similar to the one described in previous examples, (1r,4r)-N1-(6,7-dihydro-5H-cyclopenta[4,5]thieno[2,3-d]pyrimidin-4-yl)cyclohexane-1,4-diamine was obtained in a yield of 87% as a white solid. $^1$H NMR (400 MHz, DMSO-d$_6$) δ 1.16-1.23 (m, 2H), 1.44-1.53 (m, 2H), 1.80-1.92 (m, 4H), 2.40-2.43 (m, 2H), 2.58-2.63 (m, 1H), 2.92 (t, J=7.2 Hz, 2H), 3.06 (t, J=7.2 Hz, 2H), 4.00-4.04 (m, 1H), 5.97 (d, J=8.0 Hz, 1H), 8.26 (s, 1 H). MS: m/z 289.1 (M+H)$^+$.

Example 125

N-((1r,4r)-4-(pyrrolidin-1-yl)cyclohexyl)-6,7-dihydro-5H-cyclopenta[4,5]thieno[2,3-d]pyrimidin-4-amine. (I-142)

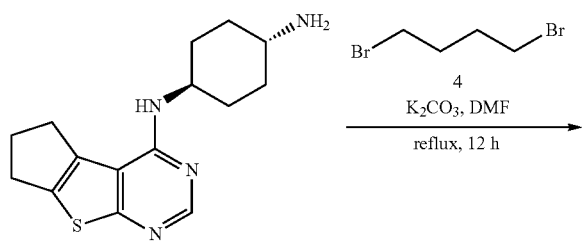

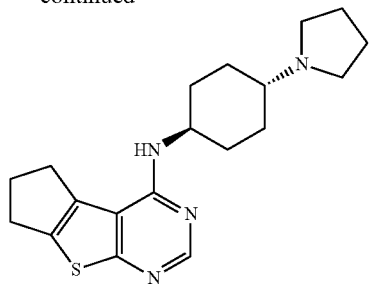

A mixture of (1r,4r)-N1-(6,7-dihydro-5H-cyclopenta[4,5]thieno[2,3-d]pyrimidin-4-yl)cyclohexane-1,4-diamine (100 mg, 0.35 mmol), 1,4-dibromobutane (89 mg, 0.42 mmol, 1.2 eq) and K$_2$CO$_3$ (232 mg, 1.68 mmol, 4.0 eq) in DMF (5 ml) was heated at reflux for 12 h and cooled down. The mixture was poured into water (40 mL) and extracted with DCM (30 mL×2). The combined organics were dried and concentrated. The crude product was purified by column chromatography on silica gel (DCM/MeOH/ammonia=100/5/1) to give N-((1r,4r)-4-(pyrrolidin-1-yl)cyclohexyl)-6,7-dihydro-5H-cyclopenta[4,5]thieno[2,3-d]pyrimidin-4-amine as white solid (13 mg, yield: 11%). $^1$H NMR (400 MHz, CDCl$_3$) δ 1.20-1.32 (m, 2H), 1.42-1.58 (m, 2H), 1.80-1.82 (m, 4H), 2.17-2.24 (m, 4H), 2.51-2.62 (m, 6H), 2.89 (t, J=4.8 Hz, 1H), 2.97-3.03 (m, 4H), 4.08-4.02 (m, 1H), 4.84 (d, J=8.4 Hz, 1H), 8.39 (s, 1H). LC/MS: calcd. for $C_{19}H_{26}N_4S$: 342.19. Found: 343.1.

Example 126

N-((1r,4r)-4-(piperidin-1-yl)cyclohexyl)-6,7-dihydro-5H-cyclopenta[4,5]thieno[2,3-d]pyrimidin-4-amine. (I-143)

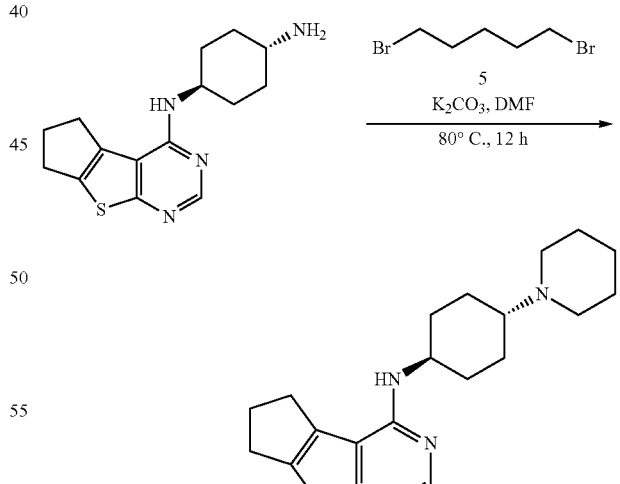

A mixture of (1r,4r)-N1-(6,7-dihydro-5H-cyclopenta[4,5]thieno[2,3-d]pyrimidin-4-yl)cyclohexane-1,4-diamine (100 mg, 0.35 mmol), 1,5-dibromopentane (95 mg, 0.42 mmol, 1.2 eq) and K$_2$CO$_3$ (232 mg, 1.68 mmol, 4.0 eq) in DMF (5 ml) was heated at 80° C. for 12 h and cooled down. The mixture was poured into water (40 mL) and extracted with DCM (30 mL×2). The combined organics were dried and concentrated.

The crude product was purified by column chromatography on silica gel (DCM/MeOH/ammonia=100/5/1) to give I-143 as white solid (12 mg, yield: 10%). $^1$H NMR (400 MHz, CDCl$_3$) δ 1.25-1.34 (m, 4H), 1.72-1.89 (m, 6H), 2.37-2.85 (m, 7H), 2.86-2.88 (m, 2H), 2.98-3.02 (m, 4H), 3.40-3.42 (m, 2H), 4.05-4.08 (m, 1H), 4.83 (d, J=7.6 Hz, 1H), 8.36 (s, 1H). LC/MS calcd. for C$_{20}$H$_{28}$N$_4$S: 356.20. Found: 357.1

Example 127

1r,4r)-N1-(6,7-dihydro-5H-cyclopenta[4,5]thieno[2,3-d]pyrimidin-4-yl)-N1,N4-dimethylcyclohexane-1,4-diamine. (I-146)

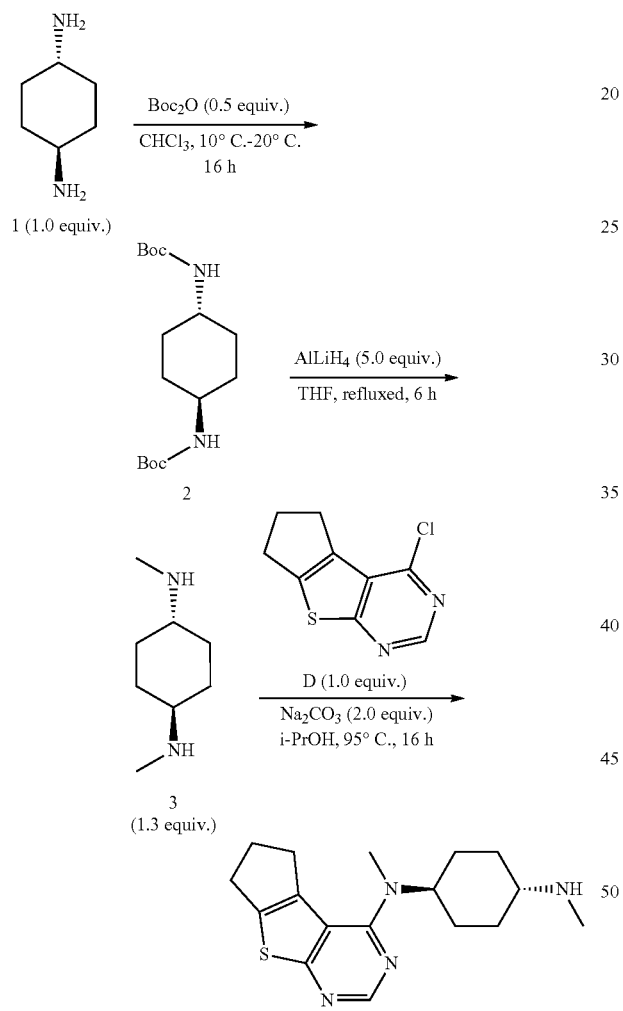

The Synthesis of Compound 2.

Into a solution of 1 (3.60 g, 31.53 mol, 1.0 eq) in CHCl$_3$ (500 mL) at 10° C. was added a solution of Boc$_2$O (3.44 g, 15.76 mol, 0.5 eq) dropwise in THF (50 mL) over 30 minutes. The reaction mixture was allowed to warm to rt and stirred for 16 h. The reaction mixture was diluted with water (200 mL) and extracted with DCM (3×500 mL). The combined organics were dried over Na$_2$SO$_4$ and concentrated under reduced pressure. The residue was purified by silica gel chromatography (PE:EA 10:1) to give 2 (875 mg, yield: 8.8%). LC/MS calcd. for C$_{16}$H$_{30}$N$_2$O$_4$: 314.2. Found: 337.1 (M+Na).

The Synthesis of Compound 3.

Into a solution of LAH (320 mg, 8.43 mmol, 5.0 eq) in THF (10 mL) was added compound 2 (530 mg, 1.69 mmol, 1.0 eq) slowly over 2 minutes under nitrogen. The mixture was stirred for 30 min at room temperature, and then heated to reflux for 6 h. The mixture was cooled down and quenched with Na$_2$SO$_4$.10H$_2$O (300 mg). The solid was filtered off and washed with THF (30 mL). The combined organic layers were dried (Na$_2$SO$_4$), filtered and concentrated under reduced pressure. The resulting residue Compound 3 was used to the next step without further purification. LC/MS calcd. for C$_8$H$_{18}$N$_2$: 142.1. Found: 143.2.

The Synthesis of Compound I-146.

A mixture of 3 (from previous step, 1.3 eq), Intermediate D (273 mg, 1.3 mmol, 1.0 eq) and Na$_2$CO$_3$ (276 mg, 2.6 mmol, 2.0 eq) in i-PrOH (10 mL) was stirred at 95° C. for 16 h. The solvent was removed and water (20 mL) was added. The aqueous phase was extracted with CH$_2$Cl$_2$ (3×40 mL). The combined organic phases was washed with brine, dried, filtered and concentrated. The residue was purified by column chromatography on silica gel (CH$_2$Cl$_2$/MeOH/Et$_3$N 20:2:1) to give (1r,4r)-N1-(6,7-dihydro-5H-cyclopenta[4,5]thieno[2,3-d]pyrimidin-4-yl)-N1,N4-dimethylcyclohexane-1,4-diamine (130 mg, 20% over two steps) as pale solid. LC/MS calcd. for C$_{17}$H$_{24}$N$_4$S: 316.2. Found: 317.2. $^1$H NMR (400 MHz, DMSO-d$_6$) δ 1.65-1.79 (m, 5H), 198-2.05 (m, 2H), 2.32-2.34 (m, 2H), 2.39-2.47 (m, 2H), 2.64 (s, 3H), 2.84-3.06 (m, 4H), 3.00 (s, 3H), 4.28-4.31 (m, 1H), 8.38 (s, 1H).

Example 128

1r,4r)-N1-(6,7-dihydro-5H-cyclopenta[4,5]thieno[2,3-d]pyrimidin-4-yl)-N1,N4,N4-trimethylcyclohexane-1,4-diamine. (I-144)

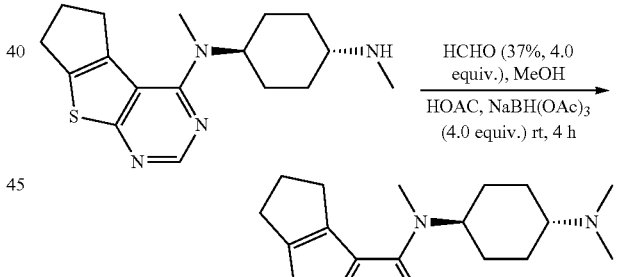

Into a solution of formaldehyde (37%, 112 mg, 1.39 mmol, 4.0 eq), acetic acid (0.08 ml, 1.39 mmol, 4.0 eq) and sodium cyanoborohydride (294 mg, 1.39 mmol, 4.0 eq) in 5 mL of MeOH was added a solution of (1r,4r)-N1-(6,7-dihydro-5H-cyclopenta[4,5]thieno[2,3-d]pyrimidin-4-yl)-N1,N4-dimethylcyclohexane-1,4-diamine (110 mg, 0.348 mmol, 1.0 equiv.) in methanol (5 ml). The resulting mixture was stirred at room temperature for 4 h. The reaction mixture was poured into a saturated aqueous sodium bicarbonate solution and extracted with ethyl acetate (3×20 mL). The combined organic layers were concentrated and the residue was crystallized with water/MeOH to give (1r,4r)-N1-(6,7-dihydro-5H-cyclopenta[2,3-d]pyrimidin-4-yl)-N1,N4,N4-trimethylcyclohexane-1,4-diamine (80 mg, 70%) as pale solid. $^1$H NMR (400 MHz, DMSO-d$_6$) δ 1.34-1.44 (m, 2H), 1.64-1.73 (m, 2H), 1.87-1.90 (m, 2H), 1.99-2.02 (m, 2H), 2.17-2.25 (m, 1H), 2.30 (s, 6H), 2.39-2.47 (m, 2H), 2.98-3.07 (m, 4H), 3.00 (s, 3H), 4.14-4.20 (m, 1H), 8.39 (s, 1H). LC/MS calcd. for $C_{18}H_{26}N_4S$: 330.2. Found: 331.2.

Example 129

1-N,1-N-dimethyl-4-N-[thieno[2,3-b]pyridin-4-yl]cyclohexane-1,4-diamine

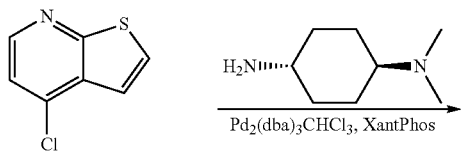

Molecular Weight: 169.63
1

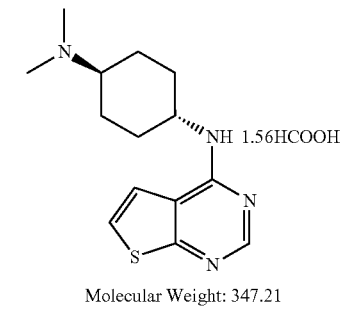

Molecular Weight: 347.21

Into a 100-mL round-bottom flask purged and maintained with an inert atmosphere of nitrogen, was placed a solution of 4-chlorothieno[2,3-b]pyridine (commercially available, 100 mg, 0.59 mmol, 1.00 equiv) in toluene (15 mL), 1-N,1-N-dimethylcyclohexane-1,4-diamine (126 mg, 0.89 mmol, 1.50 equiv), $Pd_2(dba)_3$ chloroform (30 mg, 0.03 mmol, 0.05 equiv), XantPhos (34 mg, 0.06 mmol, 0.10 equiv), t-BuONa (113 mg, 1.18 mmol, 2.00 equiv). The resulting solution was stirred overnight at 100° C. in an oil bath. The resulting mixture was concentrated under vacuum. The residue was applied onto a silica gel column with dichloromethane/methanol (6:1). The crude product (50 mg) was purified by Prep-HPLC with the following conditions: Column, SunFire Prep C18, 19*150 mm 5 um; mobile phase, $CH_3CN$ and water with 0.05% HCOOH (10.0% water with 0.05% HCOOH up to 50.0% in 10 min, up to 100.0% in 2 min down to 10.0% in 2 min); Detector, uv 254/220 nm. This resulted in 23.4 mg (14%) of 1-N,1-N-dimethyl-4-N-[thieno[2,3-b]pyridin-4-yl]cyclohexane-1,4-diamine as yellow semi-solid. MS: (ES, m/z): 276.10 [M−1.56HCOOH+H]$^+$. $^1$H NMR- (300 MHz, CDCl$_3$, ppm): δ1.20-1.47 (m, 2H), 1.60-1.72 (m, 2H), 2.21-2.38 (m, 4H), 2.69 (s, 6H), 3.00-3.13 (m, 1H) 3.71 (s, 1H), 4.72 (m, 1H), 6.38 (d, J=5.7 Hz, 1H), 7.19 (d, J=6.0 Hz, 1H), 7.30 (d, J=6.0 Hz, 1H), 8.25 (d, J=5.4 Hz, 1H), 8.48 (s, 1.56H), 9.01-9.15 (br, 1H).

Example 130

N,N-dimethyl-4-[thieno[2,3-b]pyridin-4-yloxy]cyclohexan-1-amine

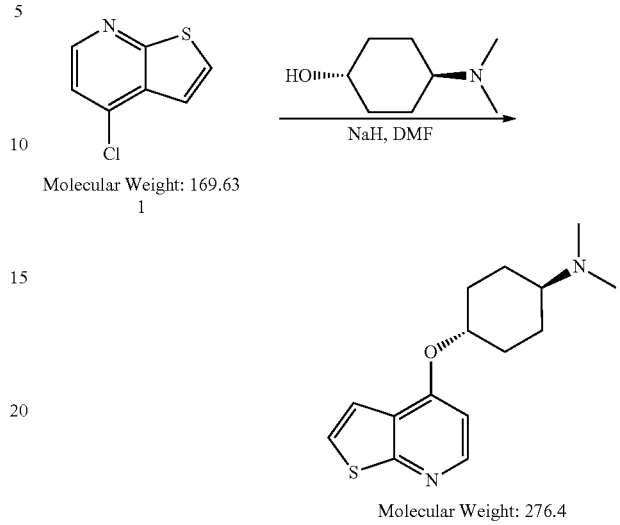

Molecular Weight: 276.4

Into a 50-mL round-bottom flask, was placed a solution of 4-(dimethylamino)cyclohexan-1-ol (127 mg, 0.89 mmol, 1.50 equiv) in N,N-dimethylformamide (15 mL). This was followed by the addition of sodium hydride (71 mg, 1.77 mmol, 3.00 equiv, 60%). The resulting solution was stirred for 30 minutes at 80° C. in an oil bath. 4-chlorothieno[2,3-b]pyridine (100 mg, 0.59 mmol, 1.00 equiv) was added to the mixture. The resulting solution was stirred for 3 h at 120° C. in an oil bath. The reaction was then quenched by the addition of 10 mL of ethanol. The resulting mixture was concentrated under vacuum. The residue was purified on a silica gel column with dichloromethane/methanol (10:1). The resulting product (50 mg) was further purified by Prep-HPLC with the following conditions: Column, SunFire Prep C18, 19*150 mm 5 um; mobile phase, $CH_3CN$ and water with 0.05% $NH_4HCO_3$ (3.0% water with 0.05% $NH_4HCO_3$ up to 3.0% in 1 min, up to 4.7.0% in 13 min, up to 100.0% in 2 min); Detector, uv 254/220 nm. This resulted in 9.6 mg (6%) of N,N-dimethyl-4-[thieno[2,3-b]pyridin-4-yloxy]cyclohexan-1-amine as a white solid.

MS: (ES, m/z): 277.10 [M+H]$^+$ $^1$H NMR (300 MHz, CD$_3$OD, ppm): δ1.49-1.69 (m, 4H), 2.06 (d, J=12.3 Hz, 2H), 2.34 (m, 9H), 4.60 (m, 1H), 7.01 (d, J=5.8 Hz, 1H), 7.38 (d, J=6.0 Hz, 1H), 7.52 (d, J=6.3 Hz, 1H), 8.36 (d, J=5.8 Hz, 1H).

Example 131

4-(4-[thieno[2,3-b]pyridin-4-yloxy]cyclohexyl)morpholine

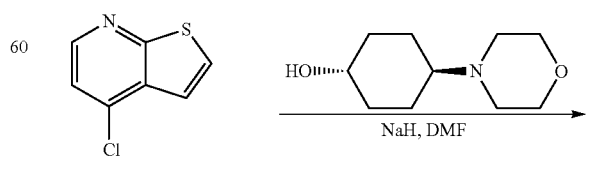

Molecular Weight: 169.63
1

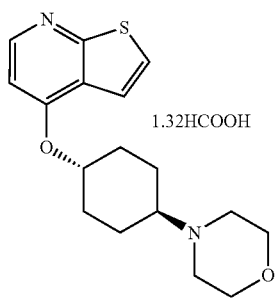

Molecular Weight: 379.19

Into a 50-mL round-bottom flask, was placed a solution of 4-(morpholin-4-yl)cyclohexan-1-ol (164 mg, 0.89 mmol, 1.50 equiv) in N,N-dimethylformamide (15 mL), sodium hydride (47 mg, 1.96 mmol, 2.00 equiv). The resulting mixture was stirred at 80° C. for 30 minutes. Then 4-chlorothieno[2,3-b]pyridine (100 mg, 0.59 mmol, 1.00 equiv) was added to the mixture. The resulting solution was stirred for 4 h at 120° C. in an oil bath. The reaction was then quenched by the addition of 5 mL of water. The resulting solution was extracted with 3×30 mL of ethyl acetate and the organic layers combined. The resulting mixture was washed with 3×15 mL of brine. The mixture was dried over anhydrous sodium sulfate and concentrated under vacuum. The residue was applied onto a silica gel column with dichloromethane/methanol (10:1). The crude product (120 mg) was purified by Prep-HPLC with the following conditions: Column, SunFire Prep C18, 19*150 mm 5 um; mobile phase, $CH_3CN$ and water with 0.05% HCOOH (10.0% water with 0.05% HCOOH up to 50.0% in 10 min, up to 100.0% in 2 min, down to 10.0% in 2 min); Detector, uv 254/220 nm. This resulted in 72.2 mg (32%) of 4-(4-[thieno[2,3-b]pyridin-4-yloxy]cyclohexyl)morpholine as a white semi-solid. MS: (ES, m/z): 319.10 $[M+H]^+$ $^1H$ NMR (400 MHz, $D_2O$, ppm): δ1.53-1.71 (m, 4H), 2.19-2.33 (dd, J1=29.7 Hz, J2=9.3 Hz, 4H), 3.24-3.30 (m, 3H), 3.51 (m, 2H), 4.07 (s, 2H), 4.60 (m, 1H), 6.98 (d, J=4.5 Hz, 1H), 7.37 (d, J=4.5 Hz, 1H), 7.52 (d, J=4.5 Hz, 1H), 8.33 (d, J=4.5 Hz, 1H).

Example 132 of 1-N,1-N-dimethyl-4-N-[thieno[2,3-b]pyridin-4-yl]cyclohexane-1,4-diamine. (I-196)

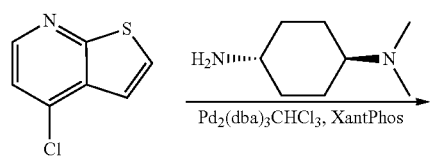

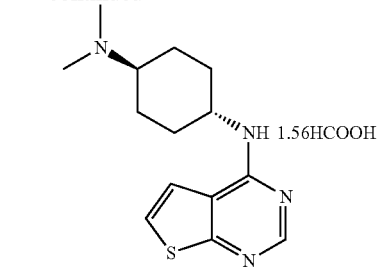

Into a 100-mL round-bottom flask purged and maintained with an inert atmosphere of nitrogen, was placed a solution of 4-chlorothieno[2,3-b]pyridine (commercially available, 100 mg, 0.59 mmol, 1.00 equiv) in toluene (15 mL), 1-N,1-N-dimethylcyclohexane-1,4-diamine (126 mg, 0.89 mmol, 1.50 equiv), $Pd_2(dba)_3$ chloroform (30 mg, 0.03 mmol, 0.05 equiv), XantPhos (34 mg, 0.06 mmol, 0.10 equiv), t-BuONa (113 mg, 1.18 mmol, 2.00 equiv). The resulting solution was stirred overnight at 100° C. in an oil bath. The resulting mixture was concentrated under vacuum. The residue was purified on a silica gel column with dichloromethane/methanol (6:1). The resulting product (50 mg) was further purified by Prep-HPLC with the following conditions: Column, SunFire Prep C18, 19*150 mm 5 um; mobile phase, $CH_3CN$ and water with 0.05% HCOOH (10.0% water with 0.05% HCOOH up to 50.0% in 10 min, up to 100.0% in 2 min down to 10.0% in 2 min); Detector, uv 254/220 nm. This resulted in 23.4 mg (14%) of 1-N,1-N-dimethyl-4-N-[thieno[2,3-b]pyridin-4-yl]cyclohexane-1,4-diamine as yellow semi-solid. MS: (ES, m/z): 276.10 $[M-1.56HCOOH+H]^+$ $^1H$ NMR (300 MHz, $CDCl_3$, ppm): δ1.20-1.47 (m, 2H), 1.60-1.72 (m, 2H), 2.21-2.38 (m, 4H), 2.69 (s, 6H), 3.00-3.13 (m, 1H) 3.71 (s, 1H), 4.72 (m, 1H), 6.38 (d, J=5.7 Hz, 1H), 7.19 (d, J=6.0 Hz, 1H), 7.30 (d, J=6.0 Hz, 1H), 8.25 (d, J=5.4 Hz, 1H), 8.48 (s, 1.56H), 9.01-9.15 (br, 1H).

Example 133

1-N-[10-chloro-7-thia-9,11-diazatricyclo[6.4.0.0[2,6]]dodeca-1(8),2(6),9,11-tetraen-12-yl]cyclohexane-1,4-diamine. (I-197)

A 50-mL round-bottom flask placed a solution of 10,12-dichloro-7-thia-9,11-diazatricyclo[6.4.0.0[2,6]]dodeca-1(8),2(6),9,11-tetraene (500 mg, 2.04 mmol, 1.00 equiv) in anhydrous CH$_3$CN (20 mL) was added trans-cyclohexane-1,4-diamine (280 mg, 2.45 mmol, 1.20 equiv) and potassium carbonate (844 mg, 6.11 mmol, 3.00 equiv) at room temperature. The resulting solution was stirred overnight at 80° C. under nitrogen. The resulting solution was diluted with EtOAc, washed with brine, dried over anhydrous sodium sulfate and concentrated under vacuum. This resulted (520 mg, crude) of 1-N-[10-chloro-7-thia-9,11-diazatricyclo[6.4.0.0[2,6]]dodeca-1(8),2(6),9,11-tetraen-12-yl]cyclohexane-1,4-diamine as a white solid which was used directly for next step without further purification.

Synthesis of 4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine. (I-198)

19*150 mm 5 um; mobile phase, water with 0.05% NH$_4$HCO$_3$ and CH$_3$CN (30% CH$_3$CN up to 64.0% in 19 min); Flow rate, 20 mL/min; UV detection at 254/220 nm. The product-containing fractions were collected and partially evaporated to remove water and CH$_3$CN under reduced pressure. The residue was lyophilized overnight to give the corresponding 4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine (380 mg, 87%) as a white solid. MS (ES, m/z): 351 [M+H]$^+$; $^1$H NMR (300 MHz, CD$_3$OD): δ 4.95 (1H, d), 4.15-4.05 (1, M), 3.01-2.96 (4H, m), 2.59-2.49 (2H, m), 2.32 (6H, s), 2.29-2.23 (3H, m), 1.96 (2H, d), 1.56-1.40 (2H, m), 1.30-1.21 (2H, m).

Example 134

4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine. (I-199)

Synthesis of 4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine

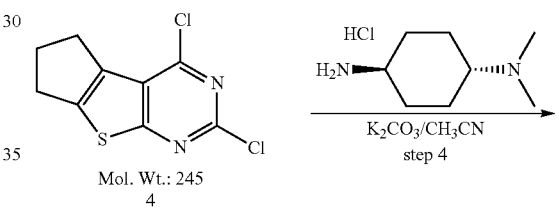

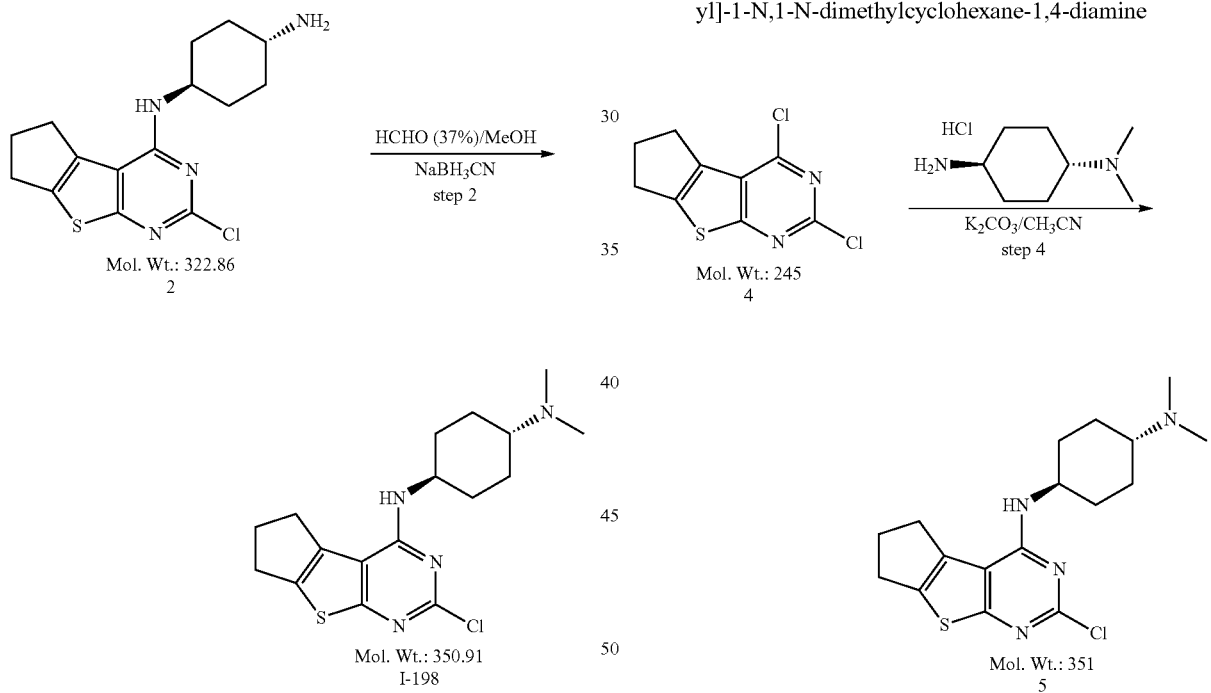

Into a 25-mL round-bottom flask containing a solution of 1-N-[10-chloro-7-thia-9,11-diazatricyclo[6.4.0.0[2,6]]dodeca-1(8),2(6),9,11-tetraen-12-yl]cyclohexane-1,4-diamine (400 mg, 1.24 mmol, 1.00 equiv) in methanol (15 mL) was added HCHO (37%, 0.5 mL) and stirred for 1 h at room temperature. Then NaBH$_3$CN (152 mg, 2.42 mmol, 2.00 equiv) was added and the resulting solution was stirred for additional 2 h at ambient temperature and diluted with EtOAc, washed with brine, dried over anhydrous sodium sulfate and concentrated under vacuum. The crude product (450 mg) was purified by Prep-HPLC with the following conditions (SHIMADZU): Column, SunFire Prep C18, A solution of 10,12-dichloro-7-thia-9,11-diazatricyclo[6.4.0.0[2,6]]dodeca-1(8),2(6),9,11-tetraene (264 mg, 1.08 mmol, 1.00 equiv) in DMF (15 mL) was added 1-N,1-N-dimethylcyclohexane-1,4-diamine hydrochloride (270 mg, 1.51 mmol, 1.40 equiv) and potassium carbonate (450 mg, 3.26 mmol, 3.00 equiv) was stirred overnight at 80° C. in an oil bath under nitrogen. The resulting solution was diluted with of EtOAc and washed with of brine. The organic layer was dried over anhydrous sodium sulfate and concentrated under vacuum to provide the resulted 4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine (300 mg, 79%) as a yellow solid. LC-MS: (ES, m/z) 252 (M+H$^+$).

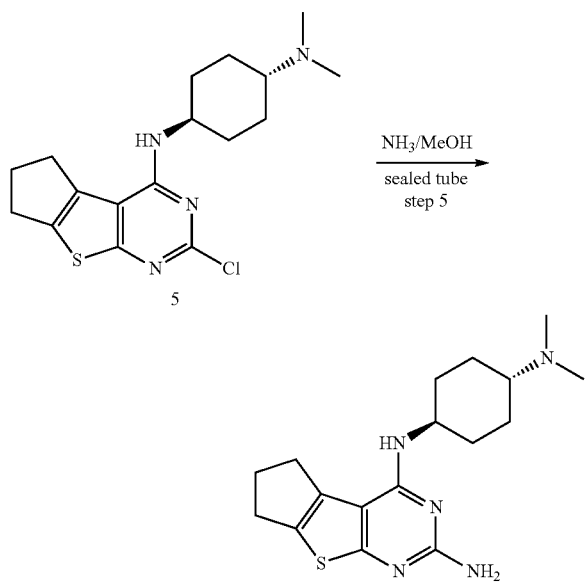

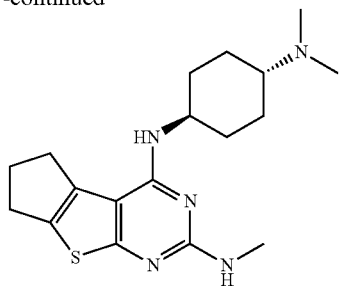

Synthesis of Compound I-199

A 20-mL sealed tube containing a solution of 4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine (80 mg, 0.23 mmol, 1.00 equiv) in 10 mL of saturated methanol-NH$_3$ solution. The resulting solution was stirred overnight at 140° C. in an oil bath and concentrated under vacuum. The crude product (80 mg) was purified by Prep-HPLC with the following conditions (SHIMADZU): Column, SunFire Prep C18, 19*150 mm 5 um; mobile phase, water with 0.05% NH$_4$HCO$_3$ and CH$_3$CN (6.0% CH$_3$CN up to 50.0% in 12 min); UV detection at 254 nm. This resulted 12-N-[4-(dimethylamino)cyclohexyl]-7-thia-9,11-diazatricyclo[6.4.0.0[2,6]]dodeca-1(8),2(6),9,11-tetraene-10,12-diamine (13 mg, 17%) was obtained as a brown solid. MS (ES, m/z) 332 [M+H]$^+$; $^1$H NMR (300 MHz, CDCl$_3$): δ 4.61 (s, 3H), 3.87-3.97 (m, 1H), 2.80-2.83 (m, 4H), 2.35-2.45 (m, 2H), 2.24 (s, 6H), 2.01-2.18 (m, 3H), 1.86 (s, 3H), 1.29-1.41 (dd, 2H), 1.14-1.18 (t, 3H).

Example 135

12-N-[4-(dimethylamino)cyclohexyl]-10-N-methyl-7-thia-9,11-diazatricyclo[6.4.0.0[2,6]]dodeca-1(8),2(6),9,11-tetraene-10,12-diamine. (I-200)

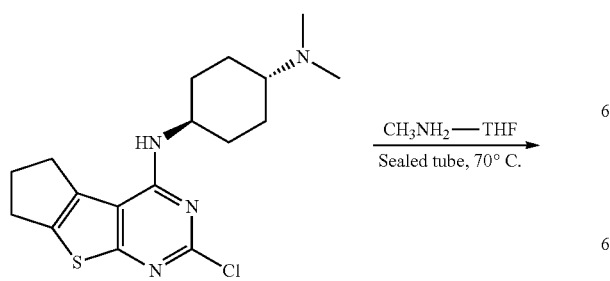

To a 10-mL sealed tube placed 4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine (120 mg, 0.34 mmol, 1.00 equiv) and CH$_3$NH$_2$—H$_2$O solution (40%, 3 mL) was stirred overnight at 70° C. in an oil bath. After completion of the reaction, the resulting mixture was concentrated under vacuum and the crude product (140 mg) was purified by Prep-HPLC with the following conditions (Waters): Column, SunFire Prep C18, 19*150 mm 5 um; mobile phase, mobile phase, water with 0.05% NH$_4$HCO$_3$ and CH$_3$CN (25% CH$_3$CN up to 100% in 15 min); Flow rate, 20 mL/min; UV detection at 254/220 nm. The product-containing fractions were collected and partially evaporated to remove water and CH$_3$CN under reduced pressure. The residue was lyophilized overnight to give the corresponding 12-N-[4-(dimethylamino)cyclohexyl]-10-N-methyl-7-thia-9,11-diazatricyclo[6.4.0.0[2,6]]dodeca-1(8),2(6),9,11-tetraene-10,12-diamine (50 mg) as a white solid. MS (ES, m/z): 346 [M+H]$^+$; $^1$H NMR (300 MHz, CD$_3$OD): δ 4.75-4.70 (1H, m), 4.64 (1H, d), 4.05-3.94 (1H, m), 3.00 (3H, d), 2.89-2.87 (4H, m), 2.54-2.38 (2H, m), 2.32 (6H, s), 2.25-2.21 (3H, m), 1.96 (2H, d), 1.50-1.35 (2H, m), 1.29-1.19 (2H, m).

Example 136

12-N-[4-(dimethylamino)cyclohexyl]-10-N-phenyl-7-thia-9,11-diazatricyclo[6.4.0.0[2,6]]dodeca-1(8),2(6),9,11-tetraene-10,12-diamine. (I-201)

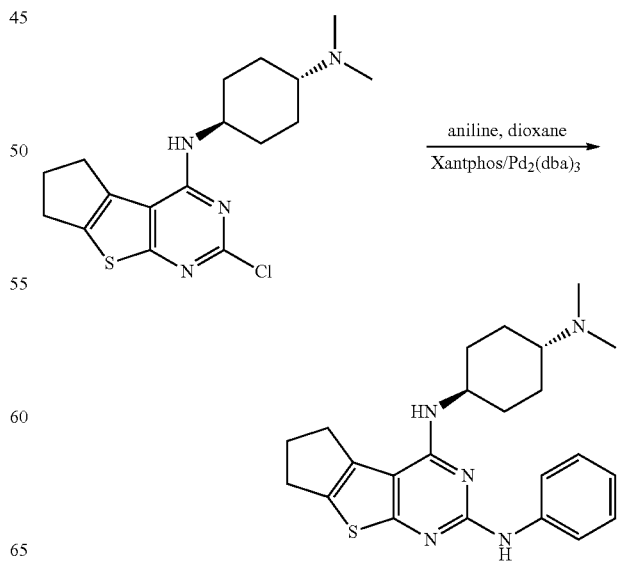

A solution of 4-N-[10-chloro-7-thia-9,11-diazatricyclo[6.4.0.0[2,6]]dodeca-1(8),2(6),9,11-tetraen-12-yl]-1-N,1-N-dimethylcyclohexane-1,4-diamine (120 mg, 0.34 mmol, 1.00 equiv) in dioxane (5 mL), was added aniline (60 mg, 0.72 mmol, 2.00 equiv), XantPhos (20 mg, 0.03 mmol, 0.10 equiv) and $Pd_2(dba)_3$ (20 mg, 0.02 mmol, 0.06 equiv) subsequently under nitrogen. The resulting solution was stirred overnight at 110° C. After completion of the reaction, the solids were filtered out and the filtrate was diluted with DCM, washed with brine. The organic layer was concentrated under vacuum and the crude product (80 mg) was purified by Prep-HPLC with the following conditions (SHIMADZU): Column, SunFire Prep C18, 19*150 mm 5 um; mobile phase, water with 0.05% $NH_4HCO_3$ and $CH_3CN$ (25% $CH_3CN$ up to 100% in 15 min); Flow rate, 20 mL/min; UV detection at 254/220 nm. The product-containing fractions were collected and partially evaporated to remove water and $CH_3CN$ under reduced pressure. The residue was lyophilized overnight to give the 12-N-[4-(dimethylamino)cyclohexyl]-10-N-phenyl-7-thia-9,11-diazatricyclo[6.4.0.0[2,6]]dodeca-1(8),2(6),9,11-tetraene-10,12-diamine (20 mg) as a grey solid. LCMS (ES, m/z): 408 [M+H]$^+$;

$^1$H NMR (400 MHz, $CD_3OD$) δ 6.67 (2H, d), 7.26 (2H, t), 6.94 (1H, t), 4.10-4.02 (1H, m), 3.01-2.92 (2 h, m), 2.91-2.87 (2H, m), 2.55-2.45 (2H, m), 2.34 (7H, m), 2.23 (2H, brs), 2.03 (2H, brs), 1.46-1.42 (4H, m).

Example 137

1r,4r)-4-((6,6-dimethyl-5,6,7,8-tetrahydrobenzo[4,5]thieno[2,3-d]pyrimidin-4-yl)oxy)-N,N-dimethylcyclohexanamine (I-202)

Synthesis of Compound 2

Into a solution of compound 1 (200 mg, 1.7 mmol, 1.0 eq) in 20 mL of methanol was added $CH_3COOH$ (510 mg, 8.5 mmol, 5.0 eq), HCHO (102 mg, 3.4 mmol, 2.0 eq) and $NaBH_3CN$ (233 mg, 3.7 mmol, 2.2 eq). The mixture was stirred at rt for 12 h then diluted with 40 mL of water, extracted with DCM (3×30 mL). The combined organics were dried and concentrated to give compound 2 as colorless oil (149 mg, 60%). LC/MS calcd. for $C_8H_{17}NO$: 143.2 Found: 144.2.

Synthesis of Compound I-202

Into a solution of compound 2 (69 mg, 0.48 mmol, 1.2 eq) in 20 mL THF was added NaH (29 g, 0.72 mmol, 1.8 eq, 60% in mineral oil) at 0° C. The resulting mixture was heated to reflux for 2 h and cooled down. To the solution was added compound 3 (100 mg, 0.40 mmol, 1 eq). The mixture was stirred at rt for 30 min then diluted with 30 mL of water and extracted with DCM (3×30 mL). The combined organics were dried and concentrated. The crude product was purified by column on silica gel (DCM/MeOH=20:1) to give compound I-202 as white solid (82 mg, 56%). LC/MS calcd. for $C_{20}H_{29}N_3OS$: 359.5 Found: 360.3

$^1$H NMR (400 MHz, $CDCl_3$) δ 1.04 (s, 6H), 1.58-1.66 (m, 4H), 2.02-2.04 (m, 2H), 2.16-2.18 (m, 2H), 2.37-2.38 (m, 2H), 2.52 (s, 6H), 2.68-2.70 (m, 2H), 2.82-2.85 (m, 3H), 5.12-5.16 (m, 1H), 8.47 (s, 1H). LC/MS calcd. for $C_{20}H_{29}N_3OS$: 359.2 Found: 360.3.

Example 138

1s,4s)-N1-(6,7-dihydro-5H-cyclopenta[4,5]thieno[2,3-d]pyrimidin-4-yl)-N4,N4-dimethylcyclohexane-1,4-diamine- (I-155)

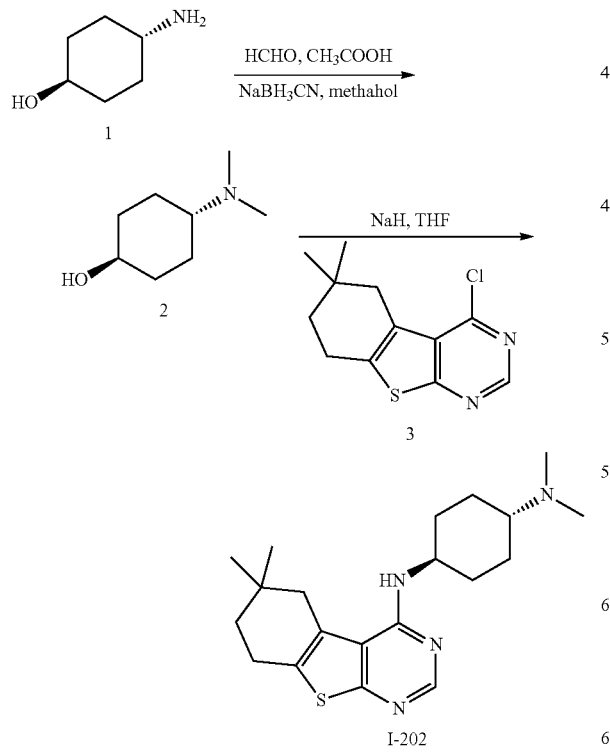

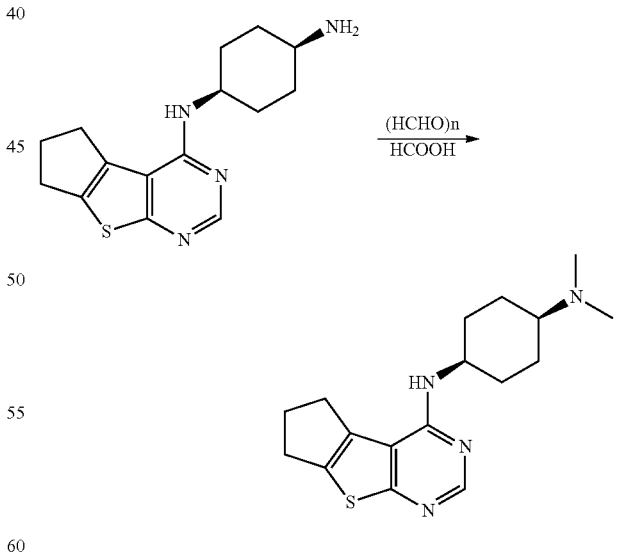

Synthesis of Cmpd I-155

A mixture of 1-N-[7-thia-9,11-diazatricyclo[6.4.0.0^[2,6]]dodeca-1(8),2(6),9,11-tetraen-12-yl]cyclohexane-1,4-diamine (500 mg, 1.73 mmol, 1.00 equiv), polyoxymethylene (520 mg, 17.31 mmol, 9.98 equiv) and formic acid (10 mL, 88%) was heated to reflux for 14 hrs. The reaction was then quenched by the addition of 80 mL of water. The solids were collected by filtration and purified on a silica gel column with dichloromethane/methanol (15/1~5/1) to give 233.8 mg (43%) of I-155 as a white solid. LC-MS: (ES, m/z): 317 [M+H]+ 1H-NMR: (400 MHz, CDCl3) δ 8.38 (1H, s), 5.24-5.26 (1H, br), 4.40 (1H, s), 2.90-3.08 (4H, dt), 2.54-2.60 (2H, m), 2.36 (6H, s), 2.24 (1H, m), 1.80-1.93 (2H, m), 1.57-1.75 (6H, m).

Example 139

N-((1s,4s)-4-(azetidin-1-yl)cyclohexyl)-6,7-dihydro-5H-cyclopenta[4,5]thieno[2,3-d]pyrimidin-4-amine- (I-159)

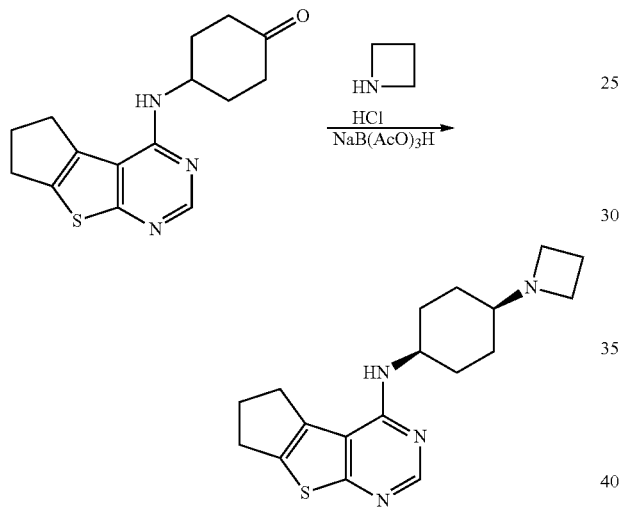

Synthesis of Compound I-159

A mixture of 4-([7-thia-9,11-diazatricyclo[6.4.0.0^[2,6]]dodeca-1(8),2(6),9,11-tetraen-12-yl]amino)cyclohexan-1-one (800 mg, 2.78 mmol, 1.00 equiv), azetidine hydrochloride (300 mg, 3.2 mmol, 1.20 equiv) and 1-[acetyl(sodio)boranyl]ethan-1-one acetic acid dihydrate (900 mg, 4.17 mmol, 1.50 equiv) in dichloromethane (10 mL) was stirred overnight at room temperature. The reaction was then quenched by the addition of 50 mL of water. The resulting solution was extracted with 3×50 mL of ethyl acetate and the organic layers combined. The resulting mixture was washed with 3×100 mL of brine. The mixture was dried over anhydrous sodium sulfate and concentrated under vacuum. The crude product was purified by Prep-HPLC with the following conditions (2#-Waters 2767-2(HPLC-08)): Column, SunFire Prep C18, 19*150 mm 5 um; mobile phase, water with 0.05% trifluoroacetic acid and acetonitrile (10.0% acetonitrile up to 17.0% in 2 min, up to 21.0% in 10 min, up to 100.0% in 2 min, down to 10.0% in 2 min); Detector, UV 220 nm. This resulted in 29.7 mg of I-159 as a white solid. LC-MS: (ES, m/z): 329 [M+H]+ 1H-NMR: (400 MHz, CDCl3) δ8.38 (1H, s), 5.18 (1H, s), 4.33 (1H, s), 3.20 (4H, s), 2.98-3.04 (4H, m), 2.51-2.58 (2H, m), 2.08-2.18 (3H, d), 1.64-1.77 (6H, d),1.45 (2H, s).

Example 140

N-((1s,4s)-4-morpholinocyclohexyl)-6,7-dihydro-5H-cyclopenta[4,5]thieno[2,3-d]pyrimidin-4-amine- (I-160)

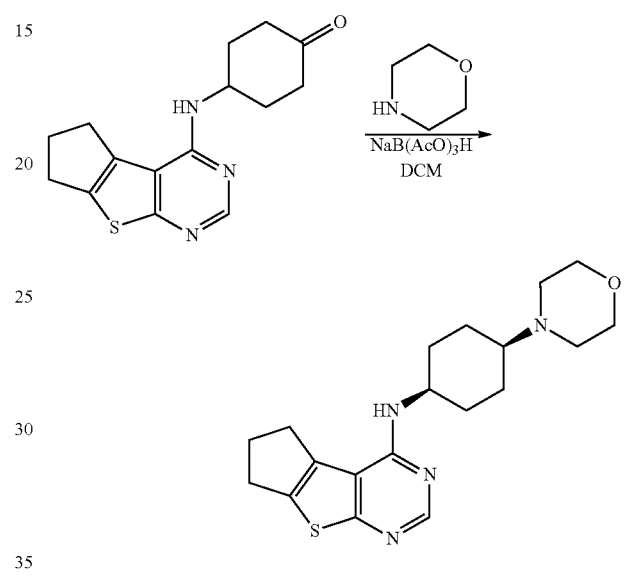

Synthesis of Compound I-160

Using a synthesis procedure similar to the one described in previous example, Compound I-160 was obtained in a yield of 87% as a white solid (103.5 mg). LC-MS: (ES, m/z): 359 [M+H]+ 1H-NMR (400 MHz, CDCl3) δ8.39 (1H, s), 5.18-5.20 (1H, d), 4.38 (1H, s), 3.76 (4H,s), 3.00-3.09 (4H, m), 2.56-2.62 (6H, m), 2.27 (1H, s), 1.92 (2H, s), 1.73-1.78 (4H, m), 1.25-1.27 (2H, m).

Example 141

1s,4s)-N1-(6,7-dihydro-5H-cyclopenta[4,5]thieno[2,3-d]pyrimidin-4-yl)-N4-isopropylcyclohexane-1,4-diamine- (I-161)

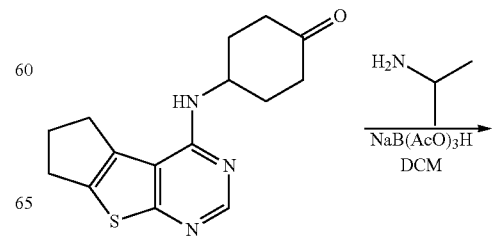

229
-continued

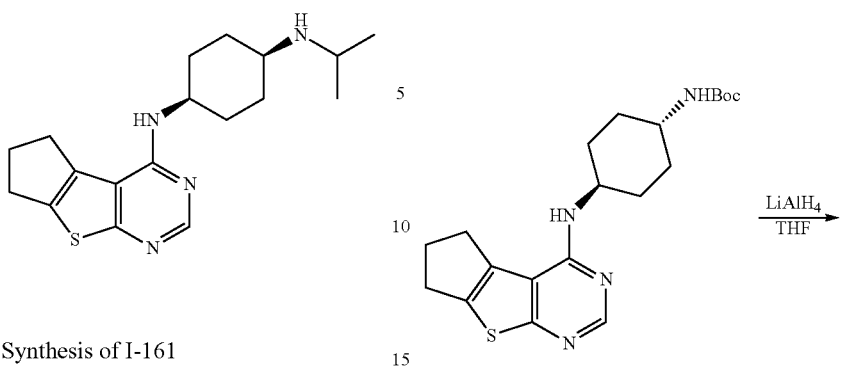

Synthesis of I-161

Using a synthesis procedure similar to the one described in previous example, Compound I-161 was obtained as a white solid (101.3 mg). LC-MS: (ES, m/z): [M+H]+ calcd for $C_{18}H_{26}N_4S$: 331, found 331 ¹HNMR (400 MHz, CDCl₃) δ 8.39 (1H, s), 5.27 (1H, s), 4.39 (1H, s), 2.92-3.10 (5H, m), 2.84 (1H, s), 2.54-2.60 (2H, m), 1.76-1.89 (7H, m), 1.16 (6H, s).

Example 142

1r,4r)-N1-(6,7-dihydro-5H-cyclopenta[4,5]thieno[2,3-d]pyrimidin-4-yl)-N4-methyl-N4-(pyridin-4-ylmethyl)cyclohexane-1,4-diamine- (I-162)

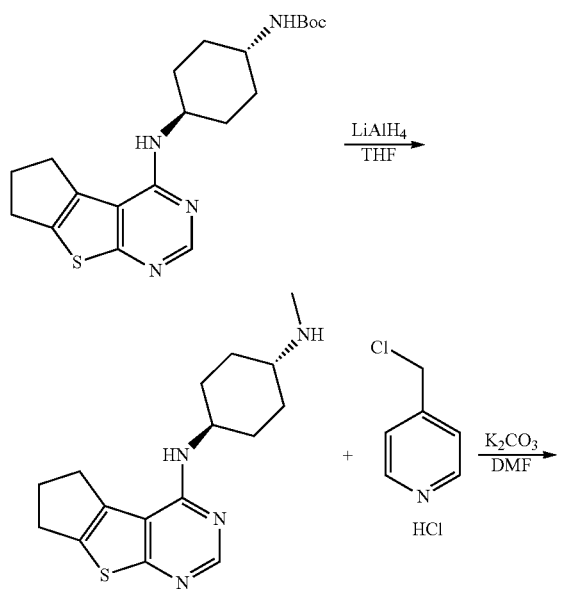

230
Synthesis of Compound I-34

A solution of tert-butyl N-[4-([7-thia-9,11-diazatricyclo [6.4.0.0ˆ[2,6]]dodeca-1(8),2(6),9,11-tetraen-12-yl]amino) cyclohexyl]carbamate (1.1 g, 2.83 mmol, 1.00 equiv) in tetrahydrofuran (20 mL) was added into a solution of lithium aluminium tetrahydride (530 mg, 13.95 mmol, 5.00 equiv) in tetrahydrofuran (30 mL) dropwise with stirring at room temperature. The resulting solution was heated to reflux for 30 min in an oil bath. The reaction was then quenched by the addition of 20 mL of tetrahydrofuran/water. The solids were filtered out. The filtrate was extracted with 3×100 mL of dichloromethane and the organic layers combined and dried over anhydrous sodium sulfate and concentrated under vacuum to give 0.86 g (crude) of 1-N-methyl-4-N-[7-thia-9,11-diazatricyclo[6.4.0.0ˆ[2,6]]dodeca-1(8), 2(6),9,11-tetraen-12-yl]cyclohexane-1,4-diamine as yellow oil. LC-MS: (ES, m/z): 303 [M+H]+

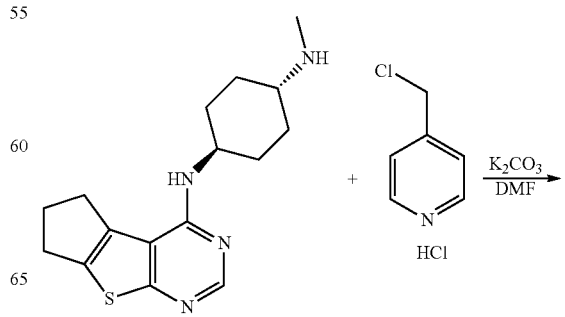

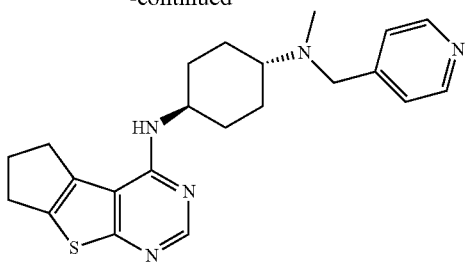

A mixture of 1-N-methyl-4-N-[7-thia-9,11-diazatricyclo[6.4.0.0^[2,6]]dodeca-1(8),2(6),9,11-tetraen-12-yl]cyclohexane-1,4-diamine (860 mg, 2.84 mmol, 1.00 equiv), 4-(chloromethyl) pyridine hydrochloride (514 mg, 3.13 mmol, 1.10 equiv) and potassium carbonate (980 mg, 7.10 mmol, 2.50 equiv) in N,N-dimethylformamide (20 mL) was stirred overnight at room temperature. The resulting solution was diluted with 150 mL of water. The resulting solution was extracted with 3×150 mL of dichloromethane and the organic layers combined. The resulting mixture was washed with 3×200 mL of brine. The mixture was dried over anhydrous sodium sulfate and concentrated under vacuum. The crude product was purified by Prep-HPLC with the following conditions (2#-Waters 2767-2(HPLC-08)): Column, SunFire Prep C18, 19*150 mm 5 um; mobile phase, water with 0.05% trifluoroacetic acid and acetonitrile (5.0% acetonitrile up to 13.0% in 2 min, up to 20.0% in 10 min, up to 100.0% in 1 min, down to 5.0% in 1 min); Detector, UV 220 nm to give 188.7 mg (17%) of Compound I-162 as a white solid. LC-MS: (ES, m/z): 394 [M+H]+ 1H-NMR: (400 MHz, CDCl3) δ8.55-8.54 (2H, d), 8.37 (1H, s), 7.31 (2H, s), 4.85-4.83 (1H, d), 4.11-4.09 (1H, q), 3.63 (2H, s), 2.99 (4H, m), 2.57-2.50 (3H, m), 2.26 (5H, m). 1.98-1.96 (2H, m), 1.64-1.55 (2H, q), 1.28-1.19 (2H, q).

Example 143

3-(((((1r,4r)-4-((6,7-dihydro-5H-cyclopenta[4,5]thieno[2,3-d]pyrimidin-4-yl)amino)cyclohexyl)(methyl)amino)methyl)benzamide- (I-166)

Synthesis of Compound I-166

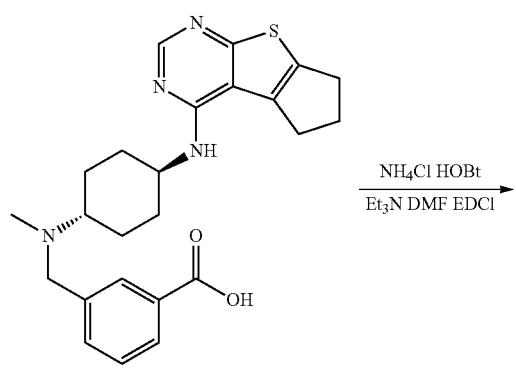

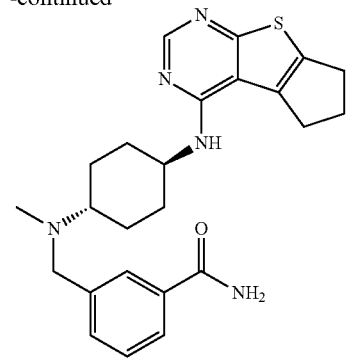

Into a 100-mL round-bottom flask, was placed 3-([methyl [4-([7-thia-9,11-diazatricyclo[6.4.0.0^[2,6]]dodeca-1(8),2(6),9,11-tetraen-12-yl]amino)cyclohexyl]amino]methyl)benzoic acid (1.3 g, 2.98 mmol, 1.00 equiv), NH4Cl (189 mg, 3.53 mmol, 1.20 equiv), HOBt (481 mg, 3.56 mmol, 1.20 equiv), EDCI (1.13 g, 5.89 mmol, 2.00 equiv) and triethylamine (900 mg, 8.89 mmol, 3.00 equiv) in N,N-dimethylformamide (20 mL). The resulting solution was stirred overnight at room temperature and then diluted with 200 mL of water. The solids were collected by filtration and dried in an oven under reduced pressure. The crude product was purified by Prep-HPLC with the following conditions (2#-Waters 2767-2(HPLC-08)): Column, Xbridge Shield RP 18, 5 um, 19*150 mm; mobile phase, water with 50 mmol NH4HCO3 and CH3CN (10.0% CH3CN up to 28.0% in 2 min, up to 46.0% in 10 min, up to 100.0% in 1 min, down to 10.0% in 1 min); Detector, UV 220 nm. This resulted in 84.2 mg (6%) of Compound I-166 as a off-white solid. LC-MS (ES, m/z): 436 [M+H]+ 1H-NMR: (400 MHz, CDCl3) δ8.40 (1H, s), 7.91 (1H, s), 7.78-7.75 (1H, d), 7.55-7.53 (1H, d), 7.47-7.42 (1H, t), 5.61 (1H, s), 4.88-4.86 (1H, d), 4.16-4.12 (1H, m), 3.72 (2H, s), 3.00-3.05 (4H, m), 2.61-2.52 (3H, m). 2.30 (4H, m), 2.04 (2H, m), 1.71-1.51 (2H, q), 1.33-1.22 (2H, q).

Example 144

1r,4r)-N1-(6,7-dihydro-5H-cyclopenta[4,5]thieno[2,3-d]pyrimidin-4-yl)-N4-ethyl-N4-phenethylcyclohexane-1,4-diamine- (I-203)

Synthesis of Compound I-203

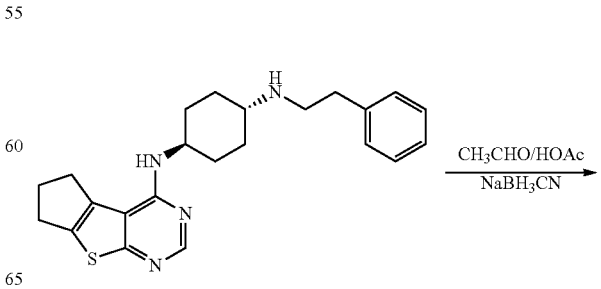

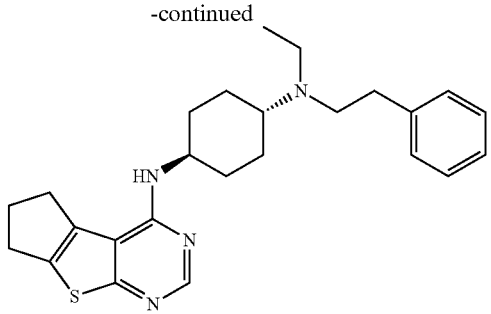

PH—NIM-0089

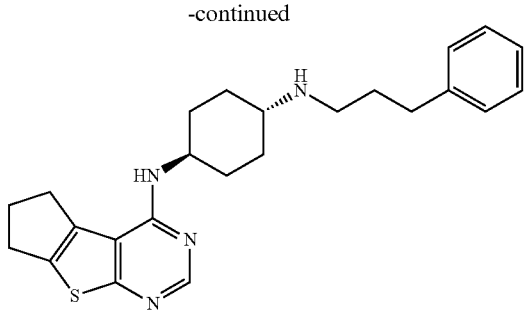

Note: For the preparation for Compound 1, see Example 68. Into a 50-mL round-bottom flask, was placed a solution of 1 (100 mg, 0.08 mmol, 1.00 equiv, 30%) in methanol (15 mL) was added acetaldehyde (0.5 mL) and acetic acid (0.5 mL), the resulting solution was stirred for 30 min at room temperature. Then NaBH$_3$CN (50 mg, 0.80 mmol, 10.00 equiv) was added and the resulting solution was stirred for 2 h at room temperature. The reaction solution was diluted with water, extracted with EtOAc. After concentration in vacuo, the crude product (100 mg) was continued to be purified by Prep-HPLC with the following conditions (Waters): Column, Xbridge Prep C18, 5 um, 19*150 mm; mobile phase, water with 50 mM NH$_4$HCO$_3$ and CH$_3$CN (10% CH$_3$CN up to 50% in 7 min, hold 50% in 1 min, up to 100% in 1.5 min); Flow rate, 20 mL/min; UV detection at 254/220 nm. The product-containing fractions were collected and partially evaporated to remove water and CH$_3$CN under reduced pressure. The residue was lyophilized overnight to give Compound I-203 (15 mg) as a white solid. LC-MS: (ES, m/z): 432 [M+H]+, 454 [M+Na]+; $^1$H-NMR (400 MHz, CDCl$_3$) δ 8.38 (1H, s), 7.34-7.22 (5H, m), 4.86 (1H, m), 4.01-3.99 (1H, m), 3.02 (4H, dd), 2.82-2.70 (6H, m), 2.59-2.52 (2H, m), 2.29-2.27 (2H, m), 2.07-0.93 (2H, m), 1.63-1.50 (2H, m), 1.32-1.17 (6H, m).

Example 145

(1r,4r)-N1-(6,7-dihydro-5H-cyclopenta[4,5]thieno[2,3-d]pyrimidin-4-yl)-N4-(3-phenylpropyl)cyclohexane-1,4-diamine Synthesis of Compound I-119

Note: For the preparation for Compound 1, see Example 147. To a solution of 1-N-[7-thia-9,11-diazatricyclo[6.4.0.0[2,6]]dodeca-1(8),2(6),9,11-tetraen-12-yl]cyclohexane-1,4-diamine (600 mg, 2.08 mmol, 1.00 equiv) in methanol (50 mL) was added 3-phenylpropanal (356 mg, 2.52 mmol, 1.20 equiv), followed by acetic acid (2.5 mL) at room temperature under nitrogen. The resulting mixture was stirred for 30 min at room temperature. Then NaBH$_3$CN (529 mg, 8.40 mmol, 4.00 equiv) was added and stirred for another 2 h at ambient temperature. The resulting solution was diluted with water and extracted with EtOAc, washed with brine, and dried with anhydrous sodium sulfate. After filtration and concentration under vacuum, 650 mg of the crude product was used for Example 146. The remaining crude product (290 mg) was purified by Prep-HPLC with the following conditions (Waters): Column, Xbridge Prep C18, 5 um, 19*150 mm; mobile phase, water with 100 mM NH$_4$CO$_3$ and CH$_3$CN (20.0% CH$_3$CN up to 60.0% in 10 min, up to 100.0% in 10 min); Flow rate, 20 mL/min; UV detection at 254/220 nm. The product-containing fractions were collected and partially evaporated to remove water and CH$_3$CN under reduced pressure. The residue was lyophilized overnight to give (1r,4r)-N1-(6,7-dihydro-5H-cyclopenta[4,5]thieno[2,3-d]pyrimidin-4-yl)-N4-(3-phenylpropyl)cyclohexane-1,4-diamine (70 mg) as a white solid. MS: (ES, m/z): 407 [M+H]$^+$; $^1$H NMR (400 MHz, CDCl$_3$): δ 8.39 (1H, s), 7.32-7.28 (2H, m), 7.22-7.19 (3H, m), 4.87 (1H, d), 4.15-4.09 (1H, m), 3.03 (4H, d), 2.71-2.67 (4H, m), 2.59-2.47 (3H, m), 2.48 (2H, d), 2.22 (2H, d), 1.39-1.21 (4H, m).

Example 146

1r,4r)-N1-(6,7-dihydro-5H-cyclopenta[4,5]thieno[2,3-d]pyrimidin-4-yl)-N4-methyl-N4-(3-phenylpropyl)cyclohexane-1,4-diamine- (I-118)

Synthesis of compound Compound I-118

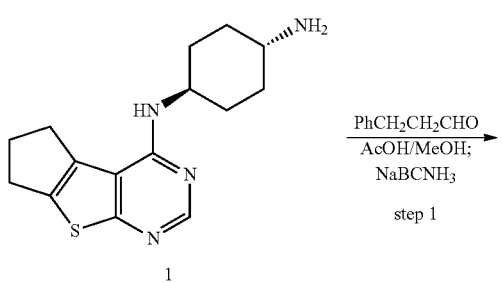

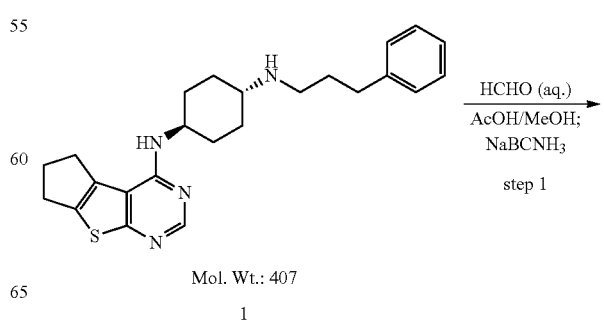

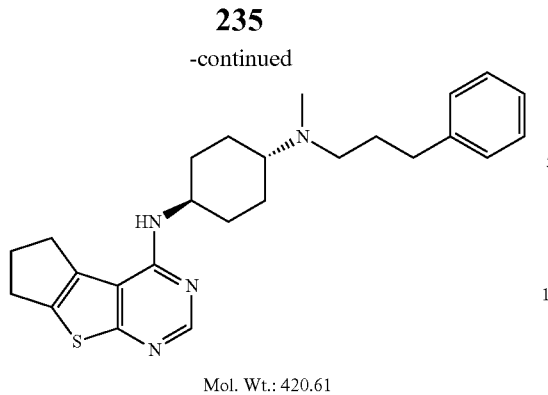

Mol. Wt.: 420.61

Note: For the preparation for Compound 1, see Example 145. Into a 100-mL round-bottom flask containing a solution of 1 (650 mg, 1.60 mmol, 1.00 equiv) in methanol (50 mL) was added HCHO solution (37%, 2 mL) and acetic acid (2 mL, 1.00 equiv) at room temperature under nitrogen. The mixture was stirred for 30 min at ambient temperature. Then NaBH$_3$CN (400 mg, 6.35 mmol, 3.97 equiv) was added and the resulting mixture was stirred for 2 h at ambient temperature. The resulting solution was neutralized with saturated aqueous K$_2$CO$_3$ and extracted with EtOAc, washed with brine, dried over anhydrous sodium sulfate. After filtration and concentration, the crude product was purified by Prep-HPLC with the following conditions (SHIMADZU): Column, SunFire Prep C18, 19*150 mm 5 um; mobile phase, water with 100 mM NH$_4$HCO$_3$ and CH$_3$CN (6.0% CH$_3$CN up to 50.0% in 13 min); Flow rate, 20 mL/min; UV detection at 254/220 nm. The product-containing fractions were collected and partially evaporated to remove water and CH$_3$CN under reduced pressure. The residue was lyophilized overnight to give Compound I-118 (124 mg) as a white solid. LC-MS: (ES, m/z): 407 [M+H]$^+$; $^1$H-NMR (400 MHz, CDDCl$_3$): δ 8.39 (1H, s), 7.32-7.28 (2H, m), 7.22-7.19 (3H, m), 4.87 (1H, d), 4.15-4.09 (1H, m), 3.03 (4H, d), 2.66 (2H, t), 2.59-2.52 (5H, m), 2.32 (3H, s), 2.26 (2H, d); 1.94-1.82 (4H, m), 1.52 (2H, d),1.27 (2H, d).

Example 147

2-(((1r,4r)-4-((6,7-dihydro-5H-cyclopenta[4,5]thieno[2,3-d]pyrimidin-4-yl)amino)cyclohexyl)(methyl)amino)-N-(pyridin-3-yl)acetamide. (I-126)

Synthesis of Compound I-126

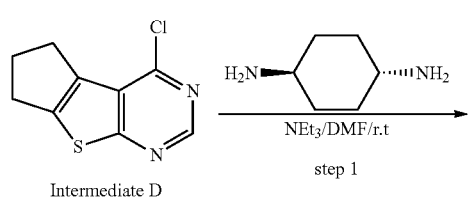

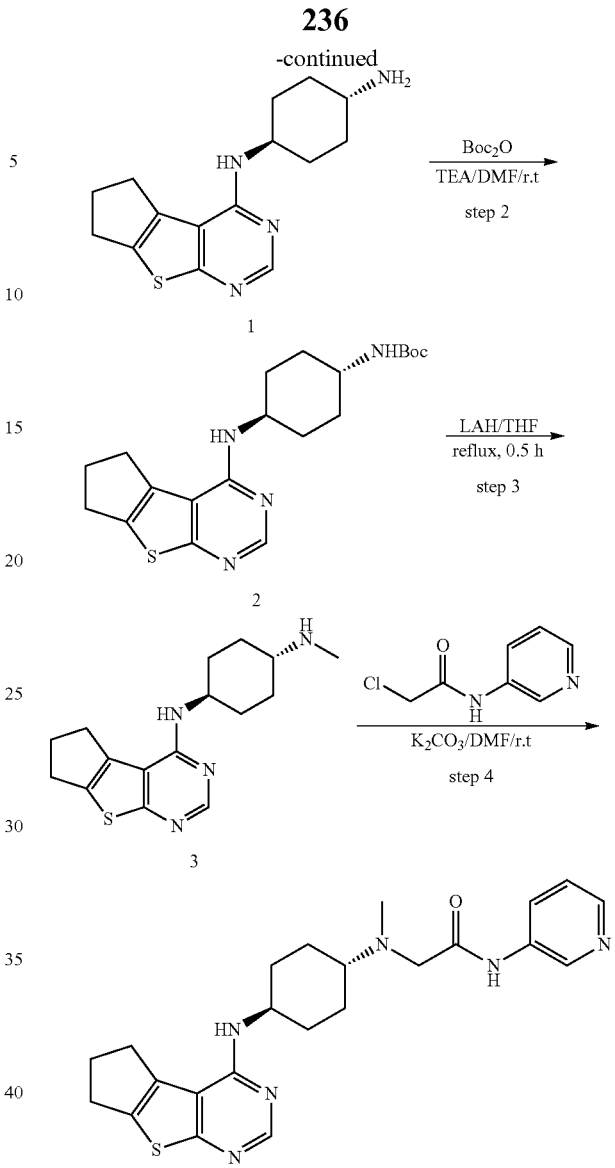

Synthesis of Compound 1

To a solution of 4 (3 g, 14.24 mmol, 1.00 equiv) in DMF (40 mL) was added cyclohexane-1,4-diamine (8.1 g, 70.94 mmol, 4.98 equiv) and triethylamine (4.3 g, 42.49 mmol, 2.98 equiv) at room temperature under nitrogen. The resulting solution was stirred overnight at ambient temperature. After completion of the reaction, the resulting solution was diluted with DCM (100 mL), washed with brine (100 mL), dried over anhydrous sodium sulfate and concentrated under vacuum to give 5 (3.4 g, 83%) as a yellow solid. LC-MS (ES, m/z): 289 (M+H$^+$).

Synthesis of Compound 2

To a solution of 5 (3.4 g, 11.79 mmol, 1.00 equiv) in DMF (50 mL) was added triethylamine (2.7 g, 26.68 mmol, 2.26 equiv) and (Boc)$_2$O (2.6 g, 11.91 mmol, 1.01 equiv) at 0° C. under nitrogen. The resulting solution was stirred for 2 h at room temperature and diluted with DCM, washed with brine, dried over anhydrous sodium sulfate and concentrated under vacuum. The residue was applied onto a silica gel column with ethyl acetate/petroleum ether (1:1) to provide 6 (4.2 g, 92%) as a yellow solid. LC-MS (ES, m/z): 389 (M+H⁺)

Synthesis of Compound 3

To a solution of 6 (200 mg, 0.51 mmol, 1.00 equiv) in THF (10 mL) was added LiAlH₄ (79 mg, 2.08 mmol, 4.00 equiv) at 0° C. The resulting solution was stirred for 30 min at 60° C. After cooled down to room temperature, the reaction was then quenched slowly with water/ice and extracted with ethyl acetate (100 mL), washed with brine, dried over anhydrous sodium sulfate and concentrated under vacuum. The desired compound 7 (200 mg, crude) was obtained as a yellow solid which was used directly to the next step without further purification. LC-MS (ES, m/z): 303 (M+H⁺).

Synthesis of Compound I-126

To a solution of 7 (200 mg, 0.33 mmol, 1.00 equiv, 50%) in DMF (5 mL) was added potassium carbonate (91.1 mg, 0.66 mmol, 2.00 equiv) and 2-chloro-N-(pyridin-3-yl)acetamide (85.5 mg, 0.50 mmol, 1.50 equiv) at room temperature under nitrogen. The resulting solution was stirred overnight at ambient temperature. The solids were filtered out and the filtrate was concentrated under vacuum. The crude product (150 mg) was purified by Prep-HPLC with the following conditions (SHIMADZU): Column, SunFire Prep C18, 19*150 mm 5 um; mobile phase, water with 0.05% NH₄HCO₃ and CH₃CN (10.0% CH₃CN up to 58.0% in 12 min); UV detection at 254/220 nm; Flow rate: 20 mL/min. The product-containing fractions were collected and partially evaporated to remove water and CH₃CN under reduced pressure. The residue was lyophilized overnight to give 2-(((1r,4r)-4-((6,7-dihydro-5H-cyclopenta[4,5]thieno[2,3-d]pyrimidin-4-yl)amino)cyclohexyl)(methyl)amino)-N-(pyridin-3-yl)acetamide (70 mg) as a white solid. LC-MS (ES, m/z): 437 (M+H⁺); ¹H NMR (400 MHz, DMSO): δ 9.86 (s, 1H), 8.83 (s, 1H), 8.27 (d, 1H), 8.25 (s, 1H), 8.11 (d, 1H), 7.35 (dd, 1H), 5.98 (d, 1H), 4.05-4.15 (m, 1H), 3.31 (s, 2H), 3.07 (t, 2H), 2.92 (t, 2H), 2.38-2.45 (m, 3H), 2.33 (s, 3H), 1.99-2.01 (m, 2H), 1.89-1.92 (m, 2H), 1.40-1.51 (m, 4H).

Example 148

2-(((1r,4r)-4-((6,7-dihydro-5H-cyclopenta[4,5]thieno[2,3-d]pyrimidin-4-yl)amino)cyclohexyl)(methyl)amino)-N-isopropylacetamide. (I-125)

Synthesis of Compound I-125

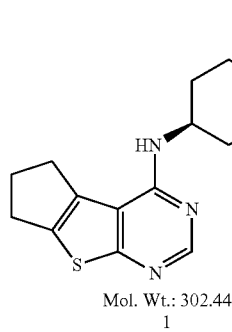

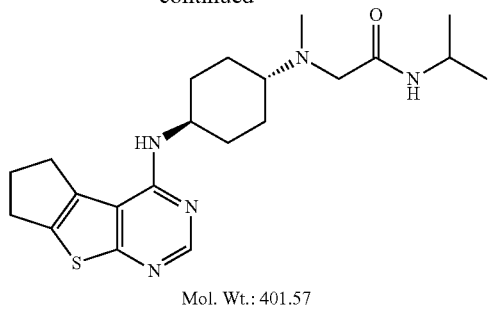

Mol. Wt.: 401.57

Note: For the preparation for Compound 1, see Example 147. To a solution of 1 (100 mg, 0.33 mmol, 1.00 equiv) in DMF (5 mL) was added potassium carbonate (91.1 mg, 0.66 mmol, 2.00 equiv) and 2-chloro-N-(propan-2-yl)acetamide (67.5 mg, 0.50 mmol, 1.50 equiv) at room temperature under nitrogen. The resulting solution was stirred overnight at ambient temperature. The solids were filtered out and the filtrate was concentrated under vacuum. The crude product (150 mg) was purified by Prep-HPLC with the following conditions (SHIMADZU): Column, X-bridge Prep C18, 19*150 mm 5 um; mobile phase, water with 0.05% NH₄HCO₃ and CH₃CN (5.0% CH₃CN up to 50.0% in 11 min); UV detection at 254/220 nm. The product-containing fractions were collected and partially evaporated to remove water and CH₃CN under reduced pressure. The residue was lyophilized overnight to give 2-(((1r,4r)-4-((6,7-dihydro-5H-cyclopenta[4,5]thieno[2,3-d]pyrimidin-4-yl)amino)cyclohexyl)(methyl)amino)-N-isopropylacetamide (36 mg) as a white solid. LC-MS (ES, m/z): 402 (M+H⁺). ¹H-NMR (400 MHz, DMSO): δ 8.25 (s, 1H), 7.42 (bs, 1H), 5.99 (d, 1H), 4.02-4.04 (m, 1H), 3.89 (sept, 1H), 3.07 (t, 2H), 2.91-2.94 (m, 4H), 2.38-2.44 (m, 3H), 2.24 (s, 3H), 1.97-2.00 (m, 2H), 1.80-1.82 (m, 2H), 1.35-1.48 (m, 4H), 1.08 (s, 6H).

Example 149

N-benzyl-2-(((1r,4r)-4-((6,7-dihydro-5H-cyclopenta[4,5]thieno[2,3-d]pyrimidin-4-yl)amino)cyclohexyl)(methyl)amino)acetamide. (I-123)

Synthesis of Compound I-123

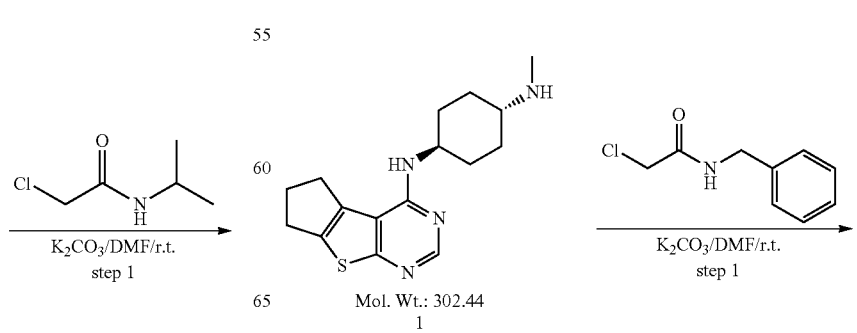

239

-continued

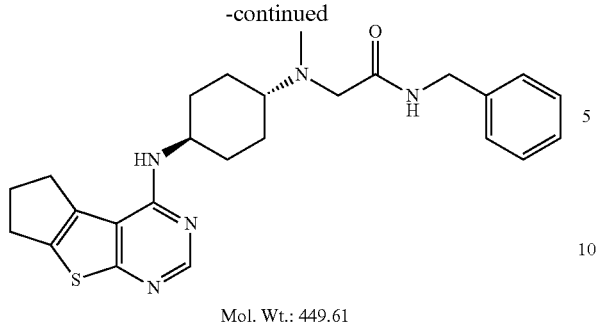

Mol. Wt.: 449.61

240

-continued

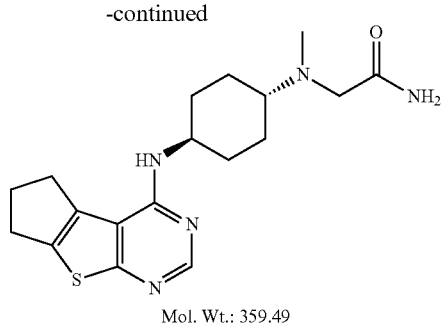

Mol. Wt.: 359.49

Note: For the preparation for Compound 1, see Example 147. To a solution of 1 (100 mg, 0.33 mmol, 1.00 equiv) in DMF (5 mL) was added N-benzyl-2-chloroacetamide (91.5 mg, 0.50 mmol, 1.51 equiv) and potassium carbonate (91.1 mg, 0.66 mmol, 2.00 equiv) at room temperature under nitrogen. The resulting solution was stirred overnight at room temperature. The solids were filtered out and the filtrate was concentrated under vacuum. The crude product (200 mg) was purified by Prep-HPLC with the following conditions (SHIMADZU): Column, SunFire Prep C18, 19*150 mm 5 um; mobile phase, water with 0.05% $NH_4HCO_3$ and $CH_3CN$ (10.0% $CH_3CN$ up to 60.0% in 10 min); Flow rate, 20 mL/min; UV detection at 254/220 nm. The product-containing fractions were collected and partially evaporated to remove water and $CH_3CN$ under reduced pressure. The residue was lyophilized overnight to give Compound I-123 (60 mg) as a white solid. LC-MS (ES, m/z): 450 (M+H$^+$); $^1$H NMR (400 MHz, DMSO): δ 8.25 (s, 1H), 8.23 (t, 1H), 7.21-7.34 (m, 5H), 5.97 (d, 1H), 4.31 (d, 2H), 4.03 (m, 1H), 3.08 (t, 2H), 3.05 (s, 2H), 2.93 (t, 2H), 2.41-2.46 (m, 3H), 2.25 (s, 3H), 1.97-2.00 (m, 2H), 1.81-1.84 (m, 2H), 1.35-1.48 (m, 4H).

Note: For the preparation for Compound 1, see Example 147. To a solution of 1 (180 mg, 0.30 mmol, 1.00 equiv, 50%) in distilled DMF (10 mL) was added potassium carbonate (83 mg, 0.60 mmol, 2.02 equiv) and 2-chloroacetamide (56 mg, 0.60 mmol, 2.01 equiv) at room temperature under nitrogen. The resulting solution was stirred overnight at 60° C. After completion of the reaction, the reaction mixture was cooled down to room temperature and diluted with water and extracted with EtOAc, washed with brine and dried over sodium sulfate. The crude product (180 mg) was purified by Prep-HPLC with the following conditions (SHIMADZU): Column, SunFire Prep C18, 19*150 mm 5 um; mobile phase, water with 0.05% $NH_4HCO_3$ and $CH_3CN$ (6.0% $CH_3CN$ up to 50.0% in 13 min); Flow rate, 20 mL/min; UV detection at 254/220 nm. The product-containing fractions were collected and partially evaporated to remove water and CH3CN under reduced pressure. The residue was lyophilized overnight to give Compound I-122 (62 mg) as a white solid. LC-MS (ES, m/z): 360 (M+H$^+$); $^1$H NMR (400 MHz, DMSO): δ 8.25 (s, 1H), 7.16 (s, 1H), 7.11 (s, 1H), 5.97 (s, 1H), 3.99-4.07 (m, 1H), 3.30 (s, 1H), 3.07 (t, 2H), 2.88-2.92 (m, 3H), 2.35-2.45 (m, 3H), 2.24 (s, 3H), 1.97-2.00 (m, 2H), 1.80-1.82 (m, 2H), 1.43-1.51 (m, 4H).

Example 150

2-(((1r,4r)-4-((6,7-dihydro-5H-cyclopenta[4,5]thieno[2,3-d]pyrimidin-4-yl)amino)cyclohexyl)(methyl)amino)acetamide- (I-122)

Synthesis of Compound I-122

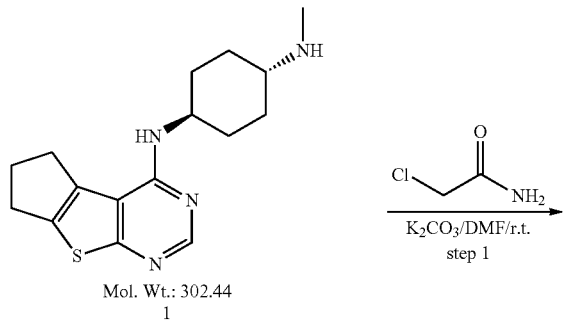

Example 151

2-[methyl[4-([7-thia-9,11-diazatricyclo[6.4.0.0[2,6]]dodeca-1(12),2(6),8,10-tetraen-12-yl]amino)cyclohexyl]amino]-1-(pyrrolidin-1-yl)ethan-1-one Synthesis of Compound I-124

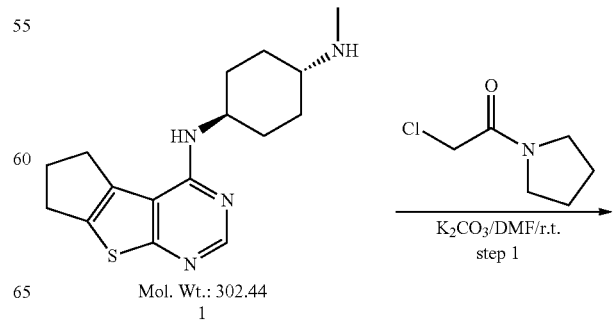

-continued

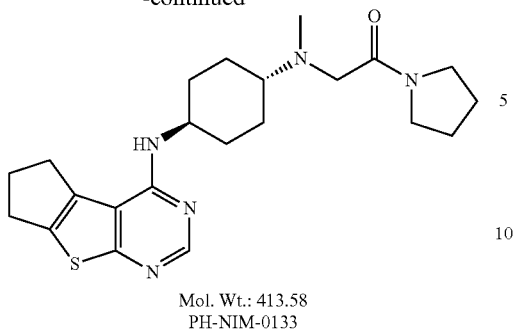

Mol. Wt.: 413.58
PH-NIM-0133

-continued

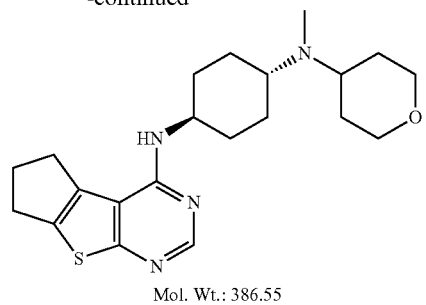

Mol. Wt.: 386.55

Note: For the preparation of the starting material compound 1, see Example 147. To a solution of 1-N-methyl-4-N-[7-thia-9,11-diazatricyclo[6.4.0.0[2,6]]dodeca-1(12),2(6),8,10-tetraen-12-yl]cyclohexane-1,4-diamine (200 mg, 0.33 mmol, 1.00 equiv, 50%) in DMF (5 mL) was added potassium carbonate (91.1 mg, 0.66 mmol, 2.00 equiv) and 2-chloro-1-(pyrrolidin-1-yl)ethan-1-one (73.5 mg, 0.50 mmol, 1.50 equiv) at room temperature under nitrogen. The resulting solution was stirred overnight at ambient temperature. The solids were filtered out and the filtrate was concentrated under vacuum. The crude product (150 mg) was purified by Prep-HPLC with the following conditions (SHIMADZU): Column, SunFire Prep C18, 19*150 mm 5 um; mobile phase, water with 0.05% NH$_3$HCO$_3$ and CH$_3$CN (5.0% CH$_3$CN up to 50.0% in 11 min); Flow rate, 20 mL/min; UV detection at 254/220 nm. The fractions containing product were collected and partially evaporated to remove water and CH$_3$CN under reduced pressure. The residue was lyophilized overnight to give the desired 2-[methyl[4-([7-thia-9,11-diazatricyclo[6.4.0.0[2,6]]dodeca-1(12),2(6),8,10-tetraen-12-yl]amino)cyclohexyl]amino]-1-(pyrrolidin-1-yl)ethan-1-one (40 mg) as a white solid. MS (ES, m/z): 414 (M+H$^+$). $^1$H NMR (400 MHz, DMSO-d$_6$): δ 8.25 (s, 1H), 5.97 (d, 1H), 4.02-4.04 (m, 1H), 3.49 (t, 2H), 3.35 (t, 2H), 3.21 (s, 2H), 3.09 (t, 2H), 2.95 (t, 2H), 2.39-2.51 (m, 3H), 2.25 (s, 3H), 1.95-2.03 (m, 2H), 1.69-1.88 (m, 6H), 1.33-1.51 (m, 4H).

Note: For the preparation of the starting material compound 1, see Example 147. To a solution of 1-N-methyl-4-N-[7-thia-9,11-diazatricyclo[6.4.0.0[2,6]]dodeca-1(8),2(6),9,11-tetraen-12-yl]cyclohexane-1,4-diamine (100 mg, 0.33 mmol, 1.00 equiv) in methanol (10 mL) was added oxan-4-one (66 mg, 0.66 mmol, 2.00 equiv), NaBH$_3$CN (104 mg, 1.65 mmol, 5.0 equiv) and acetic acid (0.1 mL) at room temperature under nitrogen. The resulting solution was stirred for 16 h at 30° C. and diluted with water, extracted with EtOAc, washed with brine. The organic layer was concentrated in vacuo. The crude product (130 mg) was purified by Prep-HPLC with the following conditions (SHIMADZU): Column, SunFire Prep C18, 19*150 mm 5 um; mobile phase, water with 0.05% NH$_4$HCO$_3$ and CH$_3$CN (6.0% CH$_3$CN up to 54.0% in 14 min); Flow rate, 20 mL/min; UV detection at 254/220 nm. The product-containing fractions were collected and partially evaporated to remove water and CH$_3$CN under reduced pressure. The residue was lyophilized overnight to give the desired 1-N-methyl-1-N-(oxan-4-yl)-4-N-[7-thia-9,11-diazatricyclo[6.4.0.0[2,6]]dodeca-1(8),2(6),9,11-tetraen-12-yl]cyclohexane-1,4-diamine (16.2 mg) as a light yellow solid. MS (ES, m/z): 387 (M+H$^+$); $^1$H NMR (400 MHz, CD$_3$OD): δ 8.35 (s, 1H), 4.20-4.33 (m, 1H), 4.05-4.16 (m, 2H), 3.61-3.70 (m, 1H), 3.47-3.56 (m, 3H), 3.17 (t, 2H, J=6.8 Hz), 3.06 (t, 2H, J=6.8 Hz), 2.85 (s, 3H), 2.56-2.65 (m, 2H), 2.27-2.32 (m, 2H), 2.18-2.25 (m, 2H), 2.01-2.16 (m, 2H), 1.91-1.97 (m, 1H), 1.79-1.89 (m, 3H), 1.69-1.75 (m, 2H).

Example 152

1-N-methyl-1-N-(oxan-4-yl)-4-N-[7-thia-9,11-diazatricyclo[6.4.0.0[2,6]]dodeca-1(8),2(6),9,11-tetraen-12-yl]cyclohexane-1,4-diamine Synthesis of Compound I-132

Example 153

2-[methyl[4-([7-thia-9,11-diazatricyclo[6.4.0.0[2,6]]dodeca-1(12),2(6),8,10-tetraen-12-yl]amino)cyclohexyl]amino]-1-(piperidin-1-yl)ethan-1-one Synthesis of Compound I-129

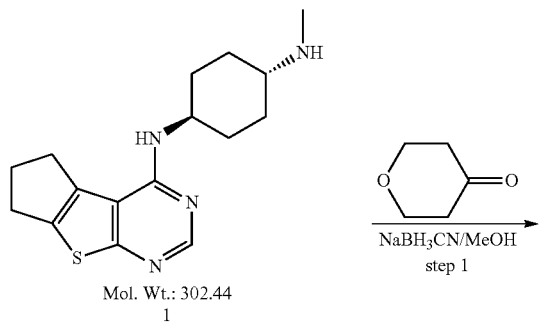

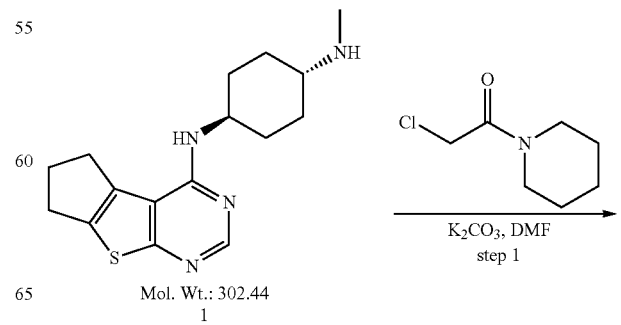

243

-continued

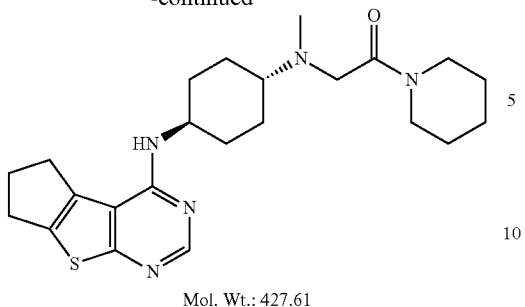

Mol. Wt.: 427.61

Note: For the preparation of the starting material compound 1, see Example 147. To a solution of 1-N-methyl-4-N-[7-thia-9,11-diazatricyclo[6.4.0.0[2,6]]dodeca-1(12),2(6),8,10-tetraen-12-yl]cyclohexane-1,4-diamine (90 mg, 0.30 mmol, 1.00 equiv) in DMF (10 mL) was added 2-chloro-1-(piperidin-1-yl)ethan-1-one (72 mg, 0.45 mmol, 1.50 equiv) and potassium carbonate (83 mg, 0.60 mmol, 2.00 equiv) at room temperature under nitrogen. The resulting solution was stirred overnight at ambient temperature. After completion of the reaction, the solids were removed by filtration and the filtrate was concentrated under vacuum. The crude product (100 mg) was purified by Prep-HPLC with the following conditions (SHIMADZU): Column, SunFire Prep C18, 19*150 mm 5 um; mobile phase, water with 0.05% $NH_4HCO_3$ and $CH_3CN$ (7.0% $CH_3CN$ up to 55.0% in 19 min); Flow rate, 20 mL/min; UV detection at 254/220 nm. The product-containing fractions were collected and partially evaporated to remove water and $CH_3CN$ under reduced pressure. The residue was lyophilized overnight to give the desired 2-[methyl[4-([7-thia-9,11-diazatricyclo[6.4.0.0[2,6]]dodeca-1(12),2(6),8,10-tetraen-12-yl]amino)cyclohexyl]amino]-1-(piperidin-1-yl)ethan-1-one (18.4 mg) as a white solid. MS (ES, m/z): 428 (M+H$^+$); $^1$H NMR (400 MHz, CD$_3$OD): δ 8.23 (s, 1H), 4.08-4.09 (m, 1H), 3.54-3.59 (m, 4H), 3.39 (s, 2H), 3.08 (t, 2H, J=6.8 Hz), 2.99 (t, 2H, J=6.8 Hz), 2.54-2.59 (m, 3H), 2.34 (s, 3H), 2.16-2.19 (m, 2H), 1.94-1.97 (m, 2H), 1.45-1.70 (m, 10H).

Example 154

2-[methyl[4-([7-thia-9,11-diazatricyclo[6.4.0.0[2,6]]dodeca-1(12),2(6),8,10-tetraen-12-yl]amino)cyclohexyl]amino]-1-(morpholin-4-yl)ethan-1-one Synthesis of Compound I-130

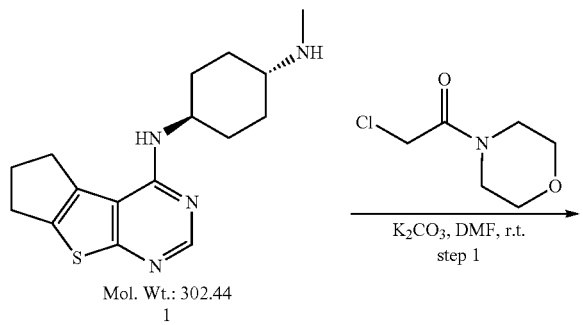

Mol. Wt.: 302.44
1

244

-continued

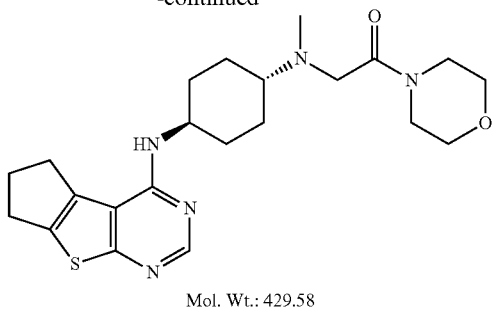

Mol. Wt.: 429.58

Note: For the preparation of the starting material compound 1, see Example 147. To a solution of 1-N-methyl-4-N-[7-thia-9,11-diazatricyclo[6.4.0.0[2,6]]dodeca-1(12),2(6),8,10-tetraen-12-yl]cyclohexane-1,4-diamine (90 mg, 0.30 mmol, 1.00 equiv) in DMF (10 mL) was added 2-chloro-1-(morpholin-4-yl)ethan-1-one (73.35 mg, 0.45 mmol, 1.50 equiv) and potassium carbonate (83 mg, 0.60 mmol, 2.00 equiv) at room temperature under nitrogen. The resulting solution was stirred overnight at ambient temperature. After completion of the reaction, the solids were removed by filtration and the filtrate was concentrated under vacuum. The crude product (100 mg) was purified by Prep-HPLC with the following conditions (SHIMADZU): Column, SunFire Prep C18, 19*150 mm 5 um; mobile phase, water with 0.05% $NH_4HCO_3$ and $CH_3CN$ (6.0% $CH_3CN$ up to 50.0% in 19 min); Flow rate, 20 mL/min; UV detection at 254/220 nm. The product-containing fractions were collected and partially evaporated to remove water and $CH_3CN$ under reduced pressure. The residue was lyophilized overnight to give the desired 2-[methyl[4-([7-thia-9,11-diazatricyclo[6.4.0.0[2,6]]dodeca-1(12),2(6),8,10-tetraen-12-yl]amino)cyclohexyl]amino]-1-(morpholin-4-yl)ethan-1-one (30.8 mg) as a white solid. MS (ES, m/z): 430 (M+H$^+$). $^1$H NMR (400 MHz, CD$_3$OD-d$_6$): δ 8.23 (s, 1H), 4.05-4.08 (m, 1H), 3.67-3.68 (m, 6H), 3.59-3.60 (m, 2H), 3.40 (s, 2H), 3.08 (t, 2H), 3.01 (t, 2H), 2.52-2.59 (m, 3H), 2.34 (s, 3H), 2.16-2.19 (m, 2H), 1.93-1.96 (m, 2H), 1.45-1.57 (m, 4H).

Example 155

N,N-dimethyl-2-[methyl[4-([7-thia-9,11-diazatricyclo[6.4.0.0[2,6]]dodeca-1(12),2(6),8,10-tetraen-12-yl]amino)cyclohexyl]amino]acetamide. (I-131)

Synthesis of Compound I-131

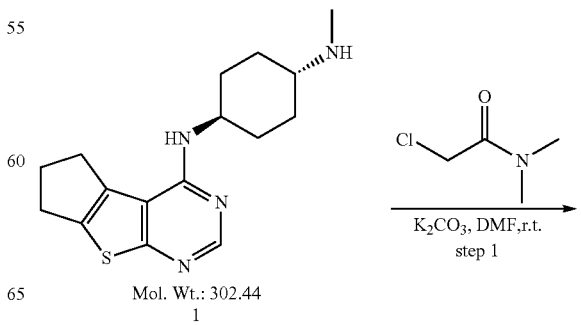

Mol. Wt.: 302.44
1

245

-continued

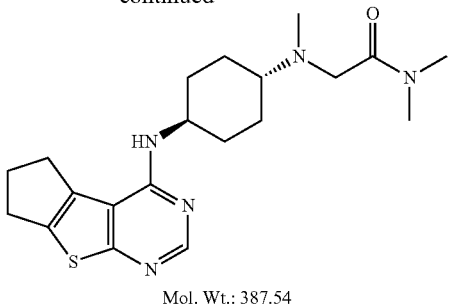

Mol. Wt.: 387.54

Note: For the preparation of the starting material compound 1, see Example 147. To a solution of 1-N-methyl-4-N-[7-thia-9,11-diazatricyclo[6.4.0.0[2,6]]dodeca-1(12),2(6),8,10-tetraen-12-yl]cyclohexane-1,4-diamine (90 mg, 0.30 mmol, 1.00 equiv) in DMF (10 mL) was added 2-chloro-N,N-dimethylacetamide (54.45 mg, 0.45 mmol, 1.50 equiv) and potassium carbonate (83 mg, 0.60 mmol, 2.00 equiv) at room temperature under nitrogen. The resulting solution was stirred overnight at ambient temperature. After completion of the reaction, the solids were removed by filtration and the filtrate was concentrated under vacuum. The crude product (120 mg) was purified by Prep-HPLC with the following conditions (SHIMADZU): Column, SunFire Prep C18, 19*150 mm 5 um; mobile phase, water with 0.05% NH$_4$HCO$_3$ and CH$_3$CN (5.0% CH$_3$CN up to 49.0% in 13 min); Flow rate, 20 mL/min; UV detection at 254/220 nm. The product-containing fractions were collected and partially evaporated to remove water and CH$_3$CN under reduced pressure. The residue was lyophilized overnight to give the desired N,N-dimethyl-2-[methyl[4-([7-thia-9,11-diazatricyclo[6.4.0.0[2,6]]dodeca-1(12),2(6),8,10-tetraen-12-yl]amino)cyclohexyl]amino]acetamide (31.8 mg) as a white solid. MS (ES, m/z): 388 (M+H$^+$). $^1$H NMR (400 MHz, DMSO): δ 8.25 (s, 1H), 5.98 (d, 1H), 4.01-4.04 (m, 1H), 3.22 (s, 2H), 3.08 (t, 2H), 3.03 (s, 3H), 2.93 (t, 2H), 2.80 (s, 3H), 2.42-2.44 (m, 3H), 2.20 (s, 3H), 1.97-2.00 (m, 2H), 1.78-1.81 (m, 2H), 1.24-1.48 (m, 4H).

Example 156

N-[4-(dimethylnitroso)cyclohexyl]-7-thia-9,11-diazatricyclo[6.4.0.0[2,6]]dodeca-1(8),2(6),9,11-tetraen-12-amine Synthesis of I-128

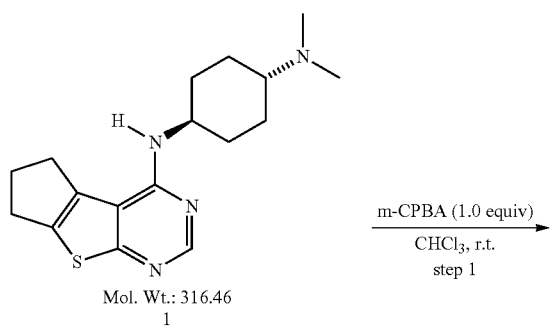

246

-continued

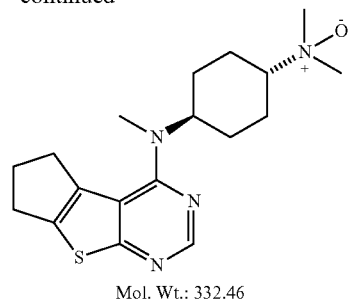

Mol. Wt.: 332.46

Note: For the preparation of the starting material compound 1, see Example 13. A solution of 1-N,1-N-dimethyl-4-N-[7-thia-9,11-diazatricyclo[6.4.0.0[2,6]]dodeca-1(8),2(6),9,11-tetraen-12-yl]cyclohexane-1,4-diamine (100 mg, 0.32 mmol, 1.00 equiv) in chloroform (5 mL) was added m-CPBA (65 mg, 0.38 mmol, 1.00 equiv) at 0° C. under nitrogen. The resulting solution was stirred for 2 h at room temperature. After completion of the reaction, the resulting solution was diluted with EtOAc and washed with water, brine. The organic layer was concentrated under vacuum. The crude product (140 mg) was purified by Prep-HPLC with the following conditions (SHIMADZU): Column, SunFire Prep C18, 19*150 mm 5 um; mobile phase, water with 0.05% NH$_4$HCO$_3$ and CH$_3$CN (6.0% CH$_3$CN up to 50.0% in 25 min); UV detection at 254/220 nm. The product-containing fractions were collected and partially evaporated to remove CH$_3$CN and water under reduced pressure. The residue was lyophilized overnight to give the resulted N-[4-(dimethylnitroso)cyclohexyl]-7-thia-9,11-diazatricyclo[6.4.0.0[2,6]]dodeca-1(8),2(6),9,11-tetraen-12-amine (98 mg, 93%) as a white solid. MS (ES, m/z): 333 (M+H)$^+$. $^1$H NMR (400 MHz, CD$_3$OD): δ 8.25 (1H, s), 4.18-4.16 (1H, m), 3.23-3.19 (1H, m), 3.15 (6H, s), 3.13-3.09 (2H, m), 3.03-2.99 (2H, m), 2.6-2.54 (2H, m), 2.43 (2H, d), 2.25 (2H, d), 1.77-1.70 (2H, m), 1.62-1.55 (2H, m).

Example 157 and Example 158

Synthesis of trans-1-(pyrrolidin-1-yl)-2-[[4-([7-thia-9,11-diazatricyclo[6.4.0.0[2,6]]dodeca-1(8),2(6),9,11-tetraen-12-yl]amino)cyclohexyl]amino]ethan-1-one and trans-2-[[2-oxo-2-(pyrrolidin-1-yl)ethyl][4-([7-thia-9,11-diazatricyclo[6.4.0.0[2,6]]dodeca-1(8),2(6),9,11-tetraen-12-yl]amino)cyclohexyl]amino]-1-(pyrrolidin-1-yl)ethan-1-one Synthesis of I-134 and I-136

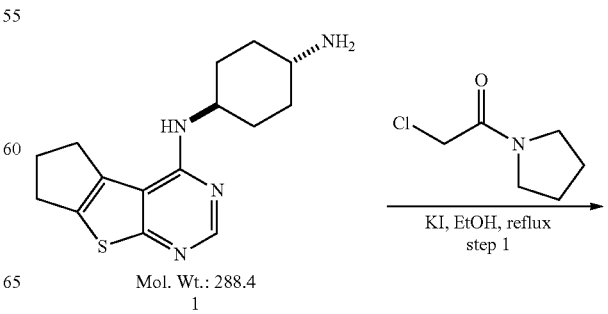

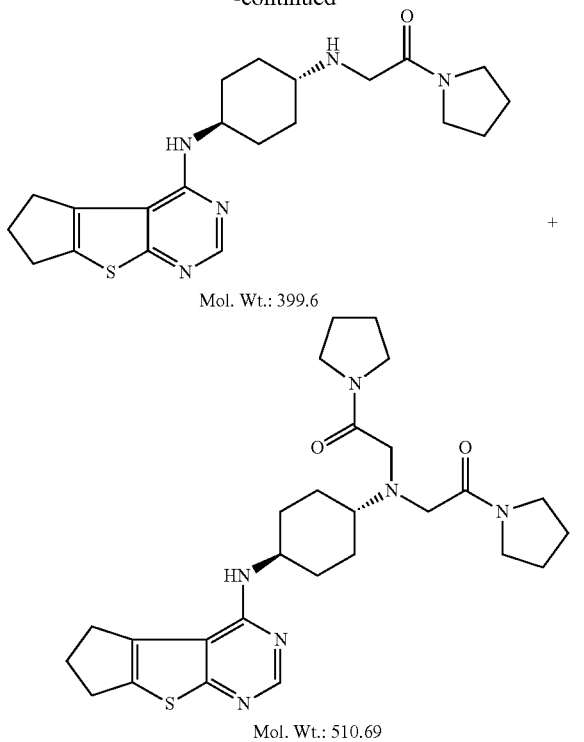

Mol. Wt.: 399.6

Mol. Wt.: 510.69

Note: For the preparation of the starting material compound 1, see Example 147. Into a 50-mL round-bottom flask, was placed 1-N-[7-thia-9,11-diazatricyclo[6.4.0.0[2,6]]dodeca-1(8),2(6),9,11-tetraen-12-yl]cyclohexane-1,4-diamine (170 mg, 0.59 mmol, 1.00 equiv), 2-chloro-1-(pyrrolidin-1-yl)ethan-1-one (89 mg, 0.60 mmol, 1.00 equiv), KI (10 mg, 1.00 equiv) and ethanol (20 mL) at room temperature under nitrogen. The resulting solution was stirred overnight at 90° C. in an oil bath. The solvent was removed under reduced pressure. The crude product (180 mg) was purified by Prep-HPLC with the following conditions (SHIMADZU): Column, SunFire Prep C18, 19*150 mm 5 um; mobile phase, water with 0.05% $NH_4HCO_3$ and $CH_3CN$ (6.0% $CH_3CN$ up to 50.0% in 21 min); Flow rate, 20 mL/min; UV detection at 254/220 nm. The product-containing fractions were collected and partially evaporated to remove water and $CH_3CN$ under reduced pressure. The residue was lyophilized overnight to give the desired trans-1-(pyrrolidin-1-yl)-2-[[4-([7-thia-9,11-diazatricyclo[6.4.0.0[2,6]]dodeca-1(8),2(6),9,11-tetraen-12-yl]amino)cyclohexyl]amino]ethan-1-one (20.5 mg) as a white solid and trans-2-[[2-oxo-2-(pyrrolidin-1-yl)ethyl][4-([7-thia-9,11-diazatricyclo[6.4.0.0[2,6]]dodeca-1(8),2(6),9,11-tetraen-12-yl]amino)cyclohexyl]amino]-1-(pyrrolidin-1-yl)ethan-1-one (26.7 mg) as a white solid, respectively.

Example 157 (I-134)

MS (ES, m/z): 400 (M+H$^+$). $^1$H NMR (300 HMz, CDCl$_3$): δ 8.37 (s, 1H), 4.83 (d, 1H), 4.11 (m, 1H), 3.50 (t, 2H), 3.38 (t, 4H), 2.99 (m, 4H), 2.53 (m, 3H), 2.22 (d, 2H), 1.98 (m, 4H), 1.86 (m, 2H), 1.40 (m, 2H), 1.27 (m, 2 H).

Example 158 (I-136)

MS: (ES, m/z): 511 (M+H$^+$). $^1$H NMR: (300 HMz, CDCl$_3$): δ 8.33 (s, 1H), 4.79 (d, 1H), 4.02 (m, 1H), 3.46 (m, 12H), 2.96 (t, 4H), 2.87 (m, 1 H), 2.55 (m, 2H), 2.18 (d, 2H), 1.89 (m, 10H), 1.78 (m, 2H), 1.65 (m, 3H).

Example 159

2-(((1r,4r)-4-((6,7-dihydro-5H-cyclopenta[4,5]thieno[2,3-d]pyrimidin-4-yl)oxy)cyclohexyl)amino)-1-(pyrrolidin-1-yl)ethanone. (I-133)

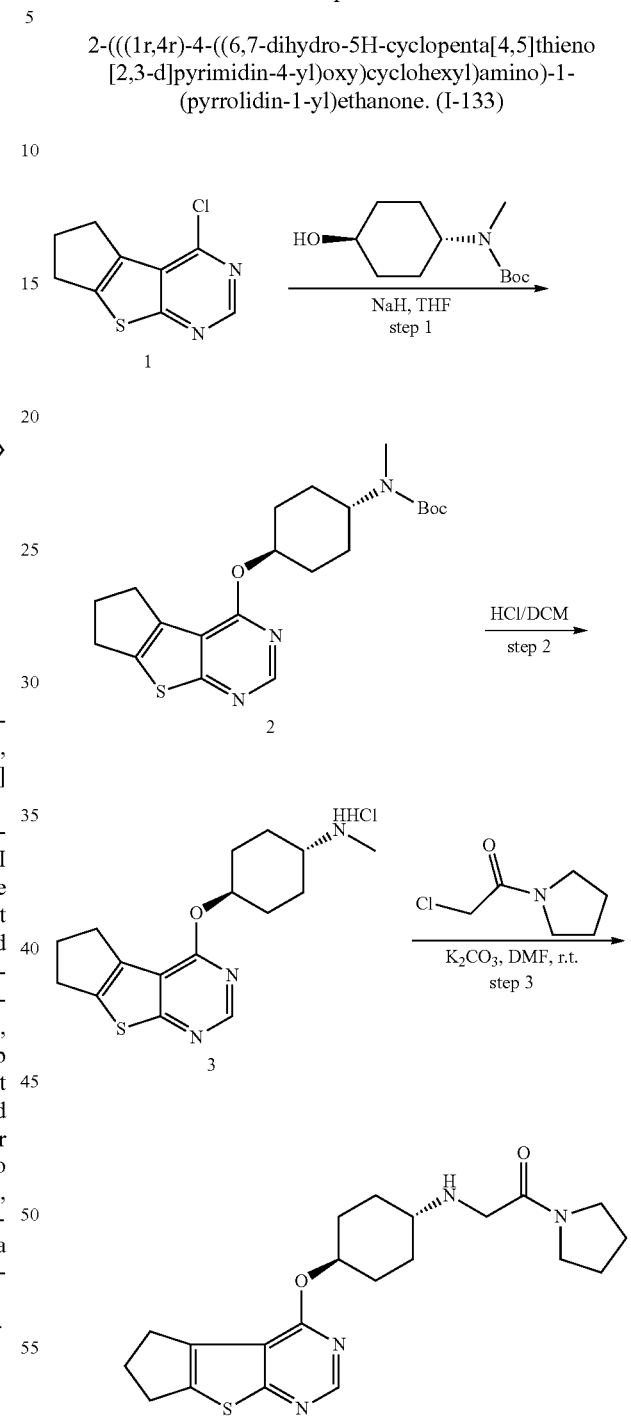

Synthesis of Compound 2

Into a 50-mL 3-necked round-bottom flask purged and maintained with an inert atmosphere of nitrogen, was placed a solution of tert-butyl N-(4-hydroxycyclohexyl)-N-methylcarbamate (447 mg, 1.95 mmol, 1.30 equiv) in anhydrous THF (30 mL), then sodium hydride (300 mg, 7.50 mmol, 5.00 equiv, 60% dispersion in mineral oil) was added and stirring for 20 min at room temperature under nitrogen. Then 12-chloro-7-thia-9,11-diazatricyclo[6.4.0.0[2,6]]dodeca-1(12),2(6),8,10-tetraene (316 mg, 1.50 mmol, 1.00 equiv) was added and stirred for 6 h at ambient temperature. The reaction mixture was quenched with NH$_4$Cl (sat.) at 0° C., diluted with brine, extracted with EtOAc. The organic layer was washed with brine and dried over anhydrous sodium sulfate. After filtration and concentration, the residue was purified by a silica gel column with EA/PE (1:10-1:4) to provide tert-butyl N-methyl-N-(4-[7-thia-9,11-diazatricyclo[6.4.0.0[2,6]]dodeca-1(12),2(6),8,10-tetraen-12-yloxy]cyclohexyl)carbamate (450 mg, 74%) as a white solid. MS: (ES, m/z): 404 [M+H]$^+$.

Synthesis of Compound 3

Into a 100-mL round-bottom flask, was placed a solution of tert-butyl N-methyl-N-(4-[7-thia-9,11-diazatricyclo[6.4.0.0[2,6]]dodeca-1(12),2(6),8,10-tetraen-12-yloxy]cyclohexyl)carbamate (450 mg, 1.12 mmol, 1.00 equiv) in dichloromethane (50 mL), hydrochloric acid (1.0 mL, 12 M) was added and the resulting solution was stirred for 3 h at room temperature. The resulting mixture was concentrated under vacuum to provide N-methyl-4-[7-thia-9,11-diazatricyclo[6.4.0.0[2,6]]dodeca-1(12),2(6),8,10-tetraen-12-yloxy]cyclohexan-1-amine hydrochloride (350 mg 92%) as a white solid.

Synthesis of Compound I-133

A solution of N-methyl-4-[7-thia-9,11-diazatricyclo[6.4.0.0ˆ[2,6]]dodeca-1(12),2(6),8,10-tetraen-12-yloxy]cyclohexan-1-amine hydrochloride (170 mg, 0.5 mmol, 1.0 equiv) in anhydrous DMF (15 mL) was added 2-chloro-1-(pyrrolidin-1-yl)ethanone (150 mg, 1.0 mmol, 2.0 equiv) and K$_2$CO$_3$ (345 mg, 2.5 mmol, 5.0 equiv) at room temperature under nitrogen. The resulting mixture was stirred over night at 60° C. After filtration and concentration in vacuo, the residue (200 mg) was purified by Prep-HPLC with the following conditions (Waters): Column, Xbridge Prep C18, 5 um, 19*150 mm; mobile phase, water with 100 mM NH$_4$HCO$_3$ and CH$_3$CN (10% CH$_3$CN up to 65% in 10 min, up to 95% in 2 min); Flow rate, 20 mL/min; UV detection at 254/220 nm. The product-containing fractions were collected and partially evaporated to remove water and CH$_3$CN under reduced pressure. The residue was lyophilized overnight to give 2-(((1r,4r)-4-((6,7-dihydro-5H-cyclopenta[4,5]thieno[2,3-d]pyrimidin-4-yl)oxy)cyclohexyl)amino)-1-(pyrrolidin-1-yl)ethanone (50 mg) as a white solid. MS: (ES, m/z): 415 [M+H]$^+$; $^1$H NMR (400 MHz, CD$_3$OD): δ 8.45 (1H, s), 5.24 (1H, m), 3.58 (2H, t), 3.45 (2H, m), 3.33 (2H, s), 3.04-3.02 (4H, m), 2.72-2.62 (1H, m), 2.52 (2H, m), 2.37 (3H, s), 2.32-2.30 (2H, m), 2.01 (4H, t), 2.01-1.88 (2H, m), 1.61-1.58 (2H, m).

Example 160 and Example 161 trans-1-(pyrrolidin-1-yl)-2-[(4-[7-thia-9,11-diazatricyclo[6.4.0.0[2,6]]dodeca-1(8),2(6),9,11-tetraen-12-yloxy]cyclohexyl)amino]ethan-1-one and trans-2-[[2-oxo-2-(pyrrolidin-1-yl)ethyl](4-[7-thia-9,11-diazatricyclo[6.4.0.0[2,6]]dodeca-1(8),2(6),9,11-tetraen-12-yloxy]cyclohexyl)amino]-1-(pyrrolidin-1-yl)ethan-1-one Synthesis of Compound I-135 and Compound I-137

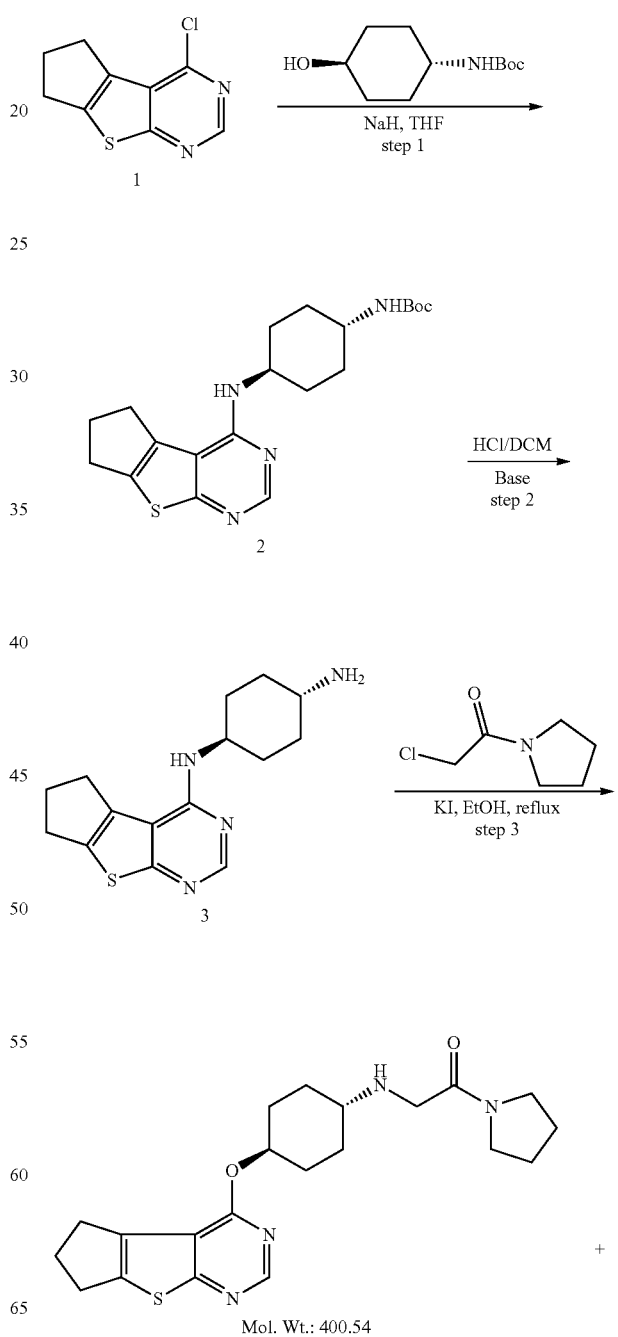

Mol. Wt.: 400.54

-continued

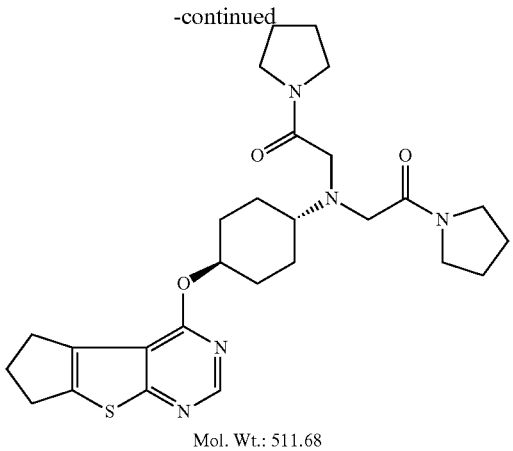

Mol. Wt.: 511.68

Synthesis of Compound 2

Note: For the preparation of the starting material compound 1, see Example 147.

A solution of tert-butyl N-(4-hydroxycyclohexyl)carbamate (194 mg, 0.90 mmol, 1.40 equiv) in anhydrous tetrahydrofuran (5 mL) was added sodium hydride (60% dispersion in mineral oil, 77 mg, 1.92 mmol, 3.00 equiv) at 0° C. under nitrogen. After stirred at room temperature for 1 h, 12-chloro-7-thia-9,11-diazatricyclo[6.4.0.0^[2,6]]dodeca-1(8),2(6),9,11-tetraene (200 mg, 0.95 mmol, 1.00 equiv) was added and the resulting solution was stirred overnight at ambient temperature for additional 5 h. The reaction was then quenched with water and extracted with 3×30 mL of ethyl acetate. The combined organic layers were washed with brine, dried over anhydrous sodium sulfate and concentrated under vacuum. The residue was applied onto a silica gel column with ethyl acetate/petroleum ether (1:5) to give the resulted tert-butyl N-(4-[7-thia-9,11-diazatricyclo[6.4.0.0[2,6]]dodeca-1(8),2(6),9,11-tetraen-12-yloxy]cyclohexyl)carbamate (308 mg, 83%) as a yellow solid. MS (ES, m/z): 390 (M+H$^+$).

Synthesis of Compound 3

Into a 50-mL round-bottom flask placed tert-butyl N-(4-[7-thiatricyclo[6.4.0.0[2,6]]dodeca-1(8),2(6),9,11-tetraen-12-yloxy]cyclohexyl)carbamate (200 mg, 0.52 mmol, 1.00 equiv) in 16 mL of dichloromethane was added hydrochloric acid (0.5 mL) at 0° C. The resulting solution was stirred for 2 h at room temperature. Then the pH value was adjusted to 8-9 with saturated aqueous sodium carbonate and extracted with 3×50 mL of ethyl acetate and the organic layers combined. The organic layers were washed with brine, dried over anhydrous sodium sulfate and concentrated under vacuum to give the resulted 4-[7-thiatricyclo[6.4.0.0[2,6]]dodeca-1(8),2(6),9,11-tetraen-12-yloxy]cyclohexan-1-amine (140 mg, 90% purity) as a white solid which was used for next step without further purification. MS (ES, m/z): 290 (M+H$^+$).

Synthesis of Compound I-135 and Compound I-137

A solution of 4-[7-thia-9,11-diazatricyclo[6.4.0.0[2,6]]dodeca-1(8),2(6),9,11-tetraen-12-yloxy]cyclohexan-1-amine (140 mg, 0.48 mmol, 1.00 equiv) in ethanol (20 mL) was added 2-chloro-1-(pyrrolidin-1-yl)ethan-1-one (72 mg, 0.49 mmol, 1.00 equiv) and KI (80 mg, 1.00 equiv) and the resulting solution was stirred for 8 h at 90° C. in an oil bath. After concentrated in vacuo, the crude product (160 mg) was purified by Prep-HPLC with the following conditions (SHIMADZU): Column, SunFire Prep C18, 19*150 mm 5 um; mobile phase, water with 0.05% HCOOH and CH$_3$CN (6.0% CH$_3$CN up to 52.0% in 14 min); Flow rate, 20 mL/min; UV detection at 254/220 nm. The product-containing fractions were collected and partially evaporated to remove water and CH$_3$CN under reduced pressure. The residue was lyophilized overnight to give the desired trans-1-(pyrrolidin-1-yl)-2-[(4-[7-thia-9,11-diazatricyclo[6.4.0.0[2,6]]dodeca-1(8),2(6),9,11-tetraen-12-yloxy]cyclohexyl)amino]ethan-1-one (14.4 mg) as a off-white solid and trans-2-[[2-oxo-2-(pyrrolidin-1-yl)ethyl](4-[7-thia-9,11-diazatricyclo[6.4.0.0[2,6]]dodeca-1(8),2(6),9,11-tetraen-12-yloxy]cyclohexyl)amino]-1-(pyrrolidin-1-yl)ethan-1-one (32.8 mg) as a off-white solid, respectively.

Example 160 (I-135)

MS: (ES, m/z): 401 [M+H]$^+$. $^1$H NMR: (300 MHz, CDCl$_3$): δ 8.50 (s, 1H), 5.28 (m, 1H), 3.42 (t, 2H), 3.39 (t, 4H), 3.02 (t, 4H), 2.66 (m, 1H), 2.50 (m, 2H), 2.25 (m, 2H), 2.04 (m, 5H), 1.85 (m, 2H), 1.56 (m, 4 H).

Example 161 (I-137)

MS: (ES, m/z): 512 [M+H]$^+$. $^1$H NMR: (300 MHz, CDCl$_3$): δ m8.48 (s, 1H), 5.18 (m, 1H), 3.48 (m, 11H), 2.95 (m, 5H), 2.53 (m, 2H), 2.23 (m, 2H), 2.10 (m, 2H), 1.99 (m, 4H), 1.84 (m, 4H), 1.63 (m, 5H).

Example 162

1-N-[7-thia-9,11-diazatricyclo[6.4.0.0^[2,6]]dodeca-1(8),2(6),9,11-tetraen-12-yl]-4-N-(2,2,2-trifluoroethyl)cyclohexane-1,4-diamine

Synthesis of Compound I-138

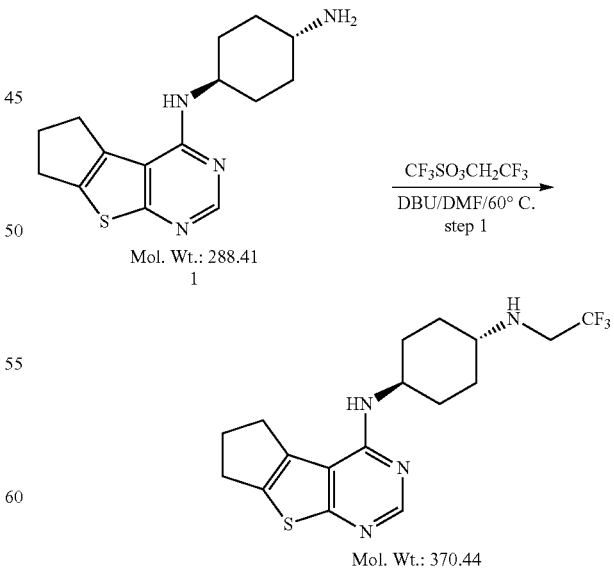

To a 50 mL round-bottom flask containing a solution of 1-N-[7-thia-9,11-diazatricyclo[6.4.0.0^[2,6]]dodeca-1(8),2(6),9,11-tetraen-12-yl]cyclohexane-1,4-diamine (288 mg, 1.00 mmol, 1.00 equiv) in DMF (10 mL) was added F$_3$CSO$_3$CH$_2$CF$_3$ (700 mg, 3.02 mmol, 3.00 equiv) and DBU (457 mg, 3.01 mmol, 3.00 equiv) in ice-water bath under nitrogen. The resulting solution was stirred overnight at 60° C. After completion of the reaction, the reaction solution was cooled down to room temperature and then quenched with water, diluted with DCM (30 mL), washed with brine, dried over anhydrous sodium sulfate and concentrated under vacuum. The residue was applied onto a silica gel column with DCM/methanol (30:1 to 20:1) to provide the desired 1-N-[7-thia-9,11-diazatricyclo[6.4.0.0^[2,6]]dodeca-1(8),2(6),9,11-tetraen-12-yl]-4-N-(2,2,2-trifluoroethyl)cyclohexane-1,4-diamine (300 mg, 81%) as a white solid. MS (electrospray) m/z 371 (M+H)$^+$; $^1$H NMR (400 MHz, CD$_3$OD): 8.22 (s, 1H), 4.06-4.14 (m, 1H), 3.24-3.32 (q, 2H), 3.01 (t, 2H), 3.07 (t, 2H), 2.51-2.78 (m, 3H), 2.04-2.15 (m, 4H), 1.43-1.55 (m, 2H), 1.28-1.35 (m, 2H).

Example 163

1-N-methyl-1-N-(2-methylpropyl)-4-N-[7-thia-9,11-diazatricyclo[6.4.0.0[2,6]]dodeca-1(8),2(6),9,11-tetraen-12-yl]cyclohexane-1,4-diamine Synthesis of Compound I-127

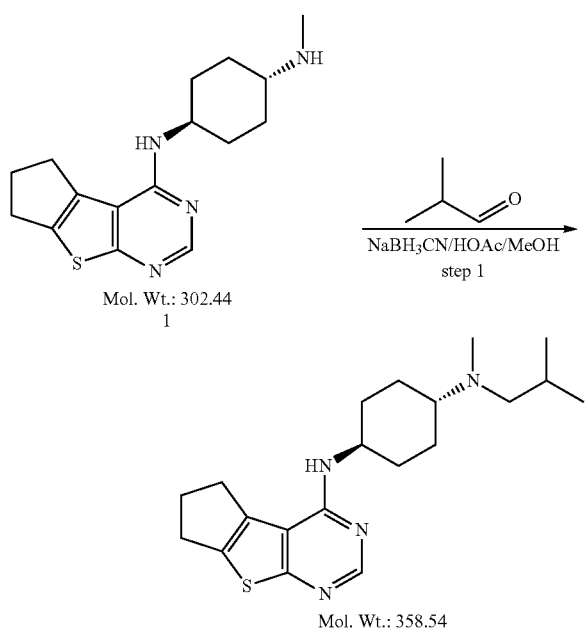

Note: For the preparation of the starting material compound 1, see Example 147.

To a solution of 1-N-methyl-4-N-[7-thia-9,11-diazatricyclo[6.4.0.0[2,6]]dodeca-1(8),2(6),9,11-tetraen-12-yl]cyclohexane-1,4-diamine (100 mg, 0.33 mmol, 1.00 equiv) in methanol (5 ml) was added 2-methylpropanal (50 mg, 0.69 mmol, 2.00 equiv) at room temperature and the reaction solution was stirred for 1 h. Then NaBH$_3$CN (45 mg, 0.72 mmol, 2.00 equiv) was added and stirred overnight at ambient temperature. The resulting solution was diluted with EtOAc (100 mL), washed with brine, dried over sodium sulfate and concentrated under vacuum. The crude product (120 mg) was purified by Prep-HPLC with the following conditions (SHIMADZU): Column, SunFire Prep C18, 19*150 mm 5 um; mobile phase, water with 0.05% NH$_4$HCO$_3$ and CH$_3$CN (6.0% CH$_3$CN up to 54.0% in 13 min); Flow rate, 20 mL/min; UV detection at 254/220 nm. The product-containing fractions were collected and partially evaporated to remove water and CH$_3$CN under reduced pressure. The residue was lyophilized overnight to give 75 mg (63%) of the desired 1-N-methyl-1-N-(2-methylpropyl)-4-N-[7-thia-9,11-diazatricyclo[6.4.0.0[2,6]]dodeca-1(8),2(6),9,11-tetraen-12-yl]cyclohexane-1,4-diamine as a white solid. MS: (ES, m/z): 359 [M+H]$^+$. $^1$H NMR (400 MHz, CD$_3$OD) δ 8.23 (s, 1H), 4.07-4.09 (m, 1H), 3.02 (t, 2H), 2.99 (t, 2H), 2.54-2.59 (m, 3H), 2.37-2.39 (m, 5H), 2.18-2.21 (m, 2H), 1.95-1.99 (m, 2H), 1.81-1.85 (m, 1H), 1.45-1.61 (m, 4H), 1.01 (s, 6H).

Example 164

1-N-(2-fluoroethyl)-1-N-methyl-4-N-[7-thia-9,11-diazatricyclo[6.4.0.0[2,6]]dodeca-1(8),2(6),9,11-tetraen-12-yl]cyclohexane-1,4-diamine Synthesis of Compound I-204

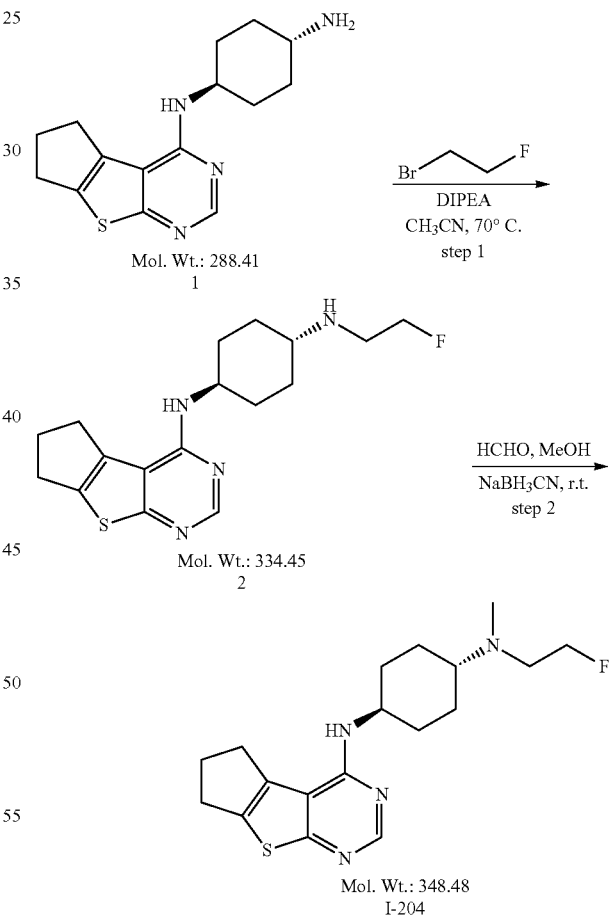

Synthesis of Compound 2

Reference: For the preparation of the starting material compound 1, see Example 147. Into a 100-mL round-bottom flask, a solution of 1-N-[7-thia-9,11-diazatricyclo[6.4.0.0[2,6]]dodeca-1(8),2(6),9,11-tetraen-12-yl]cyclohexane-1,4-diamine (250 mg, 0.87 mmol, 1.00 equiv) in CH$_3$CN (15 mL) was added 1-bromo-2-fluoroethane (220 mg, 1.73 mmol, 2.00 equiv) and DIPEA (200 mg, 1.74 mmol, 2.00 equiv) at room temperature under nitrogen. The resulting solution was stirred for 7 h at 70° C. in an oil bath. After completion, the resulting mixture was concentrated under vacuum. The residue was applied onto a silica gel column with dichloromethane/methanol (20:1) to give 240 mg (83%) of the desired 1-N-(2-fluoroethyl)-4-N-[7-thia-9,11-diazatricyclo[6.4.0.0[2,6]]dodeca-1(8),2(6),9,11-tetraen-12-yl]cyclohexane-1,4-diamine as a light yellow solid. MS (ES, m/z): 334 [M+H]$^+$.

Synthesis of Compound I-204

A solution of 1-N-(2-fluoroethyl)-4-N-[7-thia-9,11-diazatricyclo[6.4.0.0[2,6]]dodeca-1(8),2(6),9,11-tetraen-12-yl]cyclohexane-1,4-diamine (100 mg, 0.30 mmol, 1.00 equiv) in methanol (10 mL) was added HCHO (37%, 1 mL) and the resulting mixture was stirred at room temperature for 0.5 h. The NaBH(OAc)$_3$ (250 mg, 1.18 mmol, 4.00 equiv) was added and the resulting solution was stirred for additional 1 h at ambient temperature. After completion of the reaction, the reaction was then quenched with saturated aqueous sodium bicarbonate, extracted with 3×50 ml of dichloromethane. The combined organic layers were dried in an oven under reduced pressure and concentrated under vacuum. The residue was applied onto a silica gel column with dichloromethane/MeOH (10:1) to afford the corresponding 1-N-(2-fluoroethyl)-1-N-methyl-4-N-[7-thia-9,11-diazatricyclo[6.4.0.0[2,6]]dodeca-1(8),2(6),9,11-tetraen-12-yl]cyclohexane-1,4-diamine (47.8 mg, 46%) as a white solid. MS: (ES, m/z): 349 [M+H]$^+$. $^1$H NMR (400 MHz, CDCl$_3$): δ 1.23-1.32 (m, 2H), 1.50-1.60 (m, 2H), 1.76-1.95 (m, 2H), 2.27-2.35 (m, 2H), 2.40 (s, 3H), 2.50-2.60 (m, 3H), 2.84 (d, 2H), 2.99-3.05 (m, 4H), 4.05-4.15 (m, 1H), 4.57 (d, 2H), 4.86 (d, 1H), 8.39 (s, 1H).

Example 165

IRAK-4 Assay

Assay Materials

| Material | Vendor | Catalogue number |
|---|---|---|
| HEPES | Amresco | 0511 |
| Brij-35 | Sigma | B4184-100mL |
| Coating Reagent #3 | Caliper | |
| EDTA | Sigma | E5134-1KG |
| ATP | Sigma | A7699-1G |
| MgCl$_2$ | Sigma | 63068-250G |
| MnCl$_2$ | Sigma | M8054-100G |
| Peptide 8 | GL bioscience | 112396 |
| IRAK4 | CARNA Bioscience | 09-145 |
| 384-well plate | Corning | 3573 |

A 1× kinase base buffer was prepared from 50 mM HEPES, pH 7.5 and 0.0015% Brij-35. A stop buffer was prepared from 100 mM HEPES, pH 7.5, 0.015% Brij-35, 0.2% Coating Reagent #3, and 50 mM EDTA.

Test compound was diluted to 50× of the final desired highest inhibitor concentration in reaction by 100% DMSO. 100 ul of this compound dilution was transferred to a well in a 96-well plate. For example, if desired highest inhibitor concentration in IC50 determination is 100 uM, then prepare 5000 uM of compound DMSO solution in this step.

Test compound was serially diluted by transferring 30 μl to 60 μl of 100% DMSO in the next well and so forth for a total of 10 concentrations. 100 μl of 100% DMSO was added to two empty wells for no compound control and no enzyme control in the same 96-well plate.

A new 96-well plate was marked as intermediate plate. 5 μl of compound serial dilution was transferred from source plate to the corresponding wells of the intermediate plate. 45 μl of 1× kinase base buffer (KB buffer) was added to each well of the intermediate plate. The intermediate plate was placed for 10 min on a shaker.

5 μl of each well was transferred from the 96-well intermediate plate to a 384-well plate in duplicates. For example, A1 of the 96-well plate is transferred to A1 and A2 of the 384-well plate. A2 of the 96-well plate is transferred to A3 and A4 of the 384-well plate, and so on.

IRAK4 and DTT in 1× kinase base buffer was added. The 2.5× enzyme mix contained 8.8 nM IRAK4 and 5 mM DTT.

Peptide 8, ATP, MgCl$_2$ and MnC$_2$ were added in the 1× kinase base buffer. The 2.5× peptide mix contained 3.75 μM peptide 8, 92.5 μM ATP, 12.5 mM MgCl$_2$ and 2.5 mM MnC$_2$.

Assay plate already contained 5 μl of compound in 10% DMSO. Added 10 μl of 2.5× enzyme solution to each well of the 384-well assay plate, except no enzyme control wells. The final concentration of IRAK4 in reaction was 3.5 nM. Added 10 μl of 1× kinase base buffer to no enzyme control wells in the assay plate. Incubated at room temperature for 10 min.

Added 10 μl of 2.5× peptide solution to each well of the 384-well assay plate. The final concentration of Peptide 8 and ATP was 1.5 μM and 37 μM, respectively. Incubated at 28° C. for 40 minutes. Added 25 μl of stop buffer to stop reaction. Collected data on Caliper.

Copied conversion % data from Caliper program. Converted conversion % values to percent inhibition values. Percent inhibition=(max−conversion %)/(max−min)*100, where "max" means the conversion % of DMSO control and "min" means the conversion % of no enzyme control.

Tables 3 and 4 show the activity of selected compounds of this invention in the IRAK-4 activity inhibition assay. The compound numbers correspond to the compound numbers in Table 1. Compounds having an activity designated as "A" provided an IC$_{50}$≤5 μM; compounds having an activity designated as "B" provided an IC$_{50}$ of 5-20 μM; compounds having an activity designated as "C" provided an IC$_{50}$ of 20-50 μM; and compounds having an activity designated as "D" provided an IC$_{50}$≥50 μM. "NA" stands for "not assayed."

TABLE 3

IRAK-4 Activity Inhibition Data

| Cpd # | IRAK-4 |
|---|---|
| I-1 | B |
| I-2 | C |
| I-3 | B |
| I-4 | B |
| I-5 | A |
| I-6 | C |
| I-7 | B |
| I-8 | C |
| I-9 | C |
| I-10 | A |
| I-11 | B |
| I-12 | A |
| I-13 | B |
| I-14 | A |
| I-15 | B |
| I-16 | B |
| I-17 | B |

TABLE 3-continued

IRAK-4 Activity Inhibition Data

| Cpd # | IRAK-4 |
|---|---|
| I-18 | C |
| I-19 | B |
| I-20 | C |
| I-21 | B |
| I-22 | B |
| I-23 | C |
| I-24 | D |
| I-25 | B |
| I-26 | B |
| I-27 | B |
| I-28 | B |
| I-29 | B |
| I-30 | D |
| I-31 | B |
| I-32 | B |
| I-33 | C |
| I-34 | A |
| I-35 | B |
| I-36 | B |
| I-37 | B |
| I-38 | A |
| I-39 | A |
| I-40 | A |
| I-41 | A |
| I-42 | A |
| I-43 | B |
| I-44 | A |
| I-45 | B |
| I-46 | C |
| I-47 | B |
| I-48 | A |
| I-49 | A |
| I-50 | A |
| I-51 | A |
| I-52 | A |
| I-53 | A |
| I-54 | A |
| I-55 | A |
| I-56 | A |
| I-57 | A |
| I-58 | A |
| I-59 | C |
| I-60 | B |
| I-61 | A |
| I-62 | B |
| I-63 | B |
| I-64 | C |
| I-65 | B |
| I-66 | A |
| I-67 | A |
| I-68 | B |
| I-69 | D |
| I-70 | A |
| I-71 | A |
| I-72 | A |

TABLE 4

IRAK-4 Activity Inhibition Data Continued

| Cpd # | IRAK-4 |
|---|---|
| I-99 | A |
| I-100 | A |
| I-101 | A |
| I-102 | C |
| I-103 | C |
| I-104 | A |
| I-105 | A |
| I-106 | A |
| I-107 | A |
| I-108 | A |
| I-109 | A |
| I-110 | A |
| I-111 | A |
| I-112 | A |
| I-113 | B |
| I-114 | A |
| I-115 | A |
| I-116 | A |
| I-117 | A |
| I-118 | A |
| I-119 | A |
| I-120 | A |
| I-121 | A |
| I-122 | A |
| I-123 | A |
| I-124 | A |
| I-125 | A |
| I-126 | A |
| I-127 | A |
| I-128 | C |
| I-129 | A |
| I-130 | A |
| I-131 | A |
| I-132 | A |
| I-133 | A |
| I-134 | A |
| I-135 | A |
| I-136 | B |
| I-137 | B |
| I-138 | B |
| I-139 | C |
| I-140 | C |
| I-141 | B |
| I-142 | A |
| I-143 | A |
| I-144 | A |
| I-145 | C |
| I-146 | A |
| I-147 | D |
| I-148 | C |
| I-149 | A |
| I-150 | C |
| I-151 | A |
| I-153 | D |
| I-154 | B |
| I-155 | D |
| I-156 | C |
| I-157 | A |
| I-158 | A |
| I-159 | C |
| I-160 | B |
| I-161 | D |
| I-162 | A |
| I-163 | A |
| I-164 | A |
| I-165 | A |
| I-166 | A |
| I-167 | A |
| I-168 | A |
| I-169 | A |

Provided compounds were also assayed as inhibitors of IRAK-1. In certain embodiments, a provided compound inhibits IRAK-1 with an $IC_{50} \leq 5$ μM. In some embodiments, a provided compound inhibits IRAK-1 with an $IC_{50}$ of 5-20 μM. In other embodiments, a provided compound inhibits IRAK-1 with an $IC_{50}$ of 20-50 μM.

Provided compounds were also assayed in an LPS (Lipopolysacharide) induced THP-1 cell cytokine (TNFα and IL8) production assay. The protocol for this assay was as follows below.

THP-1 cells from ATCC (TIB-202) were cultured in RPMI Medium 1640 (Invitrogen, Cat No. A10491-01), 10% fetal bovine serum (Invitrogen, Cat No. 10099141, Lot No.

8172882) containing 100 U/mL Penicillin, 100 μg/mL streptomycin (Invitrogen, Cat No. 15140-122), and 50 μM 2-Mercaptoethanol (Invitrogen, Cat No. 21985023). LPS-EK ultra pure (Invivogen, Cat No. tlrl-peklps) was used to induce IL8 and TNFα production, that was detected in the cell culture supernatant by IL8 HTRF kit (Cisbio, Cat No. 62IL8PEB) and TNFα HTRF kit (Cisbio, Cat No. 62TNFPEB), as per manufacturer instructions. Cells were cultured in 96 well assay plates at 100,000 cells per well, and compounds diluted in final 0.3% DMSO were pre-incubated with cells for 1 hour prior to stimulation with 300 ng/mL LPS. Cytokine production in cell supernatant was measured at 5 hours for TNFα and IL8 production, and for 16 hours for IL8 production and assessment of cell viability.

Table 5 shows the activity of selected compounds of this invention in the TNFα and IL8 production assay. The compound numbers correspond to the compound numbers in Table 1. Compounds having an activity designated as "A" provided an $IC_{50} \leq 0.5$ μM; compounds having an activity designated as "B" provided an $IC_{50}$ of 0.5-1.0 μM; compounds having an activity designated as "C" provided an $IC_{50}$ of 1.0-5.0 μM; and compounds having an activity designated as "D" provided an $IC_{50} \geq 5$ μM. "NA" stands for "not assayed."

TABLE 5

| TNF and IL8 Production Assay | | |
|---|---|---|
| Cpd # | TNFα | IL8 |
| I-12 | B | B |
| I-124 | C | B |
| I-133 | C | C |
| I-201 | C | C |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula III-h:

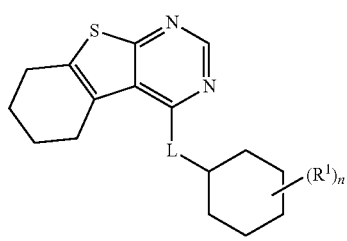

III-h or a pharmaceutically acceptable salt thereof, wherein:
n is 1-4;
each $R^1$ is independently halogen, —CN, —NO$_2$, —OR, —CH$_2$OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)R, —N(R)C(O)N(R)$_2$, Cy, or —N(R)S(O)$_2$R; or $R^1$ is selected from one of the following formulas:

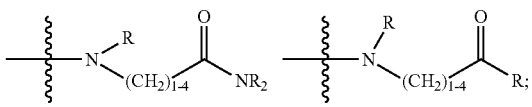

or two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen or an optionally substituted group selected from $C_{1-6}$ aliphatic, aryl, 4-7 membered saturated or partially unsaturated heterocyclic ring having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur, and L is a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —C(O)—, —OC(O)—, —C(O)O—, —S(O)—, or —S(O)$_2$—.

2. The compound of claim 1 of formula III-i:

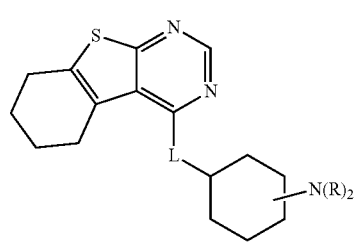

III-i or a pharmaceutically acceptable salt thereof.

3. The compound of claim 1, wherein n is 1 and $R^1$ is of one the following formulas:

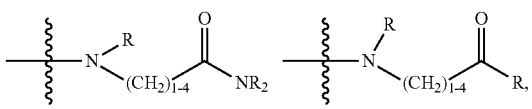

or a pharmaceutically acceptable salt thereof.

4. The compound of claim 1, wherein n is 1 and $R^1$ is —N(CH$_3$)$_2$.

5. The compound of claim 1, wherein n is 1 and $R^1$ is Cy.

6. The compound of claim 5 of formula III-j:
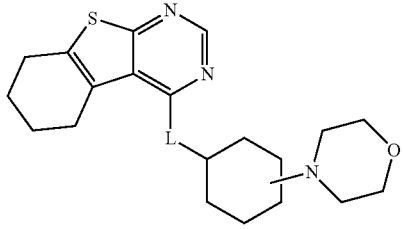
or a pharmaceutically acceptable salt thereof.
7. The compound of claim 1, wherein L is —NH—.
8. The compound of claim 1, wherein said compound is:
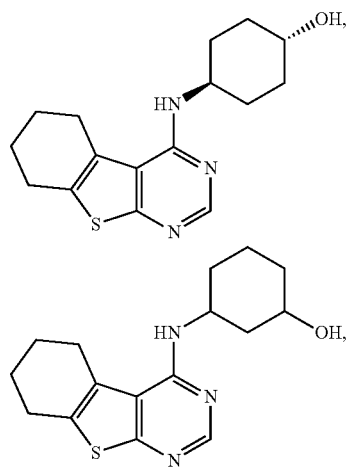
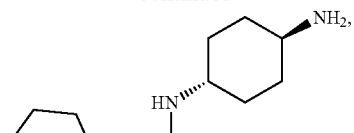
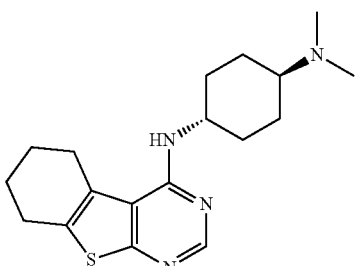
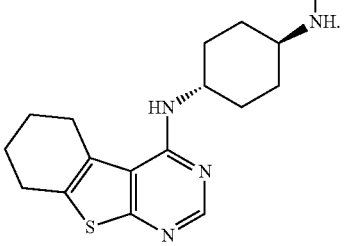
, or
9. A pharmaceutical composition comprising a compound of claim 1 and a pharmaceutically acceptable excipient, carrier or vehicle.
* * * * *